United States Patent
Albaek et al.

(10) Patent No.: US 10,077,443 B2
(45) Date of Patent: Sep. 18, 2018

(54) OLIGONUCLEOTIDE CONJUGATES

(71) Applicant: Roche Innovation Center Copenhagen A/S, Horsholm (DK)

(72) Inventors: Nanna Albaek, Birkerod (DK); Henrik Frydenlund Hansen, Roedovre (DK); Susanne Kammler, Holte (DK); Jacob Ravn, Skovlunde (DK); Henrik Orum, Vaerlose (DK)

(73) Assignee: Roche Innovation Center Copenhagen A/S, Basel (CH)

( * ) Notice: Subject to any disclaimer, the term of this patent is extended or adjusted under 35 U.S.C. 154(b) by 0 days.

(21) Appl. No.: 14/443,367

(22) PCT Filed: Nov. 14, 2013

(86) PCT No.: PCT/EP2013/073858
§ 371 (c)(1),
(2) Date: May 15, 2015

(87) PCT Pub. No.: WO2014/076195
PCT Pub. Date: May 22, 2014

(65) Prior Publication Data
US 2015/0275212 A1  Oct. 1, 2015

(30) Foreign Application Priority Data

Nov. 15, 2012 (EP) .................. 12192773
Jan. 30, 2013 (EP) .................. 13153296
Feb. 28, 2013 (EP) .................. 13157237
Jun. 27, 2013 (EP) .................. 13174092

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2310/314* (2013.01); *C12N 2310/315* (2013.01); *C12N 2310/3231* (2013.01); *C12N 2310/341* (2013.01); *C12N 2310/351* (2013.01); *C12N 2310/3515* (2013.01); *C12N 2310/3517* (2013.01); *C12N 2320/32* (2013.01); *C12N 2330/30* (2013.01)

(58) Field of Classification Search
CPC ............ C12N 15/113; C12N 2310/341; A61K 31/713
See application file for complete search history.

(56) References Cited

U.S. PATENT DOCUMENTS

| | | |
|---|---|---|
| 4,587,044 A | 5/1986 | Miller et al. |
| 4,667,025 A | 5/1987 | Miyoshi et al. |
| 4,904,582 A | 2/1990 | Tullis |
| 4,914,210 A | 4/1990 | Levenson et al. |
| 4,948,882 A | 8/1990 | Ruth |
| 4,958,013 A | 9/1990 | Letsinger |
| 4,962,029 A | 10/1990 | Levenson et al. |
| 5,112,963 A | 5/1992 | Pieles et al. |
| 5,245,022 A | 9/1993 | Weis et al. |
| 5,254,469 A | 10/1993 | Warren, III et al. |
| 5,272,250 A | 12/1993 | Spielvogel et al. |
| 5,346,696 A | 9/1994 | Kim et al. |
| 5,354,844 A | 10/1994 | Beug et al. |
| 5,391,723 A | 2/1995 | Priest |
| 5,486,603 A | 1/1996 | Buhr |
| 5,510,475 A | 4/1996 | Agrawal et al. |
| 5,512,667 A | 4/1996 | Reed et al. |
| 5,525,465 A | 6/1996 | Haralambidis et al. |
| 5,541,313 A | 7/1996 | Ruth |
| 5,545,730 A | 8/1996 | Urdea et al. |
| 5,552,538 A | 9/1996 | Urdea et al. |
| 5,574,142 A | 11/1996 | Meyer, Jr. et al. |
| 5,580,731 A | 12/1996 | Chang et al. |
| 5,608,046 A | 3/1997 | Cook et al. |
| 5,672,662 A | 9/1997 | Harris et al. |
| 5,684,142 A | 11/1997 | Mishra et al. |
| 5,714,166 A | 2/1998 | Tomalia et al. |
| 5,770,716 A | 6/1998 | Khan et al. |
| 5,776,907 A | 7/1998 | Kohn et al. |
| 5,885,968 A | 3/1999 | Biessen et al. |
| 5,994,517 A | 11/1999 | Ts'o et al. |
| 6,096,875 A | 8/2000 | Khan et al. |
| 6,268,490 B1 | 7/2001 | Imanishi et al. |
| 6,335,432 B1 | 1/2002 | Segev |
| 6,335,437 B1 | 1/2002 | Manoharan |
| 6,344,436 B1 | 2/2002 | Smith et al. |

(Continued)

FOREIGN PATENT DOCUMENTS

| | | | |
|---|---|---|---|
| CN | 102226185 A | * | 10/2011 |
| EP | 1222309 | | 12/2005 |

(Continued)

OTHER PUBLICATIONS

Elmen et al,. (Nature 2008, vol. 452, pp. 896-900).*
Dassie et al. (Nat. Biotech. 2009 vo. 27 pp. 839-849).*
Krutzfeldt et al. (Nature 2005 vol. 438 pp. 685-689).*
Baker et al., "Oligonucleotide-europium complex conjugate designed to cleave the 5' cap structure of the ICAM-1 transcript potentiates antisense activity in cell," Nucleic Acids Research, 1999, 27(6):1547-1551.
Freier et al., "The ups and downs of nucleic acid duplex stability: structure-stability studies on chemically-modified DNA:RNA duplexes," Nucleic Acids Research, 1997, 25(22):4429-4443.
Meunier et al., "The nuclear export signal-dependent localization of oligonucleopeptides enhances the inhibition of the protein expression from a gene transcribed in cytosol," Nucleic Acids Research, 1999, 27(13):2730-2736.
Wei et al., "Hybridization properties of oligodeoxynucleotide pairs bridged by polyarginine peptides," Nucleic Acids Research, 1996, 24(4):655-661.

(Continued)

*Primary Examiner* — J. E Angell
(74) *Attorney, Agent, or Firm* — Fish & Richardson P.C.

(57) ABSTRACT

The invention relates to the field of oligonucleotide therapeutics, and in particular to the use of a cleavable, e.g. a phosphodiester region covalently attached to a conjugate, a targeting group or blocking group to enhance the properties of the oligonucleotides, for example to improve the therapeutic index.

22 Claims, 28 Drawing Sheets
Specification includes a Sequence Listing.

(56) References Cited

U.S. PATENT DOCUMENTS

| | | | |
|---|---|---|---|
| 6,365,379 B1 | 4/2002 | Lima et al. |
| 6,395,492 B1 | 5/2002 | Manoharan et al. |
| 6,525,031 B2 | 2/2003 | Manoharan |
| 6,525,191 B1 | 2/2003 | Ramasamy |
| 6,528,631 B1 | 3/2003 | Cook et al. |
| 6,559,279 B1 | 5/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,087,229 B2 | 8/2006 | Zhao et al. |
| 7,399,845 B2 | 7/2008 | Seth et al. |
| 7,427,672 B2 | 9/2008 | Imanishi et al. |
| 7,723,509 B2 | 5/2010 | Manoharan |
| 7,741,457 B2 | 6/2010 | Seth et al. |
| 7,816,337 B2 | 10/2010 | Rozema et al. |
| 8,101,743 B2 | 1/2012 | Brown-Driver et al. |
| 9,132,147 B2 | 9/2015 | Bagger et al. |
| 9,181,549 B2 | 11/2015 | Prakash et al. |
| 9,290,758 B2 | 3/2016 | Nielsen et al. |
| 2003/0148985 A1 | 8/2003 | Morrissey et al. |
| 2004/0034191 A1 | 2/2004 | Manoharan et al. |
| 2004/0171570 A1 | 9/2004 | Allerson et al. |
| 2005/0009088 A1 | 1/2005 | Crooke et al. |
| 2005/0130923 A1 | 6/2005 | Bhat et al. |
| 2007/0049547 A1 | 3/2007 | Esau et al. |
| 2007/0287831 A1 | 12/2007 | Seth et al. |
| 2008/0039414 A1 | 2/2008 | McSwiggen et al. |
| 2008/0039618 A1 | 2/2008 | Allerson et al. |
| 2009/0118213 A1 | 5/2009 | Hansen et al. |
| 2009/0239814 A1 | 9/2009 | Manoharan et al. |
| 2010/0330035 A1 | 12/2010 | Hildebrandt-Ericksen et al. |
| 2011/0207799 A1 | 8/2011 | Rozema et al. |
| 2012/0122801 A1 | 5/2012 | Platenburg |
| 2015/0291958 A1 | 10/2015 | Albaek et al. |
| 2015/0368642 A1 | 12/2015 | Albaek et al. |
| 2016/0289677 A1 | 10/2016 | Albaek et al. |

FOREIGN PATENT DOCUMENTS

| | | |
|---|---|---|
| EP | 1495769 | 2/2008 |
| EP | 1984381 | 9/2010 |
| EP | 2320925 | 12/2015 |
| RU | 2009/139221 | 5/2011 |
| WO | WO1992/13570 | 8/1992 |
| WO | WO1992/17210 | 10/1992 |
| WO | WO1993/07883 | 4/1993 |
| WO | WO1994/14226 | 6/1994 |
| WO | WO1996/03152 | 2/1996 |
| WO | WO1996/11205 | 4/1996 |
| WO | WO1997/03211 | 1/1997 |
| WO | WO98/014615 | 4/1998 |
| WO | WO98/50540 | 11/1998 |
| WO | WO1998/39352 | 11/1998 |
| WO | WO1998/52614 | 11/1998 |
| WO | WO1999/14226 | 3/1999 |
| WO | WO1999/65925 | 12/1999 |
| WO | WO2000/32764 | 6/2000 |
| WO | WO2000/76554 | 12/2000 |
| WO | WO2001/025248 | 4/2001 |
| WO | WO2003/011887 | 2/2003 |
| WO | WO2003/014307 | 2/2003 |
| WO | WO03/072711 | 9/2003 |
| WO | WO2003/097662 | 11/2003 |
| WO | WO2004/000192 | 12/2003 |
| WO | WO2004/044141 | 5/2004 |
| WO | WO2004/044181 | 5/2004 |
| WO | WO2004/046160 | 6/2004 |
| WO | WO2004/087931 | 10/2004 |
| WO | WO2004/106356 | 12/2004 |
| WO | WO2005/000201 | 1/2005 |
| WO | WO2005/013901 | 2/2005 |
| WO | WO2005/019418 | 3/2005 |
| WO | WO2005/069994 | 8/2005 |
| WO | WO2005/073378 | 8/2005 |
| WO | WO2005/086775 | 9/2005 |
| WO | WO2005/021570 | 10/2005 |
| WO | WO2005/111238 | 11/2005 |
| WO | WO2005/115479 | 12/2005 |
| WO | WO2006/020676 | 2/2006 |
| WO | WO2006/036916 | 4/2006 |
| WO | WO2006/076674 | 7/2006 |
| WO | WO2006/078217 | 7/2006 |
| WO | WO2006/112872 | 10/2006 |
| WO | WO2007/027775 | 3/2007 |
| WO | WO2007/027894 | 3/2007 |
| WO | WO2007/031081 | 3/2007 |
| WO | WO2007/031091 | 3/2007 |
| WO | WO2007/035759 | 3/2007 |
| WO | WO2007/058894 | 5/2007 |
| WO | WO2007/085485 | 8/2007 |
| WO | WO2007/090071 | 8/2007 |
| WO | WO2007/107162 | 9/2007 |
| WO | WO2007/112753 | 10/2007 |
| WO | WO2007/112754 | 10/2007 |
| WO | WO2007/113531 | 10/2007 |
| WO | WO2007/131237 | 11/2007 |
| WO | WO2007/131238 | 11/2007 |
| WO | WO2007/134014 | 11/2007 |
| WO | WO2007/134181 | 11/2007 |
| WO | WO2007/136988 | 11/2007 |
| WO | WO2007/136989 | 11/2007 |
| WO | WO2007/143315 | 12/2007 |
| WO | WO2007/146511 | 12/2007 |
| WO | WO2008/034122 | 3/2008 |
| WO | WO2008/034123 | 3/2008 |
| WO | WO2008/040355 | 4/2008 |
| WO | WO2008/043753 | 4/2008 |
| WO | WO2008/051306 | 5/2008 |
| WO | WO2008/066776 | 6/2008 |
| WO | WO2008/068638 | 6/2008 |
| WO | WO2008/091703 | 7/2008 |
| WO | WO2008/101157 | 8/2008 |
| WO | WO2008/109447 | 9/2008 |
| WO | WO2008/113830 | 9/2008 |
| WO | WO2008/113831 | 9/2008 |
| WO | WO2008/113832 | 9/2008 |
| WO | WO2008/131807 | 11/2008 |
| WO | WO2008/132234 | 11/2008 |
| WO | WO2008/150729 | 12/2008 |
| WO | WO2008/154401 | 12/2008 |
| WO | WO2009/005793 | 1/2009 |
| WO | WO2009/006478 | 1/2009 |
| WO | WO2009/025669 | 2/2009 |
| WO | WO2009/043353 | 4/2009 |
| WO | WO2009/043354 | 4/2009 |
| WO | WO2009/045536 | 4/2009 |
| WO | WO2009/046141 | 4/2009 |
| WO | WO2009/068033 | 6/2009 |
| WO | WO2009/071082 | 6/2009 |
| WO | WO2009/073809 | 6/2009 |
| WO | WO2009/090182 | 7/2009 |
| WO | WO2009/100320 | 8/2009 |
| WO | WO2009/124238 | 10/2009 |
| WO | WO2009/126933 | 10/2009 |
| WO | WO2009/148605 | 12/2009 |
| WO | WO2010/000656 | 1/2010 |
| WO | WO2010/017509 | 2/2010 |
| WO | WO2010/045584 | 4/2010 |
| WO | WO2010/076248 | 7/2010 |
| WO | WO2010/142805 | 12/2010 |
| WO | WO2011/009697 | 1/2011 |
| WO | WO2011/47312 | 4/2011 |
| WO | WO2011/052911 | 5/2011 |
| WO | WO2011/085271 | 7/2011 |
| WO | WO2011/088309 | 7/2011 |
| WO | WO2011/104169 | 9/2011 |
| WO | WO2011/123621 | 10/2011 |
| WO | WO2011/126937 | 10/2011 |
| WO | WO2011/130458 | 10/2011 |
| WO | WO2011/131693 | 10/2011 |
| WO | WO2011/133871 | 10/2011 |
| WO | WO2011/139917 | 11/2011 |

(56) References Cited

FOREIGN PATENT DOCUMENTS

| WO | WO2012/012716 | 1/2012 |
|---|---|---|
| WO | WO2012/029870 | 3/2012 |
| WO | WO2012/078637 | 6/2012 |
| WO | WO2012/082046 | 6/2012 |
| WO | WO2012/083046 | 6/2012 |
| WO | WO2012/089352 | 7/2012 |
| WO | WO2012/089602 | 7/2012 |
| WO | WO2012/092373 | 7/2012 |
| WO | WO2012/099755 | 7/2012 |
| WO | WO2012/145674 | 10/2012 |
| WO | WO2012/145697 | 10/2012 |
| WO | WO2012/148952 | 11/2012 |
| WO | WO2012/174154 | 12/2012 |
| WO | WO2012/174476 | 12/2012 |
| WO | WO2013/003520 | 1/2013 |
| WO | WO2013/033230 | 3/2013 |
| WO | WO2013/070771 | 5/2013 |
| WO | WO2013/119979 | 8/2013 |
| WO | WO2013/142514 | 9/2013 |
| WO | WO2013/154798 | 10/2013 |
| WO | WO2013/159109 | 10/2013 |
| WO | WO2014/076195 | 5/2014 |
| WO | WO2014/076196 | 5/2014 |
| WO | WO2014/118267 | 8/2014 |
| WO | WO2014/179620 | 11/2014 |
| WO | WO2015/071388 | 5/2015 |

OTHER PUBLICATIONS

U.S. Appl. No. 60/979,217, filed Oct. 11, 2007, Obad et al.
U.S. Appl. No. 60/989,574, filed Nov. 21, 2007, Seth et al.
U.S. Appl. No. 61/028,062, filed Feb. 12, 2008, Obad et al.
U.S. Appl. No. 61/056,564, filed May 28, 2008, Seth et al.
U.S. Appl. No. 61/099,844, filed Sep. 24, 2008, Seth et al.
Ackermann et al., "Clinical development of an antisense therapy for the treatment of transthyretin-associated polyneuropathy," Amyloid 2012:19 Suppl. 1:43-4.
Adva Biton et al., "DNA Photocleavage by DNA and DNA-LNA Amino Acid-Dye Conjugates," Bioconjugate Chemistry, vol. 21, No. 4 (2010), pp. 616-621.
Afonina et al., "Sequence-specific arrest of primer extension on single-stranded DNA by an oligonucleotide-minor groove binder conjugate," PNAS, 1996, 93(8):3199-204.
Albaek et al., "Analogues of a locked nucleic acid with three-carbon 2',4'-linkages: synthesis by ring-closing metathesis and influence on nucleic acid duplex stability and structure," J. Org. Chem., 2006, 71(20):7731-40.
Altmann et al., "Second-generation antisense oligonucleotides: structure-activity relationships and the design of improved signal-transduction inhibitors," Biochem. Soc. Trans., 1996, 24(3):630-637.
Altmann et al., "Second Generation of Antisense Oligonucleotides: From Nuclease Resistance to Biological Efficacy in Animals," Chimia, 1996, 50, 168-176.
Altmann et al., "Second Generation Antisense Oligonucleotides-Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides," Nucleosides Nucleotides, 1997, 16, 917-926.
Antopolsky et al., "Peptide-oligonucleotide phosphorothioate conjugates with membrane translocation and nuclear localization properties," Bioconjugate Chem. 1999, 10(4):598-606.
Arar et al., "Synthesis and antiviral activity of peptide-oligonucleotide conjugates prepared by using N alpha-(bromoacetyl) peptides," Bioconjugate Chem. 1995, 6(5):573-7.
Asseline et al., "Nucleic acid-binding molecules with high affinity and base sequence specificity: intercalating agents covalently linked to oligodeoxynucleotides," PNAS, 1984, 81(11):3297-301.
Astriab-Fisher et al., "Antisense inhibition of P-glycoprotein expression using peptide-oligonucleotide conjugates," Biochem. Pharmacol, 2000, 60(1):83-90.

Baenziger and Fiete, "Galactose and N-acetylgalactosamine-specific endocytosis of glycopeptides by isolated rat hepatocytes," 1980, Cell, 22, 611-620.
Baker et al., "Oligonucleotide-europium complex conjugate designed to cleave the 5' cap structure of the ICAM-1 transcript potentiates antisense activity in cells," Nucleic Acids Res. 1999, 27(6):1547-51.
Benson et al., "Suppression of choroid plexus transthyretin levels by antisense oligonucleotide treatment," Amyloid 2010; 17(2):43-9.
Biessen et al. "Synthesis of cluster galactosides with high affinity for the hepatic asialoglycoprotein receptor," J. Med. Chem. 1995 38(9):1538-1546.
Bollig et al., "Affinity purification of ARE-binding proteins identifies polyA-binding protein 1 as a potential substrate in MK2-induced mRNA stabilization," Biochem. Biophys. Res. Commun. 2003, 301(3):665-70.
Bongartz et al., "Improved biological activity of antisense oligonucleotides conjugated to a fusogenic peptide," Nucleic Acids Res. 1994, 22(22):4681-8.
Bonora et al., "Antisense activity of an anti-HIV oligonucleotide conjugated to linear and branched high molecular weight polyethylene glycols," Farmaco, 1998, 53(10-11):634-7.
Bonora et al., "Biological Properties of Antisense Oligonucleotides Conjugated to Different High-Molecular Mass Poly(Ethylen Glycols)," Nucleosides Nucleotides, 1999, 18, 1723-1725.
Braasch et al., "Locked nucleic acid (LNA): fine-tuning the recognition of DNA and RNA," Chem. Biol, 2001, 8(1):1-7.
Branden et al., "A peptide nucleic acid-nuclear localization signal fusion that mediates nuclear transport of DNA," Nat Biotechnol, 1999, 17(8):784-7.
Cazalla et al., "Nuclear export and retention signals in the RS domain of SR proteins," Mol Cell. Biol. 2002, 22(19):6871-82.
Chaloin et al., "Design of carrier peptide-oligonucleotide conjugates with rapid membrane translocation and nuclear localization properties," Biochem. Biophys. Res. Commun., 1998, 243(2):601-8.
Chaltin et al., "Delivery of antisense oligonucleotides using cholesterol-modified sense dendrimers and cationic lipids," Bioconjugate Chem. 2005 16(4):827-836.
Chattopadhyaya et al., "Fine tuning of electrostatics around the internucleotidic phosphate through incorporation of modified 2',4'-carbocyclic-LNAs and -ENAs leads to significant modulation of antisense properties," J.Org. Chem, 2009, 74(1):118-134.
Christensen and Pedersen, "Intercalating nucleic acids containing insertions of 1-O-(1-pyrenylmethyl)glycerol: stabilization of dsDNA and discrimination of DNA over RNA," Nucl. Acids Res. 2002 30(22):4918-4925.
Connolly et al., "Binding and endocytosis of cluster glycosides by rabbit hepatocytes. Evidence for a short-circuit pathway that does not lead to degradation," 1982, J. Biol. Chern., 257(2):939-945.
Corey, "48000-fold Acceleration of Hybridization by Chemically Modified Oligonucleotides," J Am. Chem. Soc. 1995, 117, 9373-9374.
Corey, et al., "Generation of a hybrid sequence-specific single-stranded deoxyribonuclease," Science 1987, 238(4832):1401-3.
Corey et al., "Sequence-Selective Hydrolysis of Duplex DNA by an Oligonucleotide-Directed Nuclease," J. Am. Chem. Soc. 1989, 111, 8523-8525.
Duff et al., "Intrabody tissue-specific delivery of antisense conjugates in animals. ligand-linker-antisense oligomer conjugates," Methods Enzymol, 2000, 313:297-321.
Efimov et al., "Synthesis of Polyethylene Glycol-Oligonucleotide Conjugates," Bioorg. Khim 1993, 19, 800-804.
Elayadi et al., "Application of PNA and LNA oligomers to chemotherapy," Curr. Opinion Investig. Drugs, 2001, 2(4):558-561.
Esau, "miR-122 regulation of lipid metabolism revealed by in vivo antisense targeting," Cell Metab. 2006; 3(2):87-98.
Felber et al, "The interactions of amphiphilic antisense oligonucleotides with serum proteins and their effects on in vitro silencing activity," Biomaterials (2012) 33(25): 599-65.
Firestone, "Low-density lipoprotein as a vehicle for targeting antitumor compounds to cancer cells," Bioconjugate Chem., 1994, 5(2):105-13.

(56) References Cited

OTHER PUBLICATIONS

Freier & Altmann, "The ups and downs of nucleic acid duplex stability: structure-stability studies on chemically-modified DNA:RNA duplexes," Nucl. Acid Res. 1997, 25(22):4429-4443.
Frieden et al., "Expanding the design horizon of antisense oligonucleotides with alpha-L-LNA," Nucleic Acids Research, 2003, 31(21):6365-6372.
Gorlach et al., "The mRNA poly(A)-binding protein: localization, abundance, and RNA-binding specificity," Exp. Cell Res. 1994, 211(2):400-7.
Grijalvo et al., "Synthesis of oligonucleotides carrying amino lipid groups at the 3'-end for RNA interference studies," J Org Chem (2010) 75(20): 6806-13.
Guerniou et al., "Targeted inhibition of the hepatitis C internal ribosomal entry site genomic RNA with oligonucleotide conjugates," Nucleic Acids Res (2007); 35 (20): 6778-87.
Godeau et al, "Lipid-conjugated oligonucleotides via "click chemistry" efficently inhibiti hepatitis C virus translation," J. Med. Chem. (2008) 51(15): 4374-6.
Guzaev et al., "Conjugation of oligonucleotides via an electrophilic tether: N-chloroacetamidohexyl phosphoramidite reagent," Bioorg. Med. Chem. Lett., 1998, 8(24):3671-6.
Hangeland et al., "Cell-type specific and ligand specific enhancement of cellular uptake of oligodeoxynucleoside methylphosphonates covalently linked with a neoglycopeptide, YEE(ah-GalNAc)3," Bioconjug Chem. Nov.-Dec. 1995;6(6):695-701.
Hariton-Gazal, et al., "Targeting of nonkaryophilic cell-permeable peptides into the nuclei of intact cells by covalently attached nuclear localization signals," Biochemistry, 2002, 41(29):9208-14.
Henderson et al., "A comparison of the activity, sequence specificity, and CRM1-dependence of different nuclear export signals," Exp. Cell Res. 2000, 256(1):213-24.
Huang et al., "Oligonucleotide conjugates of Eu(III) tetraazamacrocycles with pendent alcohol and amide groups promote sequence-specific RNA cleavage," J. Biol. Inorg. Chem. 2000, 5(1):85-92.
Huh et al., "Design, synthesis, and evaluation of mitomycin-tethered phosphorothioate oligodeoxynucleotides," Bioconjugate Chem. 1996, 7(6):659-69.
Jaschke et al., "Synthesis and properties of oligodeoxyribonucleotide-polyethylene glycol conjugates," Nucleic Acids Res. 1994, 22(22):4810-7.
Iobst, S.T. and Drickamer, K., "Selective sugar binding to the carbohydrate recognition domains of the rat hepatic and macrophage asialoglycoprotein receptors," JB.C. 1996, 271(12):6686-93.
Juby et al., "Facile Preparation of 3'Oligonucleotide-Peptide Conjugates," Tetrahedron Letters 1991, 32(7), 879-882.
Kabanov et al., "A new class of antivirals: antisense oligonucleotides combined with a hydrophobic substituent effectively inhibit influenza virus reproduction and synthesis of virus-specific proteins in MDCK cells," FEBSLett., 1990, 259(2):327-30.
Keith T. Gagnon et al., "Antisense and Antigene Inhibition of Gene Expression by Cell-Permeable Oligonucleotide-Oligospermine Conjugates," Journal of the American Chemical Society, vol. 133, No. 22 (2011), pp. 8404-8407.
Kim et al., "PEG conjugated VEGF siRNA for anti-angiogenic gene therapy," J. Control Release (2006) 116(2):123-9.
Kobylanska et al., "Inhibition of plasminogen activator inhibitor release in endothelial cell cultures by antisense oligodeoxyribonucleotides with a 5'-end lipophilic modification," Acta Biochim Pol. (1999); 46(3); 679-91.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, 1998, 54, 3607-3630.
Koufaki et al., "Multifunctional lipoic acid conjugates," Curr Med Chem (2009) 16(35): 4728-42.
Krieg, et al, "Uptake of oligodeoxyribonucleotides by lymphoid cells is heterogeneous and inducible," Antisense Research and Development 1991, 1(2):161-71.

Krützfeldt et al., "Silencing of microRNAs in vivo with 'antagomirs'," Nature 2005, 438(7068): 685-689.
Kuijpers et al., "Specific recognition of antibody-oligonucleotide conjugates by radiolabeled antisense nucleotides: a novel approach for two-step radioimmunotheraphy of cancer," Bioconjugate Chem. 1993, 4(1):94-102.
Kumar et al., "The first analogues of LNA (locked nucleic acids): phosphorothioate-LNA and 2'-thio-LNA," Bioorg. Med. Chem. Lett., 1998, 8(16):2219-2222.
Lehmann T.J. et al., "Synthesis and Properties of Bile Acid Phosphoramidites 5'-Tethered to Antisense Oligodeoxynucleotides against HCV," Bioorganic & Medicinal Chemistry, vol. 9, No. 7 (2001), pp. 1827-1835.
Letsinger et al., "Cholesteryl-conjugated oligonucleotides: synthesis, properties, and activity as inhibitors of replication of human immunodeficiency virus in cell culture," PNAS, 1989, 86(17):6553-6.
Leumann CJ, "DNA analogues: from supramolecular principles to biological properties," Bioorg. Med. Chem. (2002) 10(4):841-854.
Li et al., "Folate-mediated targeting of antisense oligodeoxynucleotides to ovarian cancer cells," Pharm. Res. 1998, 15(10):1540-5.
Lima et al., "Highly efficient endonucleolytic cleavage of RNA by a Cys(2)His(2) zinc-finger peptide," PNAS 1999, 96(18):10010-5.
Lin et al., "A Cytosine Analogue Capable of Clamp-Like Binding to a Guanine in Helical Nucleic Acids," J. Am. Chem. Soc., 1998, 120, 8531-8532.
Lin et al., "Inhibition of collagenase type I expression by psoralen antisense oligonucleotides in dermal fibroblasts," Faseb J., 1995, 9(13):1371-7.
Liu et al., "Efficient nuclear delivery of antisense oligodeoxynucleotides and selective inhibition of CETP expression by apo E peptide in a human CETP-stably transfected CHO cell line," Arterioscler. Thromb. Vasc. Biol, 1999, 19(9):2207-13.
Lixin et al., "Novel properties of the nucleolar targeting signal of human angiogenin," Biochem. Biophys. Res. Commun. 2001, 284(1):185-93.
Lu, W. et al. "Cationic albumin-conjugated pegylated nanoparticles as novel drug carrier for brain delivery," (2005) J Control Release 107(3):428-448.
Lukhtanov et al., "Direct, solid phase assembly of dihydropyrroloindole peptides with conjugated oligonucleotides," Bioconjugate Chem. 1996, 7(5):564-7.
Manoharan et al., "Novel Functionalization of the Sugar Moiety of Nucleic Acids for Multiple Labeling in the Minor Groove," Tetrahedron Letters, 1991, 32(49):7171-7174.
Manoharan et al., "Lipidic Nucleic Acids," Tetrahedron Letters, 1995, 36(21), 3651-3654.
Martin P., "38.Ein neuer Zugang zu 2'-O-Alkylribonucleosiden und Eigenschaften deren Oligonucleotide," Helvetica Chimica Acta, 1995, 78, 486-504.
Maruenda et al., "Antisense sequence-directed cross-linking of DNA oligonucleotides by mitomycin C," Bioconjugate Chem. 1996, 7(5):541-4.
Maruenda et al., "Antisense sequence-directed cross-linking of RNA oligonucleotides by mitomycin," Anti-Cancer Drug Des. 1997, 12(6):473-9.
Meunier et al., "The nuclear export signal-dependent localization of oligonucleopeptides enhances the inhibition of the protein expression from a gene transcribed in cytosol," Nucleic Acids Res. 1999, 27(13):2730-6.
Mili et al., "Distinct RNP complexes of shuttling hnRNP proteins with pre-mRNA and mRNA: candidate intermediates in formation and export of mRNA," Mol. Cell. Biol. 2001, 21(21):7307-19.
Mishra et al., "Improved leishmanicidal effect of phosphorotioate antisense oligonucleotides by LDL-mediated delivery," Biochim. Biophys. Acta, 1995, 1264(2):229-37.
Mouna Raouane et al., "Synthesis, Characterization, and in Vivo Delivery of siRNA-Squalene Nanoparticles Targeting Fusion Oncogene in Papillary Thyroid Carcinoma," Journal of Medicinal Chemistry, vol. 54, No. 12, (2011), pp. 4067-4076.
Muthiah Manoharan, "Oligonucleotide Conjugates as Potential Antisense Drugs with Improved Uptake, Biodistribution, Targeted Deliv-

(56) References Cited

OTHER PUBLICATIONS ery, and Mechanism of Action," Antisense & Nucleic Acid Drug Development 12(2):103-128 (2002).
Nelson et al., "Bifunctional oligonucleotide probes synthesized using a novel CPG support are able to detect single base pair mutations," Nucleic Acids Res. 1989, 17(18):7187-94.
Nishina K. et al., "Efficient in vivo delivery of siRNA to the liver by conjugation of a tocopherol," Molecular Therapy, 16(4):734-740 (2008).
Oberhauser et al., "Effective incorporation of 2'-O-methyl-oligoribonucleotides into liposomes and enhanced cell association through modification with thiocholesterol," Nucl Acids Res. 1992, 20(3):533-8.
Orum et al., "Locked nucleic acids: A promising molecular family for gene-function analysis and antisense drug development," Curr. Opinion Mol. Ther., 2001, 3, 239-243.
Pettit et al., "Poly(amidoamine) polymers: soluble linear amphiphilic drug-delivery systems for genes, proteins and oligonucleotides," Ther. Deliv. (2011) 2(7); 907-17.
Pichon et al., "Intracellular routing and inhibitory activity of oligonucleopeptides containing a KDEL motif," Mol. Pharmacol. 1997, 51(3):431-8.
Prakash et al., "Synthesis of Site-Specific Oligonucleotide-Polyamine Conjugates," Bioorg. Med. Chem. Lett. 1994, 4, 1733-1738.
Rajur et al., "Covalent protein-oligonucleotide conjugates for efficient delivery of antisense molecules," Bioconjugate Chem. 1997, 8(6):935-40.
Rhodes et al., "Therapeutic potentiation of the immune system by costimulatory Schiff-base-forming drugs," Nature, 1995, 377(6544):71-5.
Rump et al., "Preparation of conjugates of oligodeoxynucleotides and lipid structures and their interaction with low-density lipoprotein," Bioconjugate Chem. 1998, 9(3):341-9.
S.T. Crooke and B. Lebleu, "Antisense Research and Applications," CRC Press, Boca Raton, FLA, 1993, p. 303-350.
Saison-Behmoaras et al., "Short modified antisense oligonucleotides directed against Ha-ras point mutation induce selective cleavage of the mRNA and inhibit T24 cells proliferation," EMBO J. 1991, 10(5):1111-8.
Sanjay Tyagi et al., "Molecular beacons: probes that fluoresce upon hybridization," Biotechnology, vol. 14, No. 3 (1996), pp. 303-308.
Seth et al., "Synthesis and biophysical evaluation of 2',4'-constrained 2'O-methoxyethyl and 2',4'-constrained 2'O-ethyl nucleic acid analogues," 2010, J. Org. Chem, 75(5):1569-81.
Shea et al., "Synthesis, hybridization properties and antiviral activity in lipid-oligodeoxynucleotide conjugates," Nuc. Acids Res. 1990, 18(13):3777-83.
Singh et al., "LNA (locked nucleic acids): synthesis and high-affinity nucleic acid recognition," Chem. Commun, 1998:455-456.
Singh et al., "Synthesis of 2'Amino-LNA: A Novel Conformationally Restricted High-Affinity Oligonucleotide Analogue with a Handle," J. Org. Chem. 1998, 63, 10035-10039.
Soutscheck et al., "Therapeutic silencing of an endogenous gene by systemic administration of modified siRNAs," Nature 2004 vol. 432(7014):173-178.
Srivastava et al., "Five-and six-membered conformationally locked 2',4'-carbocyclic ribo-thymidines: synthesis, structure, and biochemical studies," J. Am. Chem. Soc, 129(26):8362-8379 (2007).
Straarup E.M. et al., "Short locked nucleic acid antisense oligonucleotides potently reduce apolipoprotein B mRNA and serum cholesterol in mice and non-human primates," Nucleic Acids Research, 38(20):7100-7111 (2010).
Svinarchuk et al, "Inhibition of HIV proliferation in MT-4 cells by antisense oligonucleotide conjugated to lipophilic groups," Biochimie, 1993, 75(1-2): 49-54.
Third Party Observation for application No. EP20130791808, dated Apr. 4, 2016, pp. 1-7.

Uhlmann; "Recent advances in the medical chemistry of antisense oligonucleotides," *Curr. Opinion in Drug Development*, 2000, 3(2), 203-213.
Vester et al., "Chemically modified oligonucleotides with efficient RNase H response," Bioorg. Med. Chem. Lett. 2008, 18(7):2296-2300.
Wada et al., "Nuclear export of actin: a novel mechanism regulating the subcellular localization of a major cytoskeletal protein," EMBO J. 1998, 17(6):1635-41.
Wahlestedt et al., "Potent and nontoxic antisense oligonucleotides containing locked nucleic acids," PNAS, 2000, 97(10):5633-5638.
Wang et al., "Modular recognition of RNA by a human pumilio-homology domain," Cell, 2002, 110(4):501-12.
Wei et al., "Hybridization properties of oligodeoxynucleotide pairs bridged by polyarginine peptides," Nucleic Acids Res. 1996, 24(4):655-61.
Wein et al., "The 3'-UTR of the mRNA coding for the major protein kinase C substrate MARCKS contains a novel CU-rich element interacting with the mRNA stabilizing factors HuD and HuR," Eur. J. Biochem. 2003, 270(2):350-65.
Winkler et al., "Oligonucleotide-polyamine conjugates: influence of length and position of 2'-attached polyamines on duplex stability and antisense effect," (2009) Eur. J. Med Chem 44(2): 670-7.
Yang et al., "HIV-1 TAT-mediated protein transduction and subcellular localization using novel expression vectors," FEBS Letters 532 (2002) 36-44.
Yang et al., "HPMA polymer-based site-specific delivery of oligonucleotides to hepatic stellate cells," Bioconjug. Chem (2009) 20(2): 213-21.
Yu et al., "Targeted Delivery Systems for Oligonucleotide Therapeutics," The AAPS Journal, vol. II, No. 1, (2009), pp. 195-203.
Zanta et al., "Gene delivery: a single nuclear localization signal peptide is sufficient to carry DNA to the cell nucleus," PNAS, 1999, 96(1):91-6.
Zatsepin & Oretskaya, "Synthesis and applications of oligonucleotide-carbohydrate conjugates," Chem Biodivers. (2004) 1(10): 1401-17.
Zelikin et al., "Poly(vinylpyrrolidone) for bioconjugation and surface ligand immobilization," Biomacromolecules (2007) 8(9): 2950-3.
Zhao et al., "A new platform for oligonucleotide delivery utilizing the PEG prodrug approach," Bioconjugate Chem. 2005 16(4):758-766.
Zhu et al., "Oligonucleotide-poly-L-ornithine conjugates: binding to complementary DNA and RNA," Antisense Res. Dev. 1993, 3(3):265-75.
Zuckermann et al., "Site-Selective Cleavage of RNA by a Hybrid Enzyme," J. Am. Chem. Soc. 1988(110), 1614-1615.
Biessen et al., "Targeted delivery of oligodeoxynucleotides to parenchymal liver cells in vivo," Biochem J., 340 ( Pt 3):783-792, Jun. 15, 1999.
Bunnell et al., "Targeted delivery of antisense oligonucleotides by molecular conjugates," Somat Cell Mol Genet., 18(6):559-569, Nov. 1992.
Davidson and Shelness "Apolipoprotein B:mRNA editing, lipoprotein assembly, and presecretory degradation," Annu Rev Nutr., 20:169-193, 2000.
Farese et al., "Knockout of the mouse apolipoprotein B gene results in embryonic lethality in homozygotes and protection against diet-induced hypercholesterolemia in heterozygotes," Proc Natl Acad Sci U S A., 92(5):1774-1778, Feb. 28, 1995.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol Biosyst., 5(8):838-843, Epub May 19, 2009.
GenBank Accession No. NG_011793.1 GI: 226442987, "Human apolipoprotein B (apoB) mRNA: identification of two distinct apoB mRNAs, an mRNA with the apoB-100 sequence and an apoB mRNA containing a premature in-frame translational stop codon, in both liver and intestine," dated Mar. 25, 2012, 16 pages.
GenBank Accession No. NM_000131.3 GI: 116805320, "Severe FX deficiency caused by a previously unidentified 4-bp deletion compound heterozygous with a large deletion involving FVII," dated May 6, 2012, 8 pages.

(56) References Cited

OTHER PUBLICATIONS

GenBank Accession No. NM_000160.1 GI 4503946, "Three distinct epitopes on the extracellular face of the glucagon amino terminus," dated Nov. 17, 2006, 3 pages.
GenBank Accession No. NM_000314.4 GI: 110224474, "PTEN mutations as a cause of constitutive insulin sensitivity and obesity," dated Nov. 4, 2012, 7 pages.
GenBank Accession No. NM_000384.2 GI: 105990531, "Hepatic sortilin regulates both apolipoprotein B secretion and LDL catabolism," dated Oct. 28, 2012, 14 pages.
GenBank Accession No. NM_000567.1 GI: 10835134, "C-reactive protein attenuates endothelial progenitor cell survival, differentiation, and function: further evidence of a mechanistic link between C-reactive protein and cariovascular disease," dated Oct. 28, 2004, 9 pages.
GenBank Accession No. NM_002827.2 GI: 18104977, "The molecular details of WPD-loop movement differ in the protein-tyrosine phosphatases YopH and PTP1B," dated Oct. 7, 2012, 6 pages.
GenBank Accession No. NM_010172.3 GI: 225543549, "Factor VIIa binding to endothelial cell protein C receptor: differences between mouse and human systems," dated Sep. 2, 2012, 5 pages.
GenBank Accession No. NM_019616.2 GI: 116805323, "Severe FX deficiency caused by a previously unidentified 4-bp deletion compound heterozygous with a large deletion involving FVII and FX genes," dated May 6, 2012, 6 pages.
GenBank Accession No. NM_032564.2 GI: 26024196, "Increased lipid accumulation and insulin resistance in transgenic mice expressing DGAT2 in glycolytic (type II) muscle," dated Mar. 16, 2008, 4 pages.
GenBank Accession No. NM_174936.2 GI: 31317306, "Proprotein convertase subtilisin/kexin type 9 (PCSK9) affects gene expression pathways beyond cholesterol metabolism in liver cells," dated Jun. 6, 2010, 6 pages.
GenBank Accession No. XM_137955.5 GI: 82941016, "Predicted: Mus musculus apolipoprotein B, transcript variant 1 (Apob), mRNA," dated Jan. 11, 2006, 6 pages.
GenBank: BC005310.1 GI:13529049, "*Homo sapiens* transthyretin, mRNA (cDNA clone MGC:12385 Image:4071761), complete cds," 2 pages, Aug. 4, 2008.
GenBank: BC020791.1 GI:18089144, "*Homo sapiens* transthyretin, mRNA (cDNA clone MGC:23689 Image:4734010), complete cds," 2 pages, Aug. 4, 2008.
GenBank: BC031885.1, "Mus musculus glucagon receptor, mRNA (cDNA clone MGC:30235 Image:5137340), complete cds," 3 pages, Jul. 15, 2006.
GenBank: BC035723.1 "*Homo sapiens* complement component 6, mRNA (cDNA clone MGC:46183 Image:5591446), complete cds," 3 pages, Aug. 11, 2006.
GenBank: J05024.1 GI:187824, "Human MHC class III complement component C6 mRNA, complete cds," 2 pages, Jan. 7, 1995.
GenBank: J05064.1 GI:179703, "Human complement component C6 mRNA, complete cds," 2 pages, Oct. 31, 1994.
Hagedorn et al., "Hepatotoxic potential of therapeutic oligonucleotides can be predicted from their sequence and modification pattern," *Nucleic Acid Ther.*, 23(5):302-310, Epub Aug. 16, 2013.
Hajjar and Nachman, "The role of lipoprotein(a) in atherogeneis and thrombosis," *Annul Rev. Med.*, 47:423-442, 1996.
International Search Report in Application No. PCT/EP2013/073859, dated Apr. 25, 2014, 7 pages.
International Search Report in Application No. PCT/EP2014/074554, dated Feb. 9, 2015, 11 pages.
Juliano et al., "Receptors, endocytosis, and trafficking: the biological basis of targeted delivery of antisense and siRNA oligonucleotides," J Drug Target., 21(1):27-43, Epub Nov. 19, 2012, print Jan. 2013.
Kallanthottathil, "Conjugation Strategies for In Vivo siRNA Delivery," Alnylam, 8th Annual Meeting of the Oligonucleotide Therapeutics Society, Oct. 29, 2012, 30 pages.

Katan and Beynen, "Characteristics of human hypo- and hyper-responders to dietary cholesterol," *Am J Epidemiol.*, 125(3):387-399, Mar. 1987.
Kay et al., "Gene therapy for metabolic disorders," Trends Genet., Jul. 31, 1994, 10(7):253-257.
Kim and Young, "Genetically modified mice for the study of apolipoprotein B," *J Lipid Res.*, 39(4):703-723, Apr. 1998.
Lindholm et al, "PCSK9 LNA antisense oligonucleotides induce sustained reduction of LDL cholesterol in nonhuman primates," Mol Ther., 20(2):376-381, Epub Nov. 22, 2011.
Maier et al., "Synthesis of antisense oligonucleotides conjugated to a multivalent carbohydrate cluster for cellular targeting," *Bioconjug Chem.*, 14(1):18-29, Jan.-Feb. 2003.
Makino et al., "Intravenous injection with antisense oligodeoxynucleotides against angiotensinogen decreases blood pressure in spontaneously hypertensive rats," *Hypertension*, 31(5):1166-1170, May 1998.
McKee et al., "Preparation of asialoorosomucoid-polylysine conjugates," Bioconjug Chem., 5(4):306-311, Jul.-Aug. 1994.
NCBI Reference Sequence: NM_000384.1, "*Homo sapiens* apolipoprotein B (including Ag(x) antigen) (APOB), mRNA," May 28, 2006, 22 pages.
NCBI Reference Sequence: NM_003041.1, "*Homo sapiens* solute carrier family 5 (sodium/glucose cotransporter), member 2 (SLC5A2), mRNA," Nov. 17, 2006, 3 pages.
NCBI Reference Sequence: NT_027140.6, "*Homo sapiens* chromosome 13 genomic contig, GRCh37.p10 Primary Assembly," Oct. 30, 2012, 3 pages.
NCBI Reference Sequence: NT_039455.6, "Mus musculus chromosome 8 genomic contig, strain C57BL/6J," Apr. 27, 2006, 3 pages.
Nishina et al., "Synthetic low and high fat diets for the study of atherosclerosis in the mouse," *J Lipid Res.*, 31(5):859-869, May 1990.
Nowak-Gottl et al., "Lipoprotein (a): its role in childhood thromboembolism," Pediatrics, 99(6):E11, Jun. 1997.
Sandkamp et al., "Lipoprotein (a) is an independent risk factor for myocardial infarction at a young age," *Clin Chem.*, 36(1):20-23, Jan. 1990.
Seed et al., "Relation of serum lipoprotein(a) concentration and apolipoprotein(a) phenotype to coronary heart disease in patients with familial hypercholesterolemia," *N Engl J Med.*, 322(21):1494-1499, May 24, 1990.
Sendi, "Dual Role of miR-122 in Molecular Pathogenesis of Viral Hepatitis," Hepat. Mon., May 2012, 12(5):312-314.
Seth et al., "Design, synthesis and evaluation of constrained methoxyethyl (cMOE) and constrained ethyl (cEt) nucleoside analogs," *Nucleic Acids Symp Ser (Oxf).*, (52):553-554, 2008.
Singapore Search Report and Written Opinion in Application No. 11201505387P, dated Jun. 22, 2017, 9 pages.
Swayze et al., "Antisense oligonucleotides containing locked nucleic acid improve potency but cause significant hepatotoxicity in animals," Nucleic Acids Res., 35(2):687-700. Epub Dec. 19, 2006.
Third Party Observation for European Application No. 13791808.2, submitted Jul. 5, 2016, 4 pages.
Third Party Observation for European Application No. 14704307.9, submitted July Jun. 30, 2016, 94 pages.
van Poelgeest et al., "Acute kidney injury during therapy with an antisense oligonucleotide directed against PCSK9," *Am J Kidney Dis.*, 62(4):796-800, Epub Apr. 3, 2013.
Vessby et al., "Diverging effects of cholestyramine on apolipoprotein B and lipoprotein Lp(a). A dose-response study of the effects of cholestyramine in hypercholesterolaemia," *Atherosclerosis.*, 44(1):61-71, Jul. 1982.
Zheng et al., "Distribution and anti-HBV effects of antisense oligodeoxynucleotides conjugated to galactosylated poly-L-lysine," World J Gastroenterol., 9(6):1251-1255, Jun. 2003.
Zhu et al., "Site-specific delivery of oligonucleotides to hepatocytes after systemic administration," Bioconjug Chem., 19(1):290-298, Epub Sep. 13, 2007.
Bhat et al., "RG-101, a GalNAc-conjugated anti-miR Employing a Unique Mechanism of Action by Targeting Host Factor MicroRNA-

(56) References Cited

OTHER PUBLICATIONS 122 (miR-122) Demonstrates Potent Activity and Reduction of HCV in Preclinical Studies," AASLD, Nov. 7-11, 2013, 1 page. (poster).

Hangeland et al., "Tissue distribution and metabolism of the [32P]-labeled oligodeoxynucleoside methylphosphonate-neoglycopeptide conjugate, [YEE(AH-GALNAC)3]-SMCC-AET PUMPT7, in the mouse," *Antisense & Nucleic Acid Drug Development*, 7(3):141-149, Jun. 1997.

Reinis et al., "Receptor-mediated transport of oligodeoxynucleotides into hepatic cells," *J Virol Methods.*, 42(1):99-105, Apr. 1993.

Chan et al., "The complexity of antisense transcription revealed by the study of developing male germ cells," Genomics, Jun. 2006, 87(6):681-692.

Geary, "Antisense oligonucleotide pharmacokinetics and metabolism," Expert opinion on drug metabolism & toxicology, Apr. 2009, 5(4):381-391.

Higuchi et al., "Strategies for in vivo delivery of siRNAs," BioDrugs, Jun. 2010, 24(3):195-205.

Kammler et al., "LNA Antisense Oligonucleotides-A Straight-Forward Concept for RNA Therapeutics," poster presented at 7th Annual Meeting of the Oligonucleotide Therapeutics Society in Copenhagen, Denmark on Sep. 8-10, 2011; published in Nucleic Acid Therapeutics, 2011, 21(5), p. A-16, 64 pages.

Koller et al., "Mechanisms of single-stranded phosphorothioate modified antisense oligonucleotide accumulation in hepatocytes," Nucleic acids research, Feb. 2011, 39(11):4795-807.

Lapidot et al., "Genome-wide natural antisense transcription: coupling its regulation to its different regulatory mechanisms," EMBO reports, Dec. 2006, 7(12):1216-1222.

Prakash et al., "Targeted delivery of antisense oligonucleotides to hepatocytes using triantennaly Nacetyl galactosamine improves potency 10-fold in mice," Nucleic acids research, Jul. 2014, 42(13):8796-8807.

Sehgal et al., "Liver as a target for oligonucleotide therapeutics," Journal of hepatology, Dec. 2013, 59(6):1354-1359.

\* cited by examiner

A

B

A

B

A

B

Conj 4a=

A

B

SEQUENCE LISTING

<160> NUMBER OF SEQ ID NOS: 54

<210> SEQ ID NO 1
<211> LENGTH: 13
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 1
gcattggtat tca                                                          13

<210> SEQ ID NO 2
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 2
gcattggtat tca                                                          13

<210> SEQ ID NO 3
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: disulphide linked 5 cholesterol conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 3
gcattggtat tca                                                          13

<210> SEQ ID NO 4
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(4)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (4)..(16)
<223> OTHER INFORMATION: phosphorothioate lnternucleoside linkages
<220> FEATURE:
<221> NAME/KEY: misc_feature
<222> LOCATION: (4)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 4
tcagcattgg tattca                                                       16

<210> SEQ ID NO 5
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 5
cagcattggt attca                                                        15

<210> SEQ ID NO 6
<211> LENGTH: 14
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(2)
<223> OTHER INFORMATION: phosphodiester lnternucleoside linkages
<220> FEATURE:

```
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (2)..(14)
<223> OTHER INFORMATION: phosphorothioate lnternucleoside linkages
<220> FEATURE:
<221> NAME/KEY: misc_feature
<222> LOCATION: (2)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C

<400> SEQUENCE: 6
agcattggta ttca                                                     14

<210> SEQ ID NO 7
<211> LENGTH: 13
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 7
gtctgtggaa gcg                                                      13

<210> SEQ ID NO 8
<211> LENGTH: 13
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 8
gtctgtggaa gcg                                                      13

<210> SEQ ID NO 9
<211> LENGTH: 15
<212> TYPE: DNA
<213> ORGANISM: artificial
<220> FEATURE:
<223> OTHER INFORMATION: LNA antisense gapmer oligonucleotide conjugate
```

```
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 9
cagtctgtgg aagcg                                                    15

<210> SEQ ID NO 10
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 10
ctgtctgtgg aagcg                                                    15

<210> SEQ ID NO 11
<211> LENGTH: 13
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (11)..(13)
```

<223> OTHER INFORMATION: LNA nucleosides, LNA C are 5-methyl C

<400> SEQUENCE: 11 nnnnnnnnn nnn                                                          13

<210> SEQ ID NO 12
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 GalNac cluster conjugate (Conj1a)
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 12 nnnnnnnnn nnn                                                          13

<210> SEQ ID NO 13
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 GalNac cluster conjugate (Conj1a)
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (3)..(15)
<223> OTHER INFORMATION: n is a, c, g, or t
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 13
cannnnnnnn nnnnn                                                       15

<210> SEQ ID NO 14
<211> LENGTH: 13
<212> TYPE: DNA
<213> ORGANISM: artificial

-continued

```
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: disulphide linked 5 cholesterol conjugate
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 14
nnnnnnnnnn nnn                                                       13

<210> SEQ ID NO 15
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (3)..(15)
<223> OTHER INFORMATION: n is a, c, g, or t
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 15
cannnnnnnn nnnnn                                                     15

<210> SEQ ID NO 16
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(4)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 FAM conjugate
<220> FEATURE:
```

```
<221> NAME/KEY: misc_feature
<222> LOCATION: (4)..(16)
<223> OTHER INFORMATION: phosphorothioate lnternucleoside linkages
<220> FEATURE:
<221> NAME/KEY: misc_feature
<222> LOCATION: (4)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 16
tcagcattgg tattca                                                       16

<210> SEQ ID NO 17
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 FAM conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 17
cagcattggt attca                                                        15

<210> SEQ ID NO 18
<211> LENGTH: 14
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 FAM conjugate
<220> FEATURE:
<221> NAME/KEY: misc_feature
<222> LOCATION: (2)..(14)
<223> OTHER INFORMATION: phosphorothioate lnternucleoside linkages
<220> FEATURE:
<221> NAME/KEY: misc_feature
<222> LOCATION: (2)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C

<400> SEQUENCE: 18
agcattggta ttca                                                         14
```

```
<210> SEQ ID NO 19
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(4)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 FAM conjugate
<220> FEATURE:
<221> NAME/KEY: misc_feature
<222> LOCATION: (4)..(16)
<223> OTHER INFORMATION: phosphorothioate lnternucleoside linkages
<220> FEATURE:
<221> NAME/KEY: misc_feature
<222> LOCATION: (4)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 19
gacgcattgg tattca                                                   16

<210> SEQ ID NO 20
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 FAM conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 20
gcattggtat tca                                                      13

<210> SEQ ID NO 21
<211> LENGTH: 27
<212> TYPE: DNA
<213> ORGANISM: artificial
<220> FEATURE:
<223> OTHER INFORMATION: LNA antisense gapmer oligonucleotide + PO
      linker blocker
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
```

<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (13)..(27)
<223> OTHER INFORMATION: n is a, c, g, or t
<220> FEATURE:
<221> NAME/KEY: misc_feature
<222> LOCATION: (14)..(16)
<223> OTHER INFORMATION: LNA nucleosides, LNA C are 5-methyl C
<220> FEATURE:
<221> NAME/KEY: misc_feature
<222> LOCATION: (16)..(19)
<223> OTHER INFORMATION: phosphodiester lnternucleoside linkages
<220> FEATURE:
<221> NAME/KEY: misc_feature
<222> LOCATION: (19)..(27)
<223> OTHER INFORMATION: phosphorothioate lnternucleoside linkages

<400> SEQUENCE: 21 nnnnnnnnn gcnnnnnnnn nnnnnnn                                  27

<210> SEQ ID NO 22
<211> LENGTH: 27
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(27)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (1)..(27)
<223> OTHER INFORMATION: n is a, c, g, or t
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 22 nnnnnnnnn nnnnnnnnn nnnnnnn                                   27

<210> SEQ ID NO 23
<211> LENGTH: 27
<212> TYPE: DNA
<213> ORGANISM: artificial
<220> FEATURE:
<223> OTHER INFORMATION: LNA antisense gapmer oligonucleotide + PO
      linker blocker
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (13)..(27)
<223> OTHER INFORMATION: n is a, c, g, or t
<220> FEATURE:
<221> NAME/KEY: misc_feature
<222> LOCATION: (14)..(16)
<223> OTHER INFORMATION: LNA nucleosides, LNA C are 5-methyl C

```
<220> FEATURE:
<221> NAME/KEY: misc_feature
<222> LOCATION: (16)..(19)
<223> OTHER INFORMATION: phosphodiester lnternucleoside linkages
<220> FEATURE:
<221> NAME/KEY: misc_feature
<222> LOCATION: (19)..(27)
<223> OTHER INFORMATION: phosphorothioate lnternucleoside linkages

<400> SEQUENCE: 23 nnnnnnnnn gcnnnnnnnn nnnnnnn                                          27

<210> SEQ ID NO 24
<211> LENGTH: 27
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(27)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (1)..(27)
<223> OTHER INFORMATION: n is a, c, g, or t
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 24 nnnnnnnnn nnnnnnnnn nnnnnnn                                           27

<210> SEQ ID NO 25
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 folic acid conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 25
gcattggtat tca                                                        13

<210> SEQ ID NO 26
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
```

```
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 disulphide linked folic acid conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 26
gcattggtat tca                                                          13

<210> SEQ ID NO 27
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 folic acid conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 27
cagcattggt attca                                                        15

<210> SEQ ID NO 28
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 mono galnac conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 28
gcattggtat tca                                                          13
```

```
<210> SEQ ID NO 29
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 disulphide linked mono galnac conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 29
gcattggtat tca                                                            13

<210> SEQ ID NO 30
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 mono galnac conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 30
cagcattggt attca                                                          15

<210> SEQ ID NO 31
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 FAM conjugate
<220> FEATURE:
```

```
<221> NAME/KEY: misc_feature
<222> LOCATION: (11)..(13)
<223> OTHER INFORMATION: LNA nucleosides, LNA C are 5-methyl C

<400> SEQUENCE: 31
gcattggtat tca                                                         13

<210> SEQ ID NO 32
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 disulphide linked FAM conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 32
gcattggtat tca                                                         13

<210> SEQ ID NO 33
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 FAM conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 33
cagcattggt attca                                                       15

<210> SEQ ID NO 34
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
```

```
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 tocopherol conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 34
gcattggtat tca                                                        13

<210> SEQ ID NO 35
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: 5 disulphide linked tocopherol conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 35
gcattggtat tca                                                        13

<210> SEQ ID NO 36
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 tocopherol conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 36
cagcattggt attca                                                      15

<210> SEQ ID NO 37
```

```
<211> LENGTH: 14
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C

<400> SEQUENCE: 37
tgctacaaaa ccca                                                       14

<210> SEQ ID NO 38
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (13)..(16)
<223> OTHER INFORMATION: LNA nucleosides, LNA C are 5-methyl C

<400> SEQUENCE: 38
aatgctacaa aaccca                                                     16

<210> SEQ ID NO 39
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 39
aatgctacaa aaccca                                                     16

<210> SEQ ID NO 40
<211> LENGTH: 15
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
```

```
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (14)..(15)
<223> OTHER INFORMATION: LNA nucleosides, LNA C are 5-methyl C

<400> SEQUENCE: 40
gctgtgtgag cttgg                                                    15

<210> SEQ ID NO 41
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 41
tgctgtgtga gcttgg                                                   16

<210> SEQ ID NO 42
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 42
tgctgtgtga gcttgg                                                   16

<210> SEQ ID NO 43
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
```

```
<221> NAME/KEY: misc_feature
<222> LOCATION: (14)..(16)
<223> OTHER INFORMATION: LNA nucleosides, LNA C are 5-methyl C

<400> SEQUENCE: 43
tcctggtctg tgttcc                                              16

<210> SEQ ID NO 44
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (15)..(16)
<223> OTHER INFORMATION: LNA nucleosides, LNA C are 5-methyl C

<400> SEQUENCE: 44
tcctggtctg tgttcc                                              16

<210> SEQ ID NO 45
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 45
cacatgctac aaaaccca                                            18

<210> SEQ ID NO 46
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
```

```
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (15)..(18)
<223> OTHER INFORMATION: LNA nucleosides, LNA C are 5-methyl C

<400> SEQUENCE: 46
caaatgctac aaaaccca                                                       18

<210> SEQ ID NO 47
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 47
caaatgctac aaaaccca                                                       18

<210> SEQ ID NO 48
<211> LENGTH: 17
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(17)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (16)..(17)
<223> OTHER INFORMATION: LNA nucleosides, LNA C are 5-methyl C

<400> SEQUENCE: 48
```
cagctgtgtg agcttgg                                                  17

<210> SEQ ID NO 49
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 49
catgctgtgt gagcttgg                                                 18

<210> SEQ ID NO 50
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 50
catgctgtgt gagcttgg                                                 18

<210> SEQ ID NO 51
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature

```
<222> LOCATION: (1)..(1)
<223> OTHER INFORMATION: 5 cholesterol conjugate
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 51
catcctggtc tgtgttcc                                                 18

<210> SEQ ID NO 52
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (17)..(18)
<223> OTHER INFORMATION: LNA nucleosides, LNA C are 5-methyl C

<400> SEQUENCE: 52
catcctggtc tgtgttcc                                                 18

<210> SEQ ID NO 53
<211> LENGTH: 12
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(12)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (11)..(12)
<223> OTHER INFORMATION: LNA nucleosides, LNA C are 5-methyl C

<400> SEQUENCE: 53
gttgacactg tc                                                       12

<210> SEQ ID NO 54
<211> LENGTH: 14
<212> TYPE: DNA
```

```
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: 5 cholesterol conjugate
<220> FEATURE:
<221> NAME/KEY: misc_feature
<222> LOCATION: (3)..(14)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (13)..(14)
<223> OTHER INFORMATION: LNA nucleosides, LNA C are 5-methyl C

<400> SEQUENCE: 54
cagttgacac tgtc                                                     14
```

US 10,077,443 B2

OLIGONUCLEOTIDE CONJUGATES

CROSS-REFERENCE TO RELATED APPLICATIONS

This application is the U.S. national stage under 35 USC § 371 of International Application Number PCT/EP2013/073858, filed on 14 Nov. 2013, which claims priority to EP Application No. 12192773.5, filed on 15 Nov. 2012; EP Application No. 13153296.2, filed on 30 Jan. 2013; EP Application No. 13157237.2, filed on 28 Feb. 2013 and EP Application No. 13174092.0, filed on 27 Jun. 2013 the entire contents of which applications is hereby incorporated by reference.

FIELD OF INVENTION

The invention relates to the field of oligonucleotide therapeutics, and in particular to the use of a conjugate, a targeting group or blocking group to enhance the properties of the oligonucleotides, for example to improve the therapeutic index.

RELATED CASES

This application claims priority from EP12192773.5, EP13153296.2, EP13157237.2 and EP13174092.0, which are hereby incorporated by reference.

BACKGROUND

Oligonucleotide conjugates have been extensively evaluated for use in siRNAs, where they are considered essential in order to obtain sufficient in vivo potency. For example, see WO2004/044141 refers to modified oligomeric compounds that modulate gene expression via an RNA interference pathway. The oligomeric compounds include one or more conjugate moieties that can modify or enhance the pharmacokinetic and pharmacodynamic properties of the attached oligomeric compound.

In contrast, single stranded antisense oligonucleotides are typically administered therapeutically without conjugation or formulation. The main target tissues for antisense oligonucleotides are the liver and the kidney, although a wide range of other tissues are also accessible by the antisense modality, including lymph node, spleen, bone marrow.

WO2008/113832 discloses LNA phosphorothioate gapmer oligonucleotides where the flanking regions comprise at least one phosphodiester between or adjacent to a LNA nucleoside. The oligomers were preferentially targeted to the kidney.

WO2004/087931 refers to oligonucleotides comprising an acid cleavable hydrophilic polymer (PEG) conjugate.

WO 2005/086775 refers to targeted delivery of therapeutic agents to specific organs using a therapeutic chemical moiety, a cleavable linker and a labeling domain. The cleavable linker may be, for example, a disulfide group, a peptide or a restriction enzyme cleavable oligonucleotide domain.

WO 2009/126933 refers to specific delivery of siRNA nucleic acids by combining targeting ligands with endosomolytic components.

WO 2011/126937 refers to targeted intracellular delivery of oligonucleotides via conjugation with small molecule ligands.

WO2009/025669 refers to polymeric (polyethylene glycol) linkers containing pyridyl disulphide moieties. See also Zhao et al., Bioconjugate Chem. 2005 16 758-766.

Chaltin et al., Bioconjugate Chem. 2005 16 827-836 reports on cholesterol modified mono- di- and tetrameric oligonucleotides used to incorporate antisense oligonucleotides into cationic liposomes, to produce a dendrimeric delivery system. Cholesterol is conjugated to the oligonucleotides via a lysine linker.

Other non-cleavable cholesterol conjugates have been used to target siRNAs and antagomirs to the liver—see for example, Soutscheck et al., Nature 2004 vol. 432 173-178 and Krützfeldt et al., Nature 2005 vol 438, 685-689. For the partially phosphorothiolated siRNAs and antagomirs, the use of cholesterol as a liver targeting entity was found to be essential for in vivo activity.

The present invention is based upon the discovery that highly effective targeted delivery of oligonucleotides is achieved by the use of a homing device linked to the oligonucleotide by means of a short region of nuclease labile nucleosides, such as phosphodiester linked DNA or RNA nucleosides.

SUMMARY OF INVENTION

The invention provides for an oligomeric compound comprising three regions:
i) a first region (region A), which comprises 7-26 contiguous nucleotides;
ii) a second region (region B) which comprises between 1-10 nucleotides, which is covalently linked to the 5' or 3' nucleotide of the first region, such as via a internucleoside linkage group such as a phosphodiester linkage, wherein either
   a. the internucleoside linkage between the first and second region is a phosphodiester linkage and the nucleoside of the second region [such as immediately] adjacent to the first region is either DNA or RNA; and/or
   b. at least 1 nucleoside of the second region is a phosphodiester linked DNA or RNA nucleoside;
iii) a third region (C) which comprises a conjugate moiety, a targeting moiety, a reactive group, an activation group, or a blocking moiety, wherein the third region is covalent linked to the second region.

In some embodiments, region A and region B form a single contiguous nucleotide sequence of 8-35 nucleotides in length.

In some aspects the internucleoside linkage between the first and second regions may be considered part of the second region.

In some embodiments, there is a phosphorus containing linkage group between the second and third region. The phosphorus linkage group, may, for example, be a phosphate (phosphodiester), a phosphorothioate, a phosphorodithioate or a boranophosphate group.

In some embodiments, this phosphorus containing linkage group is positioned between the second region and a linker region which is attached to the third region. In some embodiments, the phosphate group is a phosphodiester.

Therefore, in some aspects the oligomeric compound comprises at least two phosphodiester groups, wherein at least one is as according to the above statement of invention, and the other is positioned between the second and third regions, optionally between a linker group and the second region.

In some embodiments, the third region is an activation group, such as an activation group for use in conjugation. In this respect, the invention also provides activated oligomers comprising region A and B and an activation group, e.g. an intermediate which is suitable for subsequent linking to the third region, such as suitable for conjugation.

In some embodiments, the third region is a reactive group, such as a reactive group for use in conjugation. In this respect, the invention also provides oligomers comprising region A and B and a reactive group, e.g. an intermediate which is suitable for subsequent linking to the third region, such as suitable for conjugation. The reactive group may, in some embodiments comprise an amine of alcohol group, such as an amine group.

In some embodiments region A comprises at least one, such as 2, 3, 4, 5, 6, 7, 8, 9, 10, 11, 12, 13, 14, 15, 16, 17, 18, 19, 20, 21, 22, 23, or 24 internucleoside linkages other than phosphodiester, such as internucleoside linkages which are (optionally independently] selected from the group consisting of phosphorothioate, phosphorodithioate, and boranophosphate, and methylphosphonate, such as phosphorothioate. In some embodiments region A comprises at least one phosphorothioate linkage. In some embodiments at least 50%, such as at least 75%, such as at least 90% of the internucleoside linkages, such as all the internucleoside linkages within region A are other than phosphodiester, for example are phosphorothioate linkages. In some embodiments, all the internucleoside linkages in region A are other than phosphodiester.

In some embodiments, the oligomeric compound comprises an antisense oligonucleotide, such as an antisense oligonucleotide conjugate. The antisense oligonucleotide may be or may comprise the first region, and optionally the second region. In this respect, in some embodiments, region B may form part of a contiguous nucleobase sequence which is complementary to the (nucleic acid) target. In other embodiments, region B may lack complementarity to the target.

Alternatively stated, in some embodiments, the invention provides a non-phosphodiester linked, such as a phosphorothioate linked, oligonucleotide (e.g. an antisense oligonucleotide) which has at least one terminal (5' and/or 3') DNA or RNA nucleoside linked to the adjacent nucleoside of the oligonucleotide via a phosphodiester linkage, wherein the terminal DNA or RNA nucleoside is further covalently linked to a conjugate moiety, a targeting moiety or a blocking moiety, optionally via a linker moiety.

The invention provides for a pharmaceutical composition comprising the oligomeric compound of the invention and a pharmaceutically acceptable diluent, carrier, salt or adjuvant.

The invention provides for the oligomeric compound according to the invention for use in the inhibition of a nucleic acid target in a cell. In some embodiments the use is in vitro. In some embodiments the use is in vivo.

The invention provides for the oligomeric compound of the invention for use in medicine, such as for use as a medicament.

The invention provides for the oligomeric compound of the invention for use in the treatment of a medical disease or disorder.

The invention provides for the use of the oligomeric compound of the invention for the preparation of a medicament for the treatment of a disease or disorder, such as a metabolic disease or disorder.

The invention provides for a method of synthesizing (or manufacture) of an oligomeric compound, such as the oligomeric compound of the invention, said method comprising either:
a) a step of providing a [solid phase] oligonucleotide synthesis support to which one of the following is attached [third region]:
   i) optionally a linker group (—Y—)
   ii) a group X comprising a group selected from the group consisting of a conjugate, a targeting group, a blocking group, a reactive group [e.g. an amine or an alcohol] or an activation group (X—), or an an —Y—X group
and
b) a step of [sequential] oligonucleotide synthesis of region B followed by region A, and/or:
c) a step of [sequential] oligonucleotide synthesis of a first region (A) and a second region (B), wherein the synthesis step is followed by
d) a step of adding a third region [phosphoramidite comprising]
   i) optionally a linker group (—Y—)
   ii) a group X comprising a group selected from the group consisting of a conjugate, a targeting group, a blocking group, a reactive group [e.g. an amine or an alcohol] or an activation group (X—) or optionally an —Y—X group
followed by
e) the cleavage of the oligomeric compound from the [solid phase] support wherein, optionally said method further comprises a further step selected from:
f) wherein the third group is an activation group, the step of activating the activation group to produce a reactive group, followed by adding a conjugate, a blocking, or targeting group to the reactive group, optionally via a linker group (Y);
g) wherein the third region is a reactive group, the step of adding a conjugate, a blocking, or targeting group to the reactive group, optionally via a linker group (Y).
h) wherein the third region is a linker group (Y), the step of adding a conjugate, a blocking, or targeting group to the linker group (Y)

wherein steps f), g) or h) are performed either prior to or subsequent to cleavage of the oligomeric compound from the oligonucleotide synthesis support. In some embodiments, the method may be performed using standard phosphoramidite chemistry, and as such the region X and/or region X or region X and Y may be provided, prior to incorporation into the oligomer, as a phosphoramidite. Please see FIGS. 5-10 which illustrate non-limiting aspects of the method of the invention.

The invention provides for a method of synthesizing (or manufacture) of an oligomeric compound, such as the oligomeric compound of the invention, said method comprising a step of [sequential] oligonucleotide synthesis of a first region (A) and optionally a second region (B), wherein the synthesis step is followed by a step of adding a third region [phosphoramidite comprising] region X (also referred to as region C), or Y such as a region comprising a group selected from the group consisting of a conjugate, a targeting group, a blocking group, a functional group, a reactive group [e.g. an amine or an alcohol] or an activation group (X), or an —Y—X group followed by the cleavage of the oligomeric compound from the [solid phase] support.

It is however recognized that the region X or X—Y may be added after the cleavage from the solid support. Alternatively, the method of synthesis may comprise the steps of synthesizing a first (A), and optionally second region (B), followed by the cleavage of the oligomer from the support, with a subsequent step of adding a third region, such as X or X—Y group to the oligomer. The addition of the third region may be achieved, by example, by adding an amino phosphoramidite unit in the final step of oligomer synthesis (on the support), which can, after cleavage from the support, be used to join to the X or X—Y group, optionally via an activation group on the X or Y (when present) group. In the embodiments where the cleavable linker is not a nucleotide region, region B may be a non-nucleotide cleavable linker for example a peptide linker, which may form part of region X (also referred to as region C) or be region Y (or part thereof).

In some embodiments of the method, region X (such as C) or (X—Y), such as the conjugate (e.g. a GalNAc conjugate) comprises an activation group, (an activated functional group) and in the method of synthesis the activated conjugate (or region x, or X—Y) is added to the first and second regions, such as an amino linked oligomer. The amino group may be added to the oligomer by standard phosphoramidite chemistry, for example as the final step of oligomer synthesis (which typically will result in amino group at the 5' end of the oligomer). For example during the last step of the oligonucleotide synthesis a protected amino-alkyl phosphoramidite is used, for example a TFA-aminoC6 phosphoramidite (6-(Trifluoroacetylamino)-hexyl-(2-cyanoethyl)-(N,N-diisopropyl)-phosphoramidite).

Region X (or region C as referred to herein), such as the conjugate (e.g. a GalNac conjugate) may be activated via NHS ester method and then the aminolinked oligomer is added. For example a N-hydroxysuccinimide (NHS) may be used as activating group for region X (or region C, such as a conjugate, such as a GalNac conjugate moiety. The invention provides an oligomer prepared by the method of the invention.

In some embodiments, region X and/or region X or region X and Y may be covalently joined (linked) to region B via a phosphate nucleoside linkage, such as those described herein, including phosphodiester or phosphorothioate, or via an alternative group, such as a triazol group.

The invention provides for a method of treatment of a disease or disorder in a subject in need of treatment, said method comprising the steps of administering a pharmaceutical composition comprising the oligomeric compound of the invention to said subject in a therapeutically effective amount.

The invention provides for a method of inhibiting the expression of a target gene in a cell, said method comprising administering the oligomeric compound according to the invention to a cell which is expressing said target gene, suitably in an amount effective to reduce the expression of the target gene in said cell. In some embodiments the method is in vitro (i.e. not in an organism, but may be in a (e.g. ex-vivo) cell or tissue). In some embodiments the method is in vivo.

The invention also provides for an LNA oligomer, comprising a contiguous region of 8-24 phosphorothioate linked nucleosides, and further comprising between 1 and 6 DNA nucleosides which are contiguous with the LNA oligomer, wherein the internucleoside linkages between the DNA, and/or adjacent to the DNA nucleoside(s), is physiologically labile, such as is/are phosphodiester linkages. Such an LNA oligomer may be in the form of a conjugate, as described herein, or may, for example be an intermediate to be used in a subsequent conjugation step. When conjugated, the conjugate may, for example be or comprise a sterol, such as cholesterol or tocopherol, or may be or comprise a (non-nucleotide) carbohydrate, such as a GalNac conjugate, such as a GalNac cluster, e.g. triGalNac, or another conjugate as described herein.

The invention provides for an LNA antisense oligomer (which may be referred to as region A herein) comprising an antisense oligomer and an asialoglycoprotein receptor targeting moiety conjugate moiety, such as a GalNAc moiety, which may form part of a further region (referred to as region C). The LNA antisense oligomer may be 7-30, such as 8-26 nucleosides in length and it comprises at least one LNA unit (nucleoside).

The invention provides for an LNA antisense oligomer covalently joined to (e.g. linked to) a (non-nucleoside) carbohydrate moiety, such as a carbohydrate conjugate moiety. In some embodiments the carbohydrate moiety is not a linear carbohydrate polymer. The carbohydrate moiety may however be multi-valent, such as, for example 2, 3, 4 or 4 identical or non-identical carbohydrate moieties may be covalently joined to the oligomer, optionally via a linker or linkers.

The invention provides for an LNA antisense oligomer (conjugate) comprising an antisense oligomer and a conjugate moiety which comprises a carbohydrate, such as a carbohydrate conjugate moiety.

The invention provides for a pharmaceutical composition comprising the LNA oligomeric compound of the invention and a pharmaceutically acceptable diluent, carrier, salt or adjuvant.

The invention provides for the oligomeric compound according to the invention for use in the inhibition of a nucleic acid target in a cell. In some embodiments the use is in vitro. In some embodiments the use is in vivo.

The invention provides for the oligomeric compound of the invention for use in medicine, such as for use as a medicament.

The invention provides for the oligomeric compound of the invention for use in the treatment of a medical disease or disorder.

The invention provides for the use of the oligomeric compound of the invention for the preparation of a medicament for the treatment of a disease or disorder, such as a metabolic disease or disorder.

DESCRIPTION OF THE INVENTION

Figure 1:
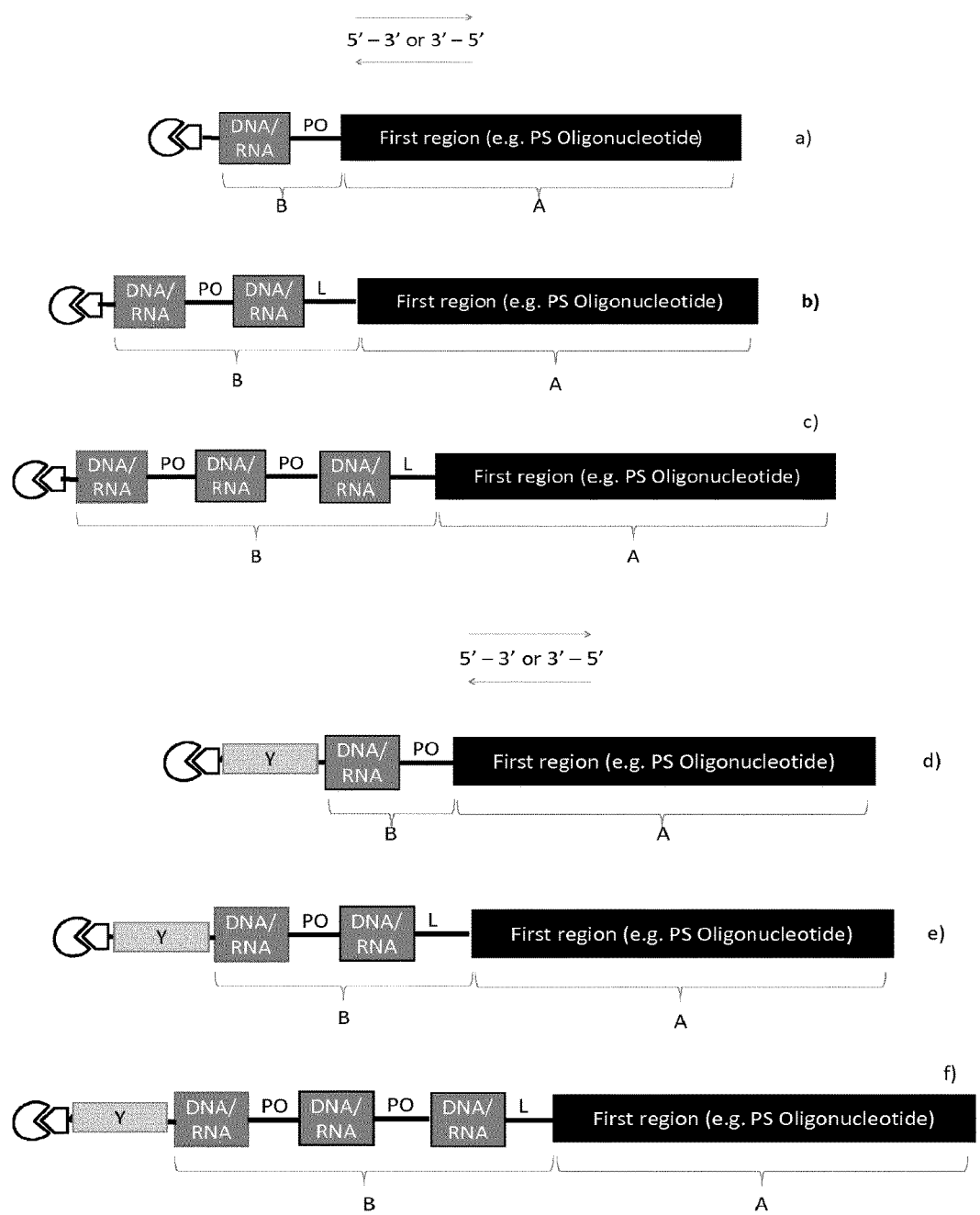
FIG. 1: Non-limiting illustration of oligomers of the invention attached to an activation group (i.e. a protected reactive group—as the third region). The internucleoside linkage L may be, for example phosphodiester, phosphorothioate, phosphorodithioate, boranophosphate or methylphosphonate, such as phosphodiester. PO is a phosphodiester linkage. Compound a) has a region B with a single DNA or RNA, the linkage between the second and the first region is PO. Compound b) has two DNA/RNA (such as DNA) nucleosides linked by a phosphodiester linkage. Compound c) has three DNA/RNA (such as DNA) nucleosides linked by a phosphodiester linkages. In some embodiments, Region B may be further extended by further phosphodiester DNA/RNA (such as DNA nucleosides). The activation group is illustrated on the left side of each compound, and may, optionally be linked to the terminal nucleoside of region B via a phosphorus nucleoside linkage group, such as phosphodiester, phosphorothioate, phosphorodithioate, boranophosphate or methylphosphonate, or in some embodiments a triazole linkage. Compounds d), e), & f) further comprise a linker (Y) between region B and the activation group, and region Y may be linked to region B via, for example, a phosphorus nucleoside linkage group, such as phosphodiester, phosphorothioate, phosphorodithioate, boranophosphate or methylphosphonate, or in some embodiments a triazole linkage.
Figure 2:
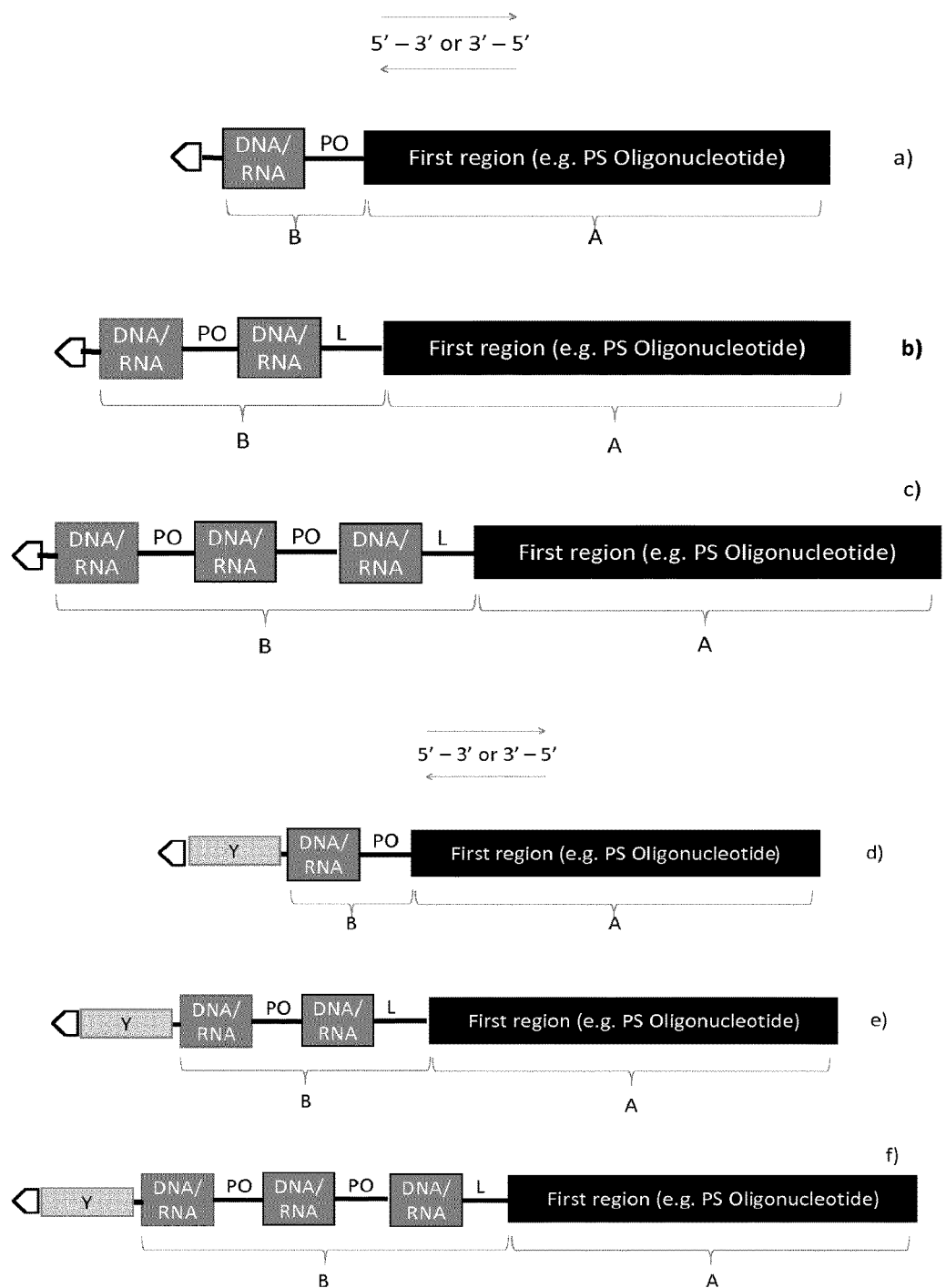
FIG. 2: Equivalent compounds as shown in FIG. 1; however a reactive group is used in place of the activation group. The reactive group may, in some embodiments be the result of activation of the activation group (e.g. deprotection). The reactive group may, in non-limiting examples, be an amine or alcohol.
Figure 3:
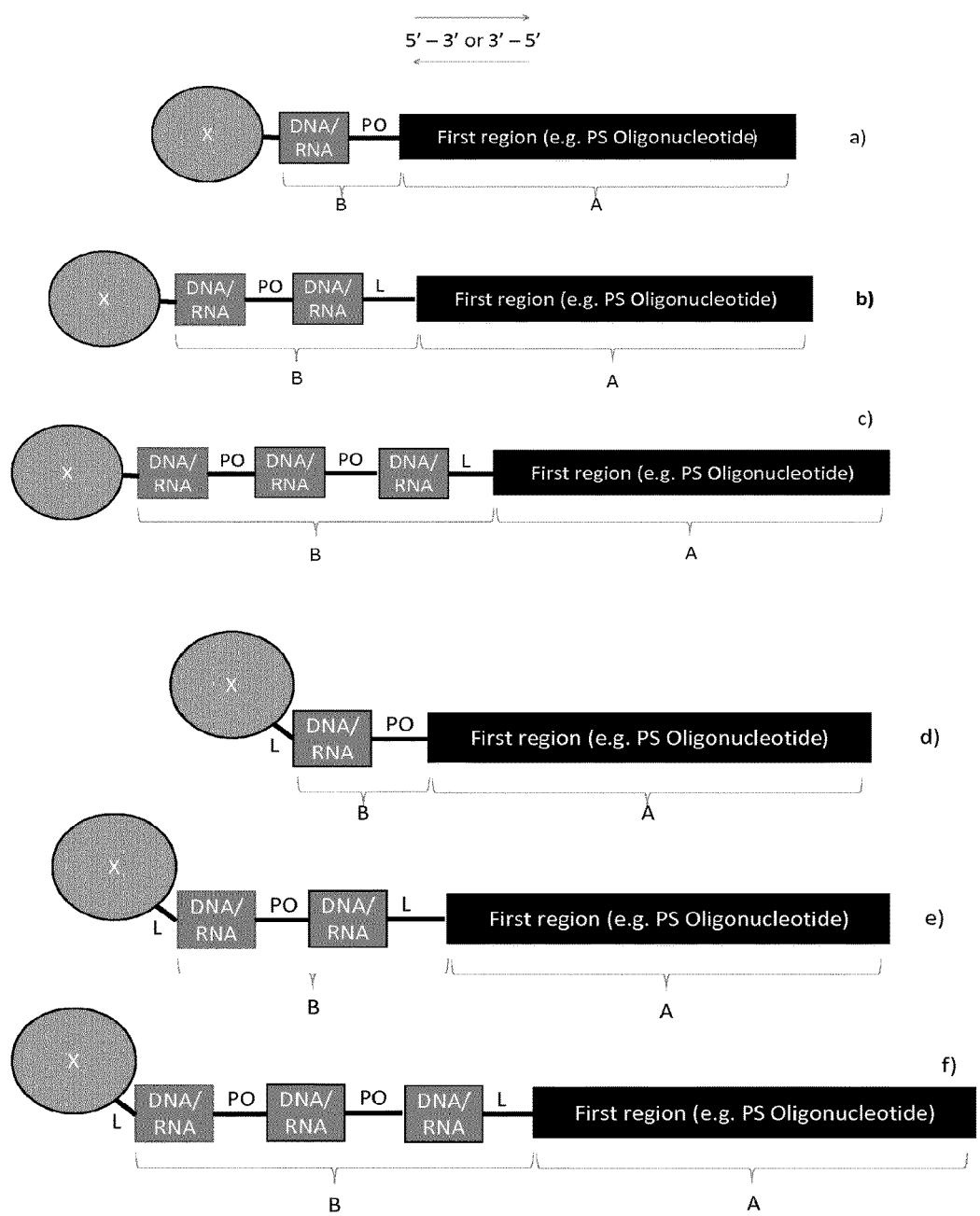
FIG. 3: Non-limiting Illustration of compounds of the invention. Same nomenclature as FIG. 1. X may in some embodiments be a conjugate, such as a lipophilic conjugate such as cholesterol, or another conjugate such as those described herein. In addition, or alternatively X may be a targeting group or a blocking group. In some aspects X may be an activation group (see FIG. 1), or a reactive group (see FIG. 2). X may be covalently attached to region B via a phosphorus nucleoside linkage group, such as phosphodiester, phosphorothioate, phosphorodithioate, boranophosphate or methylphosphonate, or may be linked via an alternative linkage, e.g. a triazol linkage (see L in compounds d), e), and f)).
Figure 4:
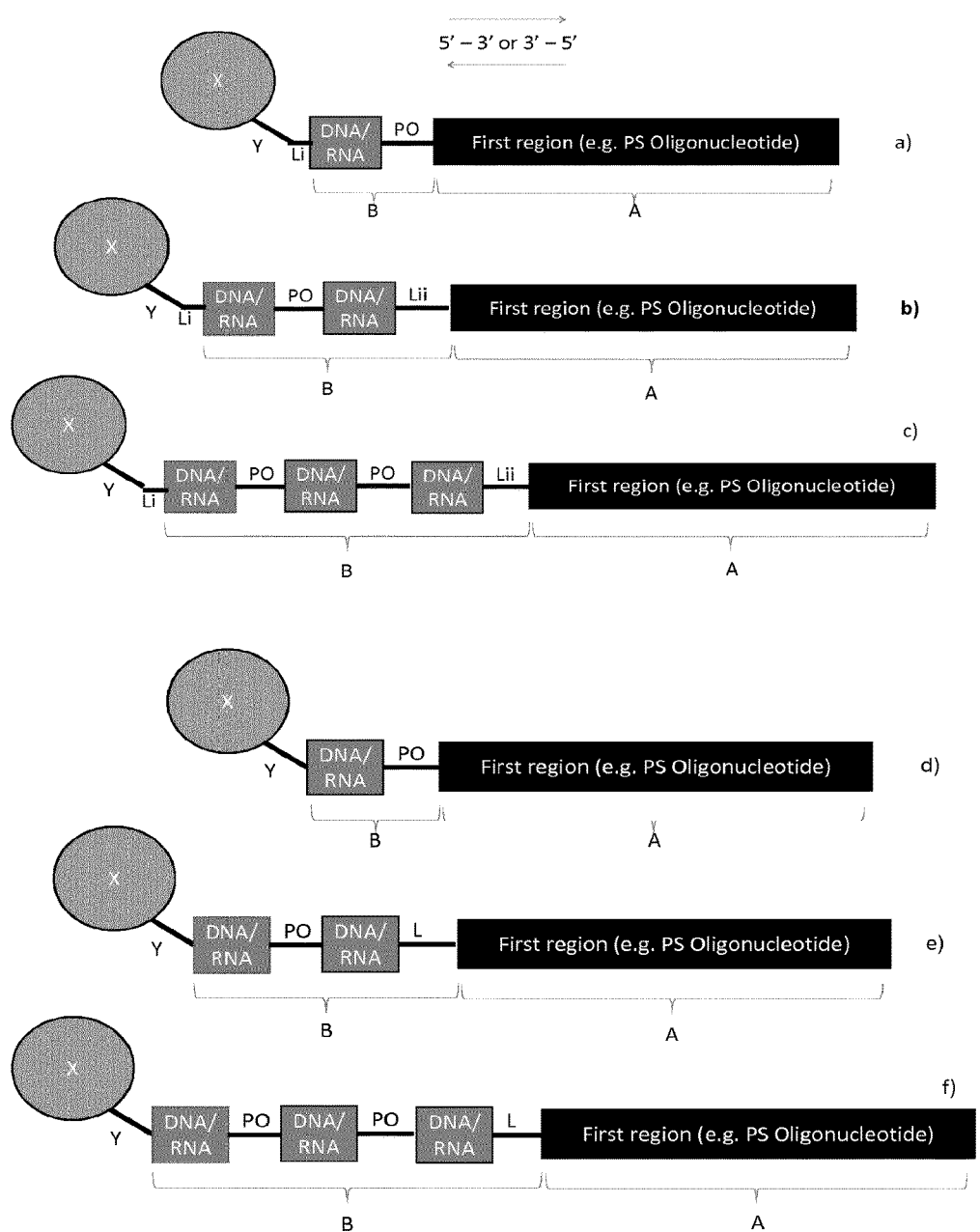
FIG. 4. Non-limiting Illustration of compounds of the invention, where the compounds comprise the optional linker between the third region (X) and the second region (region B). Same nomenclature as FIG. 1. Suitable linkers are disclosed herein, and include, for example alkyl linkers, for example C6 linkers. In compounds A, B and C, the linker between X and region B is attached to region B via a phosphorus nucleoside linkage group, such as phosphodiester, phosphorothioate, phosphorodithioate, boranophosphate or methylphosphonate, or may be linked via an alternative linkage e.g. a triazol linkage (Li). In these compounds Lii represents the internucleoside linkage between the first (A) and second regions (B).
Figure 5A:
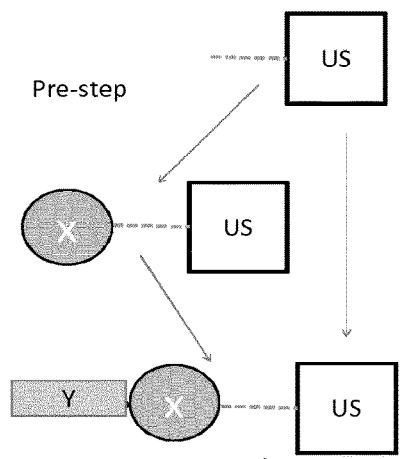
FIGS. 5a and b. 5b shows a non-limiting example of a method of synthesis of compounds of the invention. US represent a oligonucleotide synthesis support, which may be a solid support. X is the third region, such as a conjugate, a targeting group, a blocking group etc. In an optional pre-step, X is added to the oligonucleotide synthesis support. Otherwise the support with X already attached may be obtained (i). In a first step, region B is synthesized (ii), followed by region A (iii), and subsequently the cleavage of the oligomeric compound of the invention from the oligonucleotide synthesis support (iv). In an alternative method the pre-step involves the provision of a oligonucleotide synthesis support with a region X and a linker group (Y) attached (see FIG. 5a). In some embodiments, either X or Y (if present) is attached to region B via a phosphorus nucleoside linkage group, such as phosphodiester, phosphorothioate, phosphorodithioate, boranophosphate or methylphosphonate, or an alternative linkage, such as a triazole linkage.
Figure 5B:
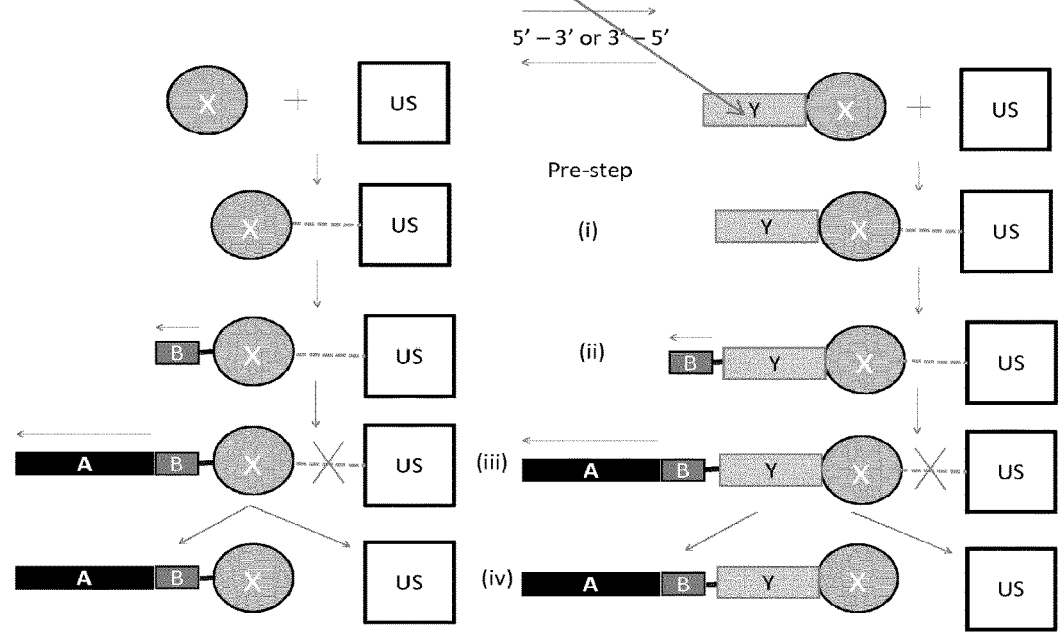
Figure 6:
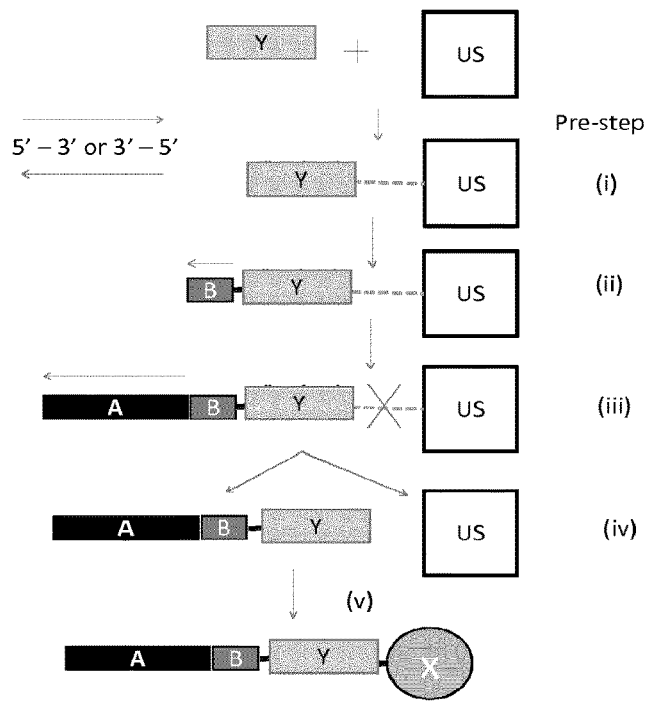
FIG. 6. A non-limiting example of a method of synthesis of compounds of the invention which comprise a linker (Y) between the third region (X) and the second region (B). US represents a oligonucleotide synthesis support, which may be a solid support. X is the third region, such as a conjugate, a targeting group, a blocking group etc. In an optional pre-step, Y is added to the oligonucleotide synthesis support. Otherwise the support with Y already attached may be obtained (i). In a first step, region B is synthesized (ii), followed by region A (iii), and subsequently the cleavage of the oligomeric compound of the invention from the oligonucleotide synthesis support (iv). In some embodiments (as shown), region X may be added to the linker (Y) after the cleavage step (v). In some embodiments, Y is attached to region B via a phosphorus nucleoside linkage group, such as phosphodiester, phosphorothioate, phosphorodithioate, boranophosphate or methylphosphonate, or an alternative linkage, such as a triazol linkage.
Figure 7:
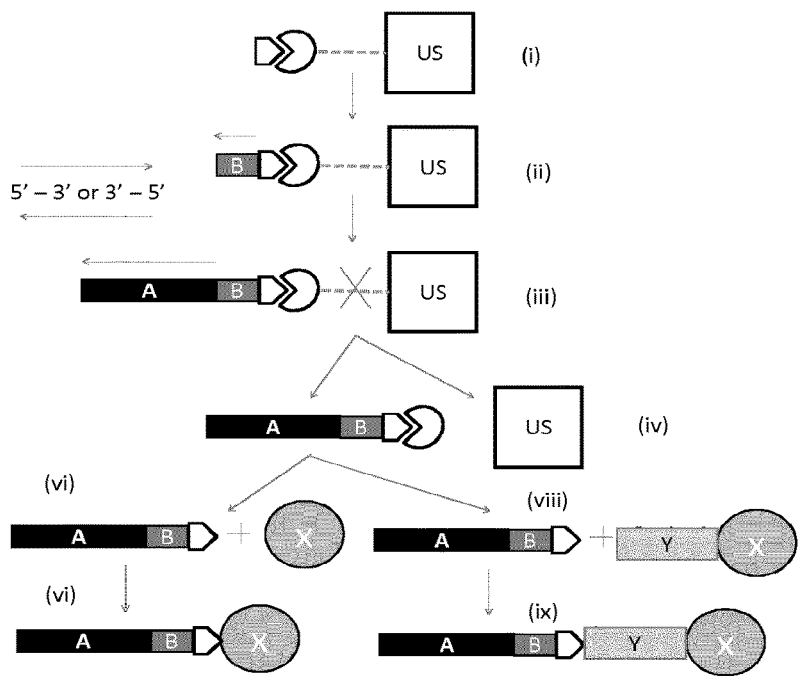
FIG. 7. A non-limiting example of a method of synthesis of compounds of the invention which utilize an activation group. In an optional pre-step, the activation group is attached the oligonucleotide synthesis support (i), or the oligonucleotide synthesis support with activation group is otherwise obtained. In step ii) region B is synthesized followed by region A (iii). The oligomer is then cleaved from the oligonucleotide synthesis support (iv). The intermediate oligomer (comprising an activation group) may then be activated (vI) or (viii) and a third region (X) added (vi), optionally via a linker (Y) (ix). In some embodiments, X (or Y when present) is attached to region B via a phosphorus nucleoside linkage group, such as phosphodiester, phosphorothioate, phosphorodithioate, boranophosphate or methylphosphonate, or an alternative linkage, such as a triazol linkage.
Figure 8:
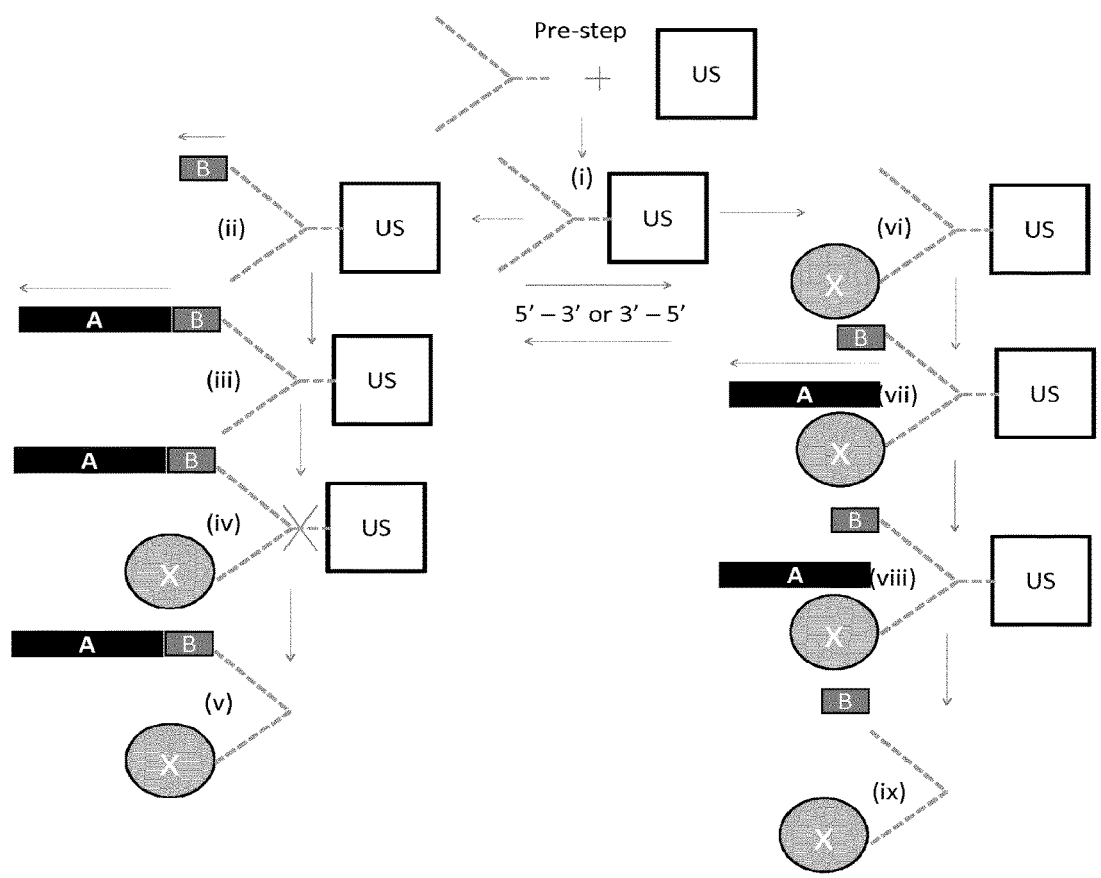
FIG. 8. A non-limiting example of a method of synthesis of compounds of the invention, wherein a bifunctional oligonucleotide synthesis support is used (i). In such a method, either the oligonucleotide is synthesized in an initial series of steps (ii)-(iii), followed by the attachment of the third region (optionally via a linker group Y), the oligomeric compound of the invention may then be cleaved (v). Alternatively, as shown in steps (vi)-(ix), the third region (optionally with a linker group (Y) is attached to the oligonucleotide synthesis support (this may be an optional pre-step)—or an oligonucleotide synthesis support with the third region (optionally with Y) is otherwise provided, the oligonucleotide is then synthesized (vii-viii). The oligomeric compound of the invention may then be cleaved (ix). In some embodiments, X (or Y when present) is attached to region B via a phosphorus nucleoside linkage group, such as phosphodiester, phosphorothioate, phosphorodithioate, boranophosphate or methylphosphonate, or an alternative linkage, such as a triazol linkage. The US may in some embodiment, prior to the method (such as the pre-step) comprise a step of adding a bidirectional (bifunctional) group which allows the independent synthesis of the oligonucleotide and the covalent attachment of group X, Y (or X and Y) to support (as shown)—this may for example be achieved using a triazol or of nucleoside group. The bidirectional (bifunctional) group, with the oligomer attached, may then be cleaved from the support.
Figure 9:
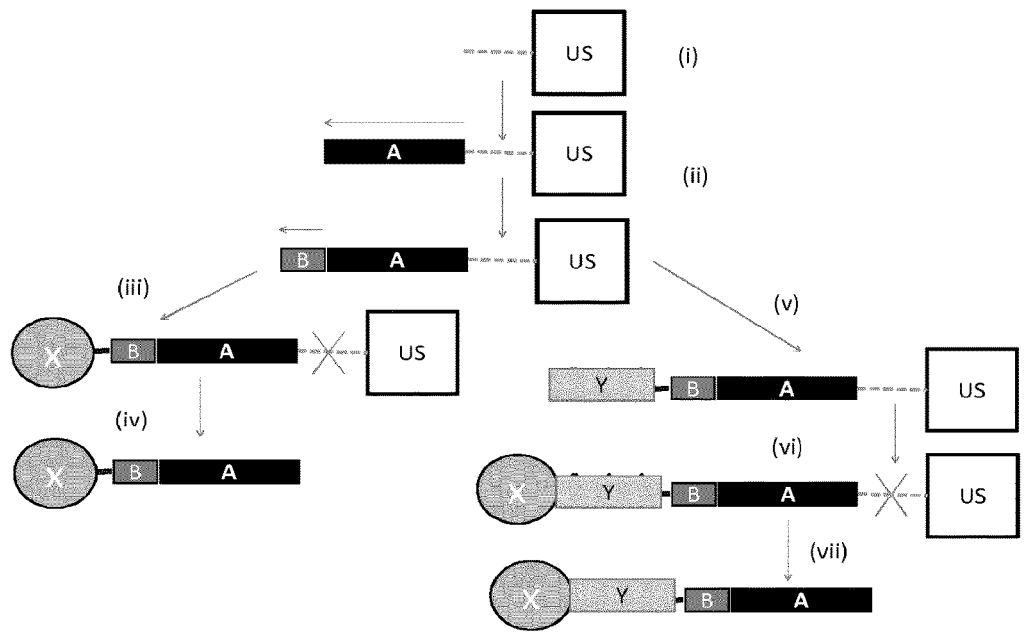
FIG. 9. A non-limiting example of a method of synthesis of compounds of the invention: In an initial step, the first region (A) is synthesized (ii), followed by region B. In some embodiments the third region is then attached to region B (iii), optionally via a phosphate nucleoside linkage (or e.g. a trialzol linkage). The oligomeric compound of the invention may then be cleaved (iv). When a linker (Y) is used, in some embodiments the steps (v)-(viii) may be followed: after synthesis of region B, the linker group (Y) is added, and then either attached to (Y) or in a subsequent step, region X is added (vi). The oligomeric compound of the invention may then be cleaved (vii). In some embodiments, X (or Y when present) is attached to region B via a phosphorus nucleoside linkage group, such as phosphodiester, phosphorothioate, phosphorodithioate, boranophosphate or methylphosphonate, or an alternative linkage, such as a triazol linkage.
Figure 10:
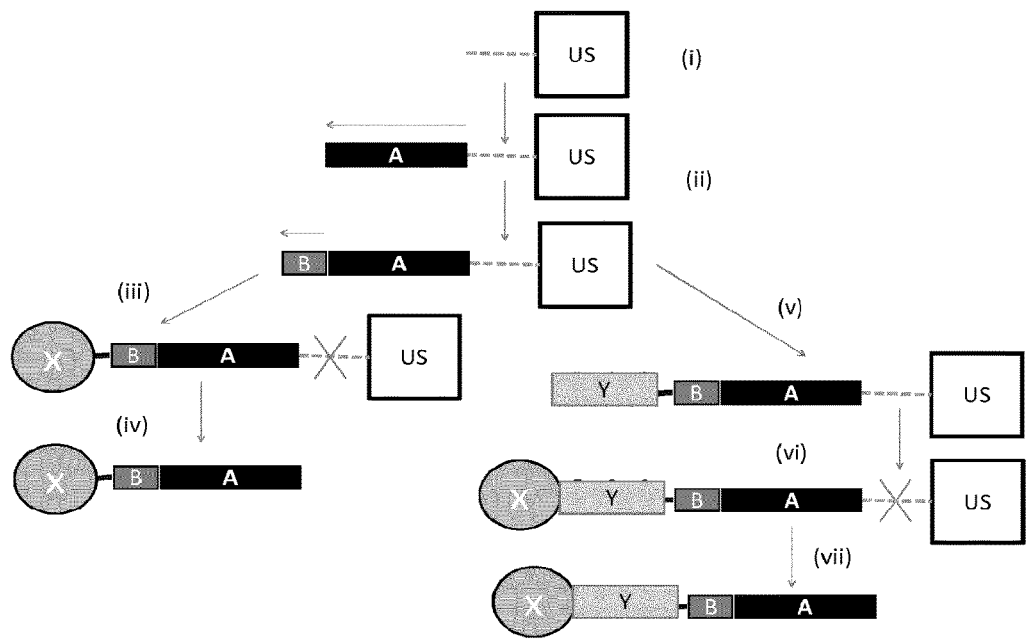
FIG. 10. A non-limiting example of a method of synthesis of compounds of the invention: In this method an activation group is used: Steps (i)-(iii) are as per FIG. 9. However after the oligonucleotide synthesis (step iii), an activation group (or a reactive group) is added to region B, optionally via a phosphate nucleoside linkage. The oligonucleotide is then cleaved from the support (v). The activation group may be subsequently activated to produce a reactive group, and then the third region (X), such as the conjugate, blocking group or targeting group, is added to the reactive group (which may be the activated activation group or the reactive group), to produce the oligomer (vi). As shown in (vii)-(viii), after cleavage, a linker group (Y) is added (vii), and then either attached to (Y) or in a subsequent step, region X is added to produce the oligomer (viii). It should be recognized that in an alternative all of the steps (ii)-(viii) may be performed on the oligonucleotide synthesis support, and in such instances a final step of cleaving the oligomer from the support may be performed. In some embodiments, the reactive group or activation group is attached to region B via a phosphorus nucleoside linkage group, such as phosphodiester, phosphorothioate, phosphorodithioate, boranophosphate or methylphosphonate, or an alternative linkage, such as a triazol linkage.

The invention relates to oligomeric compounds, such as antisense oligonucleotides, which are covalently linked to a conjugate group, a targeting group, a reactive group, an activation group, or a blocking group, via a short region comprising (e.g. 1-10) of phosphodiester linked DNA or RNA nucleoside(s).

The Oligomer

The present invention employs oligomeric compounds (also referred herein as oligomers) for use in modulating, such as inhibiting a target nucleic acid in a cell. The oligomers may have a length of 8-35 contiguous nucleotides and comprise a first region of 7-25 contiguous nucleotides, and a second region of 1-10 contiguous nucleotides, wherein, for example, either the internucleoside linkage between the first and second region is a phosphodiester linked to the first (or only) DNA or RNA nucleoside of the second region, or region B comprises at least one phosphodiester linked DNA or RNA nucleoside.

The second region may, in some embodiments, comprise further DNA or RNA nucleosides which may be phosphodiester linked. The second region is further covalently linked to a third region which may, for example, be a conjugate, a targeting group a reactive group, and/or a blocking group.

In some aspects, the present invention is based upon the provision of a labile region, the second region, linking the first region, e.g. an antisense oligonucleotide, and a conjugate or functional group, e.g. a targeting or blocking group. The labile region comprises at least one phosphodiester linked nucleoside, such as a DNA or RNA nucleoside, such as 1, 2, 3, 4, 5, 6, 7, 8, 9 or 10 phosphodiester linked nucleosides, such as DNA or RNA. In some embodiments, the oligomeric compound comprises a cleavable (labile) linker. In this respect the cleavable linker is preferably present in region B (or in some embodiments, between region A and B).

The term "oligomer" in the context of the present invention, refers to a molecule formed by covalent linkage of two or more nucleotides (i.e. an oligonucleotide). Herein, a single nucleotide (unit) may also be referred to as a monomer or unit. In some embodiments, the terms "nucleoside", "nucleotide", "unit" and "monomer" are used interchangeably. It will be recognized that when referring to a sequence of nucleotides or monomers, what is referred to is the sequence of bases, such as A, T, G, C or U.

The oligomer consists or comprises of a contiguous nucleotide sequence of from 8-25, such as 9, 10, 11, 12, 13, 14, 15, 16, 17, 18, 19, 20, 21, 22, 23, 24, 25 nucleotides in length, such as 10-20 nucleotides in length.

In various embodiments, the compound of the invention does not comprise RNA (units). In some embodiments, the compound according to the invention, the first region, or the first and second regions together (e.g. as a single contiguous sequence), is a linear molecule or is synthesized as a linear molecule. The oligomer may therefore be single stranded molecule. In some embodiments, the oligomer does not comprise short regions of, for example, at least 3, 4 or 5 contiguous nucleotides, which are complementary to equivalent regions within the same oligomer (i.e. duplexes). The oligomer, in some embodiments, may be not (essentially) double stranded. In some embodiments, the oligomer is essentially not double stranded, such as is not a siRNA.

In some embodiments, the oligomer may comprise a first region which does not comprise short regions of, for example, at least 3, 4 or 5 contiguous nucleotides, which are complementary to regions within the same first region (i.e. intra-region duplexes). In this respect, the first oligomer may, in some embodiments not form a hybridization with a non-covalently linked complementary strand, e.g. does not form part of an siRNA.

For example, in some embodiments, the oligomeric compound does comprise a region of complementarity, e.g. when the first region forms part of an siRNA, or for example, when the third region comprises an aptamer or a blocking oligonucleotide, the oligomeric compound of the invention may, in some embodiments comprise regions of double stranded nucleic acid. In such embodiments, regions of double stranded nucleic acid, for example forming a duplex of at least 3, such as at least, 4, such as at least 5, such as at least 6 nucleotides in length, may be within the third region, or between the third region and for example the first region, or in some embodiments, the second region, or a region across the first and second regions (e.g. when the third region comprises a oligonucleotide blocking region).

In some embodiments, the oligomeric compound is not in the form of a duplex with a (substantially) complementary oligonucleotide—e.g. is not an siRNA.

In some embodiments, the oligomeric compound is a LNA oligomer, for example an LNA antisense oligomer, (which may be referred to as region A herein) comprising an antisense oligomer, region B as defined herein, and a carbohydrate conjugate (which may be referred to as region C). The LNA antisense oligomer may be 7-30, such as 8-26 nucleosides in length and it comprises at least one LNA unit (nucleoside). In some embodiments the carbohydrate moiety is not a linear carbohydrate polymer.

In some embodiments, the oligomeric compound is a LNA oligomer, for example an LNA antisense oligomer, (which may be referred to as region A herein) comprising an antisense oligomer, region B as defined herein, and an asialoglycoprotein receptor targeting moiety conjugate moiety, such as a GalNAc moiety (which may be referred to as region C). The carbohydrate moiety may be multi-valent, such as, for example 2, 3, 4 or 4 identical or non-identical carbohydrate moieties may be covalently joined to the oligomer, optionally via a linker or linkers (such as region Y).

The First Region

In some embodiments, the first region may comprise a nucleic acid based oligomer, such as an antisense oligonucleotide. In some embodiments, the first region comprises or consists of a phosphorothioate linked oligonucleotide, such as an antisense oligonucleotide, of 7-25 nucleotides in length. The first region may comprise at least one modified nucleoside (a nucleoside analogue), such as at least one bicyclic nucleoside (e.g. LNA) or 2'substituted nucleoside. In some embodiments, some or all of the nucleosides of the first region may be modified nucleosides, also referred to as nucleoside analogues herein. In some embodiments, the modified nucleosides are sugar-modified (e.g. comprise a sugar or sugar surrogate moiety other than ribose or deoxyribose).

In some embodiments, the first region is an antisense oligomer (antisense oligonucleotide), such as a single stranded oligomer which comprises a sequence which is complementary to a nucleic acid target.

In some embodiments the first region comprises or is a gapmer. In some embodiments the first region comprises or is a mixmer. In some embodiments the first region comprises or is a totalmer.

In some embodiments, the first region comprises at least one, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or 25 nucleoside analogues. In some embodiments the nucleoside analogues are (optionally independently selected from the group consisting of bicyclic nucleoside analogues (such as LNA), and/or 2' substituted nucleoside analogues, such as (optionally independently) selected from the group consisting of 2'-O-alkyl-RNA units, 2'-OMe-RNA units, 2'-amino-DNA units, 2'-AP, 2'-FANA, 2'-(3-hydroxyl)propyl, and 2'-fluoro-DNA units, and/or other (optionally) sugar modified nucleoside analogues such as morpholino, peptide nucleic acid (PNA), CeNA, unlinked nucleic acid (UNA), hexitol nucleoic acid (HNA), bicyclo-HNA (see e.g. WO2009/100320), In some embodiments, the nucleoside analogues increase the affinity of the first region for its target nucleic acid (or a complementary DNA or RNA sequence). Various nucleoside analogues are disclosed in Freier & Altmann; *Nucl. Acid Res.,* 1997, 25, 4429-4443 and Uhlmann; *Curr. Opinion in Drug Development,* 2000, 3(2), 293-213, hereby incorporated by reference.

In some embodiments, the oligomer, such as the first region thereof, such as the gapmer, mixmer or totalmer comprise at least one bicyclic nucleotide analogue, such as LNA. In some embodiments, the first region comprises of at least one bicyclic nucleoside analogues (e.g. LNA) and/or 2'substituted nucleoside analogues. In some embodiments, the nucleoside analogues present in the first region all comprise the same sugar modification. In some embodiments, at least one nucleoside analogue present in the first region is a bicyclic nucleoside analogue, such as at least 2, at least 3, at least 4, at least 5, at least 6, at least 7, at least 8, at least 9, at least 10, at least 11, at least 12, at least 13, at least 14, at least 15, at least 16, for example all nucleoside analogues (or in a totalmer all nucleosides) bicyclic nucleoside analogues, such as LNA, e.g. beta-D-X-LNA or alpha-L-X-LNA (wherein X is oxy, amino or thio), or other LNAs disclosed herein including, but not limited to, (R/S) cET, cMOE or 5'-Me-LNA. In some embodiments, the oligomer, or first region thereof, comprises of DNA and sugar modified nucleoside analogues, such as bicyclic nucleoside analogues and/or 2'substituted nucleoside analogues. In some embodiments, the oligomer or first region thereof, comprises of DNA and LNA nucleoside analogues.

WO05013901, WO07/027775, WO07027894 refers to fully 2'substituted oligomers, such as fully 2'-O-MOE. In some embodiments, the first region of the oligomer may comprise of 2' substituted nucleosides. WO07/027775 also refers to MOE, LNA, DNA mixmers for use in targeting microRNAs.

In some embodiments, the first region, or the first and second region combined to not comprise a region of more than 4 or 5 consecutive DNA units. Such first regions may be (essentially) unable to recruit RNAseH.

The first region is covalently linked to the second region, such as via a 5' terminal or 3' terminal internucleoside linkage, such as a phosphodiester linkage. The phosphodiester linkage may therefore be positioned between the 5' most nucleoside of region A and the 3' most nucleoside of region B, and/or between the 3' most nucleoside of region A and the 5' most nucleoside of region B. In this respect, in some embodiments, there may be two region B covalently joined to region A, one at the 5' terminus of region A and one at the 3' terminus of region A. The two region Bs may be the same or different, and they may be covalently linked to the same or different third regions, optionally and independently via a linker (Y).

In some embodiments, some or all of the nucleosides of the first region may be modified nucleosides, also referred to as nucleoside analogues herein, such as sugar modified nucleoside analogues, for example bicyclic nucleoside analogues (e.g. LNA) and/or 2'substituted nucleoside analogues. In some embodiments, the nucleoside analogues present in the first region all comprise the same sugar modification, for example are all bicyclic nucleoside analogues, such as LNA, e.g. beta-D-X-LNA or alpha-L-X-LNA (wherein X is oxy, amino or thio), or other LNAs disclosed herein including, but not limited to, (R/S) cET, cMOE or 5'-Me-LNA.

In some embodiments, the internucleoside linkages of the first region comprise at least one internucleoside linkage other than phosphodiester, such as at least one, such as at least 50%, such as at least 75%, such as at least 90%, such as 100% of the internucleoside linkages in region A are other than phosphodiester. In some embodiments, the internucleoside linkages other than phosphodiester are sulphur containing internucleoside linkages, such as phosphorothioate, phosphorodithioate and boranophosphate, such as phosphorothioate.

The Second Region (Region B)

The second region may comprise or consists of at least one DNA or RNA nucleosides linked to the first region via a phosphodiester linkage. In some aspects, the internucleoside linkage between the first and second region is considered as part of region B.

In some embodiments, the second region comprises or consists of at least between 1 and 10 linked nucleosides, such as 1, 2, 3, 4, 5, 6, 7, 8, 9 or 10 linked DNA or RNA nucleotides. Whilst a region of DNA/RNA phosphodiester is considered important in the provision of a cleavable linker, it is possible that region B also comprises sugar-modified nucleoside analogues, such as those referred to under the first region above. However in some embodiments, the nucleosides of region B are (optionally independently) selected from the group consisting of DNA and RNA. It will be recognized that the nucleosides of region B may comprise naturally occurring or non-naturally occurring nucleobases. Region B comprises at least one phosphodiester linked DNA or RNA nucleoside (which may, in some embodiments. be the first nucleoside adjacent to region A). If region B comprises other nucleosides, region B may also comprise of other nucleoside linkages other than phosphodiester, such as (optionally independently) phosphorothioate, phosphodithioate, boranophosphate or methyl phosphonate. However, in other embodiments, all the internucleoside linkages in region B are phosphorothioate. In some embodiments, all the nucleosides of region B comprise (optionally independently) either a 2'-OH ribose sugar (RNA) or a 2'-H sugar— i.e. RNA or DNA.

In some embodiments, the second region comprises or consists of at least between 1 and 10 (e.g. phosphodiester) linked DNA or RNA nucleosides, such as 1, 2, 3, 4, 5, 6, 7, 8, 9 or 10 (e.g. phosphodiester) linked DNA or RNA nucleotides.

In some embodiments, region B comprises no more than 3 or no more than 4 consecutive DNA or RNA nucleosides (such as DNA nucleosides. As such region B may be so short as it does not recruit RNAseH, an aspect which may be important when region B does not form a part of a single contiguous nucleobase sequence which is complementary to the target. Shorter region Bs, e.g. of 1-4 nts in length may also be preferable in some embodiments, as they are unlikely to be the target of sequence specific restriction enzymes. As such it is possible to vary the susceptibility of the region B to endonuclease cleavage, and thereby fine-tune the rate of activation of the active oligomer in vivo, or even intracellular. Suitably, if very rapid activation is required, longer region Bs may be employed and/or region Bs which comprise the recognition sites of (e.g. cell or tissue specific or differentially expressed) restriction enzymes.

As illustrated in the examples, region B may be conjugated to the conjugate, targeting reactive group, an activation group, or blocking group (X) via a linker group which may, for example, comprise a phosphodiester linkage, and/ or optionally a suitable linker group, such as those provided herein. For example a phosphate nucleoside linkage (e.g. phosphodiester, phosphorothioate, phosphodithioate, boranophosphate or methylphosphonate) or a triazol group. In some aspects, the linkage group is the same as the linkage group between regions A and B, and as such may be a phosphodiester linkage. In some aspects, the linkage group is a phosphorothioate linkage.

In some embodiments the DNA or RNA nucleotides of the second region are independently selected from DNA and RNA nucleotides. In some embodiments the DNA or RNA nucleotides of the second region are DNA nucleotides. In some embodiments the DNA or RNA nucleotides of the second region are RNA nucleotides.

In the context of the second region, the term DNA and RNA nucleoside may comprise a naturally occurring or non-naturally occurring base (also referred to as a base analogue or modified base).

It will be recognized that, in some embodiments, the second region may further comprise other nucleotides or nucleotide analogues. In some embodiments, the second region comprises only DNA or RNA nucleosides. In some embodiments, when the second region comprises more than one nucleoside, the internucleoside linkages in the second region comprise phosphodiester linkages. In some embodiments, when the second region comprises more than one nucleoside, all the internucleoside linkages in the second region comprise phosphodiester linkages.

In some embodiments, at least two consecutive nucleosides of the second region are DNA nucleosides (such as at least 3 or 4 or 5 consecutive DNA nucleotides). In some embodiments the at least two consecutive nucleosides of the second region are RNA nucleosides (such as at least 3 or 4 or 5 consecutive RNA nucleotides). In some embodiments the at least two consecutive nucleosides of the second region are at least one DNA and at least one RNA nucleoside. The internucleoside linkage between region A and region B is a phosphodiester linkage. In some embodiments, when region B comprises more than one nucleoside, at least one further internucleoside linkage is phosphodiester—such as the linkage group(s) between the 2 (or 3 or 4 or 5) nucleosides adjacent to region A.

The second region is flanked on one side (either 5' or 3') by the first region, e.g. an antisense oligonucleotide, and on the other side (either 3' or 5' respectfully, via a conjugate moiety or similar group (e.g. a blocking moiety/group, a targeting moiety/group or therapeutic small molecule moiety), optionally via a linker group (i.e. between the second region and the conjugate/blocking group etc. moiety).

In such an embodiment, the oligonucleotide of the invention may be described according to the following formula:
5'-A-PO-B [Y]X-3' or 3'-A-PO-B [Y]X-5'
wherein A is region A, PO is a phosphodiester linkage, B is region B, Y is an optional linkage group, and X is a conjugate, a targeting, a blocking group or a reactive or activation group.

In some embodiments, region B comprises 3'-5' or 5'-3':
i) a phosphodiester linkage to the 5' nucleoside of region A,
ii) a DNA or RNA nucleoside, such as a DNA nucleoside, and iii) a further phosphodiester linkage
5'-A-PO-B-PO-3' or 3'-A-PO-B-PO-5'
The further phosphodiester linkage link the region B nucleoside with one or more further nucleoside, such as one or more DNA or RNA nucleosides, or may link to X (is a conjugate, a targeting or a blocking group or a reactive or activation group) optionally via a linkage group (Y).

In some embodiments, region B comprises 3'-5' or 5'-3':
i) a phosphodiester linkage to the 5' nucleoside of region A,
ii) between 2-10 DNA or RNA phosphodiester linked nucleosides, such as a DNA nucleoside, and optionally iii) a further phosphodiester linkage:
5'-A-[PO-B]n-[Y]—X 3' or 3'-A-[PO-B]n-[Y]—X 5'
5'-A-[PO-B]n-PO-[Y]—X 3' or 3'-A-[PO-B]n-PO-[Y]—X 5'
Wherein A represent region A, [PO-B]n represents region B, wherein n is 1-10, such as 1, 2, 3, 4, 5, 6, 7, 8, 9 or 10, PO is an optional phosphodiester linkage group between region B and X (or Y if present).

In some embodiments the invention provides compounds according to (or comprising) one of the following formula:

5' [Region A]-PO-[region B] 3'-Y—X
5' [Region A]-PO-[region B]-PO 3'-Y—X
5' [Region A]-PO-[region B] 3'-X
5' [Region A]-PO-[region B]-PO 3'-X
3' [Region A]-PO-[region B] 5'-Y—X
3' [Region A]-PO-[region B]-PO 5'-Y—X
3' [Region A]-PO-[region B] 5'-X
3' [Region A]-PO-[region B]-PO 5'-X
Region B, may for example comprise or consist of:
5' DNA3'
3' DNA 5'
5' DNA-PO-DNA-3'
3' DNA-PO-DNA-5'
5' DNA-PO-DNA-PO-DNA 3'
3' DNA-PO-DNA-PO-DNA 5'
5' DNA-PO-DNA-PO-DNA-PO-DNA 3'
3' DNA-PO-DNA-PO-DNA-PO-DNA 5'
5' DNA-PO-DNA-PO-DNA-PO-DNA-PO-DNA 3'
3' DNA-PO-DNA-PO-DNA-PO-DNA-PO-DNA 5'

Sequence Selection in the Second Region:

In some embodiments, region B does not form a complementary sequence when the oligonucleotide region A and B is aligned to the complementary target sequence.

In some embodiments, region B does form a complementary sequence when the oligonucleotide region A and B is aligned to the complementary target sequence. In this respect region A and B together may form a single contiguous sequence which is complementary to the target sequence.

In some embodiments, the sequence of bases in region B is selected to provide an optimal endonuclease cleavage site, based upon the predominant endonuclease cleavage enzymes present in the target tissue or cell or sub-cellular compartment. In this respect, by isolating cell extracts from target tissues and non-target tissues, endonuclease cleavage sequences for use in region B may be selected based upon a preferential cleavage activity in the desired target cell (e.g. liver/hepatocytes) as compared to a non-target cell (e.g. kidney). In this respect, the potency of the compound for target down-regulation may be optimized for the desired tissue/cell.

In some embodiments region B comprises a dinucleotide of sequence AA, AT, AC, AG, TA, TT, TC, TG, CA, CT, CC, CG, GA, GT, GC, or GG, wherein C may be 5-mthylcytosine, and/or T may be replaced with U. In some embodiments region B comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C may be 5-mthylcytosine and/or T may be replaced with U. In some embodiments region B comprises a trinucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, COAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X may be selected from the group consisting of A, T, U, G, C and analogues thereof, wherein C may be 5-mthylcytosine and/or T may be replaced with U. It will be recognized that when referring to (naturally occurring) nucleobases A, T, U, G, C, these may be substituted with nucleobase analogues which function as the equivalent natural nucleobase (e.g. base pair with the complementary nucleoside).

In some embodiments, the compound of the invention may comprise more than one conjugate group (or more than one functional group X—such as a conjugate, targeting, blocking or activated group or a reactive or activation group), such as 2 or 3 such groups. In some embodiments, region B is covalently linked, optionally via a [e.g. non-nucleotide] linker group), to at least one functional group, such as two or three functional groups. In some embodiments, the first region may be covalently linked (e.g. via internucleoside linkages, such as phosphodiester linkages), to two region Bs, for example, one 5' and one 3' to the first region, wherein each region B may be (optionally independently) selected from the region B described herein. In this respect one region B may have one or more functional groups, and the second region B may have one or more function groups, wherein the functional groups of each region B may be independently selected from a conjugate, a targeting group, a blocking group or a reactive/activation group.

Poly Oligomeric Compounds

The invention provides for a poly oligomeric compound which may comprise the first region (region A), the second region (region B) and the third region (region C), wherein the first region is covalently linked to at least one further oligomeric compound (region A'), wherein the first region (region A) and region A' are covalently linked via a bio-cleavable linker (region B'), which may be, by way of example, as according to the second region as disclosed here, for example a region of at least one phosphodiester linked DNA or RNA (such as DNA), such as two, three, four or five phosphodiester linked DNA or RNA nucleosides (such as DNA nucleosides). Regions B and B' may, in some embodiments have the same structure, e.g. the same number of DNA/RNA nucleosides and phosphodiester linkages and/or the same nucleobase sequence. In other embodiments Regions B and B' may be different. By way of example such poly oligomeric compounds may have a structure such as: (5'-3' or 3'-5') Conjugate-PO-ON-PO'-ON', wherein conjugate is region C, PO is region B, PO' is region B', and ON 1 is region A, and ON' is region A'

It should be understood that region A' may, in some embodiments, comprise multiple further oligomeric compounds (such as a further 2 or 3 oligomeric compounds) linked in series (or in parallel) via biocleavable linkers, for example: Conjugate-PO-ON-PO-ON'-PO''-ON'', or Conjugate-PO-ON-[PO-ON']n, wherein n may, for example be 1, 2 or 3, and each ON' may be the same or different, and if different may have the same or different targets.

Multi Conjugate Oligomeric Compounds

In some embodiments, the oligomeric compound may be conjugated to more than one conjugate region (region C), which may be the same or different. For example the oligomeric compound of the invention may have a structure as follows: (5'-3' or 3'-5') ON-PO'-Conj1-PO''-Conj2 wherein Conj1 and conj2 are the two conjugate groups, at least one or both of PO or PO'' are as according to region B herein, and ON is region A. Conj1 and Conj2 may be the same or may be different. For example, in some embodiments, one of Conj1 and Conj2 are a carbohydrate or sterol conjugates and the other is a lipophilic conjugate, e.g. 5'-3' or 3'-5':ON-PO'-Palmitoyl-PO''-Chol or ON-PO'-Palmitoyl-PO''-GalNac The carbohydrate conjugate moiety (represented by Gal-Nac in the preceding formulas (e.g. when used as conj1 or conj2) may for example be selected from the group consisting of galactose, galactosamine, N-formyl-galactosamine, Nacetylgalactosamine, N-propionyl-galactosamine, N-n-butanoyl-galactosamine, and N-isobutanoylgalactose-amine. The lipophilic conjugate (e.g. when used as conj1 or conj2, and represented as palmotoyl in the preceding formulas) may be a hydrophobic group, such as a C16-20 hydrophobic group, a sterol, cholesterol. Other carbohydrate and lipophilic groups which may be used are, for example, disclosed herein.

The Target

In some embodiment, for a non-limiting example, the oligomer of the invention is for use in modulating a nucleic acid (i.e. targets) selected from the group consisting of a mRNA, a microRNA, a lncRNA (long non-coding RNA), a snRNA, snoRNA, and a viral RNA.

Exemplary, but not limiting mRNA and microRNA targets include for example:

The genes indicated in cancer, such as Hif1-alpha, survivin, Bcl2, Mcl1, Her2, androgen receptor, beta-catenin, human transforming growth factor TGF-beta2, ras, TNF-alpha, c-RAF, HSPs e.g. Hsp27, elF-4E (e.g. ISIS-EIF4ER$_x$) STAT3 (e.g. ISIS-STAT3Rx), clusterin (e.g. OGX-011), AurkB, AurkA, PBK, miR-155, miR-21, miR-10b, mir-34 (see WO2011088309), miR-199a, miR-182, The mRNAs of genes involved in inflammation, e.g. ICAM-1 (e.g. Alicoforsen), CD49d, VLA-4 osteopontin, miR-21 (psoriasis), Other medically relevant mRNA targets include CTGF (local fibrosis) and c-Raf-kinase (ocular disease). miR-29 (cardiac fibrosis), Factor XI (clotting), factor VII (clotting) miR15 miR-159 (post-MI modeling (post-MI modeling), miR-138 (bone-loss), mir-21 (see WO12148952) and mir214 (fibrosis)—see WO2012012716.

Metabolic disease or disorders targets, such as Apo-B (high LDL cholesterol, ACS), ApoCIII (high serum TG, diabetes), Apo(a) (cardiovascular disease), FGFR4 (obesity), GCCR (T2 diabetes), GCGR (T2 diabetes), PTP1B (T2 diabetes), DGAT2 (NASH), PCSK9 (hyperlipidaemia and related disorders), MtGPAT (obesity and NAFLD), miR-122 (high cholesterol), miR-33 (metabolic syndrome, atherosclerosis), miR-208 (chronic heart failure), miR-499 (chronic heart failure), miR-378 (cardio metabolic disease), mir-143 (vascular disease), miR-145 (vascular disease), miR-92 (peripheral arterial disease), miR-375 (diabetes), miR-27b (diabetes), miR-34a (diabetes), miR-199a, miR-27a (heart disease, ischemia), miR-338 (diabetes).

Metabolic diseases include, for examples, metabolic syndrome, obesity, hyperlipidemia, HDL/LDL cholesterol imbalance, dyslipidemias, e.g., familial combined hyperlipidemia (FCHL), acquired hyperlipidemia, statin-resistant hypercholesterolemia, coronary artery disease (CAD), and coronary heart disease (CHD), atherosclerosis, heart disease, diabetes (I and/or II), NASH, acute coronary syndrome (ACS), Viral diseases: miR-451 (polycythemia), miR-122 (HCV), HBV, HCV, BKV, etc. Severe and rare diseases include SMN2 (spinal muscular atrophy), TTR (TTR amyloidosis), GHr (acromegaly), AAT (AATD associated liver disease), Dystophin (Duchennes muscular dystrophy).

In some embodiments, the oligomer of the invention targets a liver expressed nucleic acid, such as a liver expressed mRNA, such as PCSK9, ApoB, or MtGPAT. In some embodiments, the oligomer of the invention targets PCSK9 mRNA. In some embodiments, the oligomer of the invention targets ApoB mRNA. In some embodiments, the oligomer of the invention targets a liver expressed microRNA, such as miR-122.

In some embodiments, the oligomer of the invention is capable of down-regulating (e.g. reducing or removing) expression of the target (e.g. target nucleic acid). In this regards, the oligomer of the invention can affect the inhibition of the target. In some embodiments, the oligomers of the invention bind to the target nucleic acid and affect inhibition of expression of at least 10% or 20% compared to the normal expression level, more preferably at least a 30%, 40%, 50%, 60%, 70%, 80%, 90% or 95% inhibition compared to the normal expression level (such as the expression level in the absence of the oligomer(s) or conjugate(s)). In some embodiments, such modulation is seen when using from 0.04 and 25 nM, such as from 0.8 and 20 nM concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as from 0.04 and 25 nM, such as from 0.8 and 20 nM concentration, is, In some embodiments, typically to a level of from 10-20% the normal levels in the absence of the compound, conjugate or composition of the invention.

The invention therefore provides a method of down-regulating or inhibiting the expression of the target in a cell which is expressing the target, said method comprising administering the oligomer or conjugate according to the invention to said cell to down-regulating or inhibiting the expression of the target in said cell. Suitably the cell is a mammalian cell such as a human cell. The administration may occur, in some embodiments, in vitro. The administration may occur, in some embodiments, in vivo. Compounds of the invention, such as the oligomers and conjugates thereof, may be targeted to different targets, such as mRNA or microRNA or other nucleic acid targets which are expressed in the liver (references to NCBI Genbank/Gene IDs are given as examples of sequences which may be targeted by the compounds of the invention—the Genbank/NCBI sequences are hereby incorporated by reference).

ApoB

In some embodiments, the first region (or first and second region) forms a single contiguous nucleobase sequence which is complementary, to a corresponding region of an ApoB mRNA target (i.e. targets) ApoB-100 (NCBI Genbank ID NM_000384.2 GI:105990531, hereby incorporated by reference).

Compounds of the invention which target ApoB may be used in the treatment of acute coronary syndrome (see WO20100076248). The invention therefore provides for the oligomer according to the invention which targets ApoB100 for use in the treatment of acute coronary syndrome. The invention further provides for a method of treatment of acute coronary syndrome, wherein said method comprises the administration of the oligomer of the invention to a subject in need to said treatment.

Compounds of the invention which target ApoB may be used in the treatment atherosclerosis. The invention therefore provides for the oligomer according to the invention which targets ApoB100 for use in the treatment of atherosclerosis. The invention further provides for a method of treatment of atherosclerosis, wherein said method comprises the administration of the oligomer of the invention to a subject in need to said treatment.

Compounds of the invention which target ApoB may be used in the treatment hypercholesterolemia or hyperlipidaemia. The invention therefore provides for the oligomer according to the invention which targets ApoB100 for use in the treatment of hypercholesterolemia or hyperlipidaemia. The invention further provides for a method of treatment of hypercholesterolemia or hyperlipidaemia, wherein said method comprises the administration of the oligomer of the invention to a subject in need to said treatment.

The invention provides for an in vivo or in vitro method for the inhibition of ApoB in a cell which is expressing ApoB, said method comprising administering an oligomer or conjugate or pharmaceutical composition according to the invention to said cell so as to inhibit ApoB in said cell.

Examples of LNA oligomers which may be used as the first region in the oligomers/conjugates of the invention include, for example those disclosed in WO2007/031081, WO2008/113830, WO2007131238, and WO2010142805, which are hereby incorporated by reference. Specific preferred compounds include the following:

5'-G$_s$$^m$C$_s$a$_s$t$_s$t$_s$g$_s$g$_s$t$_s$a$_s$t$_s$T$_s$$^m$C$_s$A-3' (SEQ ID NO 1)
5'-G$_s$T$_s$t$_s$g$_s$a$_s$c$_s$a$_s$c$_s$t$_s$g$_s$T$_s$$^m$C-3' (SEQ ID NO 53)

Wherein capital letters are beta-D-oxy LNA units (nucleosides), lower case letters are DNA units, subscript s is a phosphorothioate linkage, and a superscript m before the capital C illustrates that all LNA cytosines are 5-methyl cytosine. Compounds of the invention targeting ApoB may be conjugated to a conjugate which targets the oligomer to the liver, as disclosed herein, such as a carbohydrate or lipophilic conjugate, such as a GalNac conjugate or a sterol conjugate (e.g. cholesterol or tocopherol). The conjugate may be, for example, at the 5' end or the 3' end of the oligomer compound (suitably via region B). Other oligomers which target ApoB are disclosed in WO03/011887, WO04/044181, WO2006/020676, WO2007/131238, WO2007/031081, and WO2010142805.

PCSK9

In some embodiments, the first region (or first and second region) forms a single contiguous nucleobase sequence which is complementary, to a corresponding region of a PCSK9 mRNA target (i.e. targets), such as the human PCSK9 mRNA: NCBI Genbank ID NM_174936.3 GI:299523249, hereby incorporated by reference.

The invention provides for an oligomer according to the invention which targets PCSK9, for use as a medicament, such as for the treatment of hypercholesterolemia or related disorder, such as a disorder selected from the group consisting of atherosclerosis, hyperlipidaemia, hypercholesterolemia, familiar hypercholesterolemia e.g. gain of function mutations in PCSK9, HDL/LDL cholesterol imbalance, dyslipidemias, e.g., familial hyperlipidaemia (FCHL), acquired hyperlipidaemia, statin-resistant hypercholesterolemia, coronary artery disease (CAD), and coronary heart disease (CHD).

The invention provides for the use of an oligomer of the invention which targets PCSK9, for the manufacture of a medicament for the treatment of hypercholesterolemia or a related disorder, such as a disorder selected from the group consisting of atherosclerosis, hyperlipidaemia, hypercholesterolemia, familiar hypercholesterolemia e.g. gain of function mutations in PCSK9, HDL/LDL cholesterol imbalance, dyslipidemias, e.g., familial hyperlipidaemia (FCHL), acquired hyperlipidaemia, statin-resistant hypercholesterolemia, coronary artery disease (CAD), and coronary heart disease (CHD).

The invention provides for a method of treating hypercholesterolemia or a related disorder, such as a disorder selected from the group consisting atherosclerosis, hyperlipidaemia, hypercholesterolemia, familiar hypercholesterolemia e.g. gain of function mutations in PCSK9, HDL/LDL cholesterol imbalance, dyslipidemias, e.g., familial hyperlipidaemia (FCHL), acquired hyperlipidaemia, statin-resistant hypercholesterolemia, coronary artery disease (CAD), and coronary heart disease (CHD), said method comprising administering an effective amount of an oligomer according to the invention which targets PCSK9, to a patient suffering from, or likely to suffer from hypercholesterolemia or a related disorder.

The invention provides for an in vivo or in vitro method for the inhibition of PCSK9 in a cell which is expressing PCSK9, said method comprising administering an oligomer according to the invention which targets PCSK9 to said cell so as to inhibit PCSK9 in said cell.

The following is an oligomer which targets the human PCSK9 mRNA, and may be used as region A in the compounds of the invention.

(SEQ ID NO 37)
5'-T$_s$G$_s$$^m$C$_s$t$_s$a$_s$c$_s$a$_s$a$_s$a$_s$a$_s$c$_s$$^m$C$_s$$^m$C$_s$A-3'

Wherein capital letters are beta-D-oxy LNA units (nucleosides), lower case letters are DNA units, subscript s is a phosphorothioate linkage, and a superscript m before the capital C illustrates that all LNA cytosines are 5-methyl cytosine. Compounds of the invention targeting PCSK9 may be conjugated to a conjugate which targets the oligomer to the liver, as disclosed herein, such as a carbohydrate or lipophilic conjugate, such as a GalNac conjugate or a sterol conjugate (e.g. cholesterol or tocopherol). The conjugate may be, for example, at the 5' end or the 3' end of the oligomer compound (suitably via region B). Other oligomers which target PCSK9 are disclosed as the SEQ ID NO 36-52, and others are disclosed in WO2008/043753, WO2011/009697, WO08/066776, WO07/090071, WO07/146511, WO07/143315, WO09/148605, WO11/123621, and WO11133871, which are hereby incorporated by reference.

miR-122

In some embodiments, the first region (or first and second region) form a single contiguous nucleobase sequence which is complementary, to a corresponding region of a micro-RNA-122 such as miR-122a (i.e. targets), such as the has-miR-122 sequences (miRBase release 20: MI0000442), such as:

```
>hsa-mir-122 MI0000442
CCUUAGCAGAGCUGUGGAGUGUGACAAUGGUGUUUGUGUCUAAACUAUCA

AACGCCAUUAUCACACUAAAUAGCUACUGCUAGGC

>hsa-miR-122-5p MIMAT0000421
UGGAGUGUGACAAUGGUGUUUG
``` miR-122 has been indicated in HCV infection, where it is an essential host factor required for maintenance of the infection. Inhibitors of miR-122 may therefore be used in the treatment of hepatitis C infection.

Compounds of the invention which target miR-122 may be used in the treatment of HCV infection. The invention therefore provides for the oligomer according to the invention which targets miR-122 for use in the treatment of HCV infection. The invention further provides for a method of treatment of HCV infection, wherein said method comprises the administration of the oligomer of the invention to a subject in need to said treatment.

The invention provides for the use of an oligomer of the invention which targets miR-122, for the manufacture of a medicament for the treatment of HCV infection.

The invention provides for a method of treating HCV infection, said method comprising administering an effective amount of an oligomer according to the invention which targets miR-122, to a patient suffering from HCV infection.

The invention provides for an in vivo or in vitro method for the inhibition of miR-122 in a cell which is expressing miR-122, such as an HCV infected cell or a HCV replicon expressing cell, said method comprising administering an oligomer or conjugate or pharmaceutical composition according to the invention to said cell so as to inhibit miR-122 in said cell.

miR-122 has also been indicated in cholesterol metabolism, and it has been suggested that inhibition of miR-122 may be used for a treatment to reduce plasma cholesterol levels (Esau, Cell Metab. 2006 February; 3(2):87-98.)

Inhibitors of miR-122 may therefore be used in a treatment to reduce plasma cholesterol levels, or in the treatment of a metabolic disease associated with elevated levels of cholesterol (related disorders), such as indications selected from the group consisting of atherosclerosis, hyperlipidaemia, hypercholesterolemia, familiar hypercholesterolemia, dyslipidemias, coronary artery disease (CAD), and coronary heart disease (CHD) Compounds of the invention which target miR-122 may be used in the treatment of elevated cholesterol levels or related disorders. The invention therefore provides for the oligomer according to the invention which targets miR-122 for use in the treatment of elevated cholesterol levels or related disorders. The invention further provides for a method of treatment of elevated cholesterol levels or related disorders, wherein said method comprises the administration of the oligomer of the invention to a subject in need to said treatment.

The invention provides for the use of an oligomer of the invention which targets miR-122, for the manufacture of a medicament for the treatment of elevated cholesterol levels or related disorders.

The invention provides for a method of treating elevated cholesterol levels or related disorders, said method comprising administering an effective amount of an oligomer according to the invention which targets miR-122, to a patient suffering from said disorder.

The invention provides for an in vivo or in vitro method for the inhibition of miR-122 in a cell which is expressing miR-122, such as an HCV infected cell or a HCV replicon expressing cell, said method comprising administering an oligomer or conjugate or pharmaceutical composition according to the invention to said cell so as to inhibit miR-122 in said cell.

Oligomer's targeting miR-122 are disclosed in WO2007/112754, WO2007/112753, WO2009/043353, and may be mixmers, such as SPC3649, also referred to as miravirsen see below, or a tiny LNA, such as those disclosed in WO2009/043353 (e.g. 5'-ACACTCC-3', 5'-CACACTCC-3', 5'-TCACACTCC-3', where capital letters are beta-D_oxy LNA, fully phosphorothioate and LNA C are 5-methyl cytosine). In some embodiments, the miR-122 targeting oligomers have a length of 8, 9, 10, 11, 12, 13, 14, 15, 16, 17 or 18 (or 19, 20, 21, 22 or 23 nucleotides) in length. In some embodiments, the miR-122 targeting oligomers a sequence which is fully complementary to miR-122 as measured across the length of the oligomer, and preferably include the sequence 5'-CACACTCC-3'. In some embodiments, the oligomer targeting a microRNA such as miR-122, is complementary to a corresponding region of the microRNA across the length of the oligomer and in some embodiments the 3' nucleoside of the oligomer is complementary to (i.e. aligns to) the first, second, third or fourth 5' nucleotides of the microRNA, such as miR-122, such as the second 5' nucleotide of the microRNA, such as miR-122.

The following is an oligomers which targets the has-miR-122 (human miR-122), and may be used as region A in the compounds of the invention.

Miravirsen:
5'-$^{m}C_sc_sA_{tt}G_sT_sc_A{}^mC_A{}^mC_s{}^mC_s{}^mC_sC$-3'

Other miR-122 targeting compounds which may be used in the context of the present invention (region A) are disclosed in WO2007/027894, WO2007/027775.
MtGPAT: (NCBI gene ID 57678-Chromosome: 10; NC_000010.10 (113907971 . . . 113975153, complement) Mitochondrial glycerol-3-phosphate acyltransferase 1 (EC 2.3.1.15, also known as GPAT1, mtGPAT1, GPAM, mtGPAM) plays a major role in hepatic triglyceride formation, where high levels of mtGPAT1 activity results in fatty liver (hepatosteatosis) whereas the absence of mtGPAT1 results in low levels of liver triglycerides and stimulated fatty acid oxidation (see WO2010/000656 which discloses oligomers which target mtGPAT. Compounds of the invention which target MtGPAT may be used to treat conditions such as being overweight, obesity, fatty liver, hepatosteatosis, non alcoholic fatty liver disease (NAFLD), non alcoholic steatohepatitis (NASH), insulin resistance, diabetes such as non insulin dependent diabetes mellitus (NIDDM)

FactorVII (NCBI Gene ID 2155, NCBI J02933.1 GI:180333, or EU557239.1 GI:182257998). The oligomer or conjugate of the invention may target FactorVII, and thereby inhibit the production of Factor VII, a key component of the tissue factor coagulation pathway. Compounds of the invention which target FactorVII may be used for the treatment or prevention of thrombotic diseases (typically without causing bleeding) and as heart attack, stroke and blood clots, or inflammatory conditions. WO 2013/119979 and WO 2012/174154, hereby incorporated by reference disclose oligonucleotide compounds which target FVII which may be incorporated into the conjugates of the present invention.

Factor XI (NCBI Genbank BC122863.1 GI:114108211)—Factor XI, a clotting factor that is produced in the liver. High levels of Factor XI are linked to heart attack, stroke and blood clots. WO 2013/070771, hereby incorporated by reference, discloses oligonucleotide compounds which target XI which may be incorporated into the conjugates of the present invention. Compounds of the invention which target FactorXI may be used for the treatment or prevention of thrombotic diseases, and as heart attack, stroke and blood clots, or inflammatory conditions such as arthritis and colitis.

ApoCIII (NCBI Genbank BC027977.1 GI:20379764) a protein that regulates triglyceride metabolism in blood. High levels of apoC-III are linked to inflammation, high triglycerides, atherosclerosis and metabolic syndrome. Compounds of the invention which target ApoCIII may be used to reduce serum triglyceride levels or in the treatment of e.g. familial chylomicronemia syndrome and severely high triglycerides either as a single agent or in combination with other triglyceride-lowering agents. WO11085271 hereby incorporated by reference, discloses oligonucleotide compounds which target ApoCIII which may be incorporated into the conjugates of the present invention.

Apo(a) (NCBI Genbank NM_005577.2 GI:116292749) inhibits the production of apo(a) in the liver and is designed to offer a direct approach to reducing Lp(a), an independent risk factor for cardiovascular disease. High levels of Lp(a) are associated with an increased risk of atherosclerosis, coronary heart disease, heart attack and stroke. Lp(a) promotes premature plaque buildup, or atherosclerosis, in arteries. Compounds of the invention which target Apo(a) may be used in the treatment of e.g. atherosclerosis and coronary heart disease. WO05000201 and WO03014307 hereby incorporated by reference, discloses oligonucleotide compounds which target apolipoprotein (a) which may be incorporated into the conjugates of the present invention.

Hepatitis B (HBV) (see for example NCBI D23684.1 GI:560092; D23683.1 GI: 560087; D23682.1 GI: 560082; D23681.1 GI: 560077; D23680.1 GI: 560072; D23679.1 GI: 560067; D23678.1 GI: 560062; D23677.1 GI: 560057; all of which are hereby incorporated by reference)

Oligomers which target HBV are well known in the art, for example see, WO96/03152, WO97/03211, WO2011/052911, WO2012/145674, WO2012/145697, WO2013/003520 and WO2013/159109.

Compounds of the invention which target HBV may be used in the treatment HBV infection. The invention therefore provides for the oligomer according to the invention which targets HBV for use in the treatment of HBV. The invention further provides for a method of treatment of HBV infection, wherein said method comprises the administration of the oligomer of the invention to a subject in need to said treatment.

The invention provides for the oligomer or conjugate of the invention which targets hepatitis B (HBV) for use as a medicament, such as for the treatment hepatitis B infection or a related disorder.

The invention provides for the use of an oligomer or conjugate or pharmaceutical composition according to the invention which targets hepatitis B (HBV), for the manufacture of a medicament for the treatment of hepatitis B infection or a related disorder.

The invention provides for a method of treating treatment hepatitis B infection or a related disorder, said method comprising administering an effective amount of an oligomer or conjugate of the invention which targets HBV, to a patient infected with Hepatitis B virus.

The invention provides for an in vivo or in vitro method for the inhibition of HBV replication in a cell infected with HBV, said method comprising administering an oligomer or conjugate of the invention which targets HBV to said cell so as to inhibit HBV replication. An example of an LNA oligomer which target's HBV is (as is disclosed in WO2011/47312) which may be used as the oligomer (region A) of the invention 5'-$G_sA_sG_sG_sc_sa_st_sa_sg_sc_sa_sg_s{}^mC_sA_sG_sG$-3'. Further compounds are disclosed in table 1 of WO2011/47312, and in WO2011/052911, WO2012/145674, WO2012/145697, WO2013/003520 and WO2013/159109, hereby incorporated by reference.

RG-101 is a compound which targets miR-122 and comprises a GalNac conjugate, and is being developed for treatment of HCV by Regulus Therapeutics.

ANGPTL3, (e.g. NCBI BC007059.1 GI: 14712025 or BC058287.1 GI: 34849466) ANGIOPOIETIN-LIKE 3—a protein that regulates lipid, glucose and energy metabolism. Humans with elevated levels of ANGPTL3 have hyperlipidemia associated with an increased risk of premature heart attacks, increased arterial wall thickness as well as multiple metabolic abnormalities, such as insulin resistance. In contrast, humans with lower levels of ANGPTL3 have lower LDL-C and triglyceride levels and a lower risk of cardiovascular disease. Compounds of the invention which target ANGPTL3 may be used in the treatment of e.g. hyperlipidemia and related disorders, metabolic disorder, atherosclerosis, coronary heart disease or insulin resistance. WO11085271 hereby incorporated by reference, discloses oligonucleotide compounds which target ANGPTL3 which may be incorporated into the conjugates of the present invention.

Glucagon receptor, or GCGR (BC112041.1 GI: 85567507; L20316.1 GI: 405189): Glucagon is a hormone that opposes the action of insulin and stimulates the liver to produce glucose, particularly in type 2 diabetes. In patients with advanced diabetes, uncontrolled glucagon action leads to a significant increase in blood glucose levels. Therefore, attenuating glucagon action may have a significant glucose lowering effect in patients with severe diabetes. In addition, reducing GCGR produces more active glucagon-like peptide, or GLP-1, a hormone that preserves pancreatic function and enhances insulin secretion. Compounds of the invention which target GCGR may be used in the treatment of e.g. or insulin resistance, hyperglycemia, diabetes, such as type 1 or 2 diabetes, preservation of pancreatic function, and to control of blood glucose levels. WO2007/134014 discloses oligonucleotide compounds which target GCGR which may be incorporated into the conjugates of the present invention.

Fibroblast growth factor receptor 4, or FGFR4. (NCBI Gene 2264-NC_000005.9 (176513906 . . . 176525143) FGFR4 is expressed in the liver and fat tissues, and is indicated in decreasing the body's ability to store fat while simultaneously increasing fat burning and energy expenditure. Many anti-obesity drugs act in the brain to suppress appetite, commonly resulting in CNS side effects. Compounds of the invention which target FGFR4 may be used in the treatment of e.g. or insulin resistance, hyperglycemia, diabetes, such as type 1 or 2 diabetes, preservation of obesity (e.g. when used in combination with an appetite-suppressing drug), reducing body weight, and improvement in insulin sensitivity, diabetes, such as type 1 or 2 diabetes and to control of blood glucose levels. WO09046141 and WO12174476 hereby incorporated by reference disclose oligonucleotide compounds which target FGFR4 which may be incorporated into the conjugates of the present invention.

Diacylglycerol acyltransferase-2, or DGAT-2 (NCBI GENE ID 84649): A key component in the synthesis of triglycerides. The inhibition of DGAT may reduce liver fat in patients with Nonalcoholic Steatohepatitis (NASH), and may also be used to treat type 2 diabetes and insulin resistance. Compounds of the invention which target DGAT-2 may be used to treat NASH, to reduce liver fat, to treat diabetes, such as type 2 diabetes, and treat insulin resistance. WO05019418 and WO2007136989, hereby incorporated by reference disclose oligonucleotide compounds which target DGAT-2 which may be incorporated into the conjugates of the present invention.

Glucocorticoid receptor, or GCCR (BC150257.1 GI: 152013043): Glucocorticoid hormones affect a variety of processes throughout the body, and excessive levels of glucocorticoid hormones can have a detrimental effect on many of the tissues and organs in the body. Cushing's Syndrome is an orphan disease caused by prolonged exposure to high levels of glucocorticoids. If untreated, patients with Cushing's Syndrome can develop hypertension, diabetes and impaired immune functions and have an increased risk of early death. Although there are approved treatments for Cushing's Syndrome, current medicines are associated with significant side effects, such as hypertension and diabetes, and there remains a high unmet medical need for new therapies for these patients. Compounds of the invention which target GCCR-2 may be used to treat Cushing's Syndrome and associated conditions (such as those listed above). WO07035759 and WO2007136988, which are hereby incorporated by reference disclose oligonucleotide compounds which target GCCR which may be incorporated into the conjugates of the present invention.

Complement component C5 (M57729.1 GI: 179982): The complement system plays a central role in immunity as a protective mechanism for host defense, but its dysregulation results in serious, life-threatening complications in a broad range of human diseases including paroxysmal nocturnal hemoglobinuria (PNH), atypical hemolytic-uremic syndrome (aHUS), myasthenia gravis, neuromyelitis optica, amongst others. Compounds of the invention which target complement component C5 may be used to treat one or more of these disorders. C5 is a genetically and clinically validated target; loss of function human mutations are associated with an attenuated immune defense against certain infections and intravenously administered anti-C5 monoclonal antibody therapy has demonstrated clinical activity and tolerability in a number of complement-mediated diseases. transmembrane protease, serine 6 (Tmprss6) for the treatment of beta-thalassemia and iron-overload disorders.

Alpha-1 antitrypsin (AAT): (M11465.1 GI: 177826) Liver disease associated with—WO13142514 which is hereby incorporated by reference disclose oligonucleotide compounds which target AAT which may be incorporated into the oligomers or conjugates of the present invention. Compounds of the invention which target AAT may be used in methods for decreasing A1AT mRNA and protein expression and treating, ameliorating, preventing, slowing progression, or stopping progression of fibrosis, such as, A1ATD associated liver disease, and pulmonary disease, such as, A1ATD associated pulmonary disease in an individual in need thereof.

Transthyretin—TTR (BC005310.1 GI: 13529049): The oligomers of the invention which target TTR may be used to treat transthyretin amyloidosis, or TTR amyloidosis, a severe and rare genetic disease in which the patient inherits a mutant gene that produces a misfolded form of TTR, which progressively accumulates in tissues. In patients with TTR amyloidosis, both the mutant and normal forms of TTR can build up as fibrils in tissues, including heart, peripheral nerves, and the gastrointestinal tract. The presence of TTR fibrils interferes with the normal functions of these tissues, and as the TTR protein fibrils enlarge more tissue damage occurs and the disease worsens. TTR is a carrier protein that transports a thyroid hormone and retinol in the blood. In patients with TTR amyloidosis, both the mutant and normal forms of TTR can build up as fibrils in tissue. The compounds of the invention may be used to treat TTR amyloidosis. See Benson et al., Amyloid. 2010 June; 17(2):43-9, and Ackermann et al., Amyloid. 2012 June; 19 Suppl 1:43-4.). Antisense compounds targeting TTR which may be used in the oligomers or conjugates of the invention are disclosed in U.S. Pat. No. 8,101,743, WO11139917 and WO10017509, which are hereby incorporated by reference.

Aminolevulinate synthase-1 (ALAS-1) (BC011798.2 GI: 33877783; AK312566.1 GI: 164690365; NM_199166.2 GI:

362999012; NM_000688.5 GI: 362999011). ALAS1 is a validated target for the treatment of porphyria, such as the treatment of hepatic porphyrias including acute intermittent porphyria (AIP). Compounds of the invention which target ALAS-1 may be used in the treatment of these disorders.

Vascular endothelial growth factor, or VEGF (GENE ID 7422, human Sequence: Chromosome: 6; NC_000006.11 (43737946 . . . 43754224)). VEGF is indicated in cancers. Compounds of the invention which target VEGF may be used in the treatment of hyperproliferative disorders, such as cancer, such as liver cancer.

Table 1 provides for a group of liver targets which may be targeted by the compounds of the invention, as well as the medical indication/disorder for which such compounds may be used to treat (such as a person suffering from the associated disorder) (See Sehgal et al., Liver as a target for oligonucleotide therapeutics, J. of Hepatology 2013, In Press).

TABLE 1

| The compound of the invention may target a nucleic acid (e.g. mRNA encoding, or miRNA) selected from the group consisting of | For the treatment of a disease or disorder such as |
|---|---|
| AAT | AAT-LivD |
| ALDH2 | Alcohol dependence |
| HAMP pathway | Anemia or inflammation/CKD |
| miR-33 | Atherosclerosis |
| Apo(a) | Atherosclerosis/high Lp(a) |
| miR-7 | Liver cancer |
| miR-378 | Cardiometabolic diseases |
| miR-21 | Liver cancer |
| Myc | Liver cancer |
| miR-122 | HCV |
| 5'UTR | HCV |
| 5'UTR & NS5B | HCV |
| NS3 | HCV |
| TMPRSS6 | Hemochromatosis |
| Antithrombin III | Hemophilia A, B |
| ApoCIII | Hypertriglyceridemia |
| ANGPLT3 | Hyperlipidemia |
| MTP | Hyperlipidemia |
| DGAT2 | NASH |
| ALAS1 | Porphyria |
| Antithrombin III | Rare Bleeding disorders |
| Serum amyloid A | SAA-amyloidosis |
| Factor VII | Thrombosis |
| Growth hormone receptor | Acromegaly |
| miR-122 | Hepatitis C virus |
| ApoB-100 | Hypercholesterolemia |
| ApoCIII | Hypertriglyceridemia |
| PCSK9 | Hypercholesterolemia |
| CRP | Inflammatory disorders |
| KSP or VEGF | Liver cancer |
| PLK1 | Liver cancer |
| miR-34 | Liver cancer |
| FGFR4 | Obesity |
| Factor IXa | Thrombosis |
| Factor XI | Thrombosis |
| TTR | TTR amyloidosis |
| GCCR | Type 2 diabetes |
| PTP-1B | Type 2 diabetes |
| GCGR | Cushing's Syndrome |
| Hepatic Glucose 6-Phosphate Transporter-1 | glucose homeostasis, diabetes, type 2 diabetes |

Sequences

In some embodiments, the oligomers, or first region thereof, comprise a contiguous nucleotide sequence which corresponds to the reverse complement of a nucleotide sequence present in the target nucleic acid (i.e. the sequence which the oligomer targets). Table 3 provides a group of mRNA and miRNA targets which are in pre-clinical or clinical development using oligonucleotide compounds for the associated indication, and are therefore suitable for targeting with the compounds of the present invention.

In some embodiments the target is selected from the group consisting of: miR-122, ApoB-100, ApoCIII, PCSK9, CRP, KSP, VEGF, PLK1, miR-34, FGFR4, Factor IXa, Factor XI, TTR, GCCR, PTP-1B, GCGR, AAT, ALDH2, HAMP pathway, miR-33, Apo(a), miR-7, miR-378, miR-21, Myc, miR-122, the HCV genome such as the HCV 5'UTR or HCV NS5B RNA or NS3 RNA, TMPRSS6, Antithrombin III, ApoCIII, ANGPLT3, MTP, DGAT2, ALAS1, Antithrombin III, Serum amyloid A and Factor VII.

In some embodiments, the contiguous nucleotide sequence comprises no more than a single mismatch when hybridizing to the target sequence.

In determining the degree of "complementarity" between oligomers of the invention (or regions thereof) and the target region of the nucleic acid, such as those disclosed herein, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

As used herein, the terms "homologous" and "homology" are interchangeable with the terms "identity" and "identical".

The terms "corresponding to" and "corresponds to" refer to the comparison between the nucleotide sequence of the oligomer (i.e. the nucleobase or base sequence) or contiguous nucleotide sequence (a first region) and the equivalent contiguous nucleotide sequence of a further sequence selected from either i) a sub-sequence of the reverse complement of the nucleic acid target. Nucleotide analogues are compared directly to their equivalent or corresponding nucleotides. A first sequence which corresponds to a further sequence under i) or ii) typically is identical to that sequence over the length of the first sequence (such as the contiguous nucleotide sequence) or, as described herein may, in some embodiments, is at least 80% homologous to a corresponding sequence, such as at least 85%, at least 90%, at least 91%, at least 92% at least 93%, at least 94%, at least 95%, at least 96% homologous, such as 100% homologous (identical).

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

The terms "reverse complement", "reverse complementary" and "reverse complementarity" as used herein are interchangeable with the terms "complement", "complementary" and "complementarity".

The contiguous nucleobase sequence of the oligomer (first region or first and second region) may therefore be complementary to a target, such as those referred to herein.

In some embodiments, the first region or first and second region form a single contiguous nucleobase sequence which is complementary to a region of a mRNA target, such as those referred to herein, including, for example, ApoB-100 (NM_000384.2 GI:105990531 or PCSK9 (NM_174936.3 GI:299523249).

Length

The oligomers may comprise or consist of a contiguous nucleotide sequence of a total of 8, 9, 10, 11, 12, 13, 14, 15, 16, 17, 18, 19, 20, 21, 22, 23, 24, 25, 26, 27, 28, 29, 30, 31, 32, 33, 34 and 35 contiguous nucleotides in length.

In some embodiments, the oligomers comprise or consist of a contiguous nucleotide sequence of a total of from 10-22, such as 12-18, such as 13-17 or 12-16, such as 13, 14, 15, 16 contiguous nucleotides in length.

In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides. It should be understood that when a range is given for an oligomer, or contiguous nucleotide sequence length it includes the lower an upper lengths provided in the range, for example from (or between) 10-30, includes both 10 and 30.

Nucleosides and Nucleoside Analogues

The term "nucleotide" as used herein, refers to a glycoside comprising a sugar moiety (or analogue thereof), a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

It will be recognized that in the context of the present invention the term nucleoside and nucleotide are used to refer to both naturally occurring nucleotides/sides, such as DNA and RNA, as well as nucleotide/side analogues.

In field of biochemistry, the term "nucleoside" is commonly used to refer to a glycoside comprising a sugar moiety and a base moiety, and may therefore be used when referring to the nucleotide units, which are covalently linked by the internucleoside linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refer to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifying the presence or nature of the linkages between the nucleosides.

As one of ordinary skill in the art would recognize, the 5' terminal nucleotide of an oligonucleotide does not comprise a 5' internucleoside linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

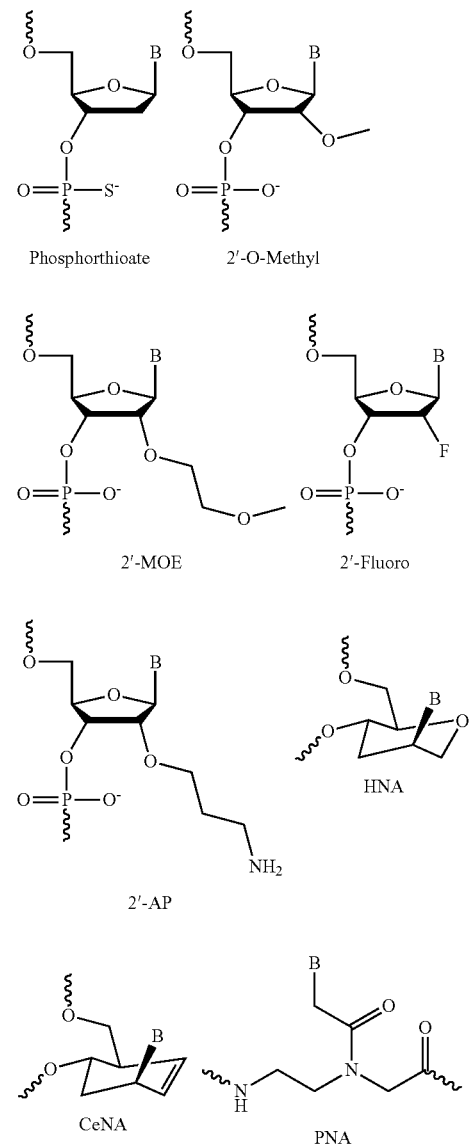

Scheme 1

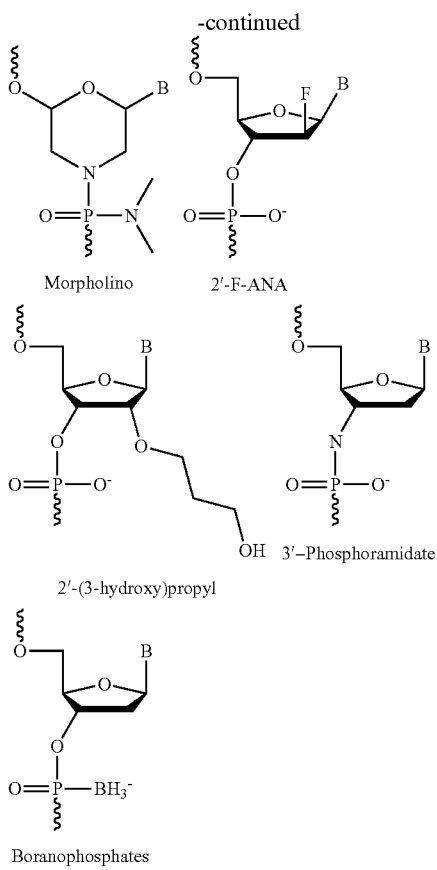

The oligomer may thus comprise or consist of a simple sequence of natural occurring nucleotides—preferably 2'-deoxynucleotides (referred here generally as "DNA"), but also possibly ribonucleotides (referred here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by WO2007/031091 or are referenced therein. Other nucleotide analogues which may be used in the oligomer of the invention include tricyclic nucleic acids, for example please see WO2013154798 and WO2013154798 which are hereby incorporated by reference.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

Oligomeric compounds, such as antisense oligonucleotides, such as the compounds referred to herein, including region A, and in some optional embodiments, region B, may contain one or more nucleosides wherein the sugar group has been modified. Such sugar modified nucleosides (nucleoside analogues) may impart enhanced nuclease stability, increased binding affinity, or some other beneficial biological property to the antisense compounds. In some embodiments, nucleosides comprise a chemically modified ribofuranose ring moiety.

In some embodiments, the oligomer, or first region thereof, comprises at least one, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or 25 nucleoside analogues, such as sugar modified nucleoside analogues.

Bicyclic nucleoside analogues include nucleoside analogues which comprise a bridge (or biradical) linking the second and forth carbon of the ribose ring, (C4*-C2* bridge or biradical). The presence of the biradical between the $2^{nd}$ and $4^{th}$ carbon locks the ribose into a 3' endo-(north) confirmation, and as such bicyclic nucleoside analogues with a C2*-C4* biradical are often referred to as Locked nucleic acid (LNA). In some embodiments the nucleoside analogues are (optionally independently selected from the group consisting of bicyclic nucleoside analogues (such as LNA), and/or 2' substituted nucleoside analogues, such as (optionally independently) selected from the group consisting of 2'-O-alkyl-RNA units, 2'-OMe-RNA units, 2'-amino-DNA units, 2'-AP, 2'-FANA, 2'-(3-hydroxyl)propyl, and 2'-fluoro-DNA units, and/or other (optionally) sugar modified nucleoside analogues such as morpholino, peptide nucleic acid (PNA), CeNA, unlinked nucleic acid (UNA), hexitol nucleoic acid (HNA), bicyclo-HNA (see e.g. WO2009/100320), In some embodiments, the nucleoside analogues increase the affinity of the first region for its target nucleic acid (or a complementary DNA or RNA sequence).

In some embodiments, the oligomer comprises at least one bicyclic nucleotide analogue, such as LNA. In some embodiments, the first region comprises of at least one bicyclic nucleoside analogues (e.g. LNA) and/or 2'substituted nucleoside analogues. In some embodiments, the nucleoside analogues present in the oligomer all comprise the same sugar modification. In some embodiments, at least one nucleoside analogue present in the first region is a bicyclic nucleoside analogue, such as at least 2, at least 3, at least 4, at least 5, at least 6, at least 7, at least 8, at least 9, at least 10, at least 11, at least 12, at least 13, at least 14, at least 15, at least 16, for example all nucleoside analogues (except the DNA and or RNA nucleosides of region B) are sugar modified nucleoside analogues, such as such as bicyclic nucleoside analogues, such as LNA, e.g. beta-D-X-LNA or alpha-L-X-LNA (wherein X is oxy, amino or thio), or other LNAs disclosed herein including, but not limited to, (R/S) cET, cMOE or 5'-Me-LNA.

Examples of chemically modified ribofuranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or $C(R_1)(R_2)$ (R=H, $C_1$-$C_2$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-$OCH_3$, and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $O(CH_2)_2SCH_3$, $O(CH_2)2$-O—N(Rm)(Rn), and O—$CH_2$—C(=O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In some embodiments, compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-($CH_2$)—O-2' (LNA); 4'-($CH_2$)—S-2'; 4'-($CH_2$)$_2$—O-2' (ENA); 4'-CH($CH_3$)—O-2' and 4'-CH($CH_2OCH_3$)—O-2*, and analogs thereof (see, U.S. Pat. No. 7,399,845, issued on Jul. 15, 2008); 4'-C($CH_3$)($CH_3$)—O-2', and analogs thereof (see, published PCT International Application WO2009/006478, published Jan. 8, 2009); 4'-$CH_2$—N($OCH_3$)-2', and analogs thereof (see, published PCT International Application WO2008/150729, published Dec. 11, 2008); 4'-$CH_2$—O—N($CH_3$)-2' (see, published U.S. Patent Application US2004/0171570, published Sep. 2, 2004); 4'-$CH_2$—N(R)—O-2', wherein R is H, $C_1$-$C_{10}$ alkyl, or a protecting group (see, U.S. Pat. No. 7,427,672, issued on Sep. 23, 2008); 4'-$CH_2$—C(H)($CH_3$)-2' (see, Chattopadhyaya, et al, J. Org. Chem., 2009, 74, 118-134); and 4'-$CH_2$—C(=$CH_2$)-2', and analogs thereof (see, published PCT International Application WO 2008/154401, published on Dec. 8, 2008). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc, 129(26) 8362-8379 (Jul. 4, 2007); Elayadi et al., Curr. Opinion Invens. Drugs, 2001, 2, 558-561; Braasch et al., Chem. Biol, 2001, 8, 1-7; Oram et al, Curr. Opinion Mol. Ther., 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent application Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example a-L-ribofuranose and beta-D-ribofuranose (see PCT international application PCT DK98/00393, published on Mar. 25, 1999 as WO 99/14226).

In some embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[$CiR_aXR_b$)]—, —C($R_a$)=C($R_b$)—, —C($R_a$)=N—, —C(=$NR_a$)—, —C(=O)—, —C(=S)—, —O—, —Si($R_a$)$_2$—, —S(=O)$_x$—, and —N(Ra)—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_6$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, C1-$C_{12}$ aminoalkyl, substituted $C_1$-$C_{12}$ aminoalkyl, or a protecting group.

In some embodiments, the bridge of a bicyclic sugar moiety is, —[C($R_a$)($R_b$)]$_n$—, —[C($R_a$)($R_b$)]$_n$—O—, —C($R_aR_b$)—N(R)—O— or, —C($R_aR_b$)—O—N(R)—. In some embodiments, the bridge is 4'-$CH_2$-2', 4'-($CH_2$)$_2$-2', 4'-($CH_2$)$_3$-2', 4'-$CH_2$—O-2', 4*-($CH_2$)2-O-2', 4'-$CH_2$—O—N(R)-2', and 4'-$CH_2$—N(R)—O-2'-, wherein each R is, independently, H, a protecting group, or $C_1$-$C_{12}$ alkyl.

In some embodiments, bicyclic nucleosides are further defined by isomeric configuration. For example, a nucleoside comprising a 4'-2' methylene-oxy bridge, may be in the a-L configuration or in the beta-D configuration. Previously, a-L-methyleneoxy (4'-$CH_2$—O-2') BNA's have been incorporated into antisense oligonucleotides that showed antisense activity (Frieden et al, Nucleic Acids Research, 2003, 21, 6365-6372).

In some embodiments, bicyclic nucleosides include, but are not limited to, (A) a-L-Methyleneoxy (4'-$CH_2$—O-2') BNA, (B) beta-D-Methyleneoxy (4'-$CH_2$—O-2') BNA, (C) Ethyleneoxy (4'-($CH_2$)$_2$—O-2') BNA, (D) Aminooxy (4'-$CH_2$—O—N(R)-2') BNA, (E) Oxyamino (4'-$CH_2$—N(R)—O-2') BNA, (F), Methyl(methyleneoxy) (4'-CH($CH_3$)—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, and (J) propylene carbocyclic (4'-($CH_2$)$_3$-2') BNA as depicted below.

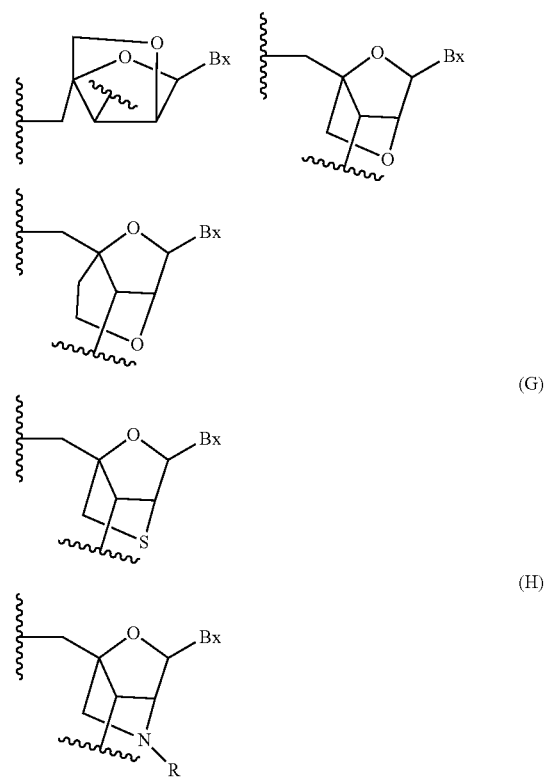

-continued

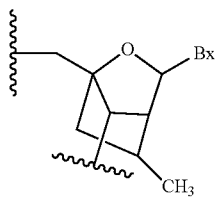
(I)

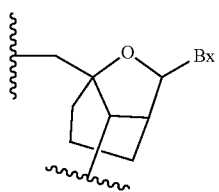
(J)

wherein Bx is the base moiety and R is, independently, H, a protecting group or $C_1$-$C_2$ alkyl. In certain embodiments, bicyclic nucleoside having Formula I:

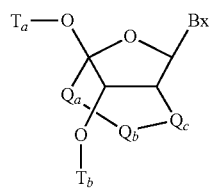
I wherein:
Bx is a heterocyclic base moiety;
-$Q_a$-$Q_b$-$Q_c$- is —$CH_2$—N(Rc)-$CH_2$—, —C(=O)—N($R_c$)—$CH_2$—, —$CH_2$—O—N(Rc)-, —$CH_2$—N(Rc)-O—, or —N(Rc)-O—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In some embodiments, bicyclic nucleoside having Formula II:

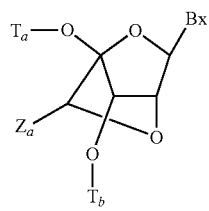
II wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium; $Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In some embodiments, each of the substituted groups is, independently, mono or poly substituted with substituent groups independently selected from halogen, oxo, hydroxyl, $OJ_c$, $NJ_d$, $SJ_c$, $N_3$, OC(=X)$J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In some embodiments, bicyclic nucleoside having Formula III:

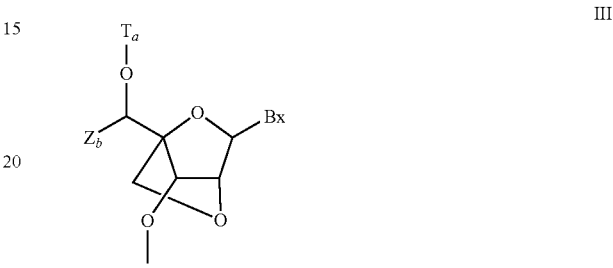
III wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$R_d$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In some embodiments, bicyclic nucleoside having Formula IV:

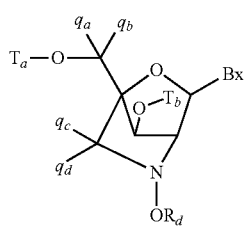
IV wherein:
Bx is a heterocyclic base moiety;
$T_a$ and $T_b$ are each, independently H, a hydroxyl protecting group, a conjugate group, a reactive phosphorus group, a phosphorus moiety, or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl; each $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted Q-$C_6$ alkoxyl, acyl, substituted acyl, $C_1$-$C_6$ aminoalkyl, or substituted $C_1$-$C_6$ aminoalkyl;

In some embodiments, bicyclic nucleoside having Formula V:

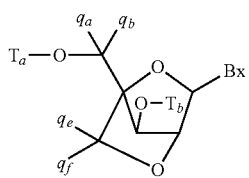

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium; $q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; or $q_e$ and $q_f$ together are =C($q_g$)($q_h$); $q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., Tetrahedron, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared {see, e.g., Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., J. Org. Chem., 1998, 63, 10035-10039). In addition, 2'-amino- and 2'-methylamino-BNA's have been prepared and the thermal stability of their duplexes with complementary RNA and DNA strands has been previously reported.

In some embodiments, the bicyclic nucleoside has Formula VI:

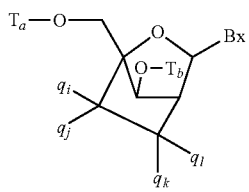

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium; each qj, qj, $q_k$ and ql is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_2$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or (H)C(=S)$NJ_jJ_k$; and qi and $q_j$ or ql and $q_k$ together are =C($q_g$)($q_h$), wherein $q_g$ and $q_h$ are each, independently, H, halogen, $C_1$-$C_{12}$ alkyl, or substituted $C_1$-$C_6$ alkyl.

One carbocyclic bicyclic nucleoside having a 4'-($CH_2$)$_3$-2' bridge and the alkenyl analog, bridge 4'-CH=CH—$CH_2$-2', have been described (see, e.g., Freier et al, Nucleic Acids Research, 1997, 25(22), 4429-4443 and Albaek et al, J. Org. Chem., 2006, 71, 7731-7740). The synthesis and preparation of carbocyclic bicyclic nucleosides along with their oligomerization and biochemical studies have also been described (see, e.g., Srivastava et al, J. Am. Chem. Soc. 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In some embodiments, the sugar moiety, or sugar moiety analogue, of a nucleoside may be modified or substituted at any position.

As used herein, "2'-modified sugar" means a furanosyl sugar modified at the 2' position. In some embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In some embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$$ONH_2$, $OCH_2$C(=O)N(H)$CH_3$, and O($CH2$)$_n$ON[($CH_2$)$_n$$CH_3$]2, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an R; a cleaving group; a reporter group; an intercalator; a group for improving pharmacokinetic properties; and a group for improving the pharmacodynamic properties of an antisense compound, and other substituents having similar properties. In some embodiments, modified nucleosides comprise a 2'-MOE side chain {see, e.g., Baker et al., J. Biol. Chem., 1997, 272, 1 1944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2-MOE substituent also have been shown to be antisense inhibitors of gene expression with promising features for in vivo use {see, e.g., Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified ?THP nucleosides include, but are not limited to, what is referred to in the art as hexitol nucleic acid (HNA), anitol nucleic acid (ANA), manitol nucleic acid (MNA) {see Leumann, C J. Bioorg. and Med. Chem. (2002) 10:841-854), fluoro HNA (F-HNA), or those compounds having Formula X:

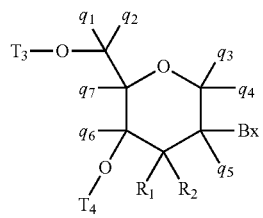

Formula X wherein independently for each of said at least one tetrahydropyran nucleoside analog of Formula X:
Bx is a heterocyclic base moiety;
$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and T4 is H, a hydroxyl protecting group, a linked conjugate group, or a 5' or 3'-terminal group; $q_1$ $q_2$ $q_3$ $q_4$ $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, NJ, $J_2$, SJ, $N_3$, OC(=X)$J_1$, OC(=X)NJ$_1$J$_2$, NJ$_3$C(=X)NJ$_1$J$_2$, and CN, wherein X is O, S, or NJ$_1$ and each $J_1$, $J_2$, and $J_3$ is, independently, H or $C_1$-$C_6$ alkyl.

In some embodiments, the modified THP nucleosides of Formula X are provided wherein $q_m$, $q_n$, $q_p$, $q_r$, $q_s$, $q_t$, and $q_n$ are each H. In some embodiments, at least one of $q_m$, $q_n$, $q_p$, $q_r$, $q_s$, $q_t$ and $q_n$ is other than H. In some embodiments, at least one of $q_m$, $q_n$, $q_p$, $q_r$, $q_s$, $g_r$ and $q_n$ is methyl. In some embodiments, THP nucleosides of Formula X are provided wherein one of $R_1$ and $R_2$ is F. In some embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to nucleosides with non-bridging 2'substituents, such as allyl, amino, azido, thio, O-allyl, O—$C_1$-$C_{10}$ alkyl, —OCF$_3$, O—(CH$_2$)$_2$—O—CH$_3$, 2'-O (CH$_2$)$_2$SCH$_3$, O—(CH$_2$)$_2$—O—N(R$_m$)(R$_n$), or O—CH$_2$—C (=O)—N(R$_m$)(R$_n$), where each R$_m$ and R$_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "oligonucleotide" refers to a compound comprising a plurality of linked nucleosides.

In some embodiments, one or more of the plurality of nucleosides is modified. In some embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds {see, e.g., review article: Leumann, J. C, Bioorganic and Medicinal Chemistry, 2002, 10, 841-854). Such ring systems can undergo various additional substitutions to enhance activity. Methods for the preparations of modified sugars are well known to those skilled in the art. In nucleotides having modified sugar moieties, the nucleobase moieties (natural, modified, or a combination thereof) are maintained for hybridization with an appropriate nucleic acid target.

In some embodiments, antisense compounds comprise one or more nucleotides having modified sugar moieties. In some embodiments, the modified sugar moiety is 2'-MOE. In some embodiments, the 2'-MOE modified nucleotides are arranged in a gapmer motif. In some embodiments, the modified sugar moiety is a cEt. In some embodiments, the cEt modified nucleotides are arranged throughout the wings of a gapmer motif.

In some embodiments, in the BNA (LNA), $R^{4*}$ and $R^{2*}$ together designate the biradical —O—CH(CH$_2$OCH$_3$)- (2'O-methoxyethyl bicyclic nucleic acid—Seth at al., 2010, J. Org. Chem)—in either the R- or S-configuration.

In some embodiments, in the BNA (LNA), $R^{4*}$ and $R^{2*}$ together designate the biradical —O—CH(CH$_2$CH$_3$)-(2'O-ethyl bicyclic nucleic acid—Seth at al., 2010, J. Org. Chem).—in either the R- or S-configuration.

In some embodiments, in the BNA (LNA), $R^{4*}$ and $R^{2*}$ together designate the biradical —O—CH(CH$_3$)—. in either the R- or S-configuration. In some embodiments, $R^{4*}$ and $R^{2*}$ together designate the biradical —O—CH$_2$—O—CH$_2$— —(Seth at al., 2010, J. Org. Chem).

In some embodiments, in the BNA (LNA), $R^{4*}$ and $R^{2*}$ together designate the biradical —O—NR—CH$_3$— —(Seth at al., 2010, J. Org. Chem).

In some embodiments, the LNA units have a structure selected from the following group:

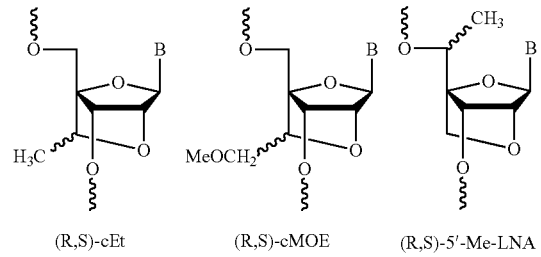

(R,S)-cEt    (R,S)-cMOE    (R,S)-5'-Me-LNA

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Incorporation of affinity-enhancing nucleotide analogues in the oligomer, such as BNA, (e.g.) LNA or 2'-substituted sugars, can allow the size of the specifically binding oligomer to be reduced, and may also reduce the upper limit to the size of the oligomer before non-specific or aberrant binding takes place.

In some embodiments, the oligomer comprises at least 1 nucleoside analogue. In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a BNA, such as locked nucleic acid (LNA); for example at least 3 or at least 4, or at least 5, or at least 6, or at least 7, or 8, of the nucleotide analogues may be BNA, such as LNA. In some embodiments all the nucleotides analogues may be BNA, such as LNA.

It will be recognized that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as BNA units or other nucleotide analogues, which raise the duplex stability/ $T_m$ of the oligomer/target duplex (i.e. affinity enhancing nucleotide analogues).

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the invention are independently selected from, for example: 2'-O-alkyl-RNA units, 2'-amino-DNA units, 2'-fluoro-DNA units, BNA units, e.g. LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, such as the first region, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the invention comprises at least one BNA, e.g. Locked Nucleic Acid (LNA) unit, such as 1, 2, 3, 4, 5, 6, 7, or 8 BNA/LNA units, such as from 3-7 or 4 to 8 BNA/LNA units, or 3, 4, 5, 6 or 7 BNA/LNA units. In some embodiments, all the nucleotide analogues are BNA, such as LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all BNA, such as LNA, cytosine units are 5'methyl-Cytosine. In some embodiments of the invention, the oligomer (such as the first and optionally second regions) may comprise both BNA and LNA and DNA units. In some embodiments, the combined total of LNA and DNA units is 10-25, such as 10-24, preferably 10-20, such as 10-18, such as 12-16. In some embodiments of the invention, the nucleotide sequence of the oligomer, of first region thereof, such as the contiguous nucleotide sequence consists of at least one BNA, e.g. LNA and the remaining nucleotide units are DNA units. In some embodiments the oligomer, or first region thereof, comprises only BNA, e.g. LNA, nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof. It will be recognized that the DNA or RNA nucleosides of region B may have a naturally occurring and/or non-naturally occurring nucleobase(s).

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine. In some embodiments the nucleobases may be independently selected from the group consisting of adenine, guanine, cytosine, thymidine, uracil, 5-methylcytosine. In some embodiments the nucleobases may be independently selected from the group consisting of adenine, guanine, cytosine, thymidine, and 5-methylcytosine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleoside analogue which comprises a C2*-C4* biradical (a bridge), and is known as "Locked Nucleic Acid". It may refer to an LNA monomer, or, when used in the context of an "LNA oligonucleotide", LNA refers to an oligonucleotide containing one or more such bicyclic nucleotide analogues. In some aspects bicyclic nucleoside analogues are LNA nucleotides, and these terms may therefore be used interchangeably, and is such embodiments, both are be characterized by the presence of a linker group (such as a bridge) between C2' and C4' of the ribose sugar ring.

In some embodiments the LNA used in the oligonucleotide compounds of the invention preferably has the structure of the general formula II:

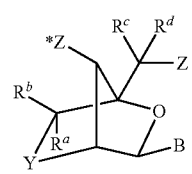

Formula II wherein Y is selected from the group consisting of —O—, —CH$_2$O—, —S—, —NH—, N(R$^e$) and/or —CH$_2$—; Z and Z* are independently selected among an internucleotide linkage, R$^H$, a terminal group or a protecting group; B constitutes a natural or non-natural nucleotide base moiety (nucleobase), and R$^H$ is selected from hydrogen and C$_{1-4}$-alkyl; R$^a$, R$^b$ R$^c$, R$^d$ and R$^e$ are, optionally independently, selected from the group consisting of hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$); and $R^H$ is selected from hydrogen and $C_{1-4}$-alkyl. In some embodiments $R^a$, $R^b$ $R^c$, $R^d$ and $R^e$ are, optionally independently, selected from the group consisting of hydrogen and $C_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

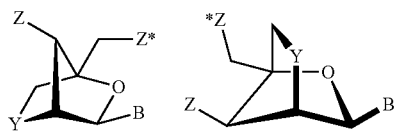

Specific exemplary LNA units are shown below:

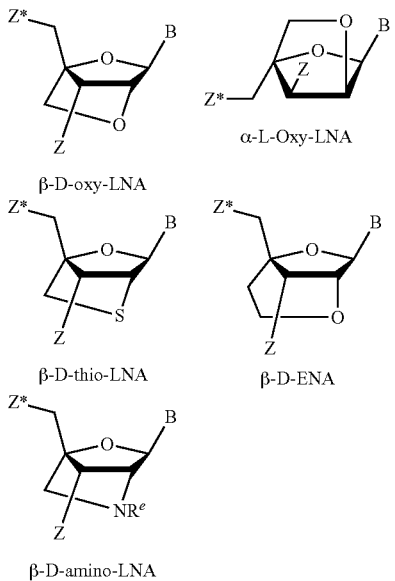

The term "thio-LNA" comprises a locked nucleotide in which Y in the general formula above is selected from S or —CH$_2$—S—. Thio-LNA can be in both beta-D and alpha-L-configuration.

The term "amino-LNA" comprises a locked nucleotide in which Y in the general formula above is selected from —N(H)—, N(R)—, CH$_2$—N(H)—, and —CH$_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH$_2$—O— (where the oxygen atom of —CH$_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

RNAse Recruitment

It is recognized that an oligomeric compound may function via non RNase mediated degradation of target mRNA, such as by steric hindrance of translation, or other methods, In some embodiments, the oligomers of the invention are capable of recruiting an endoribonuclease (RNase), such as RNase H.

It is preferable such oligomers, such as region A, or contiguous nucleotide sequence, comprises of a region of at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region Y' as referred to in the context of a gapmer as described herein. In some embodiments the size of the contiguous sequence which is capable of recruiting RNAse, such as region Y', may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or, more than 20% of the of the initial rate determined using DNA only oligonucleotide, having the same base sequence but containing only DNA monomers, with no 2' substitutions, with phosphorothioate linkage groups between all monomers in the oligonucleotide, using the methodology provided by Example 91-95 of EP 1 222 309.

In some embodiments, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target. The oligomer of the invention, such as the first region, may comprise a nucleotide sequence which comprises both nucleotides and nucleotide analogues, and may be e.g. in the form of a gapmer, a headmer or a mixmer.

A "headmer" is defined as an oligomer that comprises a region X' and a region Y' that is contiguous thereto, with the 5'-most monomer of region Y' linked to the 3'-most monomer of region X'. Region X' comprises a contiguous stretch of non-RNase recruiting nucleoside analogues and region Y' comprises a contiguous stretch (such as at least 7 contiguous monomers) of DNA monomers or nucleoside analogue monomers recognizable and cleavable by the RNase.

A "tailmer" is defined as an oligomer that comprises a region X' and a region Y' that is contiguous thereto, with the 5'-most monomer of region Y' linked to the 3'-most monomer of the region X'. Region X' comprises a contiguous stretch (such as at least 7 contiguous monomers) of DNA monomers or nucleoside analogue monomers recognizable and cleavable by the RNase, and region X' comprises a contiguous stretch of non-RNase recruiting nucleoside analogues.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNaseH) binding and cleavage. Since α-L-LNA (BNA) monomers recruit RNaseH activity to a certain extent, in some embodiments, gap regions (e.g., region Y' as referred to herein) of oligomers containing α-L-LNA monomers consist of fewer monomers recognizable and cleavable by the RNaseH, and more flexibility in the mixmer construction is introduced.

Gapmer Design

In some embodiments, the oligomer of the invention, such as the first region, comprises or is a gapmer. A gapmer oligomer is an oligomer which comprises a contiguous stretch of nucleotides which is capable of recruiting an RNAse, such as RNaseH, such as a region of at least 6 or 7 DNA nucleotides, referred to herein in as region Y' (Y'), wherein region Y' is flanked both 5' and 3' by regions of affinity enhancing nucleotide analogues, such as from 1-6 nucleotide analogues 5' and 3' to the contiguous stretch of nucleotides which is capable of recruiting RNAse—these regions are referred to as regions X' (X') and Z' (Z') respectively. Examples of gapmers are disclosed in WO2004/046160, WO2008/113832, and WO2007/146511.

In some embodiments, the monomers which are capable of recruiting RNAse are selected from the group consisting of DNA monomers, alpha-L-LNA monomers, C4' alkylayted DNA monomers (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), X'—Y'—Z', wherein; region X' (X') (5' region) consists or comprises of at least one nucleotide analogue, such as at least one BNA (e.g. LNA) unit, such as from 1-6 nucleotide analogues, such as BNA (e.g. LNA) units, and; region Y' (Y') consists or comprises of at least five consecutive nucleotides which are capable of recruiting RNAse (when formed in a duplex with a complementary RNA molecule, such as the mRNA target), such as DNA nucleotides, and; region Z' (Z') (3'region) consists or comprises of at least one nucleotide analogue, such as at least one BNA (e.g LNA unit), such as from 1-6 nucleotide analogues, such as BNA (e.g. LNA) units.

In some embodiments, region X' consists of 1, 2, 3, 4, 5 or 6 nucleotide analogues, such as BNA (e.g. LNA) units, such as from 2-5 nucleotide analogues, such as 2-5 LNA units, such as 3 or 4 nucleotide analogues, such as 3 or 4 LNA units; and/or region Z' consists of 1, 2, 3, 4, 5 or 6 nucleotide analogues, such as BNA (e.g. LNA) units, such as from 2-5 nucleotide analogues, such as 2-5 BNA (e.g. LNA) units), such as 3 or 4 nucleotide analogues, such as 3 or 4 BNA (e.g. LNA) units.

In some embodiments Y' consists or comprises of 5, 6, 7, 8, 9, 10, 11 or 12 consecutive nucleotides which are capable of recruiting RNAse, or from 6-10, or from 7-9, such as 8 consecutive nucleotides which are capable of recruiting RNAse. In some embodiments region Y' consists or comprises at least one DNA nucleotide unit, such as 1-12 DNA units, preferably from 4-12 DNA units, more preferably from 6-10 DNA units, such as from 7-10 DNA units, most preferably 8, 9 or 10 DNA units.

In some embodiments region X' consist of 3 or 4 nucleotide analogues, such as BNA (e.g. LNA), region X' consists of 7, 8, 9 or 10 DNA units, and region Z' consists of 3 or 4 nucleotide analogues, such as BNA (e.g. LNA). Such designs include (X'—Y'—Z') 3-10-3, 3-10-4, 4-10-3, 3-9-3, 3-9-4, 4-9-3, 3-8-3, 3-8-4, 4-8-3, 3-7-3, 3-7-4, 4-7-3.

Further gapmer designs are disclosed in WO2004/046160, which is hereby incorporated by reference. WO2008/113832, which claims priority from U.S. provisional application 60/977,409 hereby incorporated by reference, refers to 'shortmer' gapmer oligomers. In some embodiments, oligomers presented here may be such shortmer gapmers.

In some embodiments the oligomer, e.g. region X', is consisting of a contiguous nucleotide sequence of a total of 10, 11, 12, 13 or 14 nucleotide units, wherein the contiguous nucleotide sequence comprises or is of formula (5'-3'), X'—Y'—Z' wherein; X' consists of 1, 2 or 3 nucleotide analogue units, such as BNA (e.g. LNA) units; Y' consists of 7, 8 or 9 contiguous nucleotide units which are capable of recruiting RNAse when formed in a duplex with a complementary RNA molecule (such as a mRNA target); and Z' consists of 1, 2 or 3 nucleotide analogue units, such as BNA (e.g. LNA) units.

In some embodiments X' consists of 1 BNA (e.g. LNA) unit. In some embodiments X' consists of 2 BNA (e.g. LNA) units. In some embodiments X' consists of 3 BNA (e.g. LNA) units. In some embodiments Z' consists of 1 BNA (e.g. LNA) units. In some embodiments Z' consists of 2 BNA (e.g. LNA) units. In some embodiments Z' consists of 3 BNA (e.g. LNA) units. In some embodiments Y' consists of 7 nucleotide units. In some embodiments Y' consists of 8 nucleotide units. In some embodiments Y' consists of 9 nucleotide units. In certain embodiments, region Y' consists of 10 nucleoside monomers. In certain embodiments, region Y' consists or comprises 1-10 DNA monomers. In some embodiments Y' comprises of from 1-9 DNA units, such as 2, 3, 4, 5, 6, 7, 8 or 9 DNA units. In some embodiments Y' consists of DNA units. In some embodiments Y' comprises of at least one BNA unit which is in the alpha-L configuration, such as 2, 3, 4, 5, 6, 7, 8 or 9 LNA units in the alpha-L-configuration. In some embodiments Y' comprises of at least one alpha-L-oxy BNA/LNA unit or wherein all the LNA units in the alpha-L-configuration are alpha-L-oxy LNA units. In some embodiments the number of nucleotides present in X'—Y'—Z' are selected from the group consisting of (nucleotide analogue units—region Y'—nucleotide analogue units): 1-8-1, 1-8-2, 2-8-1, 2-8-2, 3-8-3, 2-8-3, 3-8-2, 4-8-1, 4-8-2, 1-8-4, 2-8-4, or, 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in X'—Y'—Z' are selected from the group consisting of: 2-7-1, 1-7-2, 2-7-2, 3-7-3, 2-7-3, 3-7-2, 3-7-4, and 4-7-3. In certain embodiments, each of regions X' and Y' consists of three BNA (e.g. LNA) monomers, and region Y' consists of 8 or 9 or 10 nucleoside monomers, preferably DNA monomers. In some embodiments both X' and Z' consists of two BNA (e.g. LNA) units each, and Y' consists of 8 or 9 nucleotide units, preferably DNA units. In various embodiments, other gapmer designs include those where regions X' and/or Z' consists of 3, 4, 5 or 6 nucleoside analogues, such as monomers containing a 2'-O-methoxyethyl-ribose sugar (2'-MOE) or monomers containing a 2'-fluoro-deoxyribose sugar, and region Y' consists of 8, 9, 10, 11 or 12 nucleosides, such as DNA monomers, where regions X'—Y'—Z' have 3-9-3, 3-10-3, 5-10-5 or 4-12-4 monomers. Further gapmer designs are disclosed in WO 2007/146511A2, hereby incorporated by reference.

Splice Switching Oligomers

In some embodiments, the antisense oligonucleotide is a splice switching oligomer—i.e. an oligomer which targets the pre-mRNA causing an alternative splicing of the pre-mRNA.

Targets for the splice switching oligomer may include TNF receptor, for example the SSO may be one or more of the TNFR SSOs disclosed in WO2007/058894, WO08051306 A1 and PCT/EP2007/061211, hereby incorporated by reference.

Splice switching oligomers are typically (essentially) not capable of recruiting RNaseH and as such gapmer, tailmer or headmer designs are generally not desirable. However, mixmer and totalmers designs are suitable designs for SSOs.

Spice switching oligomers have also been used to target dystrophin deficiency in Duchenne muscular dystrophy.

Mixmers

Most antisense oligonucleotides are compounds which are designed to recruit RNase enzymes (such as RNaseH) to degrade their intended target. Such compounds include DNA phosphorothioate oligonucleotides and gapmer, headmers and tailmers. These compounds typically comprise a region of at least 5 or 6 DNA nucleotides, and in the case of gapmers are flanked on either side by affinity enhancing nucleotide analogues.

The oligomers of the present invention may operate via an RNase (such as RNaseH) independent mechanism. Examples of oligomers which operate via a non-RNaseH (or non-RNase) mechanism are mixmers and totalmers.

The term 'mixmer' refers to oligomers which comprise both naturally and non-naturally occurring nucleotides, where, as opposed to gapmers, tailmers, and headmers there is no contiguous sequence of more than 5, and in some embodiments no more than 4 consecutive, such as no more than three consecutive, naturally occurring nucleotides, such as DNA units. In some embodiments, the mixmer does not comprise more than 5 consecutive nucleoside analogues, such as BNA (LNA), and in some embodiments no more than 4 consecutive, such as no more than three consecutive, consecutive nucleoside analogues, such as BNA (LNA). In such mixmers the remaining nucleosides may, for example by DNA nucleosides, and/or in non-bicyclic nucleoside analogues, such as those referred to herein, for example, 2' substituted nucleoside analogues, such as 2'-O-MOE and or 2'fluoro.

The oligomer according to the invention maybe mixmers—indeed various mixmer designs are highly effective as oligomer or first region thereof, particularly when targeting microRNA (antimiRs), microRNA binding sites on mRNAs (Blockmirs) or as splice switching oligomers (SSOs). See for example WO2007/112754 (LNA-AntimiRs™), WO2008/131807 (LNA splice switching oligos), In some embodiments, the oligomer or mixmer may comprise of BNA and 2' substituted nucleoside analogues, optionally with DNA nucleosides—see for example see WO07027894 and WO2007/112754 which are hereby incorporated by reference. Specific examples include oligomers or first regions which comprise LNA, 2'-O-MOE and DNA, LNA, 2'fluoro and 2'-O-MOE, 2'-O-MOE and 2'fluoro, 2'-O-MOE and 2'fluoro and LNA, or LNA and 2'-O-MOE and LNA and DNA.

In some embodiments, the oligomer or mixmer comprises or consists of a contiguous nucleotide sequence of repeating pattern of nucleotide analogue and naturally occurring nucleotides, or one type of nucleotide analogue and a second type of nucleotide analogues. The repeating pattern, may, for instance be every second or every third nucleotide is a nucleotide analogue, such as BNA (LNA), and the remaining nucleotides are naturally occurring nucleotides, such as DNA, or are a 2'substituted nucleotide analogue such as 2'MOE of 2'fluoro analogues as referred to herein, or, in some embodiments selected form the groups of nucleotide analogues referred to herein. It is recognized that the repeating pattern of nucleotide analogues, such as LNA units, may be combined with nucleotide analogues at fixed positions—e.g. at the 5' or 3' termini.

In some embodiments the first nucleotide of the oligomer or mixmer, counting from the 3' end, is a nucleotide analogue, such as an LNA nucleotide.

In some embodiments, which maybe the same or different, the second nucleotide of oligomer or mixmer, counting from the 3' end, is a nucleotide analogue, such as an LNA nucleotide.

In some embodiments, which maybe the same or different, the seventh and/or eighth nucleotide of oligomer or mixmer, counting from the 3' end, are nucleotide analogues, such as LNA nucleotides.

In some embodiments, which maybe the same or different, the ninth and/or the tenth nucleotides of the first and/or second oligomer, counting from the 3' end, are nucleotide analogues, such as LNA nucleotides.

In some embodiments, which maybe the same or different, the 5' terminal of oligomer or mixmer is a nucleotide analogue, such as an LNA nucleotide.

The above design features may, in some embodiments be incorporated into the mixmer design, such as antimiR mixmers.

In some embodiments, the oligomer or mixmer does not comprise a region of more than 4 consecutive DNA nucleotide units or 3 consecutive DNA nucleotide units. In some embodiments, the mixmer does not comprise a region of more than 2 consecutive DNA nucleotide units.

In some embodiments, the oligomer or mixmer comprises at least a region consisting of at least two consecutive nucleotide analogue units, such as at least two consecutive LNA units.

In some embodiments, the oligomer or mixmer comprises at least a region consisting of at least three consecutive nucleotide analogue units, such as at least three consecutive LNA units.

In some embodiments, the oligomer or mixmer of the invention does not comprise a region of more than 7 consecutive nucleotide analogue units, such as LNA units. In some embodiments, the oligomer or mixmer of the invention does not comprise a region of more than 6 consecutive nucleotide analogue units, such as LNA units. In some embodiments, the oligomer or mixmer of the invention does not comprise a region of more than 5 consecutive nucleotide analogue units, such as LNA units. In some embodiments, the oligomer or mixmer of the invention does not comprise a region of more than 4 consecutive nucleotide analogue units, such as LNA units. In some embodiments, the oligomer or mixmer of the invention does not comprise a region of more than 3 consecutive nucleotide analogue units, such as LNA units. In some embodiments, the oligomer or mixmer of the invention does not comprise a region of more than 2 consecutive nucleotide analogue units, such as LNA units. A mixmer is a oligomer which may comprise one or more short regions of DNA of no more than 4 consecutive DNA nucleotides, and typically comprises alternating regions of a nucleotide analogue (such as LNA units) and DNA nucleotides, optionally regions of other nucleotide analogues (e.g. non-LNA nucleotide analogues). Totalmers comprise of no DNA or RNA nucleotides (although may comprise analogues or derivatives of DNA and RNA).

In some embodiments, the oligomer (e.g. region A) of the invention may, in some embodiments, comprise of no more than 4 consecutive DNA nucleotides, or no more than 3 consecutive DNA nucleotides.

The following embodiments may apply to mixmers or totalmer oligomers (e.g. as region A): The oligomer (e.g. region A) of the invention may, in some embodiments, comprise of at least two alternating regions of LNA and non-LNA nucleotides (such as DNA or 2' substituted nucleotide analogues).

The oligomer of the invention may, in some embodiments, comprise a contiguous sequence of formula: 5' ([LNA nucleotides]$_{1-5}$ and [non-LNA nucleotides]$_{1-4}$)$_{2-12}$. 3'.

In some embodiments, the 5' nucleotide of the contiguous nucleotide sequence (or the oligomer) is an LNA nucleotide.

In some embodiments, the 3' nucleotide of the contiguous nucleotide sequence is a nucleotide analogue, such as LNA, or the 2, 3, 4, 5 3' nucleotides are nucleotide analogues, such as LNA nucleotides, or other nucleotide analogues which confer enhanced serum stability to the oligomer.

In some embodiments, the contiguous nucleotide sequence of the oligomer has a formula 5' ([LNA nucleotides]$_{1-5}$-[non-LNA nucleotides]$_{1-4}$)$_{2-12}$-[LNA nucleotides]$_{1-5}$ 3'.

In some embodiments, the contiguous nucleotide sequence of the oligomer has 2, 3 or 4 contiguous regions of LNA and non-LNA nucleotides—e.g. comprises formula 5' ([LNA nucleotides]$_{1-5}$ and [non-LNA nucleotides]$_{1-4}$)$_{2-3}$, optionally with a further 3' LNA region [LNA nucleotides]$_{1-5}$.

In some embodiments, the contiguous nucleotide sequence of the oligomer comprises 5' ([LNA nucleotides]$_{1-3}$ and [non-LNA nucleotides]$_{1-3}$)$_{2-5}$, optionally with a further 3' LNA region [LNA nucleotides]$_{1-3}$.

In some embodiments, the contiguous nucleotide sequence of the oligomer comprises 5' ([LNA nucleotides]$_{1-3}$ and [non-LNA nucleotides]$_{1-3}$)$_{3}$, optionally with a further 3' LNA region [LNA nucleotides]$_{1-3}$.

In some embodiments the non-LNA nucleotides are all DNA nucleotides.

In some embodiments, the non-LNA nucleotides are independently or dependently selected from the group consisting of DNA units, RNA units, 2'-O-alkyl-RNA units, 2'-OMe-RNA units, 2'-amino-DNA units, and 2'-fluoro-DNA units.

In some embodiments the non-LNA nucleotides are (optionally independently selected from the group consisting of 2' substituted nucleoside analogues, such as (optionally independently) selected from the group consisting of 2'-O-alkyl-RNA units, 2'-OMe-RNA units, 2'-amino-DNA units, 2'-AP, 2'-FANA, 2'-(3-hydroxyl)propyl, and 2'-fluoro-DNA units, and/or other (optionally) sugar modified nucleoside analogues such as morpholino, peptide nucleic acid (PNA), CeNA, unlinked nucleic acid (UNA), hexitol nucleic acid (HNA). bicyclo-HNA (see e.g. WO2009/100320), In some embodiments, the nucleoside analogues increase the affinity of the first region for its target nucleic acid (or a complementary DNA or RNA sequence). Various nucleoside analogues are disclosed in Freier & Altmann; *Nucl. Acid Res.*, 1997, 25, 4429-4443 and Uhlmann; *Curr. Opinion in Drug Development*, 2000, 3(2), 293-213, hereby incorporated by reference.

In some embodiments, the non-LNA nucleotides are DNA nucleotides. In some embodiments, the oligomer or contiguous nucleotide sequence comprises of LNA nucleotides and optionally other nucleotide analogues (such as the nucleotide analogues listed under non-LNA nucleotides) which may be affinity enhancing nucleotide analogues and/or nucleotide analogues which enhance serum stability.

In some embodiments, the oligomer or contiguous nucleotide sequence thereof consists of a contiguous nucleotide sequence of said nucleotide analogues.

In some embodiments, the oligomer or contiguous nucleotide sequence thereof consists of a contiguous nucleotide sequence of LNA nucleotides.

In some embodiments, the oligomer or contiguous nucleotide sequence is 8-12, such as 8-10, or 10-20, such as 12-18 or 14-16 nts in length.

In some embodiments, the oligomer or contiguous nucleotide sequence is capable of forming a duplex with a complementary single stranded RNA nucleic acid molecule with phosphodiester internucleoside linkages, wherein the duplex has a $T_m$ of at least about 60° C., such as at least 65° C.

Example of a $T_m$ Assay: The oligonucleotide: Oligonucleotide and RNA target (PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Totalmers

A totalmer is a single stranded oligomer which only comprises non-naturally occurring nucleosides, such as sugar-modified nucleoside analogues.

The first region according to the invention maybe totalmers—indeed various totalmer designs are highly effective as oligomers or first region thereof, e.g. particularly when targeting microRNA (antimiRs) or as splice switching oligomers (SSOs). In some embodiments, the totalmer comprises or consists of at least one XYX or YXY sequence motif, such as a repeated sequence XYX or YXY, wherein X is LNA and Y is an alternative (i.e. non LNA) nucleotide analogue, such as a 2'-O-MOE RNA unit and 2'-fluoro DNA unit. The above sequence motif may, in some embodiments, be XXY, XYX, YXY or YYX for example.

In some embodiments, the totalmer may comprise or consist of a contiguous nucleotide sequence of between 7 and 16 nucleotides, such as 9, 10, 11, 12, 13, 14, or 15 nucleotides, such as between 7 and 12 nucleotides.

In some embodiments, the contiguous nucleotide sequence of the totalmer comprises of at least 30%, such as at least 40%, such as at least 50%, such as at least 60%, such as at least 70%, such as at least 80%, such as at least 90%, such as 95%, such as 100% BNA (LNA) units. The remaining units may be selected from the non-LNA nucleotide analogues referred to herein in, such those selected from the group consisting of 2'-O_alkyl-RNA unit, 2'-OMe-RNA unit, 2'-amino-DNA unit, 2'-fluoro-DNA unit, LNA unit, PNA unit, HNA unit, INA unit, and a 2'MOE RNA unit, or the group 2'-OMe RNA unit and 2'-fluoro DNA unit.

In some embodiments the totalmer consist or comprises of a contiguous nucleotide sequence which consists only of LNA units. In some embodiments, the totalmer, such as the LNA totalmer, is between 7-12 nucleoside units in length. In some embodiments, the totalmer (as the oligomer or first region thereof) may be targeted against a microRNA (i.e. be antimiRs)—as referred to WO2009/043353, which are hereby incorporated by reference. In some embodiments, the oligomer or contiguous nucleotide sequence comprises of LNA nucleotides and optionally other nucleotide analogues which may be affinity enhancing nucleotide analogues and/or nucleotide analogues which enhance serum stability.

In some embodiments, the oligomer or contiguous nucleotide sequence thereof consists of a contiguous nucleotide sequence of said nucleotide analogues.

In some embodiments, the oligomer or contiguous nucleotide sequence thereof consists of a contiguous nucleotide sequence of LNA nucleotides.

MicroRNA Modulation Via the Oligomer or First Region Thereof.

In some embodiments, the oligomer or first region thereof is an antimiR, which comprises or consists of a contiguous nucleotide sequence which is corresponds to or is fully complementary to the entire mature microRNA. The use of the present invention in controlling the in vivo activity of microRNA is considered of primary importance due to the fact that microRNAs typically regulate numerous mRNAs in the subject. The ability to inactivate therapeutic antimiRs is therefore very desirable.

Numerous microRNAs are related to a number of diseases. For example: non-limiting examples of therapeutic indications which may be treated by the pharmaceutical compositions of the invention:

| microRNA | Possible medical indications |
| --- | --- |
| miR-1 | Cardiac arythmia |
| miR-21 | Glioblastoma, breast cancer, hepatocellular carcinoma, colorectal cancer, sensitization of gliomas to cytotoxic drugs, cardiac hypertrophy |
| miR-21, miR-200b and miR-141 | Response to chemotherapy and regulation of cholangiocarcinoma growth |
| miR-122 | hypercholesterolemia, hepatitis C infection, hemochromatosis |

-continued

| microRNA | Possible medical indications |
| --- | --- |
| miR-19b | lymphoma and other tumour types |
| miR-26a | Osteoblast differentiation of human stem cells |
| miR-155 | lymphoma, pancreatic tumor development, breast and lung cancer |
| miR-203 | Psoriasis |
| miR-375 | diabetes, metabolic disorders, glucose-induced insulin secretion from pancreatic endocrine cells |
| miR-181 | myoblast differentiation, auto immune disorders |
| miR-10b | Breast cancer cell invasion and metastasis |
| miR-125b-1 | Breast, lung, ovarian and cervical cancer |
| miR-221 and 222 | Prostate carcinoma, human thyroid papillary car, human hepatocellular carcinoma |
| miRNA-372 and -373 | testicular germ cell tumors. |
| miR-142 | B-cell leukemia |
| miR-17 - 19b cluster | B-cell lymphomas, lung cancer, hepatocellular carcinoma |

Tumor suppressor gene tropomysin 1 (TPM1) mRNA has been indicated as a target of miR-21. Myotrophin (mtpn) mRNA has been indicated as a target of miR 375.

The oligomer or first region thereof may therefore be an antimir which targets (i.e. comprises or consists of a contiguous nucleotide sequence which is fully complementary to (a corresponding region of) one of the microRNAs listed above or comprises of no more than a single mismatch thereto.

Hence, some aspects of the invention relates to the treatment of a disease associated with the expression of microRNAs selected from the group consisting of infectious diseases such as viral diseases such as hepatitis C virus and HIV, fragile X mental retardation, inflammatory diseases, cancer, such as chronic lymphocytic leukemia, breast cancer, lung cancer and colon cancer.

MicroRNAs (miRNAs) are an abundant class of short endogenous RNAs that act as post-transcriptional regulators of gene expression by base-pairing with their target mRNAs. The mature miRNAs are processed sequentially from longer hairpin transcripts by the RNAse III ribonucleases Drosha. Mature microRNAs (miRs) typically between 20 and 25 contiguous RNA nucleotides. It is now widely established that several microRNAs are associated with medical conditions and disease, and several companies are developing therapeutics based on oligomers which either mimic microRNAs or specifically hybridse to specific microRNAs associated with disease phenotypes—such oligomers are referred to, herein, as microRNA mimics and antimiRs respectfully, and the oligomer or first region thereof, in some embodiments may be such microRNA modulating oligomers.

In some embodiments the oligomer or first region thereof according to the invention, consists or comprises of a contiguous nucleotide sequence which corresponds to or is fully complementary to a microRNA sequence, such as a mature microRNA sequence, such as the human microRNAs published in miRBase (http://microrna.sanger.ac.uk/cgi-bin/sequences/mirna_summary.pl?org=hsa). In some embodiment the microRNA is a viral microRNA. At the time of writing, in miRbase 19, there are 1600 precursors and 2042 mature human miRNA sequences in miRBase which are all hereby incorporated by reference, including the mature microRNA sequence of each human microRNA. Other human microRNAs which may be targeted by the oligomer or first region thereof include those disclosed in WO08040355A, hereby incorporated by reference. In some embodiments the oligomer or first region thereof according to the invention, consists or comprises of a contiguous nucleotide sequence which corresponds to or is fully complementary to a microRNA sequence selected from the group consisting of hsa-miR19b, hsa-miR21, hsa-miR 122, hsa-miR 142 a7b, hsa-miR 155, and hsa-miR 375. In some embodiments the oligomer or first region thereof according to the invention, consists or comprises of a contiguous nucleotide sequence which corresponds to or is fully complementary to a microRNA sequence selected from the group consisting of hsa-miR221 and hsa-miR222. In some embodiments the oligomer or first region thereof according to the invention, consists or comprises of a contiguous nucleotide sequence which corresponds to or is fully complementary to hsa-miR122 (NR_029667.1 GI:262205241), such as the mature has-miR-122.

In some embodiments when the oligomer or first region thereof targets miR-122, the oligomer is for the use in the treatment of hepatitis C infection.

AntimiR Oligomers

Preferred oligomer or first region thereof 'antimiR' designs and oligomers are disclosed in WO2007/112754, WO2007/112753, PCT/DK2008/000344 and US provisional applications 60/979,217 and 61/028,062, all of which are hereby incorporated by reference. In some embodiments, the oligomer or first region thereof is an antimiR which is a mixmer or a totalmer.

AntimiR oligomers are oligomers which consist or comprise of a contiguous nucleotide sequence which is fully complementary to, or essentially complementary to (i.e. may comprise one or two mismatches), to a microRNA sequence, or a corresponding sub-sequence thereof. In this regards it is considered that the antimiR may be comprise a contiguous nucleotide sequence which is complementary or essentially complementary to the entire mature microRNA, or the antimiR may be comprise a contiguous nucleotide sequence which is complementary or essentially complementary to a sub-sequence of the mature microRNA or pre-microRNA—such a sub-sequence (and therefore the corresponding contiguous nucleotide sequence) is typically at least 8 nucleotides in length, such as between 8 and 25 nucleotides, such as 9, 10, 11, 12, 13, 14, 15, 16, 17, 18, 19, 20, 21, 22, 23, 24 nucleotides in length, such as between 10-17 or 10-16 nucleotides, such as between 12-15 nucleotides.

Numerous designs of AntimiRs have been suggested, and typically antimiRs for therapeutic use, such as the contiguous nucleotide sequence thereof comprise one or more nucleotide analogues units.

In some embodiments the antimiR may have a gapmer structure as herein described. However, as explained in WO2007/112754 and WO2007/112753, other designs may be preferable, such as mixmers, or totalmers.

WO2007/112754 and WO2007/112753, both hereby incorporated by reference, provide antimiR oligomers and antimiR oligomer designs where the oligomers which are complementary to mature microRNA In some embodiments, a subsequence of the antimiR corresponds to the miRNA seed region. In some embodiments, the first or second 3' nucleobase of the oligomer corresponds to the second 5' nucleotide of the microRNA sequence.

In some antimiR embodiments, nucleobase units 1 to 6 (inclusive) of the oligomer as measured from the 3' end the region of the oligomer are complementary to the microRNA seed region sequence.

In some antimiR embodiments, nucleobase units 1 to 7 (inclusive) of the oligomer as measured from the 3' end the region of the oligomer are complementary to the microRNA seed region sequence.

In some e antimiR embodiments, nucleobase units 2 to 7 (inclusive) of the oligomer as measured from the 3' end the region of the oligomer are complementary to the microRNA seed region sequence.

In some embodiments, the antimiR oligomer comprises at least one nucleotide analogue unit, such as at least one LNA unit, in a position which is within the region complementary to the miRNA seed region. The antimiR oligomer may, in some embodiments comprise at between one and 6 or between 1 and 7 nucleotide analogue units, such as between 1 and 6 and 1 and 7 LNA units, in a position which is within the region complementary to the miRNA seed region.

In some embodiments, the antimiR of the invention is 7, 8 or 9 nucleotides long, and comprises a contiguous nucleotide sequence which is complementary to a seed region of a human or viral microRNA, and wherein at least 80%, such as 85%, such as 90%, such as 95%, such as 100% of the nucleotides are LNA.

In some embodiments, the antimiR of the invention is 7, 8 or 9 nucleotides long, and comprises a contiguous nucleotide sequence which is complementary to a seed region of a human or viral microRNA, and wherein at least 80% of the nucleotides are LNA, and wherein at least 80%, such as 85%, such as 90%, such as 95%, such as 100% of the internucleotide bonds are phosphorothioate bonds.

In some embodiments, the antimiR comprises one or two LNA units in positions three to eight, counting from the 3' end. This is considered advantageous for the stability of the A-helix formed by the oligonucleotide:microRNA duplex, a duplex resembling an RNA:RNA duplex in structure.

The table on pages 48 line 15 to page 51, line 9 of WO2007/112754 provides examples of anti microRNA oligomers (i.e. antimiRs which may be the oligomer or first region thereof) and is hereby specifically incorporated by reference.

MicroRNA Mimics

In some embodiments the oligomer or first region thereof is in the form of a miRNA mimic which can be introduced into a cell to repress the expression of one or more mRNA target(s). miRNA mimics are typically fully complementary to the full length miRNA sequence. miRNA mimics are compounds comprising a contiguous nucleotide sequence which are homologous to a corresponding region of one, or more, of the miRNA sequences provided or referenced to herein. The use of miRNA mimics or antimiRs can be used to (optionally) further repress the mRNA targets, or to silence (down-regulate) the miRNA, thereby inhibiting the function of the endogenous miRNA, causing derepression and increased expression of the mRNA target.

Aptamers

In some embodiments the oligomer or first region thereof may be a therapeutic aptamer, a spiegelmer. Please note that aptamers may also be ligands, such as receptor ligands, and may therefore be used as a targeting moiety (i.e. region 3). Aptamers (also referred to as Spiegelmers) in the context of the present invention as nucleic acids of between 20 and 50 nucleotides in length, which have been selected on the basis of their conformational structure rather than the sequence of nucleotides—they elicit their therapeutic effect by binding with a target protein directly in vivo and they do not, therefore, comprise of the reverse complement of their target—indeed their target is not a nucleic acid but a protein. Specific aptamers which may be the oligomer or first region thereof include Macugen (OSI Pharmaceuticals) or ARC1779, (Archemix, Cambridge, Mass.). In some embodiments, the oligomer or first region thereof is not an aptamer. In some embodiments the oligomer or first region thereof is not an aptamer or a spiegelmer.

siRNA Complexes

In some embodiments, the oligomer or first region thereof may be part of a siRNA complex—i.e. the antisense or passenger strand of the siRNA complex. An siRNA complex is capable of mediating RNA interference.

In some embodiments the siRNA complex comprises two single stranded oligomers of between 17-25 nts in length, such as 18, 19, 20, 21, 22, 23, 24 nucleotides in length, such as between 21-23 nucleotides in length. In some embodiments, the sense and/or antisense strand of the siRNA may comprise a 3' overhang, typically of 1, 2 or 3 nucleotides. Suitably, the sense and or antisense strand may comprise one or more nucleotide analogues.

In some embodiments the siRNA complex is a siLNA, such as the siRNA designs described in WO2004/000192, WO2005/073378, WO2007/085485 all of which are hereby incorporated by reference. An siLNA is a siRNA which comprises at least one LNA unit.

In some embodiments, the siRNA complex is a sisiLNA, such as those described in WO2007/107162, hereby incorporated by reference. In some embodiments, the oligomer or first region thereof, of the invention is the sense strand of the siRNA, and as such may be non-complementary to the target (indeed, may be homologous to the intended target).

In some embodiments, the oligomer or compound of the invention is not a siRNA or a siLNA.

Internucleotide Linkages

The nucleoside monomers of the oligomers (e.g. first and second regions) described herein are coupled together via [internucleoside] linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group.

The terms "linkage group" or "internucleotide linkage" are intended to mean a group capable of covalently coupling together two nucleotides. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within WO2007/031091, for example the internucleotide linkages listed on the first paragraph of page 34 of WO2007/031091 (hereby incorporated by reference).

It is, in some embodiments, other than the phosphodiester linkage(s) or region B, the preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred, such as phosphorothioate or phosphodithioate. Phosphorothioate internucleotide linkages are also preferred, particularly for the first region, such as in gapmers, mixmers, antimirs splice switching oligomers, and totalmers.

For gapmers, the internucleotide linkages in the oligomer may, for example be phosphorothioate or boranophosphate so as to allow RNase H cleavage of targeted RNA. Phosphorothioate is preferred, for improved nuclease resistance and other reasons, such as ease of manufacture.

In one aspect, with the exception of the phosphodiester linkage between the first and second region, and optionally within region B, the remaining internucleoside linkages of the oligomer of the invention, the nucleotides and/or nucleotide analogues are linked to each other by means of phosphorothioate groups. In some embodiments, at least 50%, such as at least 70%, such as at least 80%, such as at least 90% such as all the internucleoside linkages between nucleosides in the first region are other than phosphodiester (phosphate), such as are selected from the group consisting of phosphorothioate phosphorodithioate, or boranophosphate. In some embodiments, at least 50%, such as at least 70%, such as at least 80%, such as at least 90% such as all the internucleoside linkages between nucleosides in the first region are phosphorothioate.

WO09124238 refers to oligomeric compounds having at least one bicyclic nucleoside attached to the 3' or 5' termini by a neutral internucleoside linkage. The oligomers of the invention may therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages may be phosphorothioate.

Conjugates, Targeting Moieties and Blocking Groups

The term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

In various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

In some embodiments, the conjugate may be a lipophilic conjugate or a proteins (e.g., antibodies, enzymes, serum proteins); peptides; vitamins (water-soluble or lipid-soluble); polymers (water-soluble or lipid-soluble); small molecules including drugs, toxins, reporter molecules, and receptor ligands; carbohydrate complexes; nucleic acid cleaving complexes; metal chelators (e.g., porphyrins, texaphyrins, crown ethers, etc.); intercalators including hybrid photonuclease/intercalators; crosslinking agents (e.g., photoactive, redox active), and combinations and derivatives thereof. Numerous suitable conjugate moieties, their preparation and linkage to oligomeric compounds are provided, for example, in WO 93/07883 and U.S. Pat. No. 6,395,492, each of which is incorporated herein by reference in its entirety. Oligonucleotide conjugates and their syntheses are also reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety. [0034]

Conjugation (to a conjugate moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example from 1-50, such as 2-20 such as 3-10 amino acid residues in length, and/or polyalkylene oxide such as polyethylglycol (PEG) or polypropylene glycol—see WO 2008/034123, hereby incorporated by reference.

The use of a conjugate is often associated with enhanced pharmacokinetic or pharmeodynamic dynamic properties. However, the presence of a conjugate group may interfere with the activity of the oligonucleotide against its intended target, for example via steric hindrance preventing hybridization or nuclease recruitment (e.g. RNAseH or RISC recruitment). The use of a DNA and/or RNA phosphodiester region (region B) between the oligonucleotide (region A) and the conjugate moiety (X), as according to the present invention, allows for the improved properties due to the presence of the conjugate group, whilst ensuring that once at the target tissue, the conjugate group does not prevent effective activity of the oligonucleotide.

The oligonucleotide of the invention is, in some embodiments, covalently attached to one or more conjugate group, optionally through one or more linkers. The resulting conjugate compounds may, for example have modified enhanced properties, such as modified or enhanced pharmacokinetic, pharmeodynamic, and other properties compared with non-conjugated oligomeric compounds. A conjugate moiety that can modify or enhance the pharmacokinetic properties of an oligomeric compound can improve cellular distribution, bioavailability, metabolism, excretion, permeability, and/or cellular uptake of the oligomeric compound. A conjugate moiety that can modify or enhance pharmacodynamic properties of an oligomeric compound can improve activity, resistance to degradation, sequence-specific hybridization, uptake, and the like. In some embodiments, the conjugate group may reduce or prevent in appropriate activity of the oligonucleotide, e.g. off target activity or activity in non-target tissues or organs. This may be achieved by use of a blocking moiety, which may for example be a conjugate, the presence of the blocking group covalently attached to the oligonucleotide (optionally via a linker), may prevent or hinder oligonucleotide hybridization and/or activity. The cleavage of the DNA/RNA phosphodiester region (e.g. at the intended target site), removes the blocking group, allowing delivery of the active oligonucleotide at the intended site.

In some embodiments, the compound of the invention comprises a conjugate group. It will be recognized that one conjugate group may be used, for example for targeting to a specific tissue, for example a lipophilic group for targeting to the liver, and a second conjugate group may be used to provide a further benefit, for example a blocking group or a further therapeutic entity. Suitable one or both of the conjugates/moieties may be linked to the oligonucleotide via the DNA/RNA phosphodiester region according to the present invention. In some embodiments, the conjugate is covalently bound to the oligonucleotide, optionally via a linker, at the 5' and/or 3' termini of the oligonucleotide. In this respect, if two conjugate/moiety groups are used, one may be linked to the 5' termini and one to the 3' termini.

Carbohydrate Conjugates

In some embodiments, the conjugate group is selected from the group consisting of a carbohydrate, a lipophilic moiety, a polymer, a protein or peptide, a label or dye, a small molecule, such as a small molecule therapeutic moiety, a cell surface receptor ligand.

In some embodiments, the conjugate is or may comprise a carbohydrate or comprises a carbohydrate group. In some embodiments, the carbohydrate is selected from the group consisting of galactose, lactose, n-acetylgalactosamine, mannose, and mannose-6-phosphate. In some embodiments, the conjugate group is or may comprise mannose or mannose-6-phosphate. Carbohydrate conjugates may be used to enhance delivery or activity in a range of tissues, such as liver and/or muscle. See, for example, EP1495769, WO99/65925, Yang et al., Bioconjug Chem (2009) 20(2): 213-21. Zatsepin & Oretskaya Chem Biodivers. (2004) 1(10): 1401-17.

In some embodiments, the conjugate group is a carbohydrate moiety. In addition, the oligomer may further comprise one or more additional conjugate moieties, of which lipophilic or hydrophobic moieties are particularly interesting. These may for example, act as pharmacokinetic modulators, and may be covalently linked to either the carbohydrate conjugate, a linker linking the carbohydrate conjugate to the oligomer or a linker linking multiple carbohydrate conjugates (multi-valent) conjugates, or to the oligomer, optionally via a linker, such as a bio cleavable linker.

In some embodiments, the conjugate is or may comprise a carbohydrate or comprises a carbohydrate group. In some embodiments, the carbohydrate is selected from the group consisting of galactose, lactose, n-acetylgalactosamine, mannose, and mannose-6-phosphate. In some embodiments, the conjugate group is or may comprise mannose or mannose-6-phosphate. Carbohydrate conjugates may be used to enhance delivery or activity in a range of tissues, such as liver and/or muscle. See, for example, EP1495769, WO99/65925, Yang et al., Bioconjug Chem (2009) 20(2): 213-21. Zatsepin & Oretskaya Chem Biodivers. (2004) 1(10): 1401-17.

GalNAc Conjugates

The invention also provides oligonucleotides, such as LNA antisense oligomers, which are conjugated to an asialoglycoprotein receptor targeting moiety. In some embodiments, the conjugate moiety (such as the third region or region C) comprises an asialoglycoprotein receptor targeting moiety, such as galactose, galactosamine, N-formyl-galactosamine, Nacetylgalactosamine, N-propionyl-galactosamine, N-n-butanoyl-galactosamine, and N-isobutanoyl-galactos-amine. In some embodiments the conjugate comprises a galactose cluster, such as N-acetylgalactosamine trimer. In some embodiments, the conjugate moiety comprises a GalNAc (N-acetylgalactosamine), such as a mono-valent, di-valent, tri-valent of tetra-valent GalNAc. Trivalent GalNAc conjugates may be used to target the compound to the liver. GalNAc conjugates have been used with methylphosphonate and PNA antisense oligonucleotides (e.g. U.S. Pat. No. 5,994,517 and Hangeland et al., Bioconjug Chem. 1995 November-December; 6(6):695-701) and siRNAs (e.g. WO2009/126933, WO2012/089352 & WO2012/083046). The GalNAc references and the specific conjugates used therein are hereby incorporated by reference. WO2012/083046 discloses siRNAs with GalNAc conjugate moieties which comprise cleavable pharmacokinetic modulators, which are suitable for use in the present invention, the preferred pharmacokinetic modulators are C16 hydrophobic groups such as palmitoyl, hexadec-8-enoyl, oleyl, (9E,12E)-octadeca-9,12-dienoyl, dioctanoyl, and C16-C20 acyl. The '046 cleavable pharmacokinetic modulators may also be cholesterol.

The 'targeting moieties (conjugate moieties) may be selected from the group consisting of: galactose, galactosamine, N-formyl-galactosamine, N-acetylgalactosamine, Npropionyl-galactosamine, N-n-butanoyl-galactosamine, N-iso-butanoylgalactos-amine, galactose cluster, and N-acetylgalactosamine trimer and may have a pharmacokinetic modulator selected from the group consisting of: hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. Certain GalNac clusters disclosed in '046 include: (E)-hexadec-8-enoyl (C16), oleyl (C18), (9,E,12E)-octadeca-9,12-dienoyl (C18), octanoyl (C8), dodececanoyl (C12), C-20 acyl, C24 acyl, dioctanoyl (2×C8). The targeting moiety-pharmacokinetic modulator targeting moiety may be linked to the polynucleotide via a physiologically labile bond or, e.g. a disulfide bond, or a PEG linker. The invention also relates to the use of phospodiester linkers between the oligomer and the conjugate group (these are referred to as region B herein, and suitably are positioned between the LNA oligomer and the carbohydrate conjugate group).

For targeting hepatocytes in liver, a preferred targeting ligand is a galactose cluster.

A galactose cluster comprises a molecule having e.g. comprising two to four terminal galactose derivatives. As used herein, the term galactose derivative includes both galactose and derivatives of galactose having affinity for the asialoglycoprotein receptor equal to or greater than that of galactose. A terminal galactose derivative is attached to a molecule through its C-I carbon. The asialoglycoprotein receptor (ASGPr) is unique to hepatocytes and binds branched galactose-terminal glycoproteins. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, 1. Biol. Chem., 257, 939-945). Multivalency is required to achieve nM affinity.

According to WO 2012/083046 the attachment of a single galactose derivative having affinity for the asialoglycoprotein receptor does not enable functional delivery of the RNAi polynucleotide to hepatocytes in vivo when co-administered with the delivery polymer.

A galactose cluster may comprise two or preferably three galactose derivatives each linked to a central branch point. The galactose derivatives are attached to the central branch point through the C-I carbons of the saccharides. The galactose derivative is preferably linked to the branch point via linkers or spacers (which may be region Y). A preferred spacer is a flexible hydrophilic spacer (U.S. Pat. No. 5,885, 968; Biessen et al. J. Med. Chern. 1995 Vol. 39 p. 1538-1546). A preferred flexible hydrophilic spacer is a PEG spacer. A preferred PEG spacer is a PEG3 spacer. The branch point can be any small molecule which permits attachment of the three galactose derivatives and further permits attachment of the branch point to the oligomer. An exemplary branch point group is a di-lysine. A di-lysine molecule contains three amine groups through which three galactose derivatives may be attached and a carboxyl reactive group through which the di-lysine may be attached to the oligomer. Attachment of the branch point to oligomer may occur through a linker or spacer. A preferred spacer is a flexible hydrophilic spacer. A preferred flexible hydrophilic spacer is a PEG spacer. A preferred PEG spacer is a PEG3 spacer (three ethylene units). The galactose cluster may be attached to the 3' or 5' end of the oligomer using methods known in the art.

A preferred galactose derivative is an N-acetyl-galactosamine (GalNAc). Other saccharides having affinity for the asialoglycoprotein receptor may be selected from the list comprising: galactosamine, N-n-butanoylgalactosamine, and N-iso-butanoylgalactosamine. The affinities of numerous galactose derivatives for the asialoglycoprotein receptor have been studied (see for example: Jobst, S. T. and Drickamer, K. J B. C. 1996, 271, 6686) or are readily determined using methods typical in the art.

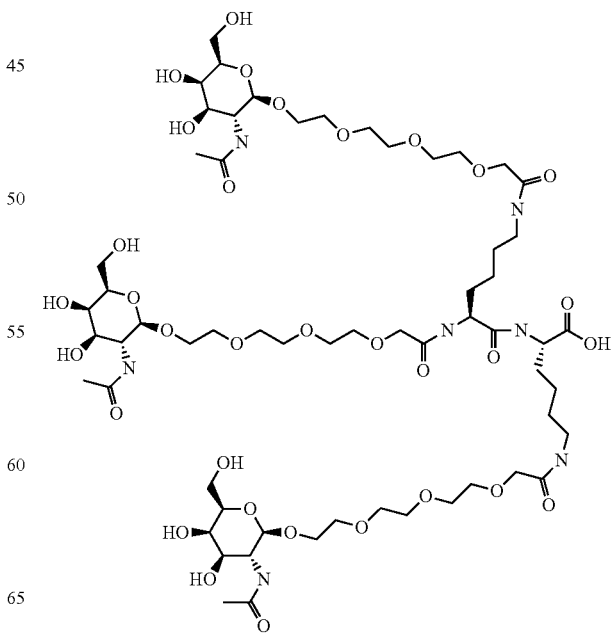

One embodiment of a Galactose cluster
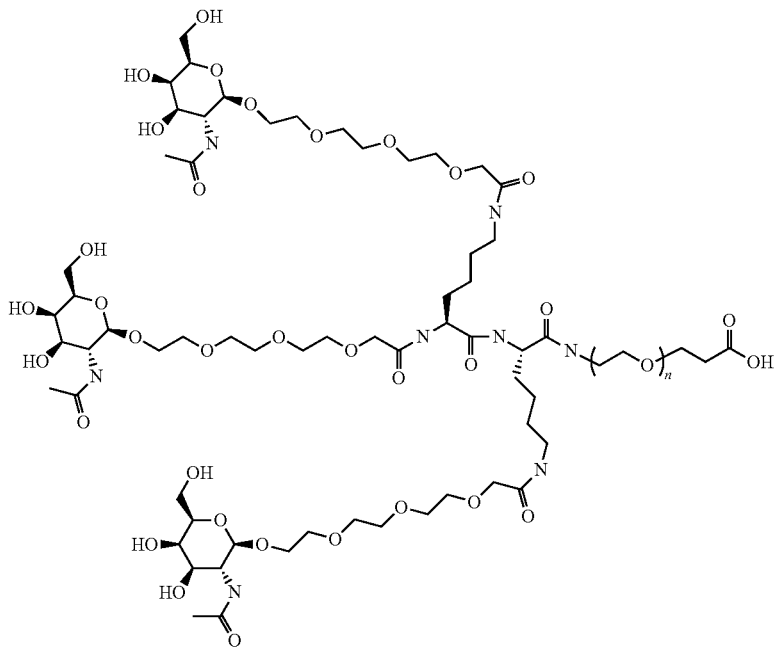
Glucose cluster with PEG spacer between branch point and nucleic acid
A GalNac conjugate is illustrated in FIG. 1. Further examples of the conjugate of the invention are illustrated below:
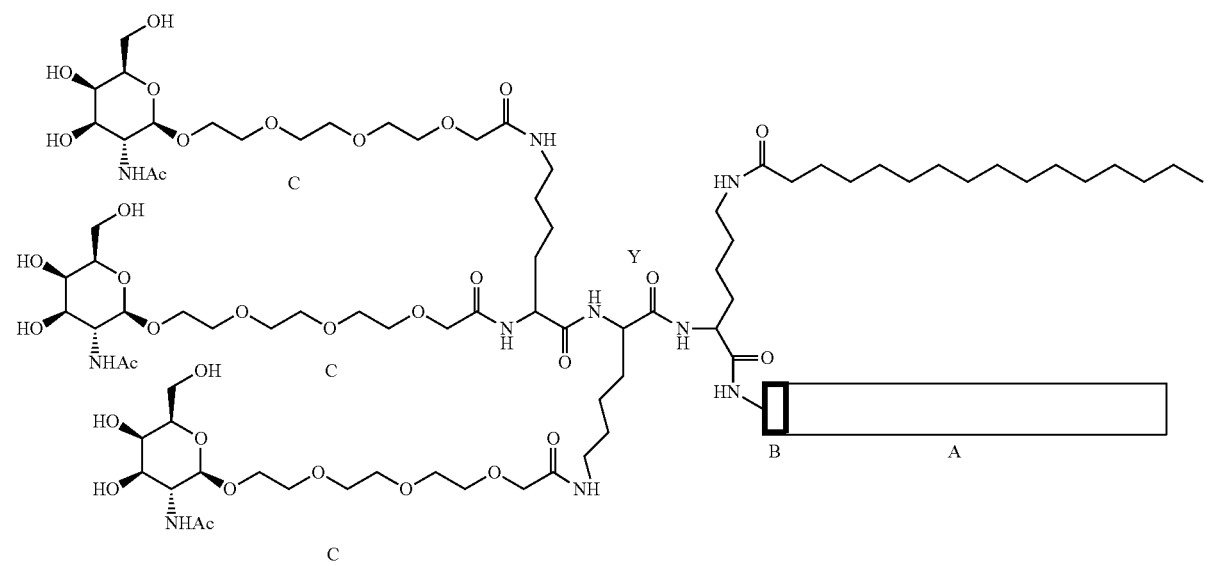

-continued

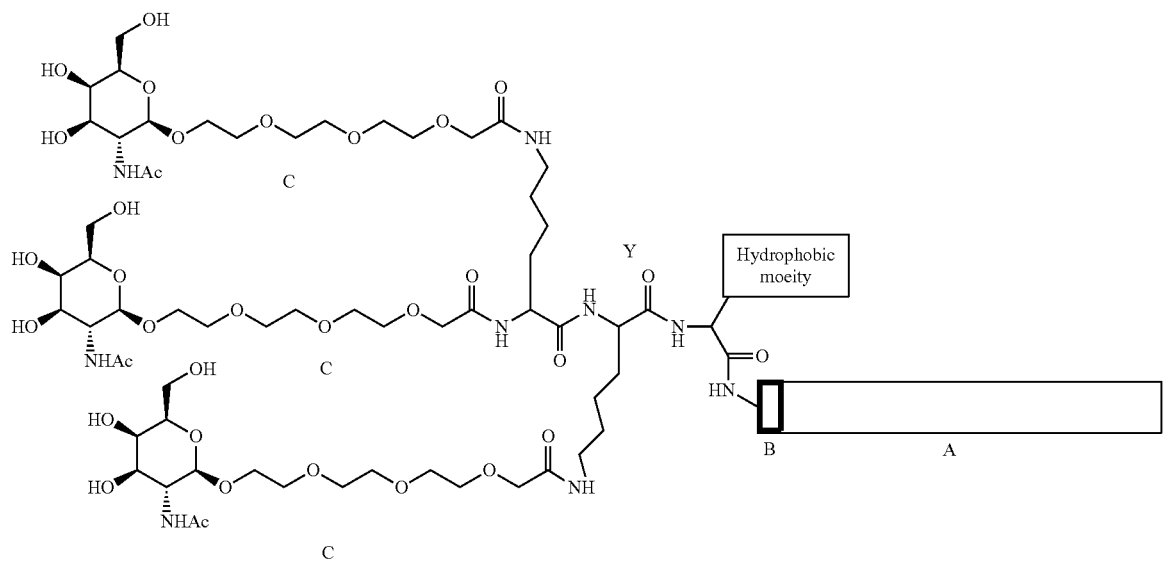

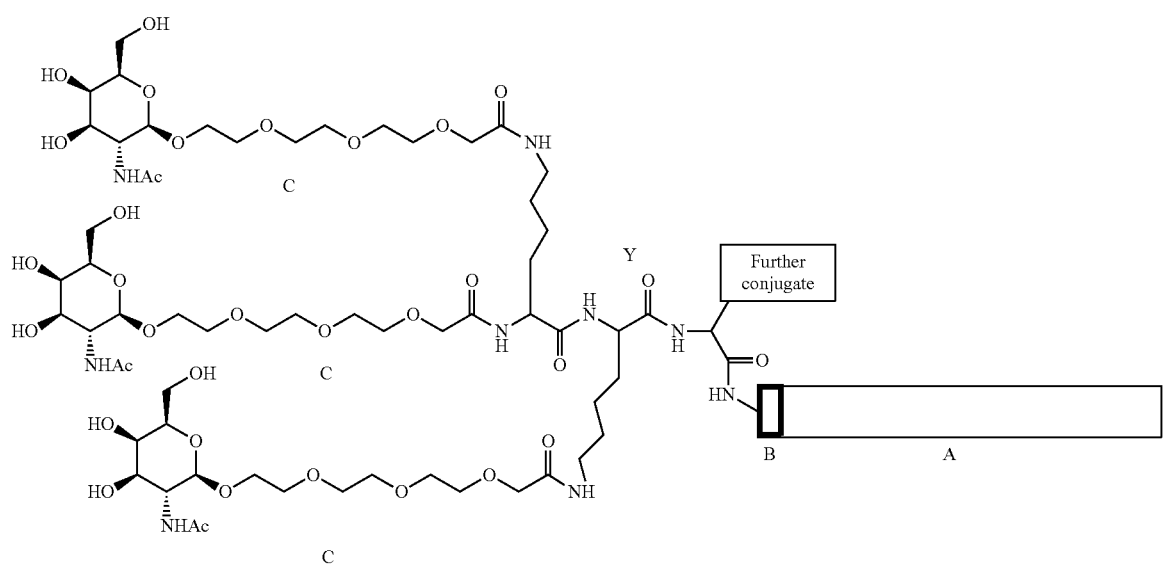

Region A may, for example, be a LNA antisense oligonucleotide.

As described herein, a carbohydrate conjugate (e.g. GalNAc) may therefore be linked to the oligomer via a biocleavable linker, such as region B as defined herein, and optionally region Y, which is illustrated as a di-lysine in the above diagrams.

Where at the hydrophobic or lipophilic (or further conjugate) moiety (i.e. pharmacokinetic modulator) in the above GalNac cluster conjugates is, when using BNA or LNA oligomers, such as LNA antisense oligonucleotides, optional.

Figure 12:
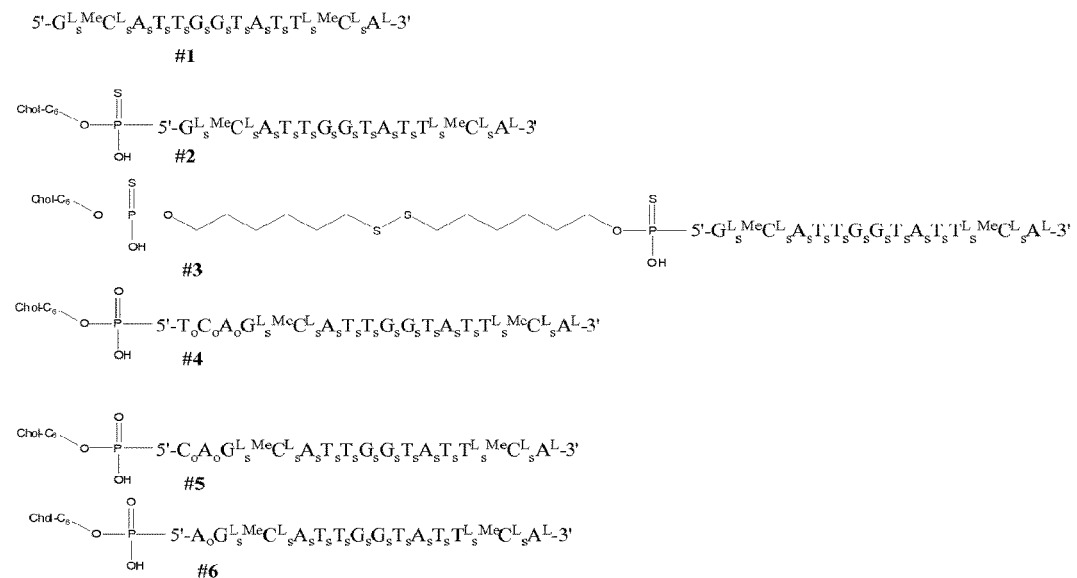
FIG. 12. Shows the cholesterol C6 conjugate which may be used as X—Y— in compounds of the invention, as well as specific compounds used in the examples, include specific compounds of the invention.
Figure 12:
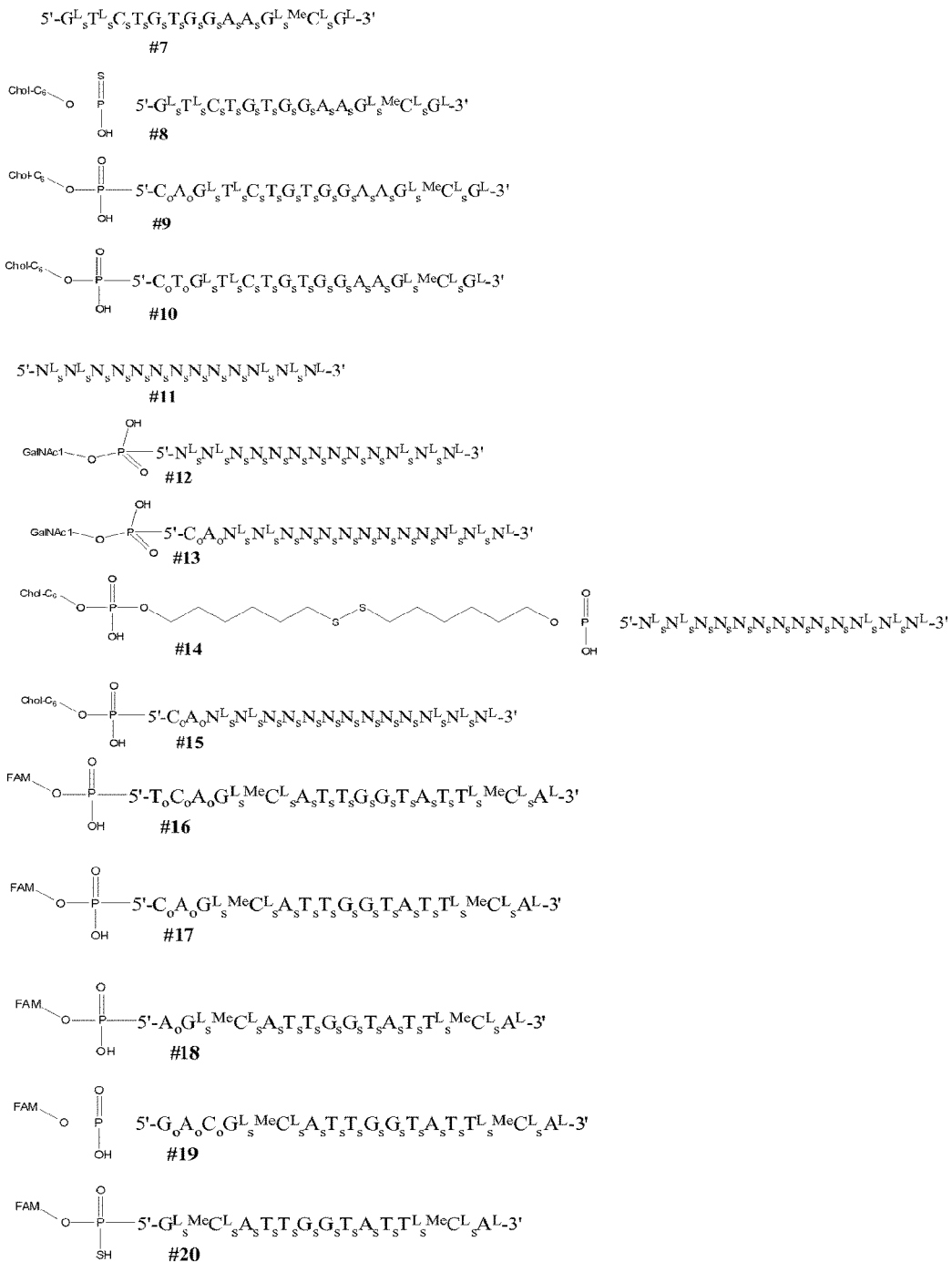
Figure 12:
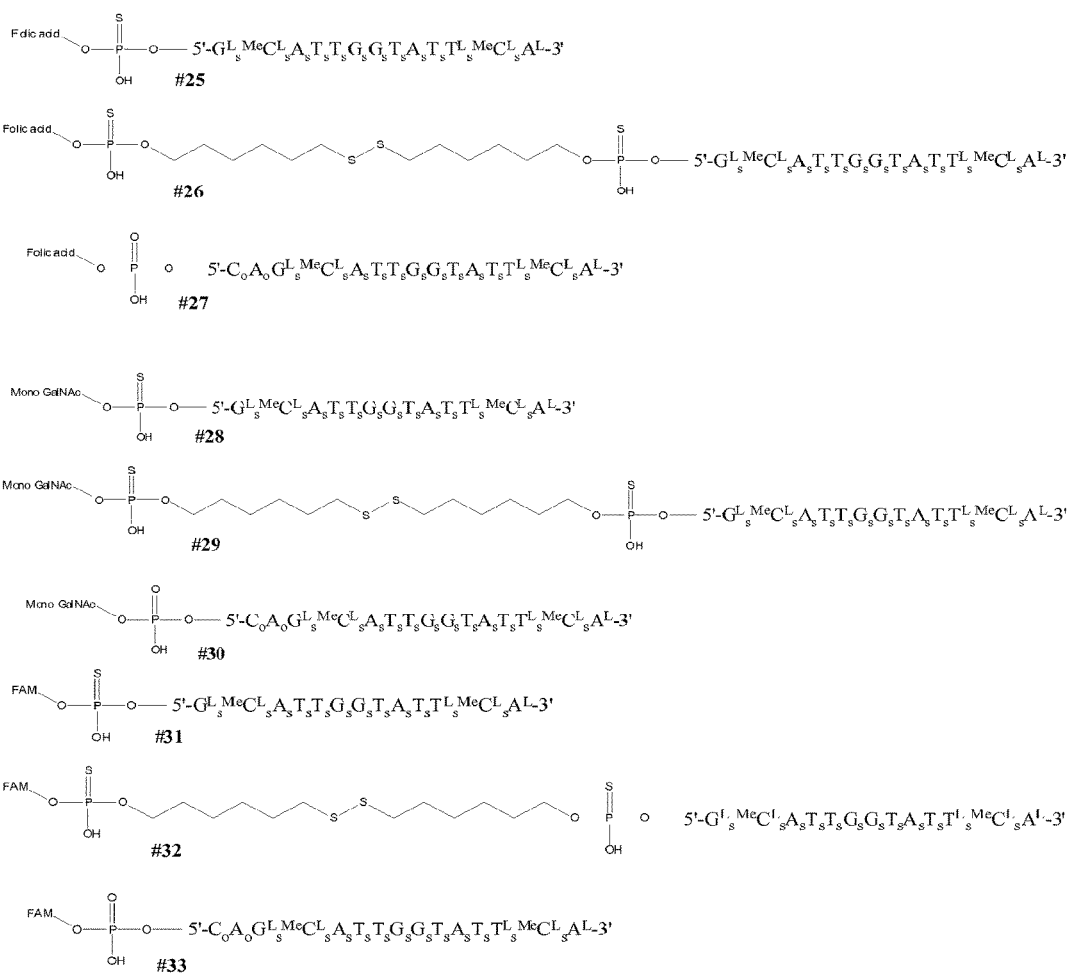
Figure 12:
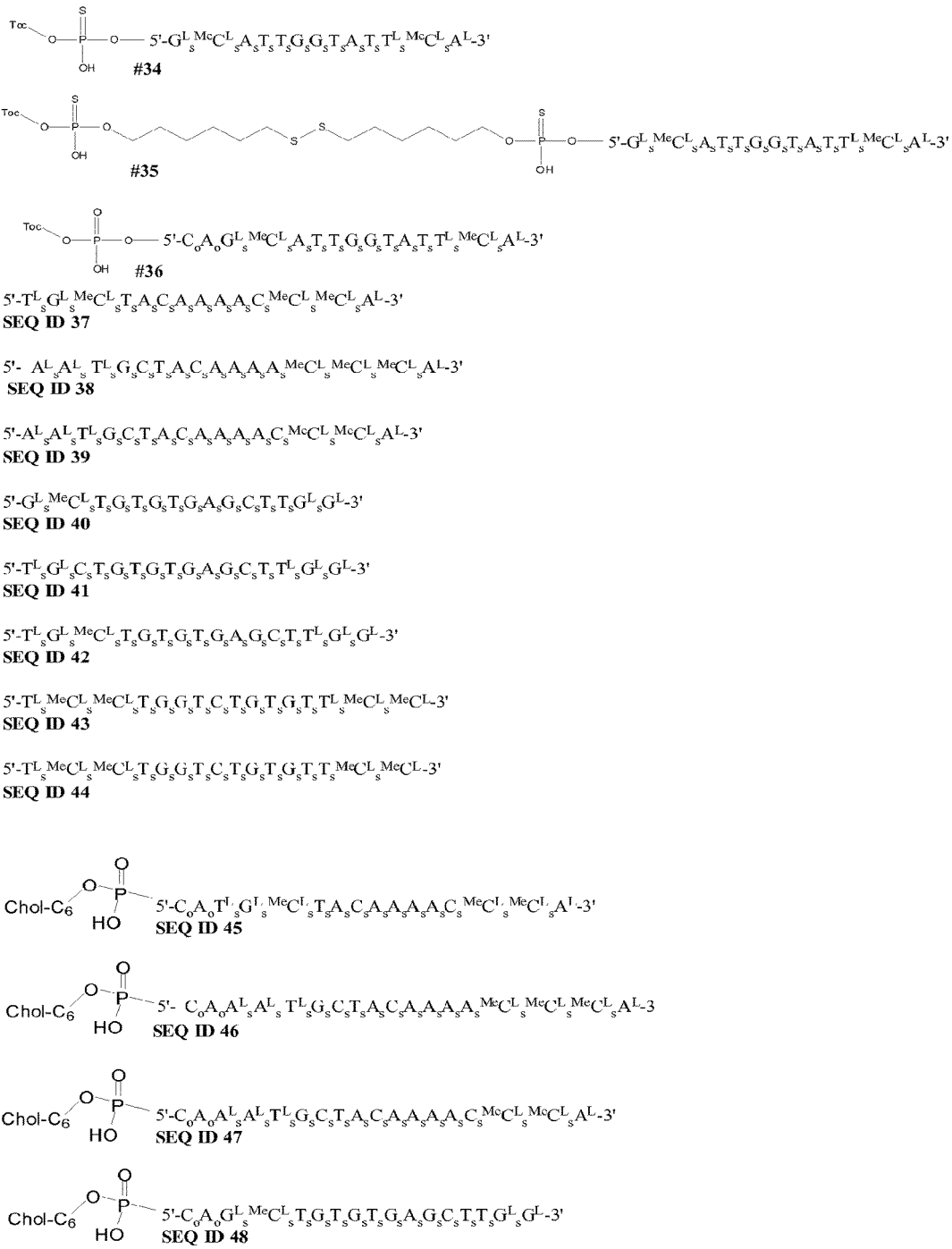
Figure 12:
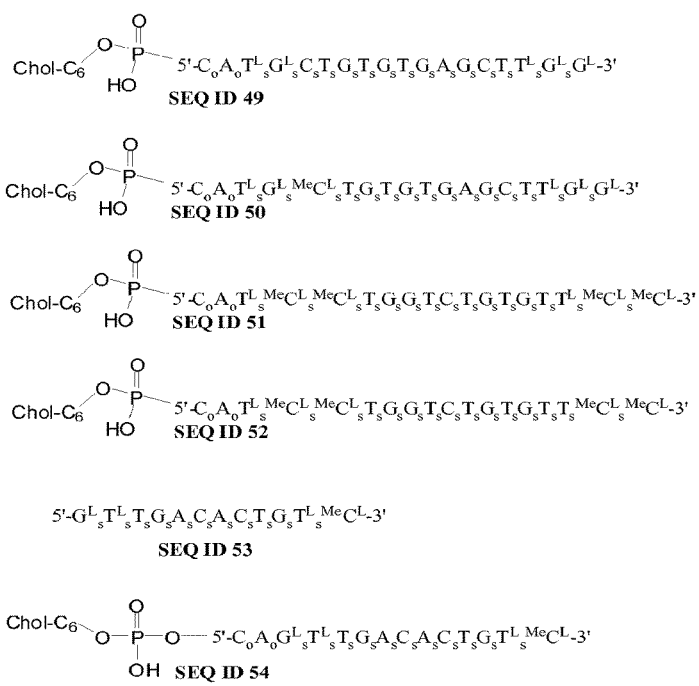
Figure 13:
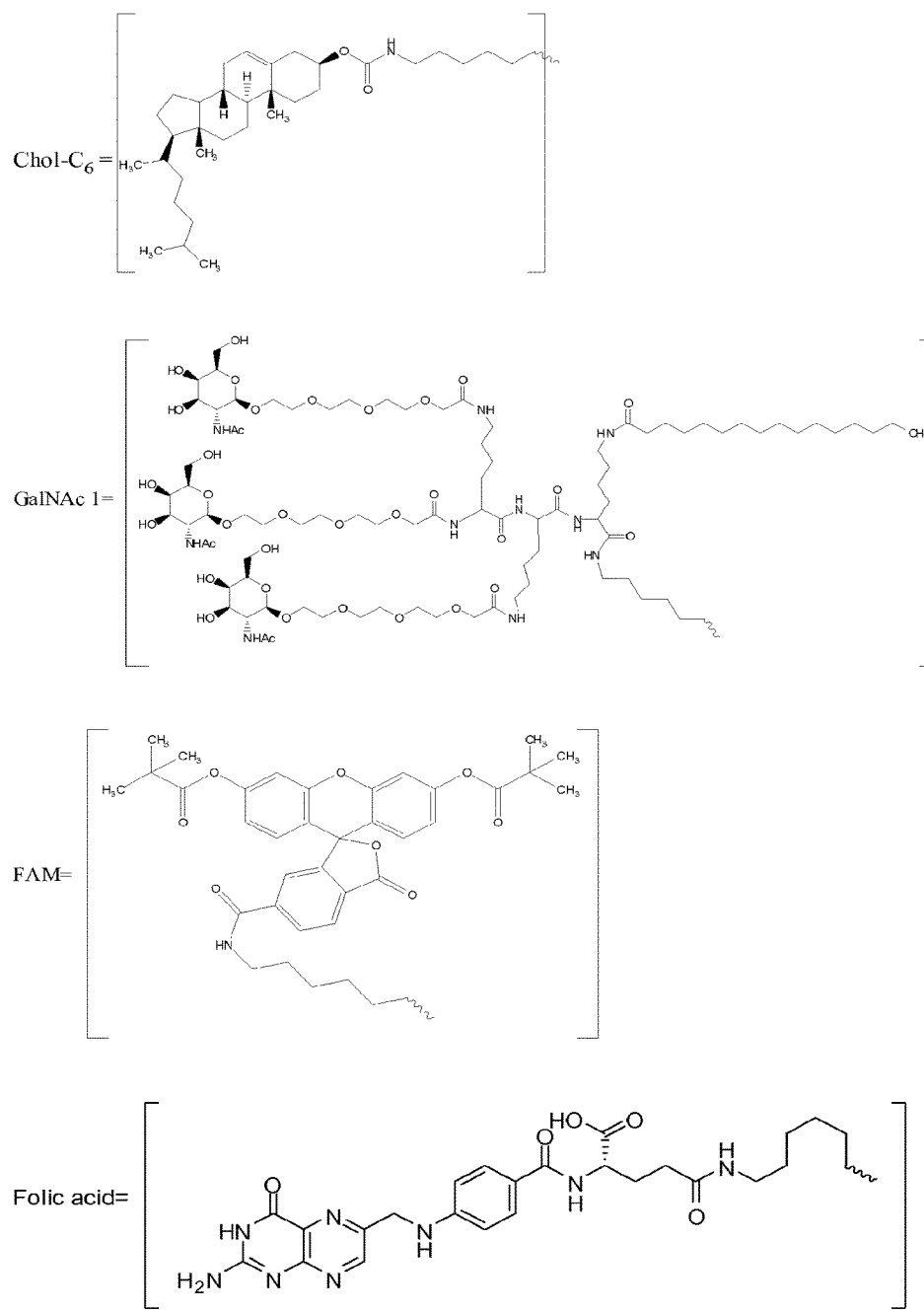
FIG. 13. Examples of cholesterol, trivalent GalNac, FAM, folic acid, monovalent GalNac and tocopherol conjugates used in the experiments (e.g. compounds of FIG. 12).
Figure 13:
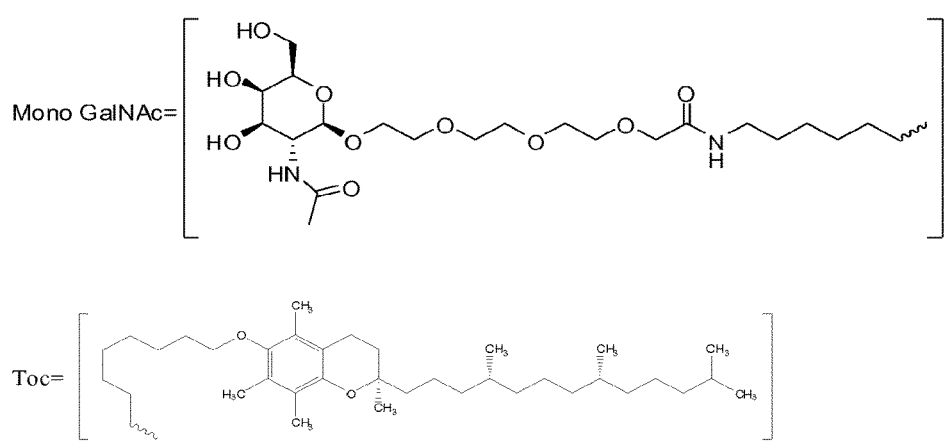
Figure 17:
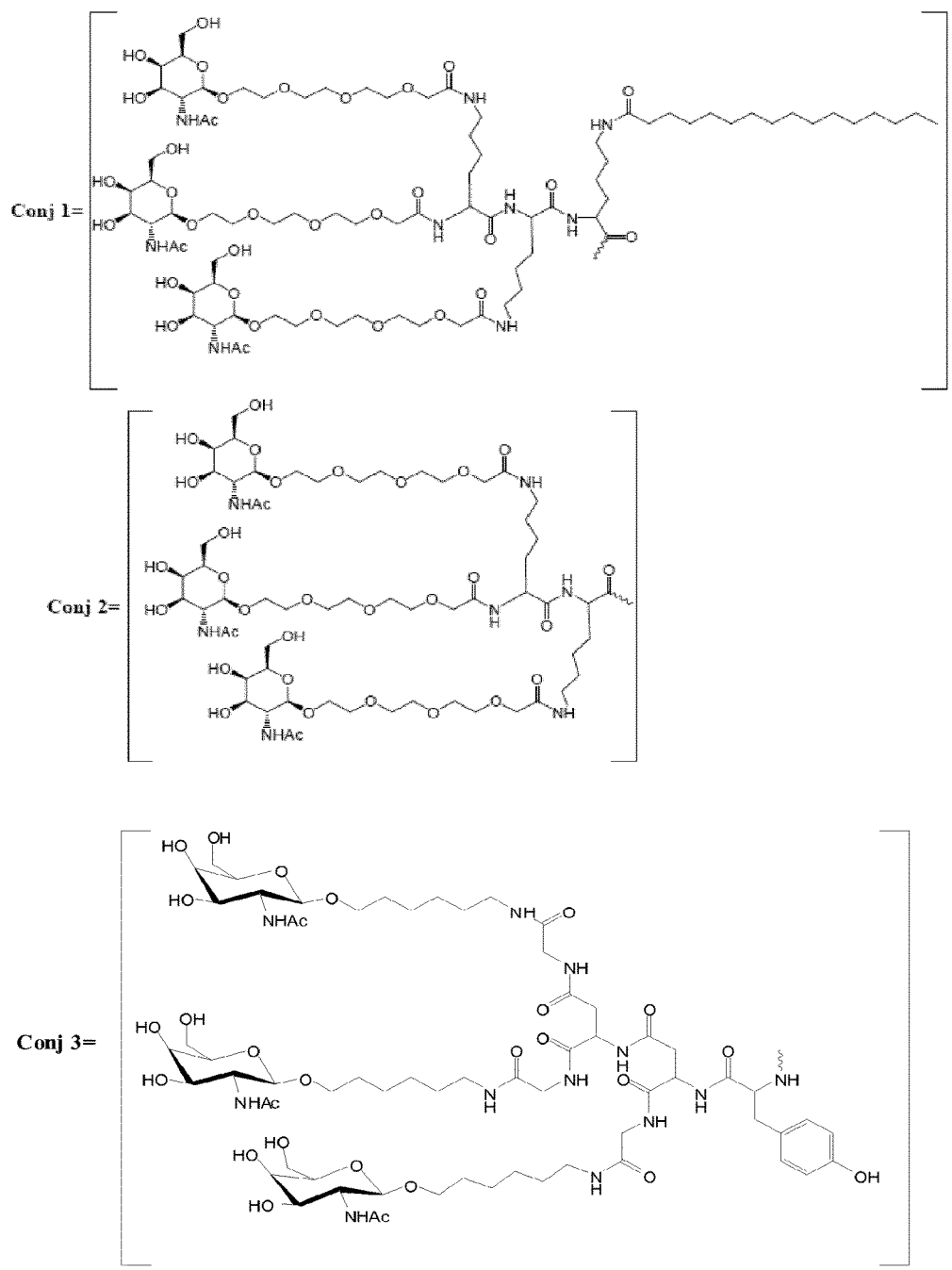
FIG. 17 Examples of tri-GalNac conjugates which may be used. Conjugates 1-4 illustrate 4 suitable GalNac conjugate moieties, and conjugates 1a-4a refer to the same conjugates with an additional linker moiety (Y) which is used to link the conjugate to the oligomer (region A or to a biocleavable linker, such as region B). The wavy line represents the covalent link to the oligomer. Also shown are examples of cholesterol and tocopherol conjugate moieties (5a and 6a). The wavy line represents the covalent link to the oligomer.
Figure 17:
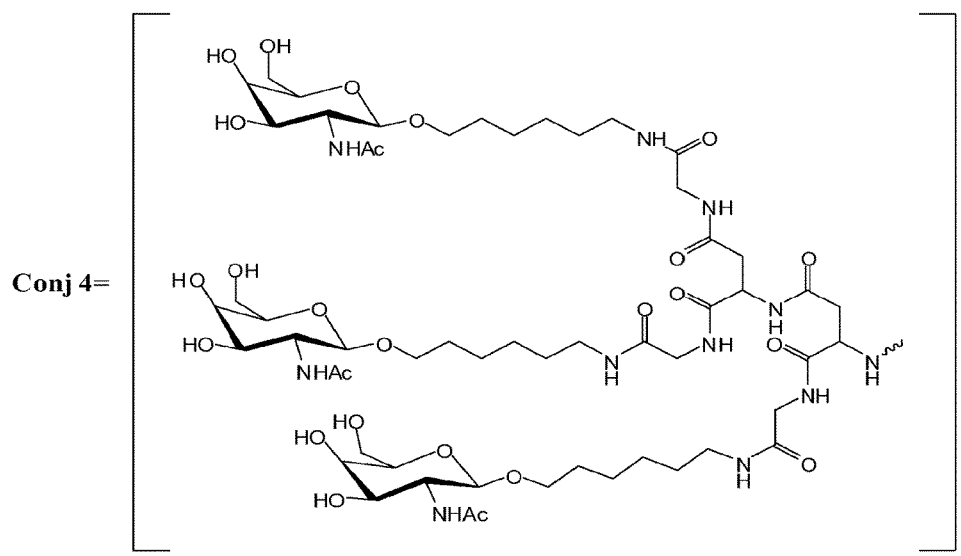
Figure 17:
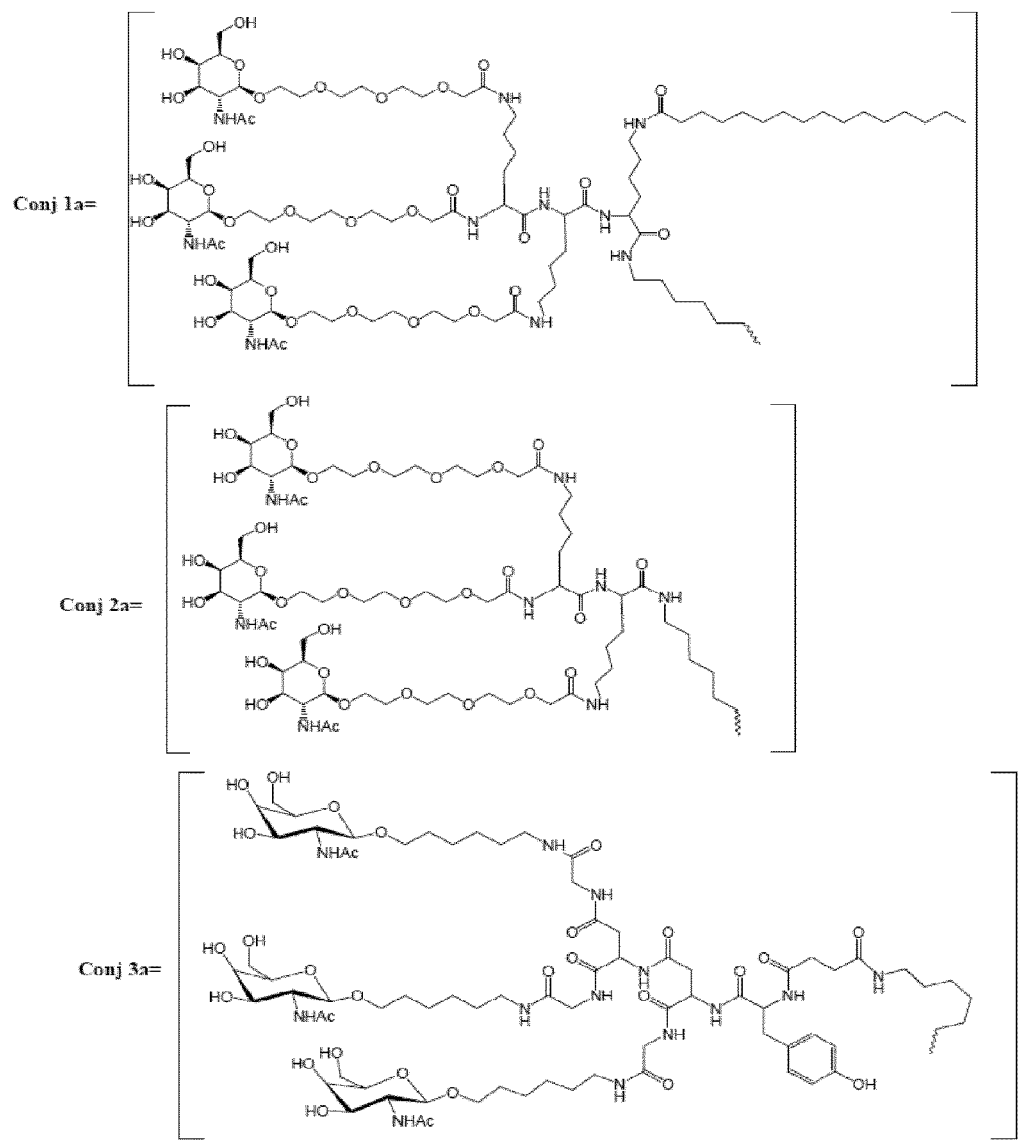
Figure 17:
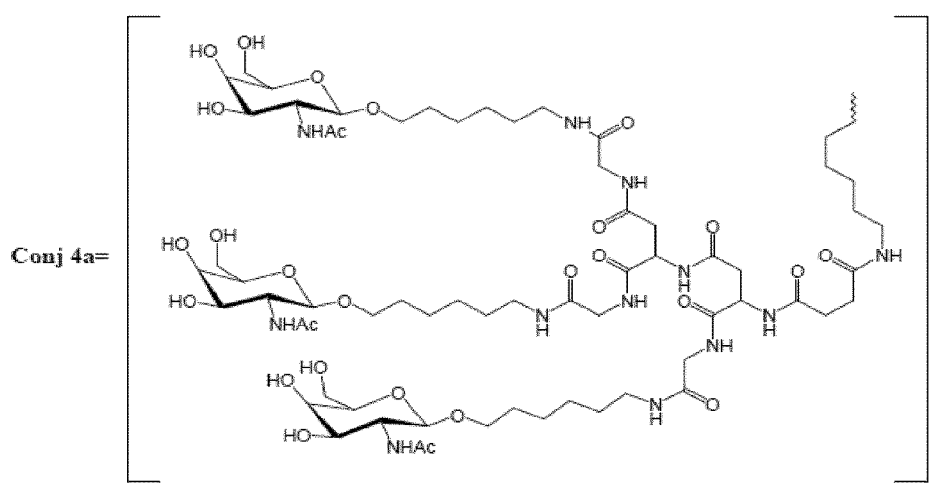

See the figures for specific GalNac clusters used in the present study, Conj 1, 2, 3, 4 and Conj1a, 2a, 3a and 4a (which are shown with an optional C6 linker which joins the GalNac cluster to the oligomer—See FIGS. 12 and 17).

Each carbohydrate moiety of a GalNac cluster (e.g. GalNAc) may therefore be joined to the oligomer via a spacer, such as (poly)ethylene glycol linker (PEG), such as a di, tri, tetra, penta, hexa-ethylene glycol linker. As is shown above the PEG moiety forms a spacer between the galactose sugar moiety and a peptide (trilysine is shown) linker.

In some embodiments, the GalNac cluster comprises a peptide linker, e.g. a Tyr-Asp(Asp) tripeptide or Asp(Asp) dipeptide, which is attached to the oligomer (or to region Y or region B) via a biradical linker, for example the GalNac cluster may comprise the following biradical linkers:

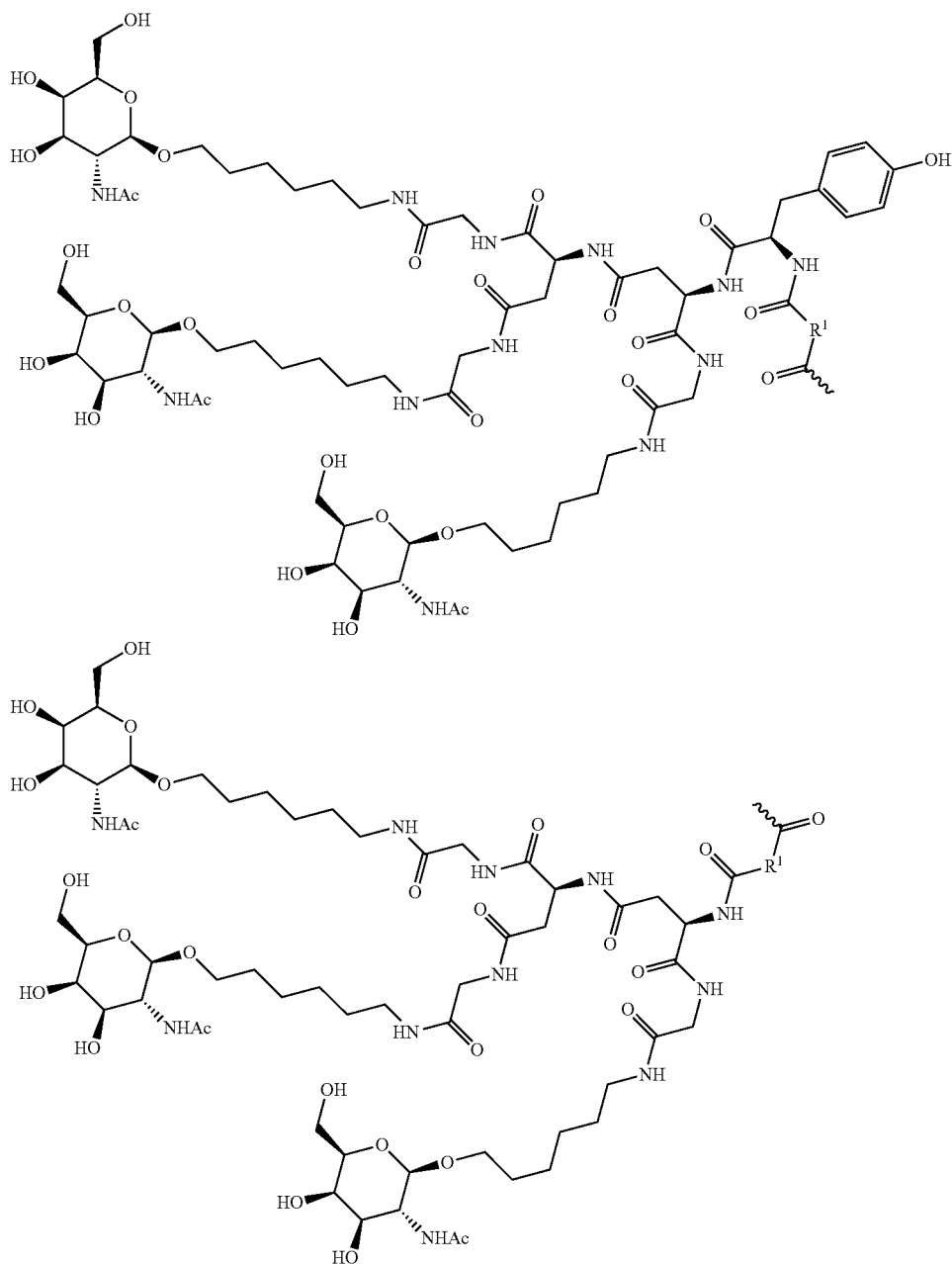

$R^1$ is a biradical preferably selected from —$C_2H_4$—, —$C_3H_6$—, —$C_4H_8$—, —$C_5H_{10}$—, —$C_6H_{12}$—, 1,4-cyclohexyl (—$C_6H_{10}$—), 1,4-phenyl (—$C_6H_4$—), —$C_2H_4OC_2H_4$—, —$C_2H_4(OC_2H_4)_2$— or —$C_2H_4(OC_2H_4)_3$—.

In addition, the carbohydrate conjugate (e.g. GalNAc), or carbohydrate-linker moiety (e.g. carbohydrate-PEG moiety) may be covalently joined (linked) to the oligomer (or region B) via a branch point group such as, an amino acid, or peptide, which suitably comprises two or more amino groups (such as 3, 4, or 5), such as lysine, di-lysine or tri-lysine or tetra-lysine. A tri-lysine molecule contains four amine groups through which three carbohydrate conjugate groups, such as galactose & derivatives (e.g. GalNAc) and a further conjugate such as a hydrophobic or lipophilic moiety/group may be attached and a carboxyl reactive group through which the tri-lysine may be attached to the oligomer. The further conjugate, such as lipophilic/hydrophobic moiety may be attached to the lysine residue that is attached to the oligomer. In some embodiments, the conjugate (C) is not a monovalent GalNac.

The invention also provides LNA antisense oligonucleotides which are conjugated to an asialoglycoprotein receptor targeting moiety. In some embodiments, the conjugate moiety (such as the third region or region C) comprises an asialoglycoprotein receptor targeting moiety, such as galactose, galactosamine, N-formyl-galactosamine, Nacetylgalactosamine, N-propionyl-galactosamine, N-n-butanoyl-galactosamine, and N-isobutanoylgalactos-amine. In some embodiments the conjugate comprises a galactose cluster, such as N-acetylgalactosamine trimer. In some embodiments, the conjugate moiety comprises a GalNac (N-acetylgalactosamine), such as a mono-valent, di-valent, tri-valent of tetra-valent GalNac. Trivalent GalNac conjugates may be used to target the compound to the liver. GalNac conjugates have been used with methylphosphonate and PNA antisense oligonucleotides (e.g. U.S. Pat. No. 5,994,517 and Hangeland et al., Bioconjug Chem. 1995 November-December; 6(6):695-701) and siRNAs (e.g. WO2009/126933, WO2012/089352 & WO2012/083046). The GalNac references and the specific conjugates used therein are hereby incorporated by reference. WO2012/083046 discloses GalNac conjugate moieties which comprise cleavable pharmacokinetic modulators, the preferred pharmacokinetic modulators are C16 hydrophobic groups such as palmitoyl, hexadec-8-enoyl, oleyl, (9E,12E)-octadeca-9,12-dienoyl, dioctanoyl, and C16-C20 acyl. The '046 cleavable pharmacokinetic modulators may also be cholesterol. The '046 targeting moieties may be selected from the group consisting of: galactose, galactosamine, N-formyl-galactosamine, N-acetylgalactosamine, Npropionyl-galactosamine, N-n-butanoyl-galactosamine, N-iso-butanoylgalactos-amine, galactose cluster, and N-acetylgalactosamine trimer and may have a pharmacokinetic modulator selected from the group consisting of: hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. Certain GalNac clusters disclosed in '046 include: (E)-hexadec-8-enoyl (016), oleyl (C18), (9,E,12E)-octadeca-9,12-dienoyl (C18), octanoyl (C8), dodececanoyl (C12), C-20 acyl, C24 acyl, dioctanoyl (2×C8). According to '046, the targeting moiety-pharmacokinetic modulator targeting moiety may be linked to the polynucleotide via a physiologically labile bond or, e.g. a disulfide bond, or a PEG linker.

Other conjugate moieties can include, for example, oligosaccharides and carbohydrate clusters such as Tyr-Glu-Glu-(aminohexyl GalNAc)3 (YEE(ahGalNAc)3; a glycotripeptide that binds to Gal/GalNAc receptors on hepatocytes, see, e.g., Duff, et al., Methods Enzymol, 2000, 313, 297); lysine-based galactose clusters (e.g., L3G4; Biessen, et al., Cardovasc. Med., 1999, 214); and cholane-based galactose clusters (e.g., carbohydrate recognition motif for asialoglycoprotein receptor). Further suitable conjugates can include oligosaccharides that can bind to carbohydrate recognition domains (CRD) found on the asiologlycoprotein-receptor (ASGP-R). Example conjugate moieties containing oligosaccharides and/or carbohydrate complexes are provided in U.S. Pat. No. 6,525,031, which is incorporated herein by reference in its entirety.

Pharmacokinetic Modulators

The compound of the invention may further comprise one or more additional conjugate moieties, of which lipophilic or hydrophobic moieties are particularly interesting, such as when the conjugate group is a carbohydrate moiety. Such lipophilic or hydrophobic moieties may act as pharmacokinetic modulators, and may be covalently linked to either the carbohydrate conjugate, a linker linking the carbohydrate conjugate to the oligomer or a linker linking multiple carbohydrate conjugates (multi-valent) conjugates, or to the oligomer, optionally via a linker, such as a bio cleavable linker.

The oligomer or conjugate moiety may therefore comprise a pharmacokinetic modulator, such as a lipophilic or hydrophobic moieties. Such moieties are disclosed within the context of siRNA conjugates in WO2012/082046. The hydrophobic moiety may comprise a C8-C36 fatty acid, which may be saturated or un-saturated. In some embodiments, C10, C12, C14, C16, C18, C20, C22, C24, C26, C28, C30, C32 and C34 fatty acids may be used. The hydrophobic group may have 16 or more carbon atoms. Exemplary suitable hydrophobic groups may be selected from the group comprising: sterol, cholesterol, palmitoyl, hexadec-8-enoyl, oleyl, (9E,12E)-octadeca-9,12-dienoyl, dioctanoyl, and C16-C20 acyl. According to WO'346, hydrophobic groups having fewer than 16 carbon atoms are less effective in enhancing polynucleotide targeting, but they may be used in multiple copies (e.g. 2×, such as 2×C8 or C10, C12 or C14) to enhance efficacy. Pharmacokinetic modulators useful as polynucleotide targeting moieties may be selected from the group consisting of: cholesterol, alkyl group, alkenyl group, alkynyl group, aryl group, aralkyl group, aralkenyl group, and aralkynyl group, each of which may be linear, branched, or cyclic. Pharmacokinetic modulators are preferably hydrocarbons, containing only carbon and hydrogen atoms. However, substitutions or heteroatoms which maintain hydrophobicity, for example fluorine, may be permitted.

Surprisingly, the present inventors have found that Gal-Nac conjugates for use with LNA oligomers do not require a pharmacokinetic modulator, and as such, in some embodiments, the GalNac conjugate is not covalently linked to a lipophilic or hydrophobic moiety, such as those described here in, e.g. do not comprise a C8-C36 fatty acid or a sterol. The invention therefore also provides for LNA oligomer GalNac conjugates which do not comprise a lipophilic or hydrophobic pharmacokinetic modulator or conjugate moiety/group.

Lipophilic Conjugates

The compounds of the invention may be conjugates comprising of the oligomer (A) and a lipophilic conjugate (C). The biocleavable linker (B) has found to be particularly effective in maintaining or enhancing the activity of such oligomer conjugates. In some embodiments the conjugate group (C) and or linker group (Y) comprises a lipophilic group.

Representative conjugate moieties can include lipophilic molecules (aromatic and non-aromatic) including sterol and steroid molecules. Lipophilic conjugate moieties can be used, for example, to counter the hydrophilic nature of an oligomeric compound and enhance cellular penetration. Lipophilic moieties include, for example, steroids and related compounds such as cholesterol (U.S. Pat. No. 4,958,013 and Letsinger et al., Proc. Natl. Acad. Sci. USA, 1989, 86, 6553), thiocholesterol (Oberhauser et al, Nucl Acids Res., 1992, 20, 533), lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone, 17-hydroxycorticosterone, their derivatives, and the like.

Other lipophilic conjugate moieties include aliphatic groups, such as, for example, straight chain, branched, and cyclic alkyls, alkenyls, and alkynyls. The aliphatic groups can have, for example, 5 to about 50, 6 to about 50, 8 to about 50, or 10 to about 50 carbon atoms. Example aliphatic groups include undecyl, dodecyl, hexadecyl, heptadecyl, octadecyl, nonadecyl, terpenes, bornyl, adamantyl, derivatives thereof and the like. In some embodiments, one or more carbon atoms in the aliphatic group can be replaced by a heteroatom such as O, S, or N (e.g., geranyloxyhexyl). Further suitable lipophilic conjugate moieties include aliphatic derivatives of glycerols such as alkylglycerols, bis (alkyl)glycerols, tris(alkyl)glycerols, monoglycerides, diglycerides, and triglycerides. In some embodiments, the lipophilic conjugate is di-hexyldecyl-rac-glycerol or 1,2-di-O-hexyldecyl-rac-glycerol (Manoharan et al., Tetrahedron Lett., 1995, 36, 3651; Shea, et al., Nuc. Acids Res., 1990, 18, 3777) or phosphonates thereof. Saturated and unsaturated fatty functionalities, such as, for example, fatty acids, fatty alcohols, fatty esters, and fatty amines, can also serve as lipophilic conjugate moieties. In some embodiments, the fatty functionalities can contain from about 6 carbons to about 30 or about 8 to about 22 carbons. Example fatty acids include, capric, caprylic, lauric, palmitic, myristic, stearic, oleic, linoleic, linolenic, arachidonic, eicosenoic acids and the like.

In further embodiments, lipophilic conjugate groups can be polycyclic aromatic groups having from 6 to about 50, 10 to about 50, or 14 to about 40 carbon atoms. Example polycyclic aromatic groups include pyrenes, purines, acridines, xanthenes, fluorenes, phenanthrenes, anthracenes, quinolines, isoquinolines, naphthalenes, derivatives thereof and the like. [0037] Other suitable lipophilic conjugate moieties include menthols, trityls (e.g., dimethoxytrityl (DMT)), phenoxazines, lipoic acid, phospholipids, ethers, thioethers (e.g., hexyl-S-tritylthiol), derivatives thereof and the like. Preparation of lipophilic conjugates of oligomeric compounds are well-described in the art, such as in, for example, Saison-Behmoaras et al, EMBO J., 1991, 10, 1111; Kabanov et al., FEBSLett., 1990, 259, 327; Svinarchuk et al., Biochimie, 1993, 75, 49; (Mishra et al., Biochim. Biophys. Acta, 1995, 1264, 229, and Manoharan et al., Tetrahedron Lett., 1995, 36, 3651.

Oligomeric compounds containing conjugate moieties with affinity for low density lipoprotein (LDL) can help provide an effective targeted delivery system. High expression levels of receptors for LDL on tumor cells makes LDL an attractive carrier for selective delivery of drugs to these cells (Rump, et al., Bioconjugate Chem., 1998, 9, 341; Firestone, Bioconjugate Chem., 1994, 5, 105; Mishra, et al., Biochim. Biophys. Acta, 1995, 1264, 229). Moieties having affinity for LDL include many lipophilic groups such as steroids (e.g., cholesterol), fatty acids, derivatives thereof and combinations thereof. In some embodiments, conjugate moieties having LDL affinity can be dioleyl esters of cholic acids such as chenodeoxycholic acid and lithocholic acid.

In some embodiments, the conjugate group is or may comprise a lipophilic moiety, such as a sterol (for example, cholesterol, cholesteryl, cholestanol, stigmasterol, cholanic acid and ergosterol). In some embodiments, the conjugate is or may comprise cholesterol. See for example, Soutschek et al., Nature (2004) 432, 173; Krützfeldt Nature 2005, NAR 2007.

In some embodiments, the conjugate is, or may comprise a lipid, a phospholipid or a lipophilic alcohol, such as a cationic lipids, a neutral lipids, sphingolipids, and fatty acids such as stearic, oleic, elaidic, linoleic, linoleaidic, linolenic, and myristic acids. In some embodiments the fatty acid comprises a C4-C30 saturated or unsaturated alkyl chain. The alkyl chain may be linear or branched.

In some embodiments, the lipophilic conjugates may be or may comprise biotin. In some embodiments, the lipophilic conjugate may be or may comprise a glyceride or glyceride ester.

Lipophilic conjugates, such as cholesterol or as disclosed herein, may be used to enhance delivery of the oligonucleotide to, for example, the liver (typically hepatocytes).

The following references refer to the use of lipophilic conjugates: Kobylanska et al., Acta Biochim Pol. (1999); 46(3): 679-91. Felber et al, Biomaterials (2012) 33(25): 599-65); Grijalvo et al., J Org Chem (2010) 75(20): 6806-13. Koufaki et al., Curr Med Chem (2009) 16(35): 4728-42. Godeau et al J. Med. Chem. (2008) 51(15): 4374-6.

Polymer Conjugates

Conjugate moieties can also include polymers. Polymers can provide added bulk and various functional groups to affect permeation, cellular transport, and localization of the conjugated oligomeric compound. For example, increased hydrodynamic radius caused by conjugation of an oligomeric compound with a polymer can help prevent entry into the nucleus and encourage localization in the cytoplasm. In some embodiments, the polymer does not substantially reduce cellular uptake or interfere with hybridization to a complementary strand or other target. In further embodiments, the conjugate polymer moiety has, for example, a molecular weight of less than about 40, less than about 30, or less than about 20 kDa. Additionally, polymer conjugate moieties can be water-soluble and optionally further comprise other conjugate moieties such as peptides, carbohydrates, drugs, reporter groups, or further conjugate moieties.

In some embodiments, polymer conjugates include polyethylene glycol (PEG) and copolymers and derivatives thereof. Conjugation to PEG has been shown to increase nuclease stability of an oligomeric compound. PEG conjugate moieties can be of any molecular weight including for example, about 100, about 500, about 1000, about 2000, about 5000, about 10,000 and higher. In some embodiments, the PEG conjugate moieties contains at least 4, at least 5, at least 6, at least 7, at least 8, at least 9, at least 10, at least 15, at least 20, or at least 25 ethylene glycol residues. In further embodiments, the PEG conjugate moiety contains from about 4 to about 10, about 4 to about 8, about 5 to about 7, or about 6 ethylene glycol residues. The PEG conjugate moiety can also be modified such that a terminal hydroxyl is replaced by alkoxy, carboxy, acyl, amido, or other functionality. Other conjugate moieties, such as reporter groups including, for example, biotin or fluorescein can also be attached to a PEG conjugate moiety. Copolymers of PEG are also suitable as conjugate moieties. [0047] Preparation and biological activity of polyethylene glycol conjugates of oligonucleotides are described, for example, in Bonora, et al., Nucleosides Nucleotides, 1999, 18, 1723; Bonora, et al., Farmaco, 1998, 53, 634; Efimov, Bioorg. Khim. 1993, 19, 800; and Jaschke, et al, Nucleic Acids Res., 1994, 22, 4810. Further example PEG conjugate moieties and preparation of corresponding conjugated oligomeric compounds is described in, for example, U.S. Pat. Nos. 4,904,582 and 5,672,662, each of which is incorporated by reference herein in its entirety. Oligomeric compounds conjugated to one or more PEG moieties are available commercially.

Other polymers suitable as conjugate moieties include polyamines, polypeptides, polymethacrylates (e.g., hydroxylpropyl methacrylate (HPMA)), poly(L-lactide), poly(DL lactide-co-glycolide (PGLA), polyacrylic acids, polyethylenimines (PEI), polyalkylacrylic acids, polyurethanes, polyacrylamides, N-alkylacrylamides, polyspermine (PSP), polyethers, cyclodextrins, derivatives thereof and co-polymers thereof. Many polymers, such as PEG and polyamines have receptors present in certain cells, thereby facilitating cellular uptake. Polyamines and other amine-containing polymers can exist in protonated form at physiological pH, effectively countering an anionic backbone of some oligomeric compounds, effectively enhancing cellular permeation. Some example polyamines include polypeptides (e.g., polylysine, polyornithine, polyhistadine, polyarginine, and copolymers thereof), triethylenetetraamine, spermine, polyspermine, spermidine, synnorspermidine, C-branched spermidine, and derivatives thereof. Preparation and biological activity of polyamine conjugates are described, for example, in Guzaev, et al, Bioorg. Med. Chem. Lett., 1998, 8, 3671;

Corey, et al, J Am. Chem. Soc, 1995, 117, 9373; and Prakash, et al, Bioorg. Med. Chem. Lett. 1994, 4, 1733. Example polypeptide conjugates of oligonucleotides are provided in, for example, Wei, et al., Nucleic Acids Res., 1996, 24, 655 and Zhu, et al., Antisense Res. Dev., 1993, 3, 265. Dendrimeric polymers can also be used as conjugate moieties, such as described in U.S. Pat. No. 5,714,166, which is incorporated herein by reference in its entirety.

[0049] As discussed above for polyamines and related polymers, other amine-containing moieties can also serve as suitable conjugate moieties due to, for example, the formation of cationic species at physiological conditions. Example amine-containing moieties include 3-aminopropyl, 3-(N,N-dimethylamino)propyl, 2-(2-(N,N-dimethylamino)ethoxy)ethyl, 2-(N-(2-aminoethyl)-N-methylaminooxy)ethyl, 2-(1-imidazolyl)ethyl, and the like. The G-clamp moiety can also serve as an amine-containing conjugate moiety (Lin, et al., J. Am. Chem. Soc, 1998, 120, 8531).

In some embodiments, the conjugate may be, or may comprise a polymer, such as a polymer selected from the group consisting of polyethyleneglycol (PEG), polyamidoamine (PAA), polyethylene oxide and polyethylenimine (PEI). Galactose, lactose, n-acetylgalactosamine, mannose, mannose-6-phosphate n some embodiments, the polymer is a polycationic polymer. In some embodiments, conjugate moieties can be, or based on (include) cationic polymers. Numerous studies have demonstrated that cationic polymers such as cationic albumin can greatly enhance delivery to particular cell types and/or tissues (e.g. brain delivery, see Lu, W. et. al. (2005) J of Control Release 107:428-448). Given the benefits of these molecules, the conjugate moieties can be cationic polymers such as polyethyleneimine, dendrimers, poly(alkylpyridinium) salts, or cationic albumin. In some embodiments is a hydrophilic polymer. In some embodiments, the polymer is Poly(vinylpyrrolidone) (PVP). In some embodiments, the polymer is a polyamine or polyamide (e.g. U.S. Pat. No. 7,816,337 & U.S. Pat. No. 5,525,465. For polymer conjugates see for example, Zhao et al., Bioconjugate Chem 2005, 16, 758-766); Kim et al., J. Control Release (2006) 116; 123. Pettit et al., Ther. Deliv. (2011) 2(7): 907-17. Yang et al., Bioconjug Chem (2009) 20(2): 213-21. Winkler et al (2009) Eur J Med Chem 44(2): 670-7. Zelikin et al, Biomacromolecules (2007) 8(9): 2950-3. See also WO12092373 which refers to enzyme cleavable polynucleotide delivery conjugates.

Protein and Peptide Conjugates

Other conjugate moieties can include proteins, subunits, or fragments thereof. Proteins include, for example, enzymes, reporter enzymes, antibodies, receptors, and the like. In some embodiments, protein conjugate moieties can be antibodies or fragments thereof (Kuijpers, et al, Bioconjugate Chem., 1993, 4, 94). Antibodies can be designed to bind to desired targets such as tumor and other disease-related antigens. In further embodiments, protein conjugate moieties can be serum proteins such as HAS or glycoproteins such as asialoglycoprotein (Rajur, et al., Bioconjugate Chem., 1997, 6, 935). In yet further embodiments, oligomeric compounds can be conjugated to RNAi-related proteins, RNAi-related protein complexes, subunits, and fragments thereof. For example, oligomeric compounds can be conjugated to Dicer or RISC. [0067] Intercalators and minor groove binders (MGBs) can also be suitable as conjugate moieties. In some embodiments, the MGB can contain repeating DPI (1,2-dihydro-3H-pyrrolo(2,3-e)indole-7-carboxylate) subunits or derivatives thereof (Lukhtanov, et al., Bioconjugate Chem., 1996, 7, 564 and Afonina, et al., Proc. Natl. Acad. Sci. USA, 1996, 93, 3199). Suitable intercalators include, for example, polycyclic aromatics such as naphthalene, perylene, phenanthridine, benzophenanthridine, phenazine, anthraquinone, acridine, and derivatives thereof. Hybrid intercalator/ligands include the photonuclease/intercalator ligand 6-[[[9-[[6-(4-nitrobenzamido)hexyl]amino]acridin-4-yl]carbonyl]amino]hexanoyl-pentafluorophenyl ester. This compound is both an acridine moiety that is an intercalator and a p-nitro benzamido group that is a photonuclease. [0069] In further embodiments, cleaving agents can serve as conjugate moieties. Cleaving agents can facilitate degradation of target, such as target nucleic acids, by hydrolytic or redox cleavage mechanisms. Cleaving groups that can be suitable as conjugate moieties include, for example, metallocomplexes, peptides, amines, enzymes, and constructs containing constituents of the active sites of nucleases such as imidazole, guanidinium, carboxyl, amino groups, etc.). Example metallocomplexes include, for example, Cu-terpyridyl complexes, Fe-porphyrin complexes, Ru-complexes, and lanthanide complexes such as various Eu(III) complexes (Hall, et al., Chem. Biol, 1994, 1, 185; Huang, et al., J. Biol. Inorg. Chem., 2000, 5, 85; and Baker, et al, Nucleic Acids Res., 1999, 27, 1547). Other metallocomplexes with cleaving properties include metalloporphyrins and derivatives thereof. Example peptides with target cleaving properties include zinc fingers (U.S. Pat. No. 6,365,379; Lima, et al., Proc. Natl. Acad. Sci. USA, 1999, 96, 10010). Example constructs containing nuclease active site constituents include bisimiazole and histamine.

Conjugate moieties can also include peptides. Suitable peptides can have from 2 to about 30, 2 to about 20, 2 to about 15, or 2 to about 10 amino acid residues. Amino acid residues can be naturally or non-naturally occurring, including both D and L isomers. In some embodiments, peptide conjugate moieties are pH sensitive peptides such as fusogenic peptides. Fusogenic peptides can facilitate endosomal release of agents such as oligomeric compounds to the cytoplasm. It is believed that fusogenic peptides change conformation in acidic pH, effectively destabilizing the endosomal membrane thereby enhancing cytoplasmic delivery of endosomal contents. Example fusogenic peptides include peptides derived from polymyxin B, influenza HA2, GALA, KALA, EALA, melittin-derived peptide, a-helical peptide or Alzheimer beta-amyloid peptide, and the like. Preparation and biological activity of oligonucleotides conjugated to fusogenic peptides are described in, for example, Bongartz, et al., Nucleic Acids Res., 1994, 22, 4681 and U.S. Pat. Nos. 6,559,279 and 6,344,436. Other peptides that can serve as conjugate moieties include delivery peptides which have the ability to transport relatively large, polar molecules (including peptides, oligonucleotides, and proteins) across cell membranes. Example delivery peptides include Tat peptide from HIV Tat protein and Ant peptide from *Drosophila* antenna protein. Conjugation of Tat and Ant with oligonucleotides is described in, for example, Astriab-Fisher, et al., Biochem. Pharmacol, 2000, 60, 83. These and other delivery peptides that can be used as conjugate moieties are provided below in Table I:

Conjugated delivery peptides can help control localization of oligomeric compounds to specific regions of a cell, including, for example, the cytoplasm, nucleus, nucleolus, and endoplasmic reticulum (ER). Nuclear localization can be effected by conjugation of a nuclear localization signal (NLS). In contrast, cytoplasmic localization can be facilitated by conjugation of a nuclear export signal (NES). [0054] Peptides suitable for localization of conjugated oligomeric compounds in the nucleus include, for example, N,N-dipalmitylglycyl-apo E peptide or N,N-dipalmitylglycyl-apolipoprotein E peptide (dpGapoE) (Liu, et al, Arterioscler. Thromb. Vasc. Biol, 1999, 19, 2207; Chaloin, et al., Biochem. Biophys. Res. Commun., 1998, 243, 601). Nucleus or nucleolar localization can also be facilitated by peptides having arginine and/or lysine rich motifs, such as in HIV-1 Tat, FXR2P, and angiogenin derived peptides (Lixin, et al, Biochem. Biophys. Res. Commun., 2001, 284, 185). Additionally, the nuclear localization signal (NLS) peptide derived from SV40 antigen T (Branden, et al., Nature Biotech, 1999, 17, 784) can be used to deliver conjugated oligomeric compounds to the nucleus of a cell. Other suitable peptides with nuclear or nucleolar localization properties are described in, for example, Antopolsky, et al., Bioconjugate Chem., 1999, 10, 598; Zanta, et al., Proc. Natl. Acad. Sci. USA, 1999 (simian virus 40 large tumor antigen); Hum. Mol. Genetics, 2000, 9, 1487; and FEBSLett., 2002, 532, 36).

In some embodiments, the delivery peptide for nucleus or nucleolar localization comprises at least three consecutive arginine residues or at least four consecutive arginine residues. Nuclear localization can also be facilitated by peptide conjugates containing RS, RE, or RD repeat motifs (Cazalla, et al., Mol Cell. Biol, 2002, 22, 6871). In some embodiments, the peptide conjugate contains at least two RS, RE, or RD motifs.

Localization of oligomeric compounds to the ER can be effected by, for example, conjugation to the signal peptide KDEL (SEQ ID NO: 18) (Arar, et al., Bioconjugate Chem., 1995, 6, 573; Pichon, et al., Mol. Pharmacol. 1997, 57, 431). [0057] Cytoplasmic localization of oligomeric compounds can be facilitated by conjugation to peptides having, for example, a nuclear export signal (NES) (Meunier, et al., Nucleic Acids Res., 1999, 27, 2730). NES peptides include the leucine-rich NES peptides derived from HIV-1 Rev (Henderson, et al., Exp. Cell Res., 2000, 256, 213), transcription factor III A, MAPKK, PKI-alpha, cyclin BI, and actin (Wada, et al., EMBO J., 1998, 17, 1635) and related proteins. Antimicrobial peptides, such as dermaseptin derivatives, can also facilitate cytoplasmic localization (Hariton-Gazal, et al., Biochemistry, 2002, 41, 9208). Peptides containing RG and/or KS repeat motifs can also be suitable for directing oligomeric compounds to the cytoplasm. In some embodiments, the peptide conjugate moieties contain at least two RG motifs, at least two KS motifs, or at least one RG and one KS motif. [0058] As used throughout, "peptide" includes not only the specific molecule or sequence recited herein (if present), but also includes fragments thereof and molecules comprising all or part of the recited sequence, where desired functionality is retained. In some embodiments, peptide fragments contain no fewer than 6 amino acids. Peptides can also contain conservative amino acid substitutions that do not substantially change its functional characteristics. Conservative substitution can be made among the following sets of functionally similar amino acids: neutral-weakly hydrophobic (A, G, P, S, T), hydrophilic-acid amine (N, D, Q, E), hydrophilic-basic (I, M, L, V), and hydrophobic-aromatic (F, W, Y). Peptides also include homologous peptides. Homology can be measured according to percent identify using, for example, the BLAST algorithm (default parameters for short sequences). For example, homologous peptides can have greater than 50, 60, 70, 80, 90, 95, or 99 percent identity. Methods for conjugating peptides to oligomeric compounds such as oligonucleotides is described in, for example, U.S. Pat. No. 6,559,279, which is incorporated herein by reference in its entirety.

In some embodiments, the conjugate moiety is or comprises a protein or peptide. In some embodiments the peptide is a cell penetrating peptides, e.g. Penetratin, transportan, Peptaibol (e.g. trichorovin-XIIa (TV-XIIa)), TAT peptide (HIV). In some embodiments, the peptide is polyarginine (e.g. stearyl-(RxR)(4)). In some embodiments the peptide is N-(2-hydroxypropyl) methacrylamide (HPMA) containing tetrapeptide Gly-Phe-Leu-Gly (GFLG). In some embodiments, the peptide is a beta-amyloid peptide. In some embodiments the protein or peptide in an antibody or antigen binding site containing fragment thereof (epitope binding site). In some embodiments the conjugate is or comprises M6P-HPMA-GFLG (see Yang et al 2009). In some embodiments, the conjugate is or comprises arginine rich peptides (WO2005/115479)—see also WO09005793 RGD peptides. In some embodiments, the conjugate is or comprises a protein carrier (e.g. albumin, albumin-PEG conjugate—RGD-PEG-albumin) (Kang et al) see also WO09045536. In some embodiments, the conjugate is or comprises histidylated oligolysine (e.g. WO0032764). In some embodiments, the conjugate is or comprises Glycoproteins: transferrin-polycation (e.g. U.S. Pat. No. 5,354,844, WO9217210, WO9213570). In some embodiments, the conjugate is or comprises asialoglycoprotein (U.S. Pat. No. 5,346,696). In some embodiments, the conjugate is or comprises a polycationic protein (e.g. U.S. Pat. No. 603,095). In some embodiments, the conjugate is or comprises polypseudo-lysine conjugates (e.g. WO07113531).

Reporter and Dye Conjugate Groups

Reporter groups that are suitable as conjugate moieties include any moiety that can be detected by, for example, spectroscopic means. Example reporter groups include dyes, flurophores, phosphors, radiolabels, and the like. In some embodiments, the reporter group is biotin, flourescein, rhodamine, coumarin, or related compounds. Reporter groups can also be attached to other conjugate moieties. In some embodiments, the conjugate is or comprises a label or dye, such as a fluorophore, such as FAM (Carboxyfluorescein).

Cross-linking agents can also serve as conjugate moieties. Cross-linking agents facilitate the covalent linkage of the conjugated oligomeric compounds with other compounds. In some embodiments, cross-linking agents can covalently link double-stranded nucleic acids, effectively increasing duplex stability and modulating pharmacokinetic properties. In some embodiments, cross-linking agents can be photoactive or redox active. Example cross-linking agents include psoralens which can facilitate interstrand cross-linking of nucleic acids by photoactivation (Lin, et al, Faseb J, 1995, 9, 1371). Other cross-linking agents include, for example, mitomycin C and analogs thereof (Maruenda, et al., Bioconjugate Chem., 1996, 7, 541; Maruenda, et al., Anti-Cancer Drug Des., 1997, 12, 473; and Huh, et al, Bioconjugate Chem., 1996, 7, 659). Cross-linking mediated by mitomycin C can be effected by reductive activation, such as, for example, with biological reductants (e.g., NADPH-cytochrome c reductase/NADPH system). Further photocrosslinking agents include aryl azides such as, for example, N-hydroxysucciniimidyl-4-azidobenzoate (HSAB) and N-succinimidyl-6-(4'-azido-2'-nitrophenyl-amino)hexanoate (SANPAH). Aryl azides conjugated to oligonucleotides effect crosslinking with nucleic acids and proteins upon irradiation. They can also crosslink with earner proteins (such as KLH or BSA).

Various Functional Conjugate Groups

Other suitable conjugate moieties include, for example, polyboranes, carboranes, metallopolyboranes, metallocarborane, derivatives thereof and the like (see, e.g., U.S. Pat. No. 5,272,250, which is incorporated herein by reference in its entirety).

Many drugs, receptor ligands, toxins, reporter molecules, and other small molecules can serve as conjugate moieties. Small molecule conjugate moieties often have specific interactions with certain receptors or other biomolecules, thereby allowing targeting of conjugated oligomeric compounds to specific cells or tissues. Example small molecule conjugate moieties include mycophenolic acid (inhibitor of inosine-5'-monophosphate dihydrogenase; useful for treating psoriasis and other skin disorders), curcumin (has therapeutic applications to psoriasis, cancer, bacterial and viral diseases). In further embodiments, small molecule conjugate moieties can be ligands of serum proteins such as human serum albumin (HSA). Numerous ligands of HSA are known and include, for example, arylpropionic acids, ibuprofen, warfarin, phenylbutazone, suprofen, carprofen, fenfufen, ketoprofen, aspirin, indomethacin, (S)-(+)-pranoprofen, dansylsarcosine, 2,3,5-triiodobenzoic acid, flufenamic acid, folinic acid, benzothiadiazide, chlorothiazide, diazepines, indomethicin, barbituates, cephalosporins, sulfa drugs, antibacterials, antibiotics (e.g., puromycin and pamamycin), and the like. Oligonucleotide-drug conjugates and their preparation are described in, for example, WO 00/76554, which is incorporated herein by reference in its entirety.

In some embodiments, the conjugate may be or comprise a small molecule, such as a small molecule drug or pro-drug. Certain drugs are highly effective at targeting specific target tissue or cells, and as such they may be used to target an oligonucleotide to its intended site of action. Furthermore, the small molecule may in itself have a therapeutic activity, typically once cleaved from the oligonucleotide component of the conjugate. Examples include bisphosphonates (widely used for the treatment of osteoporosis and effective in targeting bone tissues), anti-cancer drugs and chemotherapeutic agents (e.g. doxorubicin or mitomycein C—see U.S. Pat. No. 5,776,907). In some embodiments, the drug may be a nucleoside analogue, such as a nucleoside polymerase inhibitor.

In yet further embodiments, small molecule conjugates can target or bind certain receptors or cells. T-cells are known to have exposed amino groups that can form Schiff base complexes with appropriate molecules. Thus, small molecules containing functional groups such as aldehydes that can interact or react with exposed amino groups can also be suitable conjugate moieties. Tucaresol and related compounds can be conjugated to oligomeric compounds in such a way as to leave the aldehyde free to interact with T-cell targets. Interaction of tucaresol with T-cells in believed to result in therapeutic potentiation of the immune system by Schiff-base formation (Rhodes, et al., Nature, 1995, 377, 6544).

In some embodiments, the conjugate is or comprises a (e.g. cell surface) receptor ligand. In some embodiments the conjugate is or comprises a folate receptor ligand, such as a folic acid group—see for example, EP1572067 or WO2005/069994, WO2010/045584). Other cell surface receptor ligands include antibodies and fragments thereof, prostate-specific membrane antigen, neuron surface antigens (see WO2011/131693)

In some embodiments, the conjugate moieties are ligands for receptors or can associate with molecules that (in turn) associate with receptors. Included in this class are bile acids, small molecule drug ligands, vitamins, aptamers, carbohydrates, peptides (including but not limited to hormones, proteins, protein fragments, antibodies or antibody fragments), viral proteins (e.g. capsids), toxins (e.g. bacterial toxins), and more. Also included in this class are conjugates that are steroidal in nature e.g. cholesterol, cholestanol, cholanic acid, stigmasterols, pregnolones, progesterones, corticosterones, aldosterones, testosterones, estradiols, ergosterols, and more), Preferred conjugate moieties of the disclosure are cholesterol (CHOL), cholestanol (CHLN), cholanic acid (CHLA), stigmasterol (STIG), and ergosterol (ERGO). In certain preferred embodiments, the conjugate moiety is cholesterol.

In some embodiments the conjugate comprises a sterol, such as cholesterol or tocopherol, optionally including a linker, such as a fatty acid linker, e.g. a C6 linker. In some embodiments the conjugates comprise Conj5a or Conj 6a.

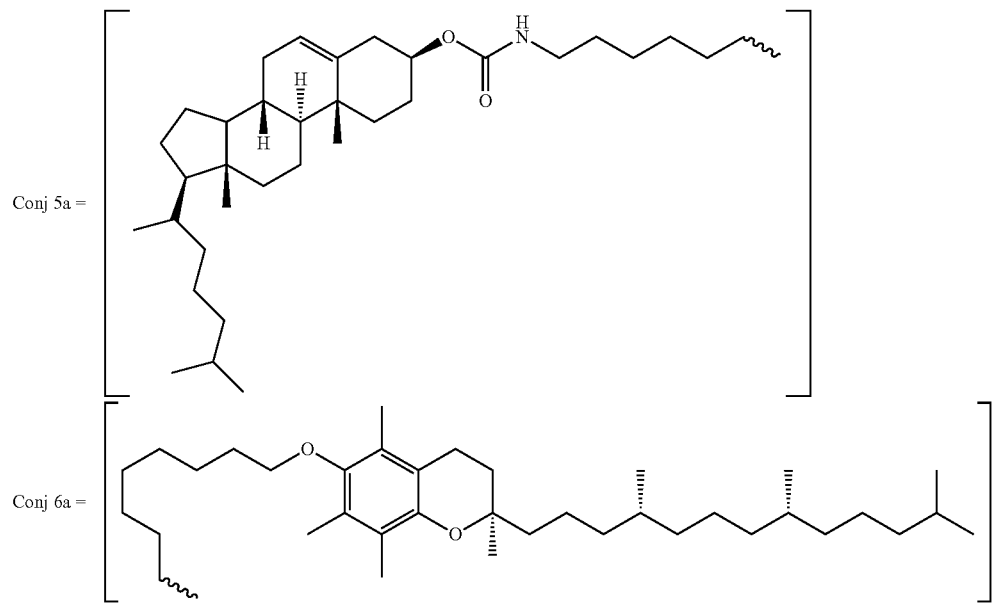

Conjugate moieties can also include vitamins. Vitamins are known to be transported into cells by numerous cellular transport systems. Typically, vitamins can be classified as water soluble or lipid soluble. Water soluble vitamins include thiamine, riboflavin, nicotinic acid or niacin, the vitamin B6 pyridoxal group, pantothenic acid, biotin, folic acid, the B]2 cobamide coenzymes, inositol, choline and ascorbic acid. Lipid soluble vitamins include the vitamin A family, vitamin D, the vitamin E tocopherol family and vitamin K (and phytols). Related compounds include retinoid derivatives such as tazarotene and etretinate. [0040] In some embodiments, the conjugate moiety includes folic acid folate) and/or one or more of its various forms, such as dihydrofolic acid, tetrahydrofolic acid, folinic acid, pteropolyglutamic acid, dihydrofolates, tetrahydrofolates, tetrahydropterins, 1-deaza, 3-deaza, 5-deaza, 8-deaza, 10-deaza, 1,5-dideaza, 5,10-dideaza, 8,10-dideaza and 5,8-dideaza folate analogs, and antifolates. Folate is involved in the biosynthesis of nucleic acids and therefore impacts the survival and proliferation of cells. Folate cofactors play a role in the one-carbon transfers that are needed for the biosynthesis of pyrimidine nucleosides. Cells therefore have a system of transporting folates into the cytoplasm. Folate receptors also tend to be overexpressed in many human cancer cells, and folate-mediated targeting of oligonucleotides to ovarian cancer cells has been reported (Li, et al, Pharm. Res. 1998, 15, 1540, which is incorporated herein by reference in its entirety). Preparation of folic acid conjugates of nucleic acids are described in, for example, U.S. Pat. No. 6,528,631, which is incorporated herein by reference in its entirety.

Vitamin conjugate moieties include, for example, vitamin A (retinol) and/or related compounds. The vitamin A family (retinoids), including retinoic acid and retinol, are typically absorbed and transported to target tissues through their interaction with specific proteins such as cytosol retinol-binding protein type II (CRBP-II), retinol-binding protein (RBP), and cellular retinol-binding protein (CRBP). The vitamin A family of compounds can be attached to oligomeric compounds via acid or alcohol functionalities found in the various family members. For example, conjugation of an N-hydroxy succinimide ester of an acid moiety of retinoic acid to an amine function on a linker pendant to an oligonucleotide can result in linkage of vitamin A compound to the oligomeric compound via an amide bond. Also, retinol can be converted to its phosphoramidite, which is useful for 5' conjugation. alpha-Tocopherol (vitamin E) and the other tocopherols (beta through zeta) can be conjugated to oligomeric compounds to enhance uptake because of their lipophilic character. Also, vitamin D, and its ergosterol precursors, can be conjugated to oligomeric compounds through their hydroxyl groups by first activating the hydroxyl groups to, for example, hemisuccinate esters. Conjugation can then be effected directly to the oligomeric compound or to an arninolinker pendant from the oligomeric compound. Other vitamins that can be conjugated to oligomeric compounds in a similar manner on include thiamine, riboflavin, pyridoxine, pyridoxamine, pyridoxal, deoxypyridoxine. Lipid soluble vitamin K's and related quinone-containing compounds can be conjugated via carbonyl groups on the quinone ring. The phytol moiety of vitamin K can also serve to enhance binding of the oligomeric compounds to cells.

Other functional groups which may be used as conjugates in compounds of the invention, include imidazole conjugate—RNase A catalytic center mimics (polyamine-imidazole conjugates)—see Guerniou et al Nucleic Acids Res (2007); 35 (20): 6778-87.

Conjugates are typically non-nucleotide moieties. However, in the context of blocking groups or targeting groups, or nucleotide analog small therapeutics, it is recognized that the oligonucleotide may be covalently linked to a nucleotide moiety via the DNA/RNA phosphodiester region of the invention. Suitably, a nucleic acid group, as used in the context of the invention may, in some embodiments, lack complementarity to the target of the oligonucleotide (region A).

In some embodiments, the blocking or targeting moiety is an aptamer (see e.g. Meng et al., PLoS One (2012) 7(4): e33434, WO2005/111238 & WO12078637).

A blocking group may also be or comprise a oligonucleotide region which is complementary to, e.g. part of, the antisense oligonucleotide. In this regard the blocking oligonucleotide is covalently bound to an antisense oligonucleotide via the DNA/RNA phosphodiester region (region b), and optionally a linker. The blocking oligonucleotide is, in some embodiments, therefore able to form a duplex with the antisense oligonucleotide. Suitably the blocking nucleotide sequence (as third region or region C) is a short oligonucleotide sequence of e.g. 3-10 nucleotides in length which forms a duplex (i.e. is complementary to) with an equivalent length of the first region. In some embodiments a linker is used between the second region and the blocking region.

Like delivery peptides, nucleic acids can also serve as conjugate like moieties that can affect localization of conjugated oligomeric compounds in a cell. For example, nucleic acid conjugate moieties can contain poly A, a motif recognized by poly A binding protein (PABP), which can localize poly A-containing molecules in the cytoplasm (Gorlach, et al., Exp. Cell Res., 1994, 211, 400. In some embodiments, the nucleic acid conjugate moiety contains at least 3, at least 4, at least 5, at least 6, at least 7, at least 8, at least 9, at least 10, at least 15, at least 20, and at least 25 consecutive A bases. The nucleic acid conjugate moiety can also contain one or more AU-rich sequence elements (AREs). AREs are recognized by ELAV family proteins which can facilitate localization to the cytoplasm (Bollig, et al, Biochem. Bioophys. Res. Commun., 2003, 301, 665). Example AREs include UUAUUUAUU and sequences containing multiple repeats of this motif. In other embodiments, the nucleic acid conjugate moiety contains two or more AU or AUU motifs. Similarly, the nucleic acid conjugate moiety can also contain one or more CU-rich sequence elements (CREs) (Wein, et al, Eur. J. Biochem., 2003, 270, 350) which can bind to proteins HuD and/or HuR of the ELAV family of proteins. As with AREs, CREs can help localize conjugated oligomeric compounds to the cytoplasm. In some embodiments, the nucleic acid conjugate moiety contains the motif (CUUU)n, wherein, for example, n can be 1 to about 20, 1 to about 15, or 1 to about 11. The (CUUU)n motif can optionally be followed or preceded by one or more U. In some embodiments, n is about 9 to about 12 or about 11. The nucleic acid conjugate moiety can also include substrates of hnRNP proteins (heterogeneous nuclear ribonucleoprotein), some of which are involved in shuttling nucleic acids between the nucleus and cytoplasm, (e.g., nhRNP AI and nhRNP K; see, e.g., Mili, et al, Mol. Cell Biol, 2001, 21, 7307). Some example hnRNP substrates include nucleic acids containing the sequence UAGGA/U or (GG)ACUAGC(A). Other nucleic acid conjugate moieties can include Y strings or other tracts that can bind to, for example, IinRNP I. In some embodiments, the nucleic acid conjugate can contain at least 3, at least 4, at least 5, at least 6, at least 7, at least 8, at least 9, at least 10, at least 15, at least 20, and at least 25 consecutive pyrimidine bases. In other embodiments the nucleic acid conjugate can contain greater than 50, greater than 60, greater than 70, greater than 80, greater than 90, or greater than 95 percent pyrimidine bases.

Other nucleic acid conjugate-like moieties can include pumilio (puf protein) recognition sequences such as described in Wang, et al., Cell, 2002, 110, 501. Example pumilio recognition sequences can include UGUANAUR, where N can be any base and R can be a purine base. Localization to the cytoplasm can be facilitated by nucleic acid conjugate moieties containing AREs and/or CREs. Nucleic acid conjugate-like moieties serving as substrates of hnRNPs can facilitate localization of conjugated oligomeric compounds to the cytoplasm (e.g., hnRNP AI or K) or nucleus (e.g., hnRNP I). Additionally, nucleus localization can be facilitated by nucleic acid conjugate-like moieties containing polypyrimidine tracts.

A Reactive Group

A reactive group is a group which is used in chemical synthesis, which in the context of the present invention may be used "conjugate" the oligonucleotide, or otherwise covalently link the oligonucleotide to the third region (X), such as the conjugate, blocking group or targeting group, or optionally the linker (Y). An example of a reactive group is a phosphoramidite, which is widely used in oligonucleotide synthesis.

An Activation Group

An activation group is a group which may be activated to form a reactive group. In this respect, an activation group may be considered as a protected reactive group, which may be deprotected prior to enable use of the reactive group, for example in the methods of synthesis/manufacture disclosed herein.

Linkage Group

A nucleoside linkage is the linkage group either between nucleosides in the oligonucleotide, or, when present, may also describe the group which attaches the third region (X or C) or the linker (Y) to region B—for example this linker may be a phosphate (containing) linkage group or a triazol group.

Blocker Group (Also Referred to as a Blocking/Blocker Moiety)

In some aspects, the third region is a blocking region. A blocker is typically a conjugate or an oligonucleotide (typically not complementary to the target region), which, for example (but not limited to) either through steric hindrance, or through hybridization to the first region (or first and second regions), prevents or reduces activity of the oligomer. The (blocked) activity may be against its intended target (the target) or in some embodiments unintended targets (off-targets).

The oligomeric compound of the invention may therefore comprise a first region, such as a gapmer or LNA gaper oligonucleotide (such as a gapmer of formula X'Y'Z), a second region which is a biocleavable linker, such as region B as described herein, and a third region, region C, which comprises a region of at least 2 consecutive nucleosides, such as 3, 4, 5, 6, 7, 8, 9, 10, 11, 12, 13, 14, 15, 16 nucleotides which are complementary to a corresponding part of the first region. In some embodiments at least 2 nucleosides of region C, such as 3, 4, 5, 6, 7, 8, 9, or 10 nucleosides are high affinity nucleoside analogues, such as LNA (BNA)—in some embodiments, these may form the distal part of region C. The high affinity nucleoside analogues of region C may form a contiguous sequence of high affinity nucleoside analogues, which may be flanked by other nucleosides, such as DNA nucleosides (also part of region C, referred to as the proximal part of region C). In some embodiments, region C comprises between 2-8 (such as 3, 4, 5, 6, & 7 LNA (BNA) nucleotides, and in the same or in a different embodiment a region of between 2-16 DNA nucleotides (such as 3, 4, 5, 6, 7, 8, 9, 10, 11, 12, 13, 14, 15). In some embodiments, the distal part of region B comprises a contiguous region of high affinity nucleotide analogues, for example a contiguous region of 2, 3, 4, 5, 6, 7, or 8 LNA nucleotides. The proximal region may comprise a contiguous region of non-LNA nucleotides, such as those referred to herein, such as DNA nucleotides, such as a region of 2-16 non-LNA nucleotides. It is however also understood that the proximal region may comprise high affinity nucleotide analogues including LNA, but as contiguous regions of LNA can restrict the conformational flexibility of the proximal region (which is thought to act as a loop) it may, in some embodiments be useful to limit the use of long stretches of LNA in the proximal (or loop forming part), such as no more than 4 consecutive LNAs, such as no more than 3 consecutive LNAs, or no more than 2 consecutive LNAs.

In some embodiments, the region of other nucleotides in region C (such as DNA nucleotides) forms a contiguous sequence with region B, i.e. is proximal to the terminal nucleotide of region B), so that the region of high affinity nucleotides is distal to region B. In such an embodiment, region B and the proximal part of region C (e.g. the region comprising DNA nucleotides) may form a flexible loop, which allows the distal part of region C to hybridize with the first region. The proximal part of region C may or may not be complementary to a corresponding part of region A. In some embodiments, the distal part of region C is complementary to nucleotides which form a region which is capable of recruiting RNaseH, such as the gap region of a gapmer (referred to herein region Y'). In such an embodiment, the blocking region (region C) forms a duplex with the gap region, or part thereof, thereby blocking the availability of the central region of the gapmer to interact with other molecules or the target or off-targets. The invention therefore provides a solution to the inherent toxicity of DNA phosphorothioate oligonucleotides (which are typically used for the gap region of gapmers), as it allows for the controlled activation of gapmer oligomers (region A) within the target tissue or cells. In this respect, the use of a blocking region can act as a pro-drug. It is recognized that the blocking region (region C or distal part thereof), may also be directed towards other regions of an oligomer, including a mixmer or totalmer oligomer, or the flanking regions of a gapmer, or across the wing region and the gap region of a gapmer. In such an embodiment, the hybridization or region C (or distal part thereof) to region A (or part of region A), prevents the hybridization of the corresponding part of region A to biomolecules, and may therefore also be used to prevent unintended interaction with other biomolecules, enhancing specificity, tissue specific activity, and diminishing the risk of toxicity. The internucleoside linkages between the nucleotides of region C may be other than phosphodiester, such as may be phosphorothioate.

Targeting Group (Also Referred to as a Targeting Moiety)

A targeting moiety is a group whose presence on the oligomeric compound causes a differential pattern of biodistribution and/or cellular uptake of the oligomeric compound. Targeting groups may be, for example, receptor ligands, antibodies, hormones or hormone analogues, aptamers etc. The examples show the use of cholesterol as a targeting group—cholesterol is recognized by the LDL receptor in the surface of hepatocytes, resulting in the preferential uptake of cholesterol conjugated oligonucleotides into the liver. The examples also illustrate the use of GalNac, tocopherol, and folic acid as targeting groups.

Oligomer Linked Biocleavable Conjugates

The oligomeric compound may optionally, comprise a second region (region B) which is positioned between the oligomer (referred to as region A) and the conjugate (referred to as region C). Region B may be a linker such as a cleavable linker (also referred to as a physiologically labile linkage).

In some embodiments, the compound of the invention comprises a biocleavable linker (also referred to as the physiologically labile linker, Nuclease Susceptible Physiological Labile Linkages, or nuclease susceptible linker), for example the phosphate nucleotide linker (such as region B) or a peptide linker, which joins the oligomer (or contiguous nucleotide sequence or region A), to a conjugate moiety (or region C).

Biocleavable linkers according to the present invention refers to linkers which are susceptible to cleavage in a target tissue (i.e. physiologically labile), for example liver and/or kidney. It is preferred that the cleavage rate seen in the target tissue is greater than that found in blood serum. Suitable methods for determining the level (%) of cleavage in tissue (e.g. liver or kidney) and in serum are found in example 6. In some embodiments, the biocleavable linker (also referred to as the physiologically labile linker, or nuclease susceptible linker), such as region B, in a compound of the invention, are at least about 20% cleaved, such as at least about 30% cleaved, such as at least about 40% cleaved, such as at least about 50% cleaved, such as at least about 60% cleaved, such as at least about 70% cleaved, such as at least about 75% cleaved, in the the liver or kidney homogenate assay of Example 6. In some embodiments, the cleavage (%) in serum, as used in the assay in Example 6, is less than about 20%, such as less than about 10%, such as less than 5%, such as less than about 1%.

Biocleavable linkers according to the present invention refers to linkers which are susceptible to cleavage in a target tissue (i.e. physiologically labile), for example liver and/or kidney. It is preferred that the cleavage rate seen in the target tissue is greater than that found in blood serum. Suitable methods for determining the level (%) of cleavage in tissue (e.g. liver or kidney) and in serum are found in example 6. In some embodiments, the biocleavable linker (also referred to as the physiologically labile linker, or nuclease susceptible linker), such as region B, in a compound of the invention, are at least about 20% cleaved, such as at least about 30% cleaved, such as at least about 40% cleaved, such as at least about 50% cleaved, such as at least about 60% cleaved, such as at least about 70% cleaved, such as at least about 75% cleaved, in the liver or kidney homogenate assay of Example 6. In some embodiments, the cleavage (%) in serum, as used in the assay in Example 6, is less than about 30%, is less than about 20%, such as less than about 10%, such as less than 5%, such as less than about 1%.

In some embodiments, which may be the same of different, the biocleavable linker (also referred to as the physiologically labile linker, or nuclease susceptible linker), such as region B, in a compound of the invention, are susceptible to S1 nuclease cleavage. Susceptibility to S1 cleavage may be evaluated using the S1 nuclease assay shown in Example 6. In some embodiments, the biocleavable linker (also referred to as the physiologically labile linker, or nuclease susceptible linker), such as region B, in a compound of the invention, are at least about 30% cleaved, such as at least about 40% cleaved, such as at least about 50% cleaved, such as at least about 60% cleaved, such as at least about 70% cleaved, such as at least about 80% cleaved, such as at least about 90% cleaved, such as at least 95% cleaved after 120 min incubation with S1 nuclease according to the assay used in Example 6.

Nuclease Susceptible Physiological Labile Linkages: In some embodiments, the oligomer (also referred to as oligomeric compound) of the invention (or conjugate) comprises three regions:
  i) a first region (region A), which comprises 10-18 contiguous nucleotides;
  ii) a second region (region B) which comprises a biocleavable linker
  iii) a third region (C) which comprises a conjugate moiety, a targeting moiety, an activation moiety, wherein the third region is covalent linked to the second region.

In some embodiments, region B may be a phosphate nucleotide linker. For example such linkers may be used when the conjugate is a lipophilic conjugate, such as a lipid, a fatty acid, sterol, such as cholesterol or tocopherol. Phosphate nucleotide linkers may also be used for other conjugates, for example carbohydrate conjugates, such as GalNac.

Peptide and Other Linkers

In some embodiments, the biocleavable linker (region B) is a peptide, such as a trilysine peptide linker which may be used in a polyGalNac conjugate, such a triGalNac conjugate. Other linkers known in the art which may be used, including disulfide linkers (also referred to as dithio or disulphide herein). Other peptide linkers include, e.g. a Tyr-Asp(Asp) tripeptide or Asp(Asp) dipeptide.

Phosphate Nucleotide Linkers

In some embodiments, region B comprises between 1-6 nucleotides, which is covalently linked to the 5' or 3' nucleotide of the first region, such as via a internucleoside linkage group such as a phosphodiester linkage, wherein either
  a. the internucleoside linkage between the first and second region is a phosphodiester linkage and the nucleoside of the second region [such as immediately] adjacent to the first region is either DNA or RNA; and/or
  b. at least 1 nucleoside of the second region is a phosphodiester linked DNA or RNA nucleoside;

In some embodiments, region A and region B form a single contiguous nucleotide sequence of 10-22, such as 12-20 nucleotides in length.

In some aspects the internucleoside linkage between the first and second regions may be considered part of the second region.

Linkers

A linkage or linker is a connection between two atoms that links one chemical group or segment of interest to another chemical group or segment of interest via one or more covalent bonds. Conjugate moieties (or targeting or blocking moieties) can be attached to the oligomeric compound directly or through a linking moiety (linker or tether)—a linker. Linkers are bifunctional moieties that serve to covalently connect a third region, e.g. a conjugate moiety, to an oligomeric compound (such as to region B). In some embodiments, the linker comprises a chain structure or an oligomer of repeating units such as ethylene glyol or amino acid units. The linker can have at least two functionalities, one for attaching to the oligomeric compound and the other for attaching to the conjugate moiety. Example linker functionalities can be electrophilic for reacting with nucleophilic groups on the oligomer or conjugate moiety, or nucleophilic for reacting with electrophilic groups. In some embodiments, linker functionalities include amino, hydroxyl, carboxylic acid, thiol, phosphoramidate, phophate, phosphite, unsaturations (e.g., double or triple bonds), and the like. Some example linkers include 8-amino-3,6-dioxaoctanoic acid (ADO), succinimidyl 4-(N-maleimidomethyl)cyclohexane-l-carboxylate (SMCC), 6-aminohexanoic acid (AHEX or AHA), 6-aminohexyloxy, 4-aminobutyric acid, 4-aminocyclohexylcarboxylic acid, succinimidyl 4-(N-maleimidomethyl)cyclohexane-1-carboxy-(6-amido-caproate) (LCSMCC), succinimidyl m-maleimido-benzoylate (MBS), succinimidyl N-e-maleimido-caproylate (EMCS), succinimidyl 6-(beta-maleimido-propionamido) hexanoate (SMPH), succinimidyl N-(a-maleimido acetate) (AMAS), succinimidyl 4-(p-maleimidophenyl)butyrate (SMPB), beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like.

A wide variety of further linker groups are known in the art that can be useful in the attachment of conjugate moieties to oligomeric compounds. A review of many of the useful linker groups can be found in, for example, Antisense Research and Applications, S. T. Crooke and B. Lebleu, Eds., CRC Press, Boca Raton, Fla., 1993, p. 303-350. A disulfide linkage has been used to link the 3' terminus of an oligonucleotide to a peptide (Corey, et al., Science 1987, 238, 1401; Zuckermann, et al, J Am. Chem. Soc. 1988, 110, 1614; and Corey, et al., J Am. Chem. Soc. 1989, 111, 8524). Nelson, et al., Nuc. Acids Res. 1989, 17, 7187 describe a linking reagent for attaching biotin to the 3'-terminus of an oligonucleotide. This reagent, N-Fmoc-O-DMT-3-amino-1, 2-propanediol is commercially available from Clontech Laboratories (Palo Alto, Calif.) under the name 3'-Amine. It is also commercially available under the name 3'-Amino-Modifier reagent from Glen Research Corporation (Sterling, Va.). This reagent was also utilized to link a peptide to an oligonucleotide as reported by Judy, et al., Tetrahedron Letters 1991, 32, 879. A similar commercial reagent for linking to the 5'-terminus of an oligonucleotide is 5'-Amino-Modifier C6. These reagents are available from Glen Research Corporation (Sterling, Va.). These compounds or similar ones were utilized by Krieg, et al, Antisense Research and Development 1991, 1, 161 to link fluorescein to the 5'-terminus of an oligonucleotide. Other compounds such as acridine have been attached to the 3'-terminal phosphate group of an oligonucleotide via a polymethylene linkage (Asseline, et al., Proc. Natl. Acad. Sci. USA 1984, 81, 3297). [0074] Any of the above groups can be used as a single linker or in combination with one or more further linkers.

Linkers and their use in preparation of conjugates of oligomeric compounds are provided throughout the art such as in WO 96/11205 and WO 98/52614 and U.S. Pat. Nos. 4,948,882; 5,525,465; 5,541,313; 5,545,730; 5,552,538; 5,580,731; 5,486,603; 5,608,046; 4,587,044; 4,667,025; 5,254,469; 5,245,022; 5,112,963; 5,391,723; 5,510475; 5,512,667; 5,574,142; 5,684,142; 5,770,716; 6,096,875; 6,335,432; and 6,335,437, each of which is incorporated by reference in its entirety.

As used herein, a physiologically labile bond is a labile bond that is cleavable under conditions normally encountered or analogous to those encountered within a mammalian body (also referred to as a cleavable linker). Physiologically labile linkage groups are selected such that they undergo a chemical transformation (e.g., cleavage) when present in certain physiological conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. In some embodiments, the cleavable linker is susceptible to nuclease(s) which may for example, be expressed in the target cell—and as such, as detailed herein, the linker may be a short region (e.g. 1-10) phosphodiester linked nucleosides, such as DNA nucleosides, Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond. As used herein, a pH-labile bond is a labile bond that is selectively broken under acidic conditions (pH<7). Such bonds may also be termed endosomally labile bonds, since cell endosomes and lysosomes have a pH less than 7.

Activated Oligomers

In some embodiments, the invention provides an activated oligomer—i.e. an intermediate used in the synthesis of the oligomer of the invention—e.g. the conjugated oligomer. In this respect, the oligomer of the invention may, in some embodiments comprise region A and region B as described herein, and region B in covalently linked to an activation (or reactive) group, suitable for use in conjugation of the oligomer.

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH)

In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Methods of Synthesis and Manufacture

The invention also provides methods of synthesis or manufacture of the oligomer of the invention. The oligomer may be made using standard oligonucleotide synthesis, which is typically performed on a solid support, such as a universal support. As illustrated in FIGS. 5-10, the oligomer of the invention may be synthesized, for example, by the sequential synthesis of the first region and the second region, followed by the addition (e.g. conjugation) of the third region (X) optionally via a linker (Y). Region Y, when present may be joined to the region B, and region X subsequently added to region Y, or region Y and X may be added to region B in a single reaction step.

Alternatively, the oligomer synthesis my occur via the initial coupling of region X, or region X and Y to the oligonucleotide support column, followed by sequential oligonucleotide synthesis of region B and then region A.

Alternatively, the use of a cleavable bidirectional group attached to the oligonucleotide synthesis support (in an initial or pre-step), allows for a method where the oligonucleotide regions B and A are synthesized on one reactive group of the bifunctional group, and region X or region X and Y are synthesized on a second reactive group of the bifunctional group, wherein the oligonucleotide synthesis or addition of X (or X and Y) to the support may occur in any order or even together. The cleavage of the bifunctional group from the support then produces the oligomer of the invention. The bifunctional group may for example be a nucleoside, where one entity (e.g. region B or X or X—Y—) is attached to a phosphate containing group on the nucleoside (e.g. a 5' or 3' group), and the other (e.g. region B or X or X—Y—), is attached, for example to an reactive group present on the nucleobase.

Alternatively region X or X—Y may be joined to the oligomer (region B) after oligonucleotide synthesis, such as after the cleavage step. The invention therefore also relates to the intermediate oligomer, which comprises regions A and B, and a reactive or activation group attached to region B, which is subsequently used to join region X or regions X and Y to region B.

Region Y or region X may be linked to region B as a phosphoramidite, for example—allowing for the formation of the oligomer in a single oligonucleotide synthesis, followed by cleavage of the oligomer from the oligonucleotide synthesis support (US). In this regard, in some embodiments, the linkage group between region B and region X or Y may be a phosphate containing group, such as a nucleoside linkage, such as phosphodiester, phosphorothioate, phosphorodithioate, boranophosphate, methylphosphonate or others, such as those referred to herein. Alternatively other chemical linkages may be used such as a triazol group.

In some embodiments, the third region (X) or X—Y— may be linked to region B via a group other than a 5' or 3' phosphate, for example via a reactive group at another position, for example a reactive group, such as an amine on the base of a nucleoside in region B.

Oligonucleotide synthesis may occur in the 5'-3' direction, or, as is typical of most oligonucleotide synthesis, in the 3'-5' direction.

In some non-limiting examples, the oligonucleotide-conjugate construct can be assembled in different ways, e.g.

A) The B-A part of the construct can be made on an oligonucleotide synthesis machine capable of synthesizing both phosphorothioate and phosphorodiester linkages. B-A can then optionally be elongated by standard phosphoramidite chemistry using a building block X-A-P (conjugate moiety with linker attached) to create X-A-B-A or with building block X-P (conjugate moiety with no linker) to create X-B-A

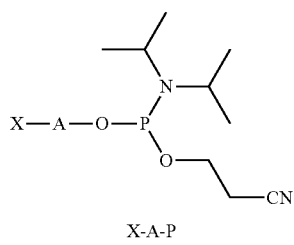

X-A-P

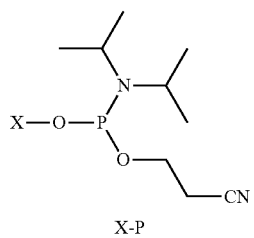

X-P

B) The B-A part of the construct can be made on an oligonucleotide synthesis machine capable of synthesizing both phosphorthioate and phosphordiester linkages. B-A can then optionally be sequentially elongated by standard phosphoramidite chemistry using a building block DMTrO-A-P followed by building block X—P to create X-A-B-A with a PO or PS linkage between the X and A part.

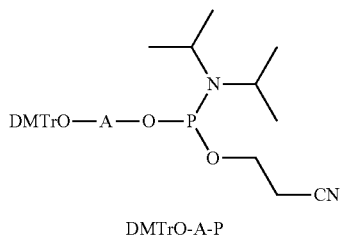

DMTrO-A-P

The B-A part of the construct can be made on an oligonucleotide synthesis machine capable of synthesizing both phosphorthioate and phosphordiester linkages. B-A can then optionally be sequentially elongated by standard phosphoramidite chemistry using a building block PGN-A-P to create $H_2N$-A-B-A. After cleavage and deprotection of the oligonucleotide the free amine of the oligonucleotide can be conjugated with moiety X in which a functional group of X has been activated in order to react with the terminal primary amine of the oligonucleotide.

Compositions

The oligomer of the invention may be used in pharmaceutical formulations and compositions. Suitably, such compositions comprise a pharmaceutically acceptable diluent, carrier, salt or adjuvant. WO2007/031091 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in WO2007/031091—which are also hereby incorporated by reference.

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of an antisense compound which are cleaved by endogenous nucleases within the body, to form the active antisense compound. In this regard the prodrug may comprise region B and a conjugate, targeting or blocking moiety as according to the present invention. In some embodiments, the oligomer of the invention is a pro-drug.

The use of lipophilic conjugates according to the invention allows for the incorporation of the oligomer of the invention into lipidoids or liposomes, e.g. cationic liposomes (e.g. cationic liposome SNALPs (stable nucleic acid lipid particle), which are particularly useful for delivery of oligomers e.g. to the liver, e.g. siRNAs.

Applications

The oligomers of the invention may be utilized as research reagents for, for example, diagnostics, therapeutics and prophylaxis.

In research, in some embodiments, such oligomers may be used to specifically inhibit the synthesis of protein (typically by degrading or inhibiting the mRNA and thereby prevent protein formation) in cells and experimental animals thereby facilitating functional analysis of the target or an appraisal of its usefulness as a target for therapeutic intervention.

For therapeutics, an animal or a human, suspected of having a disease or disorder, which can be treated by modulating the expression of the target is treated by administering oligomeric compounds in accordance with this invention. Further provided are methods of treating a mammal, such as treating a human, suspected of having or being prone to a disease or condition, associated with expression of the target by administering a therapeutically or prophylactically effective amount of one or more of the oligomers or compositions of the invention. The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Medical Indications

In some embodiments, the disease is cancer. In some embodiments, the disease is an inflammatory disease. In some embodiments, the disease is a cardiovascular disease, such as In some embodiments the disease or disorder is myocardial infarction (MI).

In some embodiments, the disease or disorder is, or results in or is associated with fibrosis, such as liver-fibrosis, cardiac fibrosis or local fibrosis.

In some embodiments, the disease or disorder is blood clotting disorder.

In some embodiments the disease or disorder is or comprises (results in or is associated with) bone-lose.

In some embodiments, the disease or disorder is a liver disease or disorder.

In some embodiments the disease or disorder is a metabolic disorder, which may for example be a liver disease or disorder, and/or in some aspects a cardiovascular disease or disorder).

Cardiovascular/Metabolic diseases include, for examples, metabolic syndrome, obesity, hyperlipidemia, HDL/LDL cholesterol imbalance, dyslipidemias, e.g., familial combined hyperlipidemia (FCHL), acquired hyperlipidemia, statin-resistant, hypercholesterolemia, coronary artery disease (CAD), and coronary heart disease (CHD), atherosclerosis, heart disease, diabetes (I and/or II), NASH, acute coronary syndrome (ACS), NASH, chronic heart failure, cardiovascular disease, cardio metabolic disease, hyperlipidaemia and related disorders, metabolic syndrome, atherosclerosis, chronic heart failure, vascular disease, peripheral arterial disease, heart disease, ischemia, type 2 diabetes, type 1 diabetes, In some embodiments, the disease or disorder is selected from the group consisting of metabolic syndrome, obesity, hyperlipidemia, atherosclerosis, HDL/LDL cholesterol imbalance, dyslipidemias, e.g., familial combined hyperlipidemia (FCHL), acquired hyperlipidemia, statin-resistant, hypercholesterolemia, coronary artery disease (CAD), and coronary heart disease (CHD).

In some embodiments, the disease or disorder is selected from the group consisting of chronic heart failure, cardiovascular disease, cardio metabolic disease, chronic heart failure, vascular disease, peripheral arterial disease, heart disease, ischemia, acute coronary syndrome (ACS).

In some embodiments, the disease or disorder is type 2 diabetes, type 1 diabetes, In some embodiments, the disease or disorder is a viral disease, such as polycythemia, hepatitis C, hepatitis B, BKV, HIV.

In some embodiments, the disease or disorder is a severe and rare diseases (or genetic disorder).

The invention further provides use of a compound of the invention in the manufacture of a medicament for the treatment of a disease, disorder or condition, such as those as referred to herein.

Generally stated, some aspects of the invention is directed to a method of treating a mammal suffering from or susceptible to conditions associated with abnormal levels of the target, comprising administering to the mammal and therapeutically effective amount of an oligomer targeted to the target that comprises one or more LNA units. The oligomer, a conjugate or a pharmaceutical composition according to the invention is typically administered in an effective amount.

An interesting aspect of the invention is directed to the use of the compound as defined herein for the preparation of a medicament for the treatment of a disease, disorder or condition as referred to herein.

Moreover, the invention relates to a method of treating a subject suffering from a disease or condition such as those referred to herein.

A patient who is in need of treatment is a patient suffering from or likely to suffer from the disease or disorder.

In some embodiments, the term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

EXAMPLES

Oligonucleotide List

In the following list, Capital letters represent LNA nucleosides, such as beta-D-oxy LNA, lower case letters represent DNA nucleosides. Capital L is a LNA, such as beta-D-oxy, and lower case d is a DNA nucleoside. LNA cytosines are optionally 5'methyl cytosine. The internucleosides within region A are phosphorothioate, and within region B are phosphodiester (as shown). The internucleoside linkage between region A and B is phoshodiester, but where region B is >1 DNA nucleotide, may optionally be other than phosphodiester (e.g. may be phosphorothioate). There is, optionally a further linker (Y), between region B and region C, such as a C6 linker. # refers to SEQ ID No.

ApoB Targeting Compounds

| # | Seq (5'-3') (Region A) | Cleavable Linker (Region B) | Region C - Conjugate |
|---|---|---|---|
| 1 | GCattggtatTCA | no | no |
| 2 | GCattggtatTCA | no | Cholesterol |
| 3 | GCattggtatTCA | SS | Cholesterol |
| 4 | GCattggtatTCA | 3PO-DNA (5'tca3') | Cholesterol |
| 5 | GCattggtatTCA | 2PO-DNA (5'ca3') | Cholesterol |
| 6 | GCattggtatTCA | 1PO-DNA (5'a3') | Cholesterol |

PCSK9—Mouse Specific Compounds

| # | Seq (5'-3')(A) | Cleavable Linker (B) | Conjugate (C) |
|---|---|---|---|
| 7 | GTctgtggaaGCG | no | no |
| 8 | GTctgtggaaGCG | no | Cholesterol |
| 9 | GTctgtggaaGCG | 2PO-DNA (5'ca3') | Cholesterol |
| 10 | GTctgtggaaGCG | 2PO-DNA (5'ct3') | Cholesterol |

FVII (Mouse FVII)

| # | Seq (5'-3') | Cleavable linker (B) | Conjugate (C) |
|---|---|---|---|
| 11 | LLdddddddddLLL | no | no |
| 12 | LLdddddddddLLL | | GalNAc cluster |
| 13 | LLdddddddddLLL | 2PO (ca) | GalNAc cluster |
| 14 | LLdddddddddLLL | SS | Cholesterol |
| 15 | LLdddddddddLLL | 2PO (ca) | Cholesterol |

ApoB Targeting Compounds with FAM Label Conjugates

| # | Seq (5'-3') | Cleavable linker (B) | Conjugate (C) |
|---|---|---|---|
| 16 | GCattggtatTCA | 3PO-DNA (5'tca3') | FAM |
| 17 | GCattggtatTCA | 2PO-DNA (5'ca3') | FAM |
| 18 | GCattggtatTCA | 1PO-DNA (5'a3') | FAM |
| 19 | GCattggtatTCA | 3PO-DNA (5'gac3') | FAM |
| 20 | GCattggtatTCA | no | FAM |

Target X Compounds (A Human Therapeutic Target)

| # | Seq (5'-3') | Cleavable Linker (B) | Region C (in 3'-end) |
|---|---|---|---|
| 21 | LLLdddddddddddLLL | 3PO-DNA (5'tgc3') | 5'-dddddLLLL-3' |
| 22 | LLLdddddddddddLLL | | 5'-dddddddLLLL-3' |
| 23 | LLLdddddddddddLLL | 3PO-DNA (5'tgc3') | 5'-dddddLLLL-3' |
| 24 | LLLdddddddddddLLL | | 5'-dddddddLLLL-3' |

In the above compounds, region C comprises the complement to the Seq (Region A) so that the 3' nucleotide of region C aligns (forms a base pair) with the 8$^{th}$ nucleotide of region A from the 5' end. Region C therefore loops back and forms an 8 base hybridization with region A across the 3' wing of the gapmer and 5 bases of the DNA gap region, thereby creating a "pro-drug" which is inactive until the linker region (B) is cleaved.

ApoB Targeting Compounds

| # | Seq (5'-3') | Cleavable Linker (B) | Conjugate |
|---|---|---|---|
| 25 | GCattggtatTCA | no | Folic acid |
| 26 | GCattggtatTCA | SS | Folic acid |
| 27 | GCattggtatTCA | 2PO-DNA (5'ca3') | Folic acid |
| 28 | GCattggtatTCA | no | monoGalNAc |
| 29 | GCattggtatTCA | SS | monoGalNAc |
| 30 | GCattggtatTCA | 2PO-DNA (5'ca3') | monoGalNAc |
| 31 | GCattggtatTCA | no | FAM |
| 32 | GCattggtatTCA | SS | FAM |
| 33 | GCattggtatTCA | 2PO-DNA (5'ca3') | FAM |
| 34 | GCattggtatTCA | no | Tocopherol |
| 35 | GCattggtatTCA | SS | Tocopherol |
| 36 | GCattggtatTCA | 2PO-DNA (5'ca3') | Tocopherol |

PCSK9 Compounds

| # | Seq (5'-3') | linker | Conjugate |
|---|---|---|---|
| 37 | TGCtacaaaacCCA | no | |
| 38 | AATgctacaaaaCCCA | no | |
| 39 | AATgctacaaaacCCCA | no | |
| 40 | GCtgtgtgagcttGG | no | |
| 41 | TGctgtgtgagctTGG | no | |
| 42 | TGCtgtgtgagctTGG | no | |
| 43 | TCCtggtctgtgtTCC | no | |
| 44 | TCCtggtctgtgttCC | no | |
| 45 | TGCtacaaaacCCA | 2PO-DNA (5'ca3') | Cholesterol |
| 46 | AATgctacaaaaCCCA | 2PO-DNA (5'ca3') | Cholesterol |
| 47 | AATgctacaaaacCCCA | 2PO-DNA (5'ca3') | Cholesterol |
| 48 | GCtgtgtgagcttGG | 2PO-DNA (5'ca3') | Cholesterol |
| 49 | TGctgtgtgagctTGG | 2PO-DNA (5'ca3') | Cholesterol |
| 50 | TGCtgtgtgagctTGG | 2PO-DNA (5'ca3') | Cholesterol |
| 51 | TCCtggtctgtgtTCC | 2PO-DNA (5'ca3') | Cholesterol |
| 52 | TCCtggtctgtgttCC | 2PO-DNA (5'ca3') | Cholesterol |

Monkey Study Compounds ApoB

| | | | |
|---|---|---|---|
| 53 | GTtgacactgTC | No | no |
| 5 | GCattggtatTCA | 2PO-DNA (5'ca3') | Cholesterol |
| 54 | GTtgacactgTC | 2PO-DNA (5'ca3') | Cholesterol |
| 46 | AATgctacaaaaCCCA | 2PO-DNA (5'ca3') | Cholesterol |
| 49 | TGctgtgtgagctTGG | 2PO-DNA (5'ca3') | Cholesterol |

SEQ ID NO 53 is provided as the parent compound of SEQ ID NO 54.

Mouse Experiments: Unless otherwise specified, the mouse experiments may be performed as follows:

Dose Administration and Sampling:

7-10 week old C57B16-N mice were used, animals were age and sex matched (females for study 1, 2 and 4, males in study 3). Compounds were injected i.v. into the tail vein. For intermediate serum sampling, 2-3 drops of blood were collected by puncture of the vena facialis, final bleeds were taken from the vena cava inferior. Serum was collected in gel-containing serum-separation tubes (Greiner) and kept frozen until analysis.

C57BL6 mice were dosed i.v. with a single dose of 1 mg/kg ASO (or amount shown) formulated in saline or saline alone according to the information shown. Animals were sacrificed at e.g. day 4 or 7 (or time shown) after dosing and liver and kidney were sampled. RNA isolation and mRNA analysis: mRNA analysis from tissue was performed using the Qantigene mRNA quantification kit ("bDNA-assay", Panomics/Affimetrix), following the manufacturers protocol. For tissue lysates, 50-80 mg of tissue was lysed by sonication in 1 ml lysis-buffer containing Proteinase K. Lysates were used directly for bDNA-assay without RNA extraction. Probesets for the target and GAPDH were obtained custom designed from Panomics. For analysis, luminescence units obtained for target genes were normalized to the housekeeper GAPDH.

Serum analysis for ALT, AST and cholesterol was performed on the "Cobas INTEGRA 400 plus" clinical chemistry platform (Roche Diagnostics), using 10 μl of serum.

For quantification of Factor VII serum levels, the BIO-PHEN FVII enzyme activity kit (#221304, Hyphen BioMed) was used according to the manufacturer's protocol.

For oligonucleotide quantification, a fluorescently-labeled PNA probe is hybridized to the oligo of interest in the tissue lysate. The same lysates are used as for bDNA-assays, just with exactly weighted amounts of tissue. The heteroduplex is quantified using AEX-HPLC and fluorescent detection.

Example 1

Synthesis of Compounds SEQ ID NO 1, SEQ ID NO 2, SEQ ID NO 3, SEQ ID NO 4 and SEQ ID NO 5

Oligonucleotides were synthesized on uridine universal supports using the phosphoramidite approach on an Expedite 8900/MOSS synthesizer (Multiple Oligonucleotide Synthesis System) or equivalent at 4 μmol scale. At the end of the synthesis, the oligonucleotides were cleaved from the solid support using aqueous ammonia for 1-2 hours at room temperature, and further deprotected for 16 hours at 65° C. The oligonucleotides were purified by reverse phase HPLC (RP-HPLC) and characterized by UPLC, and the molecular mass was further confirmed by ESI-MS. See below for more details.

Elongation of the Oligonucleotide

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), LNA-T or C6-S-S linker) is performed by using a solution of 0.1 M of the 5'-O-DMT-protected amidite in acetonitrile and DCl (4,5-dicyanoimidazole) in acetonitrile (0.25 M) as activator. For the final cycle a commercially available C6-linked cholesterol phosphoramidite was used at 0.1 M in DCM. Thiolation for introduction of phosphorthioate linkages is carried out by using xanthane hydride (0.01 M in acetonitrile/pyridine 9:1). Phosphordiester linkages are introduced using 0.02 M iodine in THF/Pyridine/water 7:2:1. The rest of the reagents are the ones typically used for oligonucleotide synthesis.

Purification by RP-HPLC:

The crude compounds were purified by preparative RP-HPLC on a Phenomenex Jupiter C18 10μ 150×10 mm column. 0.1 M ammonium acetate pH 8 and acetonitrile was used as buffers at a flowrate of 5 mL/min. The collected fractions were lyophilized to give the purified compound typically as a white solid.

ABBREVIATIONS

DCl: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography Example 2

Design of LNA Antisense Oligonucleotides

Oligomers used in the examples and figures. The SEQ# is an identifier used throughout the examples and figures

TABLE 2

| SEQ ID NO | Compound Sequence | Comment |
|---|---|---|
| #1 | 5'- $c_s^{me} c_s^{me}$ $a_s$ $t_s$ $t_s$ $g_s$ $g_s$ $t_s$ $a_s$ $t_s$ $t_s^{me} c_s^{me} a$ -3' | Mother compound without conjugated Cholesterol |
| #2 | 5'-CHOL $c_s^{me} c_s^{me}$ $a_s$ $t_s$ $t_s$ $g_s$ $g_s$ $t_s$ $a_s$ $t_s$ $t_s^{me} c_s^{me} a$ -3' | Chol-3833 |
| #3 | 5'- Chol_C6 C6SSC6 $c_s^{me} c_s^{me}$ $a_s$ $t_s$ $t_s$ $g_s$ $g_s$ $t_s$ $a_s$ $t_s$ $t_s^{me} c_s^{me} a$ -3' | Chol-SS-3833 |

TABLE 2-continued

| SEQ ID NO | Compound Sequence | Comment |
|---|---|---|
| #4 | 5'-Chol_C6 t c a $^m$C$^m$C' a$_s$ t$_s$ t$_s$ g$_s$ g$_s$ t$_s$ a$_s$ t$_s$ T$^m$C$^m$A-3' | Chol-3PO-3833 |
| #5 | 5'-Chol_C6 c a $^m$C$^m$C' a$_s$ t$_s$ t$_s$ g$_s$ g$_s$ t$_s$ a$_s$ t$_s$ T$^m$C$^m$A-3' | Chol-2PO-3833 |
| #6 | 5'- Chol_C6 a G$_s^o$ $^m$C$_s^o$ a$_s$ t$_s$ t$_s$ g$_s$ g$_s$ t$_s$ a$_s$ t$_s$ T$_s^o$ $^m$C$_s^o$ A$^o$-3' | Chol-1PO-3833 |
| #7 | 5'- G$_s^o$ T$_s^o$ c$_s$ t$_s$ g$_s$ t$_s$ g$_s$ g$_s$ a$_s$ a$_s$ G$_s$o $^m$C$_s$o Go -3' | Mother compound without conjugate |
| #8 | 5'- Chol_C6 G$_s^o$ T$_s^o$ c$_s$ t$_s$ g$_s$ t$_s$ g$_s$ g$_s$ a$_s$ a$_s$ G$_s^o$ $^m$C$_s^o$ G$^o$ -3' | Chol-4061 |
| #9 | 5'- Chol_C6 c a G$_s^o$ T$_s^o$ c$_s$ t$_s$ g$_s$ t$_s$ g$_s$ g$_s$ a$_s$ a$_s$ G$_s^o$ $^m$C$_s^o$ G$^o$ -3' | Chol-2PO(ca)-4061 |
| #10 | 5'- Chol_C6 c t G$_s^o$ T$_s^o$ c$_s$ t$_s$ g$_s$ t$_s$ g$_s$ g$_s$ a$_s$ a$_s$ G$_s^o$ $^m$C$_s^o$ G$^o$ -3' | Chol-2PO(ct)-4061 |

Example 3

Knock Down of ApoB mRNA with Cholesterol-Conjugates In Vivo

C57BL6/J mice were injected with a single dose saline or 1 mg/kg unconjugated LNA-antisense oligonucleotide (SEQ ID #1) or equimolar amounts of LNA antisense oligonucleotides conjugated to Cholesterol with different linkers and sacrificed at days 1-10 according to Tab. 3.

RNA was isolated from liver and kidney and subjected to qPCR with ApoB specific primers and probe to analyze for ApoB mRNA knockdown.

Figure 11:
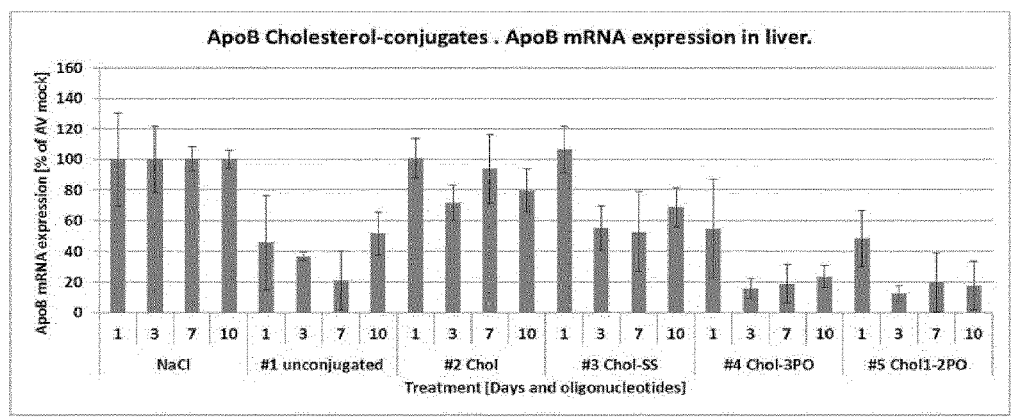
FIG. 11. Silencing of ApoB mRNA with Cholesterol-conjugates in vivo. Mice were injected with a single dose of 1 mg/kg unconjugated LNA-antisense oligonucleotide (#3833) or equimolar amounts of LNA antisense oligonucleotides conjugated to Cholesterol with different linkers (Tab. 3) and sacrificed at days 1, 3, 7 and 10 after dosing. RNA was isolated from liver and kidney and subjected to ApoB specific RT-qPCR A. Quantification of ApoB mRNA from liver samples normalized to GAPDH and shown as percentage of the average of equivalent saline controls B. Quantification of ApoB mRNA from kidney samples normalized to GAPDH and shown as percentage of the average of equivalent saline controls.
Figure 11:
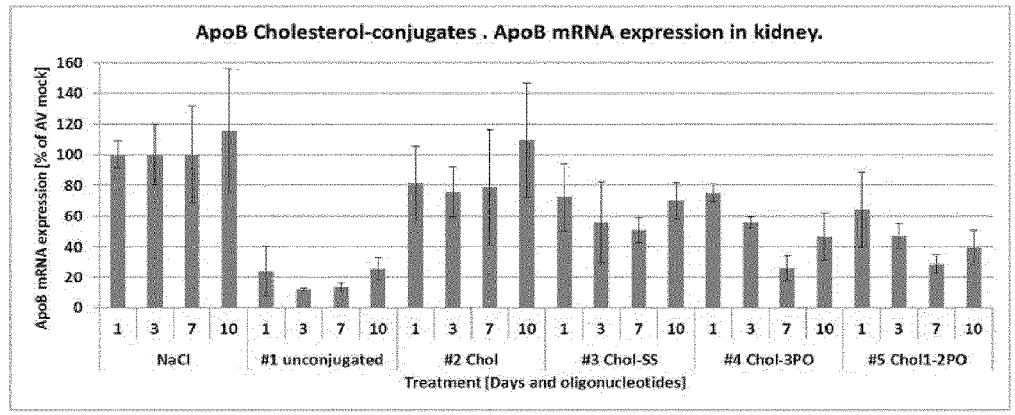

Conclusions:

Cholesterol conjugated to an ApoB LNA antisense oligonucleotide with a linker composed of 2 or 3 DNA with Phophodiester-backbone (Seq#4 and 5) showed a preference for liver specific knock down of ApoB (FIG. 11). This means increases efficiency and duration of ApoB mRNA knock down in liver tissue compared to the unconjugated compound (Seq #1), as well as compared to Cholesterol conjugates with stable linker (Seq#2) and with disulphide linker (Seq. #3) and concomitant less knock down activity of Seq#4 and #5 in kidney tissue.

Materials and Methods:
Experimental Design:

TABLE 3

| Gr. no. | Animal ID no. | No. of animals | Animal strain/ gender/feed | Compound Dose level per day | Conc. at dose vol. 10 ml/kg | Body weight | Sacrifice |
|---|---|---|---|---|---|---|---|
| A | 1 | 1-4 | 4 | C57BL/6J-♀- Chow | NaCl 0.9% | — | Day −1, 7 and 10 | Day 10 |
| | 2 | 5-8 | 4 | C57BL/6J-♀- Chow | SEQ ID NO 1 1 mg/kg | 0.1 mg/ml | Day −1, 7 and 10 | Day 10 |
| | 3 | 9-12 | 4 | C57BL/6J-♀- Chow | SEQ ID NO 2 1.2 mg/kg | 0.12 mg/ml | Day −1, 7 and 10 | Day 10 |
| | 4 | 13-16 | 4 | C57BL/6J-♀- Chow | SEQ ID NO 3 1.2 mg/kg | 0.12 mg/ml | Day −1, 7 and 10 | Day 10 |
| | 5 | 17-20 | 4 | C57BL/6J-♀- Chow | SEQ ID NO 4 1.3 mg/kg | 0.13 mg/ml | Day −1, 7 and 10 | Day 10 |
| | 6 | 21-24 | 4 | C57BL/6J-♀- Chow | SEQ ID NO 5 1.3 mg/kg | 0.13 mg/ml | Day −1, 7 and 10 | Day 10 |
| B | 7 | 25-28 | 4 | C57BL/6J-♀- Chow | NaCl 0.9% | — | Day −1, 7 | Day 7 |
| | 8 | 29-32 | 4 | C57BL/6J-♀- Chow | SEQ ID NO 1 1 mg/kg | 0.1 mg/ml | Day −1, 7 | Day 7 |
| | 9 | 33-36 | 4 | C57BL/6J-♀- Chow | SEQ ID NO 2 1.2 mg/kg | 0.12 mg/ml | Day −1, 7 | Day 7 |
| | 10 | 37-40 | 4 | C57BL/6J-♀- Chow | SEQ ID NO 3 1.2 mg/kg | 0.12 mg/ml | Day −1, 7 | Day 7 |
| | 11 | 41-44 | 4 | C57BL/6J-♀- Chow | SEQ ID NO 4 1.3 mg/kg | 0.13 mg/ml | Day −1, 7 | Day 7 |
| | 12 | 45-48 | 4 | C57BL/6J-♀- Chow | SEQ ID NO 5 1.3 mg/kg | 0.13 mg/ml | Day −1, 7 | Day 7 |
| C | 13 | 49-52 | 4 | C57BL/6J-♀- Chow | NaCl 0.9% | — | Day 0, 3 | Day 3 |
| | 14 | 53-56 | 4 | C57BL/6J-♀- Chow | SEQ ID NO 1 1 mg/kg | 0.1 mg/ml | Day 0, 3 | Day 3 |
| | 15 | 57-60 | 4 | C57BL/6J-♀- Chow | SEQ ID NO 2 1.2 mg/kg | 0.12 mg/ml | Day 0, 3 | Day 3 |
| | 16 | 61-64 | 4 | C57BL/6J-♀- Chow | SEQ ID NO 3 1.2 mg/kg | 0.12 mg/ml | Day 0, 3 | Day 3 |
| | 17 | 65-68 | 4 | C57BL/6J-♀- Chow | SEQ ID NO 4 1.3 mg/kg | 0.13 mg/ml | Day 0, 3 | Day 3 |
| | 18 | 69-72 | 4 | C57BL/6J-♀- Chow | SEQ ID NO 5 1.3 mg/kg | 0.13 mg/ml | Day 0, 3 | Day 3 |

TABLE 3-continued

| Gr. no. | Animal ID no. | No. of animals | Animal strain/ gender/feed | Compound Dose level per day | Conc. at dose vol. 10 ml/kg | Body weight | Sacrifice |
|---|---|---|---|---|---|---|---|
| D 19 | 73-76 | 4 | C57BL/6J- ♀- Chow | NaCl 0.9% | — | Day −1, 1 | Day 1 |
| 20 | 77-80 | 4 | C57BL/6J- ♀- Chow | SEQ ID NO 1 1 mg/kg | 0.1 mg/ml | Day −1, 1 | Day 1 |
| 21 | 81-84 | 4 | C57BL/6J- ♀- Chow | SEQ ID NO 2 1.2 mg/kg | 0.12 mg/ml | Day −1, 1 | Day 1 |
| 22 | 85-88 | 4 | C57BL/6J- ♀- Chow | SEQ ID NO 3 1.2 mg/kg | 0.12 mg/ml | Day −1, 1 | Day 1 |
| 23 | 89-92 | 4 | C57BL/6J- ♀- Chow | SEQ ID NO 4 1.3 mg/kg | 0.13 mg/ml | Day −1, 1 | Day 1 |
| 24 | 93-96 | 4 | C57BL/6J- ♀- Chow | SEQ ID NO 5 1.3 mg/kg | 0.13 mg/ml | Day −1, 1 | Day 1 |

Dose Administration.

C57BL/6JBom female animals, app. 20 g at arrival, were dosed with 10 ml per kg BW (according to day 0 bodyweight) i.v. of the compound formulated in saline or saline alone according to table 3.

Sampling of Liver and Kidney Tissue.

The animals were anaesthetized with 70% $CO_2$-30% $O_2$ and sacrificed by cervical dislocation according to Table 3. One half of the large liver lobe and one kidney were minced and submerged in RNAlater.

Total RNA Isolation and First strand synthesis. Total RNA was extracted from maximum 30 mg of tissue homogenized by bead-milling in the presence of RLT-Lysis buffer using the Qiagen RNeasy kit (Qiagen cat. no. 74106) according to the manufacturer's instructions. First strand synthesis was performed using Reverse Transcriptase reagents from Ambion according to the manufacturer's instructions.

For each sample 0.5 µg total RNA was adjusted to (10.8 µl) with RNase free $H_2O$ and mixed with 2 µl random decamers (50 µM) and 4 µl dNTP mix (2.5 mM each dNTP) and heated to 70° C. for 3 min after which the samples were rapidly cooled on ice. 2 µl 10× Buffer RT, 1 µl MMLV Reverse Transcriptase (100 U/µl) and 0.25 µl RNase inhibitor (10 U/µl) were added to each sample, followed by incubation at 42° C. for 60 min, heat inactivation of the enzyme at 95° C. for 10 min and then the sample was cooled to 4° C. cDNA samples were diluted 1:5 and subjected to RT-QPCR using Taqman Fast Universal PCR Master Mix 2× (Applied Biosystems Cat #4364103) and Taqman gene expression assay (mApoB, Mn01545150_m1 and mGAPDH #4352339E) following the manufacturers protocol and processed in an Applied Biosystems RT-qPCR instrument (7500/7900 or ViiA7) in fast mode.

Example 4

Knock Down of ApoB mRNA with Cholesterol-Conjugates In Vivo and LNA Distribution to Liver and Kidney C57BL6/J mice were injected with a single dose saline or 1 mg/kg unconjugated LNA-antisense oligonucleotide (SEQ ID #1) or equimolar amounts of LNA antisense oligonucleotides conjugated to Cholesterol with different linkers and sacrificed at days 1-16 according to Tab. 4. RNA was isolated from liver and kidney and subjected to qPCR with ApoB specific primers and probe to analyze for ApoB mRNA knockdown.

The LNA oligonucleotide content was measured in liver and kidney using LNA based sandwich ELISA method.

Figure 14:
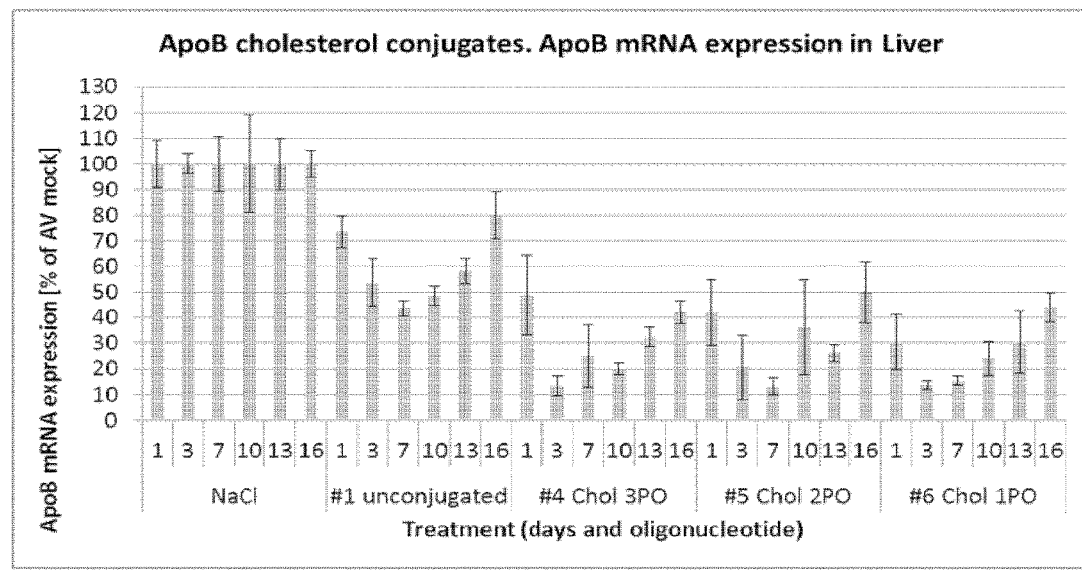
FIG. 14. Silencing of ApoB mRNA with cholesterol-conjugates in vivo. Mice were injected with a single dose of 1 mg/kg unconjugated LNA-antisense oligonucleotide (#3833) or equimolar amounts of LNA antisense oligonucleotides conjugated to Cholesterol with different linkers (Tab. 3) and sacrificed at days 1, 3, 7, 10, 13 and 16 after dosing. RNA was isolated from liver and kidney and subjected to ApoB specific RT-qPCR A. Quantification of ApoB mRNA from liver samples normalized to GAPDH and shown as percentage of the average of equivalent saline controls B. Quantification of ApoB mRNA from kidney samples normalized to GAPDH and shown as percentage of the average of equivalent saline controls.
Figure 14:
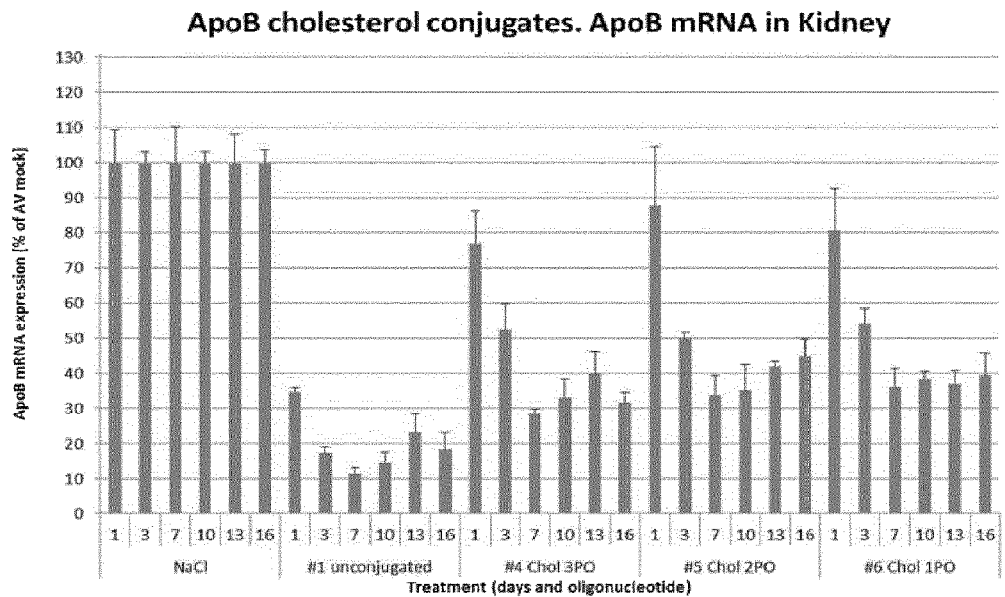
Figure 15:
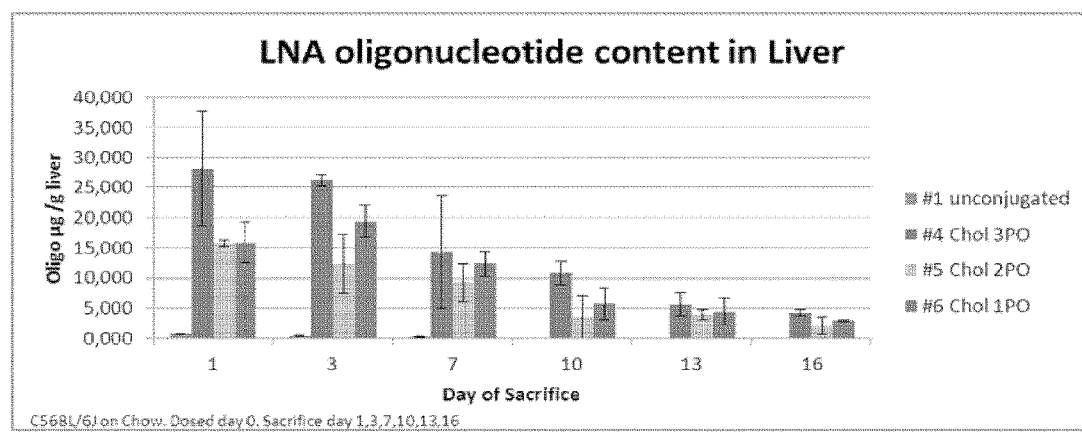
FIG. 15. Content of the specific LNA oligonucleotide in liver and kidney in vivo. Mice were injected with a single dose of 1 mg/kg unconjugated LNA-antisense oligonucleotide (#1) or equimolar amounts of LNA antisense oligonucleotides conjugated to Cholesterol with different linkers (Tab. 4) and sacrificed at days 1, 3, 7, 10, 13 and 16 after dosing. LNA oligonucleotide content was measured using LNA based sandwich ELISA method.
Figure 15:
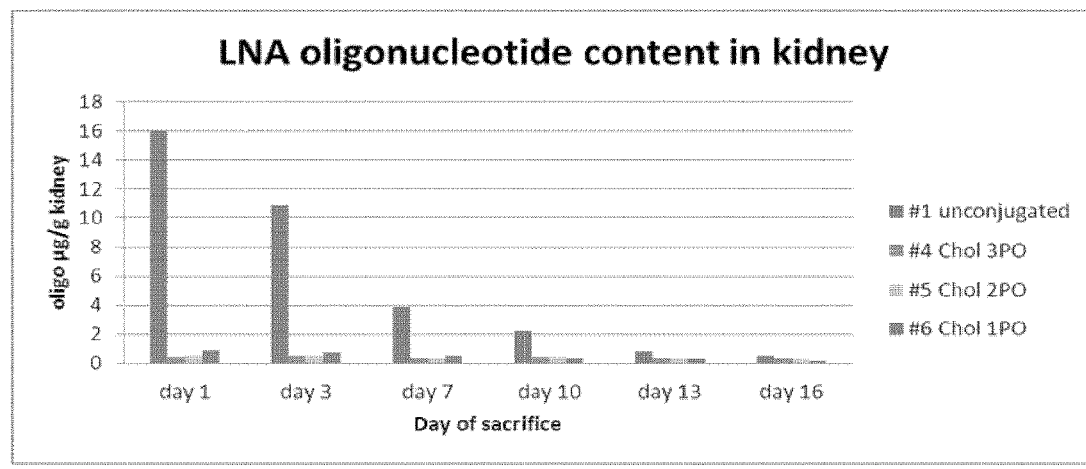

Conclusions:

Cholesterol conjugated to an ApoB LNA antisense oligonucleotide with a linker composed of 1, 2 or 3 DNA with Phophodiester-backbone (Seq#4, #5 and #6) showed a preference for liver specific knock down of ApoB (FIG. 14). This means increased efficiency and duration of ApoB mRNA knock down in liver tissue compared to the unconjugated compound (Seq #1), and concomitant less knock down activity of Seq#4, #5 and #6 in kidney tissue. The Cholesterol conjugated LNA antisense oligonucleotides have a much higher uptake in the liver and much lower uptake in the kidney as compared to the unconjugated LNA oligonucleotide (FIG. 15).

Materials and Methods:

Experimental Design:

TABLE 4

| Part | Group no. | Animal id no. | No. of Animals | Animal strain/ gender/feed | Compound Dose level per day | Conc. at dose vol. 10 ml/kg | Adm. Route | Dosing day | Body weight day | Sacrifice day |
|---|---|---|---|---|---|---|---|---|---|---|
| A | 1 | 1-3 | 3 | C57BL/6J/♀/Chow | Saline | — | iv | 0 | 0, 1 | 1 |
|  | 2 | 4-6 | 3 | C57BL/6J/♀/Chow | SEQ ID NO 1 1 mg/kg | 0.1 mg/ml | iv | 0 | 0, 1 | 1 |
|  | 3 | 7-9 | 3 | C57BL/6J/♀/Chow | SEQ ID NO 4 equimolar 1.35 mg/kg | 0.135 mg/ml | iv | 0 | 0, 1 | 1 |
|  | 4 | 10-12 | 3 | C57BL/6J/♀/Chow | SEQ ID NO 5 equimolar 1.28 mg/kg | 0.128 mg/ml | iv | 0 | 0, 1 | 1 |
|  | 5 | 13-15 | 3 | C57BL/6J/♀/Chow | SEQ ID NO 6 equimolar 1.21 mg/kg | 0.121 mg/ml | iv | 0 | 0, 1 | 1 |
| B | 6 | 16-18 | 3 | C57BL/6J/♀/Chow | Saline | — | iv | 0 | 0, 3 | 3 |

TABLE 4-continued

| Part | Group no. | Animal id no. | No. of Animals | Animal strain/ gender/feed | Compound Dose level per day | Conc. at dose vol. 10 ml/kg | Adm. Route | Dosing day | Body weight day | Sacrifice day |
|---|---|---|---|---|---|---|---|---|---|---|
| | 7 | 19-21 | 3 | C57BL/6J/♀/Chow | SEQ ID NO 1 1 mg/kg | 0.1 mg/ml | iv | 0 | 0, 3 | 3 |
| | 8 | 22-24 | 3 | C57BL/6J/♀/Chow | SEQ ID NO 4 equimolar 1.35 mg/kg | 0.135 mg/ml | iv | 0 | 0, 3 | 3 |
| | 9 | 25-27 | 3 | C57BL/6J/♀/Chow | SEQ ID NO 5 equimolar 1.28 mg/kg | 0.128 mg/ml | iv | 0 | 0, 3 | 3 |
| | 10 | 28-30 | 3 | C57BL/6J/♀/Chow | SEQ ID NO 6 equimolar 1.21 mg/kg | 0.121 mg/ml | iv | 0 | 0, 3 | 3 |
| C | 11 | 31-33 | 3 | C57BL/6J/♀/Chow | Saline | — | iv | 0 | 0, 3 | 3 |
| | 12 | 34-36 | 3 | C57BL/6J/♀/Chow | SEQ ID NO 1 1 mg/kg | 0.1 mg/ml | iv | 0 | 0, 7 | 7 |
| | 13 | 37-39 | 3 | C57BL/6J/♀/Chow | SEQ ID NO 4 equimolar 1.35 mg/kg | 0.135 mg/ml | iv | 0 | 0, 7 | 7 |
| | 14 | 40-42 | 3 | C57BL/6J/♀/Chow | SEQ ID NO 5 equimolar 1.28 mg/kg | 0.128 mg/ml | iv | 0 | 0, 7 | 7 |
| | 15 | 43-45 | 3 | C57BL/6J/♀/Chow | SEQ ID NO 6 equimolar 1.21 mg/kg | 0.121 mg/ml | iv | 0 | 0, 7 | 7 |
| D | 16 | 46-48 | 3 | C57BL/6J/♀/Chow | Saline | — | iv | 0 | 0, 7, 10 | 10 |
| | 17 | 49-51 | 3 | C57BL/6J/♀/Chow | SEQ ID NO 1 1 mg/kg | 0.1 mg/ml | iv | 0 | 0, 7, 10 | 10 |
| | 18 | 52-54 | 3 | C57BL/6J/♀/Chow | SEQ ID NO 4 equimolar 1.35 mg/kg | 0.135 mg/ml | iv | 0 | 0, 7, 10 | 10 |
| | 19 | 55-57 | 3 | C57BL/6J/♀/Chow | SEQ ID NO 5 equimolar 1.28 mg/kg | 0.128 mg/ml | iv | 0 | 0, 7, 10 | 10 |
| | 20 | 58-60 | 3 | C57BL/6J/♀/Chow | SEQ ID NO 6 equimolar 1.21 mg/kg | 0.121 mg/ml | iv | 0 | 0, 7, 10 | 10 |
| E | 21 | 61-63 | 3 | C57BL/6J/♀/Chow | Saline | — | iv | 0 | 0, 7, 13 | 13 |
| | 22 | 64-66 | 3 | C57BL/6J/♀/Chow | SEQ ID NO 1 1 mg/kg | 0.1 mg/ml | iv | 0 | 0, 7, 13 | 13 |
| | 23 | 67-69 | 3 | C57BL/6J/♀/Chow | SEQ ID NO 4 equimolar 1.35 mg/kg | 0.135 mg/ml | iv | 0 | 0, 7, 13 | 13 |
| | 24 | 70-72 | 3 | C57BL/6J/♀/Chow | SEQ ID NO 5 equimolar 1.28 mg/kg | 0.128 mg/ml | iv | 0 | 0, 7, 13 | 13 |
| | 25 | 73-75 | 3 | C57BL/6J/♀/Chow | SEQ ID NO 6 equimolar 1.21 mg/kg | 0.121 mg/ml | iv | 0 | 0, 7, 13 | 13 |
| F | 26 | 76-78 | 3 | C57BL/6J/♀/Chow | Saline | — | iv | 0 | 0, 7, 14, 16 | 16 |
| | 27 | 79-81 | 3 | C57BL/6J/♀/Chow | SEQ ID NO 1 1 mg/kg | 0.1 mg/ml | iv | 0 | 0, 7, 14, 16 | 16 |
| | 28 | 82-84 | 3 | C57BL/6J/♀/Chow | SEQ ID NO 4 equimolar 1.35 mg/kg | 0.135 mg/ml | iv | 0 | 0, 7, 14, 16 | 16 |
| | 29 | 85-87 | 3 | C57BL/6J/♀/Chow | SEQ ID NO 5 equimolar 1.28 mg/kg | 0.128 mg/ml | iv | 0 | 0, 7, 14, 16 | 16 |
| | 30 | 88-90 | 3 | C57BL/6J/♀/Chow | SEQ ID NO 6 equimolar 1.21 mg/kg | 0.121 mg/ml | iv | 0 | 0, 7, 14, 16 | 16 |

Dose Administration.

C57BL/6JBom female animals, app. 20 g at arrival, were dosed with 10 ml per kg BW (according to day 0 bodyweight) i.v. of the compound formulated in saline or saline alone according to Table 4.

Sampling of Liver and Kidney Tissue.

The animals were anaesthetized with 70% $CO_2$-30% $O_2$ and sacrificed by cervical dislocation according to Table 4. One half of the large liver lobe and one kidney were minced and submerged in RNAlater.

Total RNA Isolation and First Strand Synthesis.

Total RNA was extracted from maximum 30 mg of tissue homogenized by bead-milling in the presence of RLT-Lysis buffer using the Qiagen RNeasy kit (Qiagen cat. no. 74106) according to the manufacturer's instructions. First strand synthesis was performed using Reverse Transcriptase reagents from Ambion according to the manufacturer's instructions.

For each sample 0.5 μg total RNA was adjusted to (10.8 μl) with RNase free $H_2O$ and mixed with 2 μl random decamers (50 μM) and 4 μl dNTP mix (2.5 mM each dNTP) and heated to 70° C. for 3 min after which the samples were rapidly cooled on ice. 2 μl 10× Buffer RT, 1 μl MMLV Reverse Transcriptase (100 U/μl) and 0.25 μl RNase inhibitor (10 U/μl) were added to each sample, followed by incubation at 42° C. for 60 min, heat inactivation of the enzyme at 95° C. for 10 min and then the sample was cooled to 4° C. cDNA samples were diluted 1:5 and subjected to RT-QPCR using Taqman Fast Universal PCR Master Mix 2× (Applied Biosystems Cat #4364103) and Taqman gene expression assay (mApoB, Mn01545150_m1 and mGAPDH #4352339E) following the manufacturers protocol and processed in an Applied Biosystems RT-qPCR instrument (7500/7900 or ViiA7) in fast mode.

Oligo Content Sandwich ELISA:

Liver and kidney samples (100 mg) were collected in tubes at different times after dosing. The samples were added buffer, (pH 8.0 100 mM NaCl, 25 mM EDTA, 0.25 mM Tris), protease k (1%, Sigma P4850-5) and 2 Tungsten Carbide Beads (3 mm) (Qiagen) and homogenized for 8 min (Retsch MM300, 25 Hz [l/s]) and incubated the homogenate at 37° C. over night. The samples are spun at 14000 g for 15 minutes before use.

Standards 1-100 µg/g of LNA oligonucleotides in kidney and liver were prepared and treated as above. Standards and samples were diluted to (100-5000 ng/L) into 150 µl of a 35 nM solution of a biotinylated and digoxigenin modified capture and detection probe (5×SSCT buffer [(750 mM NaCl, and 75 mM sodium citrate, containing 0.05% (v/v) Tween-20 pH 7.0)] and mixed for an hour. Streptavidin-coated (Nunc Immobilizer Streptavidin F96 CLEAR module plate Nunc Cat. No. 436014) were washed three times (5×SSCT buffer, 300 µL). The samples 100 µL was transferred to the streptavidin coated plates and incubated for one hour under gentle shaking. The wells were aspirated and washed three times with 300 µl of 2×SSCT buffer (300 mM NaCl+30 mM sodium citrate containing 0.05% (v/v) Tween-20, pH 7.0). One hundred microliters of anti-Dig-AP Fab fragments (Roche Applied Science, Cat. No. 11 093 274 910) diluted 1:4000 in PBST (Phosphate buffered saline, pH 7.2) were added to the wells and incubated for 1 hour at room temperature under gentle agitation. The wells were aspirated and washed three times with 300 µl of 2×SSCT buffer. One hundred microliters of substrate solution (KPL BluePhos Microwell Phosphatase substrate system 50-88-00) were added to each well. The intensity of the color development was measured spectrophotometrically at 615 nm every 5 minutes after shaking. The test samples were referenced against the standard samples.

Example 5

Knock Down of PCSK9 mRNA with Cholesterol Conjugates In Vivo

NMRI mice were injected with a single dose saline or 10 mg/kg unconjugated LNA-antisense oligonucleotide (SEQ ID 7) or equimolar amounts of LNA antisense oligonucleotides conjugated to Cholesterol with different linkers and sacrificed at days 1-10 according to Tab. 5.

RNA was isolated from liver and kidney and subjected to qPCR with PCSK9 specific primers and probe to analyze for PCSK9 mRNA knockdown.

Figure 16:
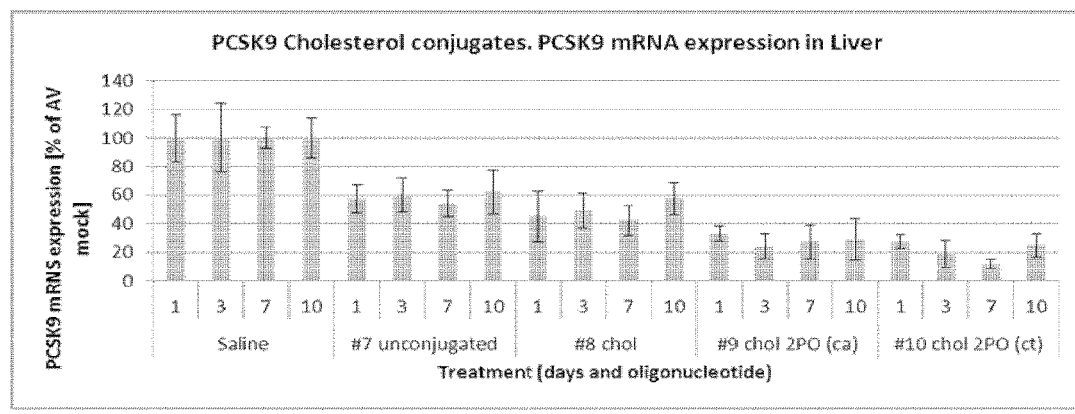
FIG. 16. Silencing of PCSK9 mRNA with cholesterol-conjugates in vivo. Mice were injected with a single dose of 10 mg/kg unconjugated LNA-antisense oligonucleotide (#7) or equimolar amounts of LNA antisense oligonucleotides conjugated to Cholesterol with different linkers (Tab. 5) and sacrificed at days 1, 3, 7 and 10 after dosing. RNA was isolated from liver and kidney and subjected to PCSK9 specific RT-qPCR A. Quantification of PCSK9 mRNA from liver samples normalized to BACT and shown as percentage of the average of equivalent saline controls B. Quantification of PCSK9 mRNA from kidney samples normalized to BACT and shown as percentage of the average of equivalent saline controls.
Figure 16:
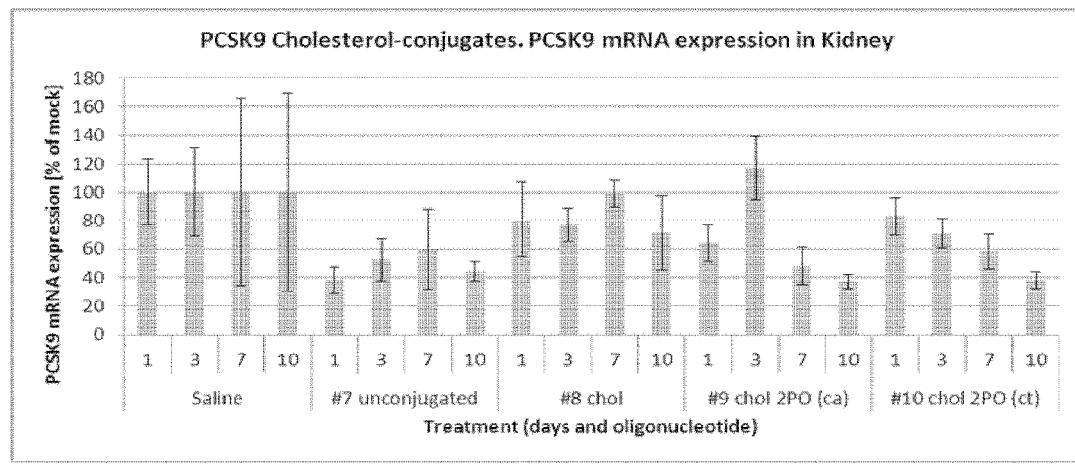

Conclusions:

Cholesterol conjugated to an PCSK9 LNA antisense oligonucleotide with a linker composed of 2 DNA with Phophodiester-backbone (Seq#9 and #10) showed an enhanced liver knock down of PCSK9 (FIG. 16) compared to the unconjugated compound (Seq #7), as well as compared to Cholesterol conjugates with stable linker (Seq#8).

Materials and Methods:

Experimental Design:

TABLE 5

| Part | Group no. | Animal id no. | No. of Animals | Animal strain/ gender/feed | Compound Dose level per day | Conc. at dose vol. 10 ml/kg | Adm. Route | Dosing day | Body weight day | Sacrifice day |
|---|---|---|---|---|---|---|---|---|---|---|
| A | 1 | 1-3 | 3 | NMRI/♀/Chow | Saline | — | iv | 0 | 0, 1 | 1 |
|   | 2 | 4-6 | 3 | NMRI/♀/Chow | SEQ ID NO 7 10 mg/kg | 1 mg/ml | iv | 0 | 0, 1 | 1 |
|   | 3 | 7-9 | 3 | NMRI/♀/Chow | SEQ ID NO 8 equimolar 11.3 mg/kg | 1.13 mg/ml | iv | 0 | 0, 1 | 1 |
|   | 5 | 13-15 | 3 | NMRI/♀/Chow | SEQ ID NO 9 equimolar 12.7 mg/kg | 1.27 mg/ml | iv | 0 | 0, 1 | 1 |
|   | 6 | 16-18 | 3 | NMRI/♀/Chow | SEQ ID NO 10 equimolar 12.7 mg/kg | 1.27 mg/ml | iv | 0 | 0, 1 | 1 |
| B | 7 | 19-21 | 3 | NMRI/♀/Chow | Saline | — | iv | 0 | 0, 3 | 3 |
|   | 8 | 22-24 | 3 | NMRI/♀/Chow | SEQ ID NO 7 10 mg/kg | 1 mg/ml | iv | 0 | 0, 3 | 3 |
|   | 9 | 25-27 | 3 | NMRI/♀/Chow | SEQ ID NO 8 equimolar 11.3 mg/kg | 1.13 mg/ml | iv | 0 | 0, 3 | 3 |
|   | 11 | 31-33 | 3 | NMRI/♀/Chow | SEQ ID NO 9 equimolar 12.7 mg/kg | 1.27 mg/ml | iv | 0 | 0, 3 | 3 |
|   | 12 | 34-36 | 3 | NMRI/♀/Chow | SEQ ID NO 10 equimolar 12.7 mg/kg | 1.27 mg/ml | iv | 0 | 0, 3 | 3 |
| C | 13 | 37-39 | 3 | NMRI/♀/Chow | Saline | — | iv | 0 | 0, 7 | 7 |
|   | 14 | 40-42 | 3 | NMRI/♀/Chow | SEQ ID NO 7 10 mg/kg | 1 mg/ml | iv | 0 | 0, 7 | 7 |
|   | 15 | 43-45 | 3 | NMRI/♀/Chow | SEQ ID NO 8 equimolar 11.3 mg/kg | 1.13 mg/ml | iv | 0 | 0, 7 | 7 |
|   | 17 | 49-51 | 3 | NMRI/♀/Chow | SEQ ID NO 9 equimolar 12.7 mg/kg | 1.27 mg/ml | iv | 0 | 0, 7 | 7 |

TABLE 5-continued

| Part | Group no. | Animal id no. | No. of Animals | Animal strain/ gender/feed | Compound Dose level per day | Conc. at dose vol. 10 ml/kg | Adm. Route | Dosing day | Body weight day | Sacrifice day |
|------|-----------|---------------|----------------|----------------------------|------------------------------|------------------------------|------------|------------|------------------|----------------|
|      | 18        | 52-54         | 3              | NMRI/♀/Chow                | SEQ ID NO 10 equimolar 12.7 mg/kg | 1.27 mg/ml | iv | 0 | 0, 7 | 7 |
| D    | 19        | 55-57         | 3              | NMRI/♀/Chow                | Saline                       | —                            | iv         | 0          | 0, 7, 10         | 10             |
|      | 20        | 58-60         | 3              | NMRI/♀/Chow                | SEQ ID NO 7 10 mg/kg         | 1 mg/ml                      | iv         | 0          | 0, 7, 10         | 10             |
|      | 21        | 61-63         | 3              | NMRI/♀/Chow                | SEQ ID NO 8 equimolar 11.3 mg/kg | 1.13 mg/ml | iv | 0 | 0, 7, 10 | 10 |
|      | 24        | 70-72         | 3              | NMRI/♀/Chow                | SEQ ID NO 10 equimolar 12.7 mg/kg | 1.27 mg/ml | iv | 0 | 0, 7, 10 | 10 |
| A    | 25        | 73-75         | 3              | NMRI/♀/Chow                | Saline                       | —                            | iv         | 0          | 0, 1             | 1              |

Dose Administration.

NMRI female animals, app. 20 g at arrival, were dosed with 10 ml per kg BW (according to day 0 bodyweight) i.v. of the compound formulated in saline or saline alone according to Table 5.

Sampling of Liver and Kidney Tissue.

The animals were anaesthetized with 70% $CO_2$-30% $O_2$ and sacrificed by cervical dislocation according to Table 4. One half of the large liver lobe and one kidney were minced and submerged in RNAlater.

Total RNA was extracted from maximum 10 mg of tissue homogenized by bead-milling in the presence of MagNA Pure LC RNA Isolation Tissue buffer (Roche cat. no 03 604 721 001) using the MagNa Pure 96 Cellular RNA Large Volume Kit (Roche cat no. 5467535001), according to the manufacturer's instructions. First strand synthesis was performed using Reverse Transcriptase reagents from Ambion according to the manufacturer's instructions. For each sample 0.5 µg total RNA was adjusted to (10.8 µl) with RNase free $H_2O$ and mixed with 2 µl random decamers (50 µM) and 4 µl dNTP mix (2.5 mM each dNTP) and heated to 70° C. for 3 min after which the samples were rapidly cooled on ice. 2 µl 10× Buffer RT, 1 µl MMLV Reverse Transcriptase (100 U/µl) and 0.25 µl RNase inhibitor (10 U/µl) were added to each sample, followed by incubation at 42° C. for 60 min, heat inactivation of the enzyme at 95° C. for 10 min and then the sample was cooled to 4° C. cDNA samples were diluted 1:5 and subjected to RT-QPCR using Taqman Fast Universal PCR Master Mix 2× (Applied Biosystems Cat #4364103) and Taqman gene expression assay (mPCSK9, Mn00463738_m1 and mActin #4352341E) following the manufacturers protocol and processed in an Applied Biosystems RT-qPCR instrument (7500/7900 or ViiA7) in fast mode.

Example 6

In Vitro Cleavage of Different DNA/PO-Linkers

FAM-labeled ASOs with different DNA/PO-linkers (PO linkers) were subjected to in vitro cleavage either in S1 nuclease extract (FIG. 6A), Liver or kidney homogenates or Serum FAM-labeled ASOs 100 µM with different DNA/PO-linkers were subjected to in vitro cleavage by S1 nuclease in nuclease buffer (60 U pr. 100 µL) for 20 and 120 minutes (A). The enzymatic activity was stopped by adding EDTA to the buffer solution. The solutions were then subjected to AIE HPLC analyses on a Dionex Ultimate 3000 using an Dionex DNApac p-100 column and a gradient ranging from 10 mM-1 M sodium perchlorate at pH 7.5. The content of cleaved and non cleaved oligonucleotide were determined against a standard using both a fluoresense detector at 615 nm and a uv detector at 260 nm.

| SEQ ID NO | Linker sequence | % cleaved after 20 min S1 | % cleaved after 120 min S1 |
|-----------|-----------------|---------------------------|-----------------------------|
| 20        | —               | 2                         | 5                           |
| 18        | a               | 29.1                      | 100                         |
| 17        | ca              | 40.8                      | 100                         |
| 16        | tca             | 74.2                      | 100                         |
| 19        | gac             | 22.9                      | n.d                         |

CONCLUSION

The PO linkers (or region B as referred to herein) results in the conjugate (or group C) being cleaved off, and both the length and/or the sequence composition of the linker can be used to modulate susceptibility to nucleolytic cleavage of region B. The Sequence of DNA/PO-linkers can modulate the cleavage rate as seen after 20 min in Nuclease S1 extract Sequence selection for region B (e.g. for the DNA/PO-linker) can therefore also be used to modulate the level of cleavage in serum and in cells of target tissues.

Liver, kidney and Serum (B) were spiked with oligonucleotide SEQ ID NO 16 to concentrations of 200 µg/g tissue. Liver and kidney samples collected from NMRI mice were homogenized in a homogenisation buffer (0.5% Igepal CA-630, 25 mM Tris pH 8.0, 100 mM NaCl, pH 8.0 (adjusted with 1 N NaOH). The homogenates were incubated for 24 hours at 37° and thereafter the homogenates were extracted with phenol-chloroform. The content of cleaved and non cleaved oligonucleotide in the extract from liver and kidney and from the serum were determined against a standard using the above HPLC method.

| Seq ID | Linker Sequence | % cleaved after 24 hrs liver homogenate | % cleaved after 24 hrs kidney homogenate | % cleaved after 24 hours in serum |
|--------|-----------------|------------------------------------------|-------------------------------------------|-----------------------------------|
| 16     | tca             | 83                                       | 95                                        | 0                                 |

CONCLUSION

The PO linkers (or region B as referred to herein) results in cleavage of the conjugate (or group C) from the oligonucleotide, in liver or kidney homogenate, but not in serum.

Note: cleavage in the above assays refers to the cleavage of the cleavable linker, the oligomer or region A should remain functionally intact. The susceptibility to cleavage in the above assays can be used to determine whether a linker is biocleavable or physiologically labile.

Example 7a

In Vivo Inhibition of FVII (1 Mg/Kg)

An in vivo mouse study was prepared using a total of 6 groups of mice (n=3). Each mouse was administered a single i.v. dose of LNA compound targeting FVII mRNA, at 1 mg/kg or equimolar compared to SEQ ID #12. A saline control group was included. The mice were pre-bled 1 day before administration, and subsequent bleeds were taken at day 1 and 2 after administration. The mice were sacrificed at days 4, liver, kidney, and blood samples were taken. See table 7 for study setup.

Factor VII serum levels, mRNA levels, and oligonucleotide tissue content were measured using standard assay techniques.

Figure 18:
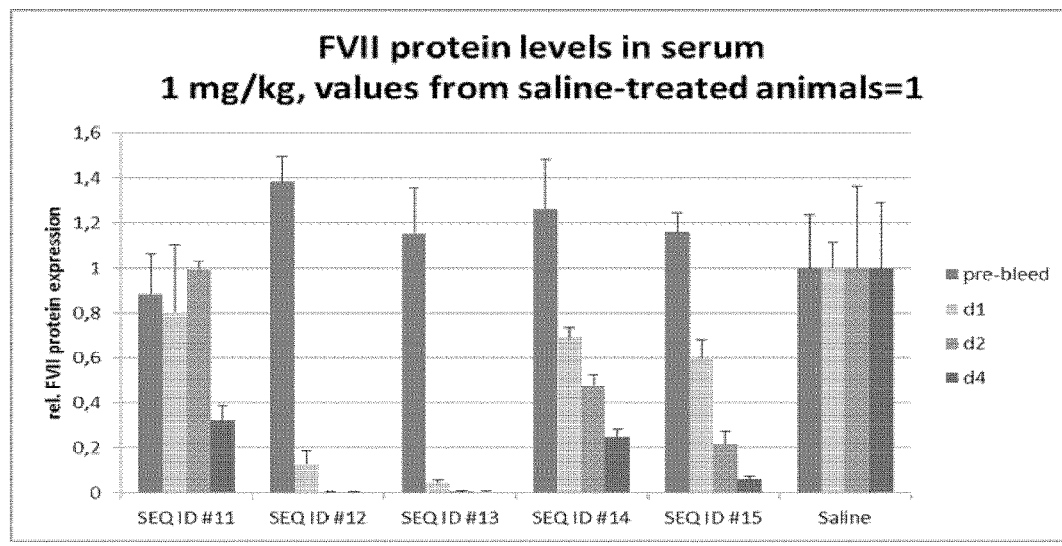
FIG. 18: Example 7a: FVII serum protein levels
Figure 19:
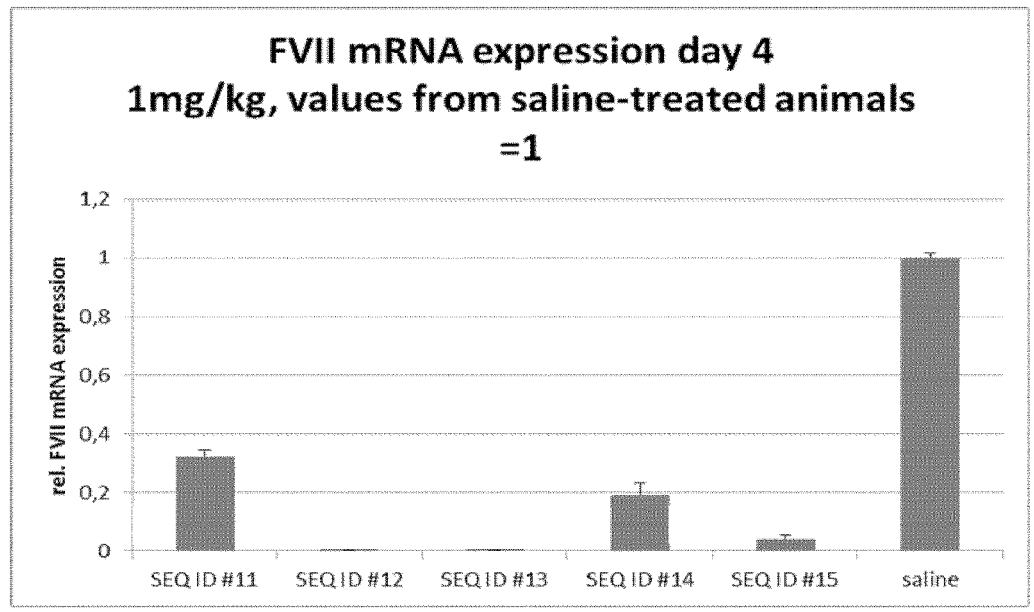
FIG. 19: Example 7a: FVII mRNA levels in liver day 4
Figure 20:
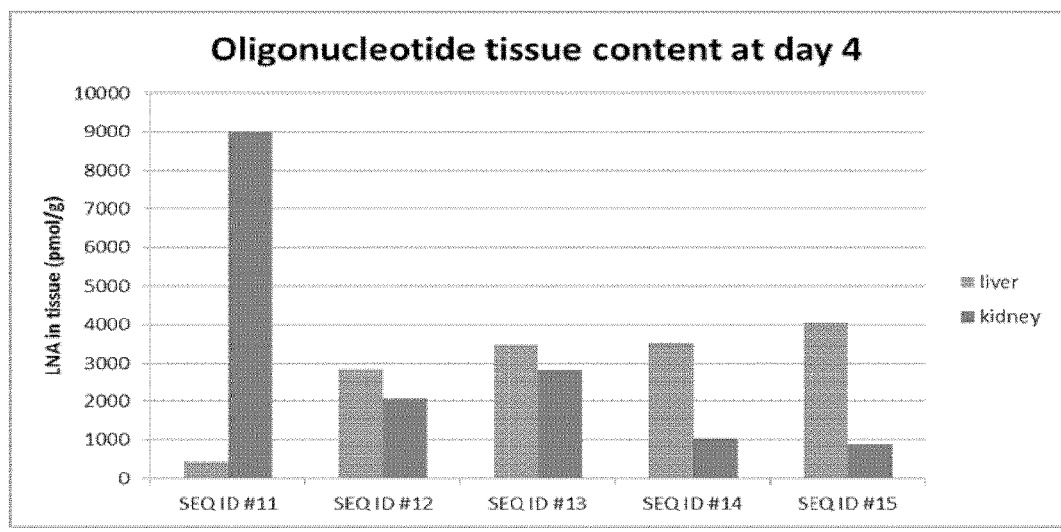
FIG. 20: Example 7a: Oligonucleotide content in liver and kidney day 4

Conclusions:

The DNA/PO-linker (PO) improves the FVII protein down regulation in serum (FIG. 18) for FVII mRNA targeting LNA oligonucleotides with cholesterol conjugates when comparing to the widely used dithio linker (disulphide) (PO linker SEQ ID #15 compare to SS linker SEQ ID #14). Using GalNAc as conjugate it is apparent that the PO linker improves the down regulation of FVII protein when compared to the aminolinked conjugated LNA oligonucleotide (PO linker SEQ ID #13 compare to amino linked SEQ ID #12). The GalNac conjugate is known to be biocleavable (possibly due to the peptide linker), and as such it appears that the PO linker further enhances the release of active and potent compound in the target cell. These data corresponds to the mRNA expression data (FIG. 19). The tissue content of oligonucleotide in kidney and liver shows how the conjugates change the distribution (FIG. 20). It is seen that the two cholesterol conjugated compounds gives similar distribution (compare SEQ ID #14 and #15) so with the enhanced mRNA and FVII protein down regulation of the PO linker compound (SEQ ID #15) it is seen how the PO linker enhances the activity of the FVII targeting LNA oligonucleotide when comparing to SEQ ID #14.

Materials and Methods:
Experimental Design:

TABLE 7

| group | compound | termination time point post dose | group size | dose (d0) mg/kg |
|---|---|---|---|---|
| 1 | saline | d4 | 3 | none |
| 2 | SEQ ID #11 | d4 | 3 | 1 |
| 3 | SEQ ID #12 | d4 | 3 | 1 |
| 4 | SEQ ID #13 | d4 | 3 | 1 |
| 5 | SEQ ID #14 | d4 | 3 | 1 |
| 6 | SEQ ID #15 | d4 | 3 | 1 |

Female mice were administered iv and liver, kidney, and blood were sampled at sacrifice on day 4, Additional blood draws were made before dosing and also on day 1 and 2 after dosing.

Example 7b

In Vivo Inhibition of FVII (0.1 and 0.25 Mg/Kg)

Figure 21:
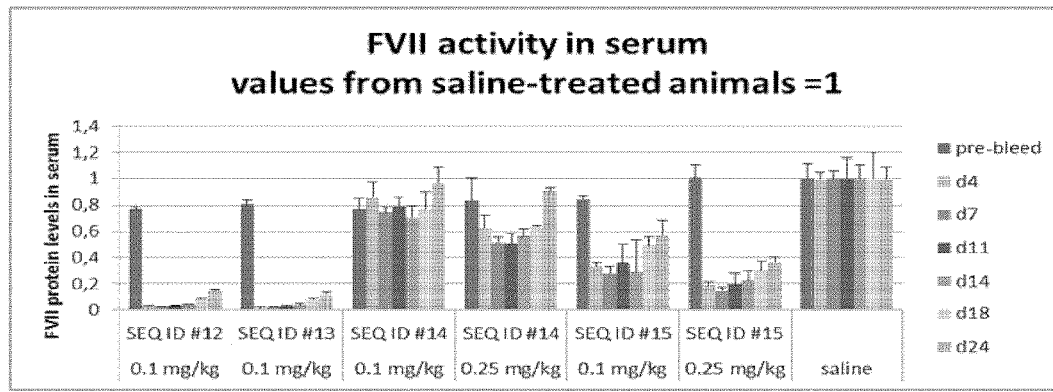
FIG. 21: Example 7b—FVII serum protein levels
Figure 22:
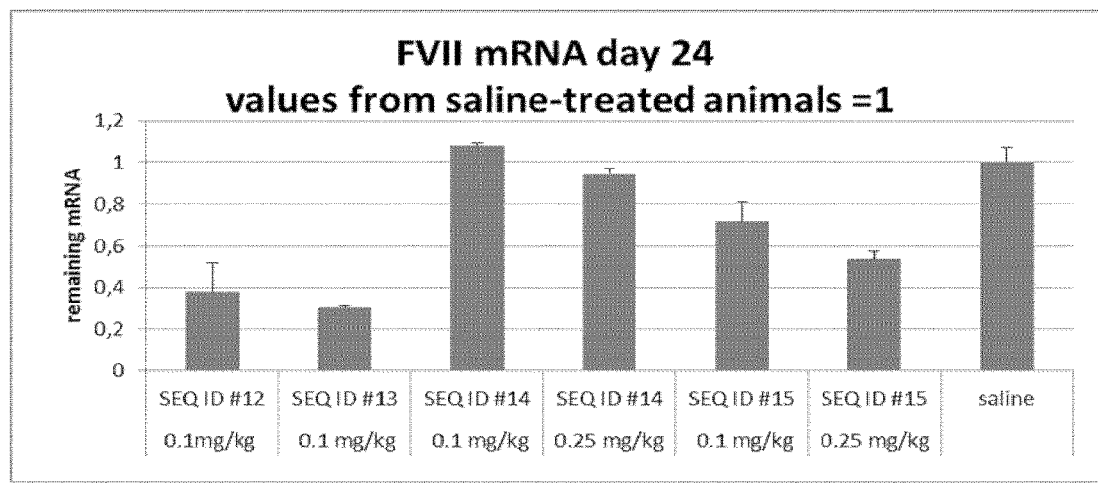
FIG. 22: FVII mRNA levels in liver day 24
Figure 23:
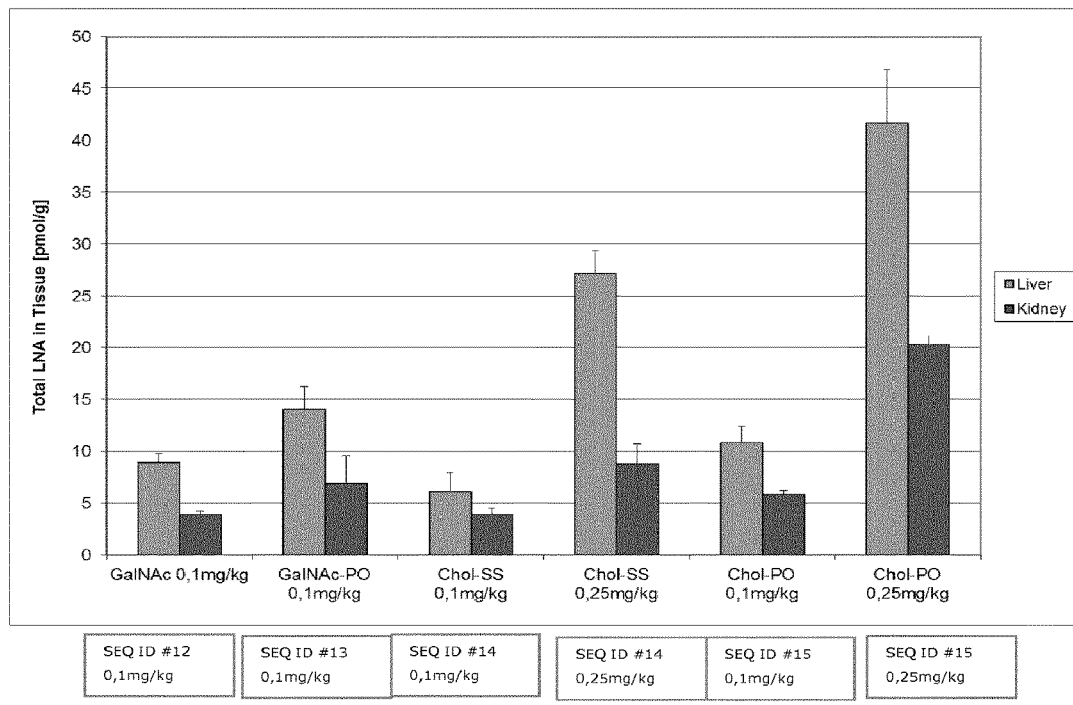
FIG. 23: Oligonucleotide content in liver and kidney day 4

An in vivo mouse study was prepared using a total of 7 groups of mice (n=3). Each mouse was administered a single i.v. dose of LNA compound targeting FVII mRNA, at either 0.1 mg/kg or 0.25 mg/kg in equimolar amount compared to SEQ ID #12. A saline control group was included. The mice were pre-bled 1 day before administration, and subsequent bleeds were taken at days 4, 7, 11, 14, and 18 after administration. The mice were sacrificed at days 24, liver, kidney, and blood samples were taken. See table 8 for study setup. Factor VII serum levels, mRNA levels, and oligonucleotide tissue content were measured using standard assay techniques Conclusions:

The DNA/PO-linker (PO) improves the FVII protein down regulation (FIG. 21) for FVII mRNA targeting LNA oligonucleotides with cholesterol conjugates when comparing to the widely used dithio linker (PO linker SEQ ID #15 compare to SS linker SEQ ID #14) at both 0.1 mg/kg and 0.25 mg/kg. Using GalNAc as conjugate mRNA data (FIG. 22) suggest that the PO linker improves the down regulation when compared to the aminolinked conjugated LNA oligonucleotide (PO linker SEQ ID #13 compare to amino linked SEQ ID #12). The mRNA expression data (FIG. 22) supports the improved activity of the PO linker compound (SEQ ID #15) compared to the dithio linked conjugate (SEQ ID #14). The tissue content of oligonucleotide in kidney and liver shows how the conjugates change the distribution (FIG. 23). Data suggest that the PO linker enhances the uptake both in liver and kidney at these dose ranges for both Cholesterol conjugate and GalNAc conjugate (compare SEQ ID #14 and #15 and compare SEQ ID #13 to #12)

Materials and Methods:
Experimental Design:

TABLE 8

| group | compound | termination time point post dose | group size | dose (d0) mg/kg |
|---|---|---|---|---|
| 1 | Saline | d24 | 3 | none |
| 2 | SEQ ID #12 | d24 | 3 | 0.1 |
| 3 | SEQ ID #13 | d24 | 3 | 0.1 |
| 4 | SEQ ID #14 | d24 | 3 | 0.1 |
| 5 | SEQ ID #14 | d24 | 3 | 0.25 |
| 6 | SEQ ID #15 | d24 | 3 | 0.1 |
| 7 | SEQ ID #15 | d24 | 3 | 0.25 |

Male mice were administered iv and liver, kidney, and blood were sampled at sacrifice on day 24, Additional blood draws were made before dosing and also on day 4, 7, 11, 14, and 18 after dosing.

Example 8

In Vivo Silencing of ApoB mRNA with Different Conjugates and PO-Linker

Figure 24:
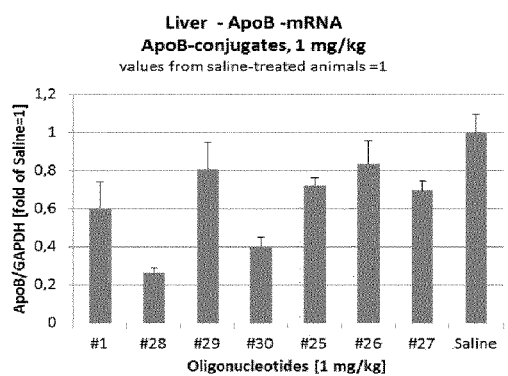
FIG. 24. In vivo silencing of ApoB mRNA with different conjugates and PO-linker. Mice were treated with 1 mg/kg of ASO with different conjugates either without biocleavable linker, with Dithio-linker (SS) or with DNA/PO-linker (PO). RNA was isolated from liver (A) and kidney samples (B) and analyzed for ApoB mRNA knock down. Data is shown compared to Saline (=1).
Figure 24:
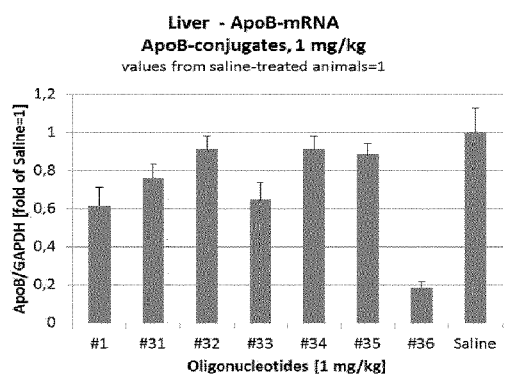
Figure 24:
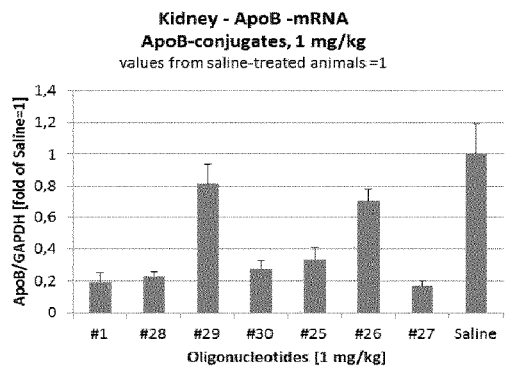
Figure 24:
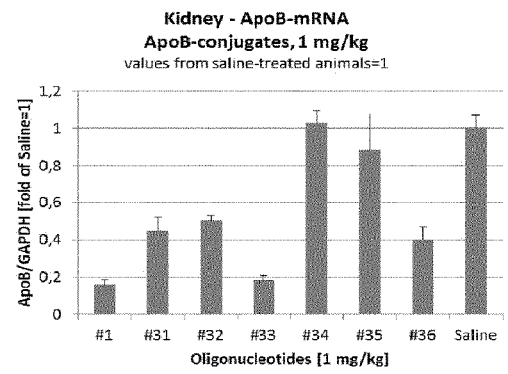

To explore the impact of the biocleavable DNA/PO-linker on additional conjugates C57BL6l mice were treated i.v. with saline control or with a single dose of 1 mg/kg kg for parent compound #1 or equimolarly of ASO conjugated to Mono-GalNAc, Folic acid, Fam or Tocopherol, either without bioleavable linker, with Dithio-linker (SS) or with DNA/PO-linker (PO). After 7 days animals were sacrificed and RNA was isolated from liver and kidney samples and analyzed for ApoB mRNA expression (FIG. 24)

Conclusions:

For all 4 conjugates the DNA/PO-linker improves ApoB knock down in the liver compared to the widely used dithio-linker (compare #27 with #26, #30 with #29, #33 with

32 and #36 with #35). For mono-GalNAc and Tocopherol the DNA/PO-linker improves knock down of ApoB in the liver even compared to unconjugated compound (compare #30 and #36 with #1). Tocopherol combined with a DNA/PO-linker shows capability of redirecting a compound from kidney to liver (compare A and B, #36 with #1)

Materials and Methods:
Experimental Design:

TABLE 9

| Gr. no. | Animal ID no. | Animal strain/ gender/ feed | Compound Seq ID, dose 1 mg/kg | Adm. Route | Dosing Day | Sacrifice Day |
|---|---|---|---|---|---|---|
| 1 | 1-5 | NMRI ♀- Chow | 1 | i.v. | 0 | 7 |
| 2 | 5-10 | NMRI ♀- Chow | 28 | i.v. | 0 | 7 |
| 3 | 11-15 | NMRI ♀- Chow | 29 | i.v. | 0 | 7 |
| 4 | 16-20 | NMRI ♀- Chow | 30 | i.v.. | 0 | 7 |
| 5 | 21-25 | NMRI ♀- Chow | 25 | i.v. | 0 | 7 |
| 6 | 26-30 | NMRI ♀- Chow | 26 | i.v. | 0 | 7 |
| 7 | 31-35 | NMRI ♀- Chow | 27 | i.v. | 0 | 7 |
| 8 | 36-40 | NMRI ♀- Chow | NaCl 0.9% | i.v. | 0 | 7 |
| 1 | 1-5 | NMRI ♀- Chow | 1 | i.v. | 0 | 7 |
| 2 | 5-10 | NMRI ♀- Chow | 31 | i.v. | 0 | 7 |
| 3 | 11-15 | NMRI ♀- Chow | 32 | i.v. | 0 | 7 |
| 4 | 16-20 | NMRI ♀- Chow | 33 | i.v.. | 0 | 7 |
| 5 | 21-25 | NMRI ♀- Chow | 34 | i.v. | 0 | 7 |
| 6 | 26-30 | NMRI ♀- Chow | 35 | i.v. | 0 | 7 |
| 7 | 31-35 | NMRI ♀- Chow | 36 | i.v. | 0 | 7 |
| 8 | 36-40 | NMRI ♀- Chow | NaCl 0.9% | i.v. | 0 | 7 |

Dose Administration and Sampling.

C57BL6 mice were dosed i.v. with a single dose of 1 mg/kg ASO formulated in saline or saline alone according to the above table. Animals were sacrificed at day 7 after dosing and liver and kidney were sampled.

RNA isolation and mRNA analysis. Total RNA was extracted from liver and kidney samples and ApoB mRNA levels were analyzed using a branched DNA assay.

Example 9

In Vitro Silencing of Target X mRNA with Looped LNA ASO with PO-Linker

Figure 25:
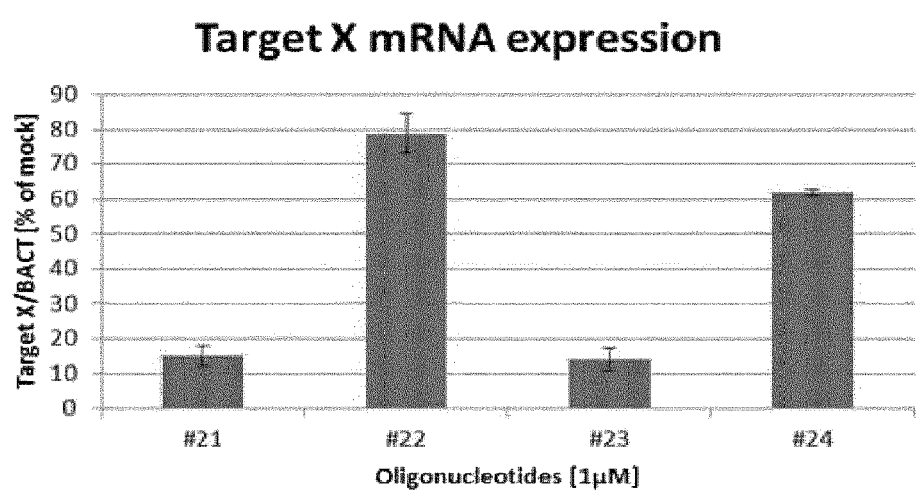
FIG. 25. In vitro silencing of Target X mRNA with looped LNA ASO with PO-linker. Neuro 2a cells were treated with looped LNA ASOs with or without PO-linker, respectively. After 6 days gymnosis mRNA was extracted and analyzed for target X mRNA knock down. mRNA expression is shown as percentage of mock treated samples.

Blocker groups might be beneficial regarding tolerability, specificity or reduced off-target effect of ASOs but challenging in terms of preserving the activity of the original, unblocked ASO. As an example for a blocker group we used a complementary sequence which is connected to the oligonucleotide by a non-complementary nucleotide stretch generating a hairpin loop. The unpaired bases in the loop where either 3 DNA nucleotides with Phophodiester-backbone (PO-linker) or the same DNA nucleotides with Phosphorothioate-backbone. To test the activity of the looped LNA-ASOs Neuro 2a cells were treated with 1 µM ASO in a gymnosis assay and RNA was extracted and subjected to RT-QPCR to analyze for target X mRNA knock down (FIG. 25).

Conclusion:

Looped ASOs with PO-linker (Seq ID #21 and #23) showed improved target X mRNA knock down compared to the same ASO sequence without PO-linker (Seq ID #22 and #24).

Materials and Methods:
Gymnosis Assay in N2a Cells:

Neuro 2a (mouse neuroblastoma) cells were seeded in 24 well plates with $1.8 \times 10^4$ cells/well and treated with 1 µM looped LNA ASOs with and without PO-linker, respectively in DMEM+Glutamax (gibco-life, #61965-026), 2 mM Glutamine, 10% FBS, 1 mM Sodium Pyruvate, 25 µg/ml Gentamicin.

Total RNA Isolation and First Strand Synthesis.

Total RNA was extracted after 6 days gymnosis using the Qiagen RNeasy kit (Qiagen cat. no. 74106) according to the manufacturer's instructions. First strand synthesis was performed using Reverse Transcriptase reagents from Ambion according to the manufacturer's instructions.

For each sample 0.5 µg total RNA was mixed with 2 µl random decamers (50 µM) and 4 µl dNTP mix (2.5 mM each dNTP) and heated to 70° C. for 3 min after which the samples were rapidly cooled on ice. 2 µl 10× Buffer RT, 1 µl MMLV Reverse Transcriptase (100 U/µl) and 0.25 µl RNase inhibitor (10 U/µl) were added to each sample, followed by incubation at 42° C. for 60 min, heat inactivation of the enzyme at 95° C. for 10 min and then the sample was cooled to 4° C. cDNA samples were diluted 1:5 and subjected to RT-QPCR using Taqman Fast Universal PCR Master Mix 2× (Applied Biosystems Cat #4364103) and Taqman gene expression assay against target X following the manufacturers protocol and processed in an Applied Biosystems RT-qPCR instrument (ViiA7) in fast mode. Target X mRNA expression was normalized to Beta actin mRNA expression (mBACT #4352341E) and compared to mock mRNA levels.

Example 10

Non-Human Primate Study

The primary objective for this study is to investigate selected lipid markers over 7 weeks after a single slow bolus injection of anti-PCSK9 and anti-ApoB LNA conjugated compounds to cynomolgus monkeys and assess the potential toxicity of compounds in monkey. The compounds used in this study are SEQ ID NOs 46 and 49, 5 and 54, which were prepared in sterile saline (0.9%) at an initial concentration of 0.625 and 2.5 mg/ml).

Male (PCSK9) or female monkeys (ApoB) monkeys of at least 24 months old are used, and given free access to tap water and 180 g of MWM(E) SQC SHORT expanded diet (Dietex France, SDS, Saint Gratien, France) will be distributed daily per animal. The total quantity of food distributed in each cage will be calculated according to the number of animals in the cage on that day. In addition, fruit or vegetables will be given daily to each animal. The animals will be acclimated to the study conditions for a period of at least 14 days before the beginning of the treatment period. During this period, pre-treatment investigations will be performed. The animals are dosed i.v. at a dose if, for example, 0.25 mg/kg or 1 mg/kg. The dose volume will be 0.4 mL/kg. 2 animals are used per group. After three weeks, the data will be analyzed and a second group of animals using a higher or lower dosing regimen may be initiated—preliminary dose setting is 0.5 mg/kg and 1 mg/kg, or lower than that based on the first data set.

The dose formulations will be administered once on Day 1. Animals will be observed for a period of 7 weeks following treatment, and will be released from the study on Day 51. Day 1 corresponds to the first day of the treatment period. Clinical observations and body weight and food intake (per group) will be recorded prior to and during the study.

Blood is sampled and analysis at the following time points:

| Study Day | Parameters |
| --- | --- |
| −8 | RCP, L, Apo-B, PCSK9*, OA |
| −1 | L, Apo-B, PCSK9*, PK, OA |
| 1 | Dosing |
| 4 | LSB, L, Apo-B, PCSK9*, OA |
| 8 | LSB, L, Apo-B, PCSK9* , PK, OA |
| 15 | RCP, L, Apo-B, PCSK9* PK, OA |
| 22 | LSB, L, Apo-B, PCSK9* PK, OA |
| 29 | L, Apo-B, PCSK9* PK, OA |
| 36 | LSB, L, Apo-B, PCSK9* PK, OA |
| 43 | L, PK, Apo-B, PCSK9* PK, OA |
| 50 | RCP, L, Apo-B, PCSK9* PK, OA |

RCP 0 routine clinical pathology,
LSB = liver safety biochemistry,
PK = pharmacokinetics,
OA = other analysis,
L = Lipids.

Blood Biochemistry

The following parameters will be determined for all surviving animals at the occasions indicated below:
- full biochemistry panel (complete list below)—on Days −8, 15 and 50,
- liver Safety (ASAT, ALP, ALAT, TBIL and GGT only)—on Days 4, 8, 22 and 36,
- lipid profile (Total cholesterol, HDL-C, LDL-C and Triglycerides) and Apo-B only—on Days −1, 4, 8, 22, 29, 36, and 43.

Blood (approximately 1.0 mL) is taken into lithium heparin tubes (using the ADVIA 1650 blood biochemistry analyzer): Apo-B, sodium, potassium, chloride, calcium, inorganic phosphorus, glucose, HDL-C, LDL-C, urea, creatinine, total bilirubin (TBIL), total cholesterol, triglycerides, alkaline phosphatase (ALP), alanine aminotransferase (ALAT), aspartate aminotransferase (ASAT), creatine kinase, gamma-glutamyl transferase (GGT), lactate dehydrogenase, total protein, albumin, albumin/globulin ratio.

Analysis of blood: Blood samples for PCSK9 analysis will be collected from Group 16 animals only on Days −8, −1, 4, 8, 15, 22, 29, 36, 43 and 50.

Venous blood (approximately 2 mL) will be collected from an appropriate vein in each animal into a Serum Separating Tube (SST) and allowed to clot for at least 60±30 minutes at room temperature. Blood will be centrifuged at 1000 g for 10 minutes under refrigerated conditions (set to maintain +4° C.). The serum will be transferred into 3 individual tubes and stored at −80° C. until analyzed at CitoxLAB France using an ELISA method (Circulex Human PCSK9 ELISA kit, CY-8079, validated for samples from cynomolgus monkey).

Other Analysis: WO2011009697 & WO2010142805 provides the methods for the following analysis: qPCR, PCSK9/ApoB mRNA analysis, Other analysis includes PCSK9/ApoB protein ELISA, serum Lp(a) analysis with ELISA (Mercodia No. 10-1106-01), tissue and plasma oligonucleotide analysis (drug content), Extraction of samples, standard—and QC-samples, Oligonucleotide content determination by ELISA.

Example 11

Liver and Kidney Toxicity Assessment in Rat

Compounds of the invention can be evaluated for their toxicity profile in rodents, such as in mice or rats. By way of example the following protocol may be used: Wistar Han CrI:WI(Han) are used at an age of approximately 8 weeks old. At this age, the males should weigh approximately 250 g. All animals have free access to SSNIFF R/M-H pelleted maintenance diet (SSNIFF Spezialdiaten GmbH, Soest, Germany) and to tap water (filtered with a 0.22 μm filter) contained in bottles. The dose level of 10 and 40 mg/kg/dose is used (sub-cutaneous administration) and dosed on days 1 and 8. The animals are euthanized on Day 15. Urine and blood samples are collected on day 7 and 14. A clinical pathology assessment is made on day 14. Body weight is determined prior to the study, on the first day of administration, and 1 week prior to necropsy. Food consumption per group will be assessed daily. Blood samples are taken via the tail vein after 6 hours of fasting. The following blood serum analysis is performed: erythrocyte count mean cell volume packed cell volume hemoglobin mean cell hemoglobin concentration mean cell hemoglobin thrombocyte count leucocyte count differential white cell count with cell morphology reticulocyte count, sodium potassium chloride calcium inorganic phosphorus glucose urea creatinine total bilirubin total cholesterol triglycerides alkaline phosphatase alanine aminotransferase aspartate aminotransferase total protein albumin albumin/globulin ratio. Urinalysis are performed α-GST, β-2 Microglobulin, Calbindin, Clusterin, Cystatin C, KIM-1, Osteopontin, TIMP-1, VEGF, and NGAL. Seven analytes (Calbindin, Clusterin, GST-α, KIM-1, Osteopontin, TIMP-1, VEGF) will be quantified under Panel 1 (MILLIPLEX® MAP Rat Kidney Toxicity Magnetic Bead Panel 1, RKTX1 MAG-37K). Three analytes (β-2 Microglobulin, Cystatin C, Lipocalin-2/NGAL) will be quantified under Panel 2 (MILLIPLEX® MAP Rat Kidney Toxicity Magnetic Bead Panel 2, RKTX2MAG-37K). The assay for the determination of these biomarkers' concentration in rat urines is based on the Luminex xMAP® technology. Microspheres coated with anti-α-GST/β-2 microglobulin/calbindin/clusterin/cystacin C/KIM-1/osteopontin/TIMP-1/VEGF/NGAL antibodies are color-coded with two different fluorescent dyes. The following parameters are determined (Urine using the ADVIA 1650): Urine protein, urine creatinine. Quantitative parameters: volume, pH (using 10-Multistix SG test strips/Clinitek 500 urine analyzer), specific gravity (using a refractometer). Semi-quantitative parameters (using 10-Multistix SG test strips/Clinitek 500 urine analyzer): proteins, glucose, ketones, bilirubin, nitrites, blood, urobilinogen, cytology of sediment (by microscopic examination). Qualitative parameters: Appearance, color. After sacrifice, the body weight and kidney, liver and spleen weight are determined and organ to body weight ratio calculated. Kidney and liver samples will be taken and either frozen or stored in formalin. Microscopic analysis is performed.

The invention claimed is:

1. An oligomeric compound of 8-35 nucleotides in length, comprising three regions:
   i) a first region (region A), which is an antisense oligomer of 7-26 contiguous nucleotides complementary to a nucleic acid target, wherein the first region comprises at least four nucleoside analogues and wherein the internucleoside linkages of the first region are internucleoside linkage other than phosphodiester;
   ii) a second region (region B) which is covalently linked to the 5' or 3' nucleotide of the first region via a phosphodiester internucleoside linkage, wherein the second region consists of 2-10 phosphodiester linked DNA or RNA nucleosides; and
   iii) a third region which comprises a conjugate moiety or a targeting moiety, wherein the third region is covalent linked to the second region.

2. The oligomeric compound according to claim 1, wherein the internucleoside linkages other than phosphodiester are selected from the group consisting of phosphorothioate, phosphorodithioate and boranophosphate.

3. The oligomeric compound according to claim 1, wherein the nucleic acid target is selected from the group consisting of a microRNA, a mRNA, a lncRNA (long non-coding RNA), a snRNA, snoRNA, and a viral RNA.

4. The oligomeric compound according to claim 1, wherein the first region is a gapmer, a mixmer, or a totalmer.

5. The oligomeric compound according of claim 1, wherein the first region comprises at least one bicyclic nucleotide analogue (LNA).

6. The oligomeric compound according to claim 1, wherein the first region and the second region form a contiguous nucleotide sequence.

7. The oligomeric compound according to claim 1, wherein the second region is 5' to the first region.

8. The oligomeric compound according to claim 1, wherein the second region is 3' to the first region.

9. The oligomeric compound according to claim 1, wherein the second region is covalently linked to the third region at the terminal nucleoside of the second region.

10. The oligomeric compound according to claim 1, wherein the third region comprises a non-nucleotide moiety selected from a sterol and a carbohydrate.

11. The oligomeric compound according to claim 10, wherein the third region comprises a moiety selected from the group consisting of: a lipophilic group, a protein, a peptide, an antibody or fragment thereof, a polymer, a reporter group, a dye, a receptor ligand, a small molecule drug, a prodrug, and a vitamin.

12. The oligomeric compound according to claim 1, wherein the third region comprises a targeting group.

13. The oligomeric compound according to claim 1, wherein the second and third regions are covalently joined by a linker group.

14. The oligomeric compound according to claim 13, wherein the linker group between the second and third regions comprises a group selected from phosphodiester, a phosphorothioate, a phosphorodithioate and a boranophosphate group.

15. A pharmaceutical composition comprising the oligomeric compound of claim 1, and a pharmaceutically acceptable diluent, carrier, salt or adjuvant.

16. The oligomeric compound according to claim 1 for use in the inhibition of a nucleic acid target in a cell.

17. The oligomeric compound according to claim 1 for use in medicine.

18. The oligomeric compound according to claim 1 for use in the treatment of a medical disease or disorder.

19. The oligomeric compound according to claim 1, wherein region B consists of a dinucleotide of sequence AA, AT, AC, AG, TA, TT, TC, TG, CA, CT, CC, CG, GA, GT, GC, or GG.

20. The oligomeric compound according to claim 1, wherein region B consists of a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, or GGG.

21. The oligomeric compound according to claim 10, wherein the third region comprises cholesterol.

22. The oligomeric compound according to claim 10, wherein the third region comprises a GalNac cluster.

* * * * *

UNITED STATES PATENT AND TRADEMARK OFFICE
CERTIFICATE OF CORRECTION

PATENT NO.       : 10,077,443 B2
APPLICATION NO.  : 14/443367
DATED            : September 18, 2018
INVENTOR(S)      : Nanna Albaek et al.

Page 1 of 1

It is certified that error appears in the above-identified patent and that said Letters Patent is hereby corrected as shown below:

In the Claims

Column 151, Line 55, Claim 5, delete "of" and insert -- to --

Signed and Sealed this
Fifth Day of February, 2019

Andrei Iancu
*Director of the United States Patent and Trademark Office*